(12) United States Patent
Sadelain et al.

(10) Patent No.: US 12,259,390 B2
(45) Date of Patent: Mar. 25, 2025

(54) CANCER ANTIGEN TARGETS AND USES THEREOF

(71) Applicant: MEMORIAL SLOAN-KETTERING CANCER CENTER, New York, NY (US)

(72) Inventors: Michel Sadelain, New York, NY (US); Fabiana Perna, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 321 days.

(21) Appl. No.: 16/795,346

(22) Filed: Feb. 19, 2020

(65) Prior Publication Data

US 2020/0182880 A1 Jun. 11, 2020

Related U.S. Application Data

(60) Division of application No. 15/966,992, filed on Apr. 30, 2018, now Pat. No. 11,193,938, which is a continuation of application No. PCT/US2017/045632, filed on Aug. 4, 2017.

(60) Provisional application No. 62/371,199, filed on Aug. 4, 2016.

(51) Int. Cl.
| | |
|---|---|
| *A61P 35/00* | (2006.01) |
| *A61K 39/00* | (2006.01) |
| *A61P 35/02* | (2006.01) |
| *C07K 14/47* | (2006.01) |
| *C07K 14/705* | (2006.01) |
| *C07K 14/715* | (2006.01) |
| *C07K 14/72* | (2006.01) |
| *C07K 16/00* | (2006.01) |
| *C07K 16/28* | (2006.01) |
| *G01N 33/566* | (2006.01) |
| *G01N 33/569* | (2006.01) |
| *G01N 33/574* | (2006.01) |
| *G01N 33/68* | (2006.01) |
| *G16B 5/00* | (2019.01) |
| *G16B 20/00* | (2019.01) |
| *G16B 20/20* | (2019.01) |
| *G16B 20/30* | (2019.01) |
| *G16B 20/50* | (2019.01) |
| *G16B 30/00* | (2019.01) |
| *A61K 48/00* | (2006.01) |

(52) U.S. Cl.
CPC .... *G01N 33/57492* (2013.01); *A61K 39/4611* (2023.05); *A61K 39/4631* (2023.05); *A61K 39/464429* (2023.05); *A61K 39/464431* (2023.05); *A61P 35/00* (2018.01); *A61P 35/02* (2018.01); *C07K 14/4748* (2013.01); *C07K 14/705* (2013.01); *C07K 14/70503* (2013.01); *C07K 14/70575* (2013.01); *C07K 14/7158* (2013.01); *C07K 14/723* (2013.01); *C07K 16/00* (2013.01); *C07K 16/2875* (2013.01); *C07K 16/2878* (2013.01); *G01N 33/566* (2013.01); *G01N 33/56972* (2013.01); *G01N 33/6845* (2013.01); *G16B 5/00* (2019.02); *G16B 20/00* (2019.02); *G16B 20/20* (2019.02); *G16B 20/30* (2019.02); *G16B 20/50* (2019.02); *G16B 30/00* (2019.02); *A61K 2039/804* (2018.08); *A61K 48/00* (2013.01); *C07K 2317/622* (2013.01); *C07K 2319/03* (2013.01); *C07K 2319/70* (2013.01); *G06F 2218/00* (2023.01)

(58) Field of Classification Search
CPC .............. G01N 33/57492; A61K 35/17; A61K 39/0011; A61K 2039/804; A61P 35/00; A61P 35/02
USPC ....................................................... 424/138.1
See application file for complete search history.

(56) References Cited

U.S. PATENT DOCUMENTS

| | | | |
|---|---|---|---|
| 2003/0148951 A1 | 8/2003 | Hsi-Hsien et al. | |
| 2009/0203538 A1* | 8/2009 | Sugioka | C07K 16/2803 506/18 |
| 2015/0342993 A1 | 12/2015 | Kloss et al. | |
| 2015/0368342 A1 | 12/2015 | Wu et al. | |
| 2016/0108108 A1* | 4/2016 | Wang | A61K 31/69 514/17.7 |

FOREIGN PATENT DOCUMENTS

| | | |
|---|---|---|
| WO | WO 2014/055668 A1 | 4/2014 |
| WO | WO 2015/077789 A2 | 5/2015 |
| WO | WO 2015/095895 A1 | 6/2015 |
| WO | WO 2015/142675 A2 | 9/2015 |
| WO | WO 2016/090034 A2 | 6/2016 |
| WO | WO 2016/093878 A1 | 6/2016 |

OTHER PUBLICATIONS

Extended European Search Report for European Patent Application No. 17837803.0 dated Jun. 5, 2020.
Perna et al., "Integrating Proteomics and Transcriptomics for Systematic Combinatorial Chimeric Antigen Receptor Therapy of AML," Cancer Cell 32 506-519 (2017).

(Continued)

*Primary Examiner* — Yan Xiao
(74) *Attorney, Agent, or Firm* — Baker Botts L.L.P.

(57) ABSTRACT

The presently disclosed subject matter provides methods and compositions for treating myeloid disorders (e.g., acute myeloid leukemia (AML)). It relates to immunoresponsive cells bearing antigen recognizing receptors (e.g., chimeric antigen receptors (CARs)) targeting AML-specific antigens.

13 Claims, 64 Drawing Sheets

Specification includes a Sequence Listing.

(56) References Cited

OTHER PUBLICATIONS

U.S. Appl. No. 15/966,992 (US 2018/0348227), filed Apr. 30, 2018.
U.S. Appl. No. 15/966,992, Apr. 27, 2020 Non-Final Action.
U.S. Appl. No. 15/966,992, Feb. 11, 2020 Response Restriction Requirement.
U.S. Appl. No. 15/966,992. Nov. 21, 2019 Restriction Requirement.
"ADCs Show Promise in Leukemias," Cancer Discov 6:939 (2016), 2 pages.
"Q9UHX3-AGRE2, Adhesion G protein-coupled receptor E2," UniProtKB, Mar. 1, 2004 (Mar. 1, 2004), pp. 1-16. Retrieved from Internet: www.uniprotorg/uniprot/Q9UHX3> on Jul. 2, 2018.
Anderson et al., "C—C Chemokine Receptor 1 Expression in Human Hematolymphoid Neoplasia," Am J Clin Pathol. 133(3):473-483 (2010).
Arcangeli et al., "Balance of Anti-CD123 Chimeric Antigen Receptor Binding Affinity and Density for the Targeting of Acute Myeloid Leukemia," Mol Ther. 25(8):1933-1945 (2017).
Bagger et al., "BloodSpot: a database of gene expression profiles and transcriptional programs for healthy and malignant haematopoiesis," Nucleic Acids Res 44:D917-924 (2016).
Bakker et al., "C-type Lectin-Like Molecule-1: A Novel Myeloid Cell Surface Marker Associated with Acute Myeloid Leukemia," Cancer Res 64:8443-8450 (2004).
Baud et al., "EMR1, an Unusual Member in the Family of Hormone Receptors with Seven Transmembrane Segments," Genomics 26:334-344 (1995).
Becker et al., "Clofarabine with high dose cytarabine and granulocyte colony-stimulating factor (G-CSF) priming for relapsed and refractory acute myeloid leukaemia," Br J Haematol 155(2):182-189 (2011).
Bendall et al., "Expression of CD44 variant exons in acute myeloid leukemia is more common and more complex than that observed in normal blood, bone marrow or CD34+ cells," Leukemia 14:1239-1246 (2000).
Bolker, Tools for General Maximum Likelihood Estimation (Feb. 3, 2020).
Bowman et al., "The cloning of CD70 and its identification as the ligand for CD27," J Immunol 152:1756-1761 (1994).
Breems et al., "Prognostic Index for Adult Patients with Acute Myeloid Leukemia in First Relapse," J Clin Oncol 23(9):1969-1978 (2005).
Brentjens et al., "CD19-targeted T cells rapidly induce molecular remissions in adults with chemotherapy-refractory acute lymphoblastic leukemia," Sci Transl Med 5:177ra38 (2013).
Cancer Genome Atlas Research Network, "Genomic and Epigenomic Landscapes of Adult De Novo Acute Myeloid Leukemia," N Engl. J Med 368(22):2059-2074 (2013).
Casucci et al. "CD44v6-targeted T cells mediate potent antitumor effects against acute myeloid leukemia and multiple myeloma," Blood 122(20):3461-3472 (2013).
Chung et al., "CD99 is a Therapeutic Target on Disease Stem Cells in Myeloid Malignancies," Sci Transl Med 9(374):27 pages (2017).
Couzin-Frankel, "Cancer Immunotherapy. Breakthrough of the Year 2013," Science 342:1432-1433 (2013).
Curran et al., "Chimeric antigen receptors for T cell immunotherapy: current understanding and future directions," J Gene Med 14:405-415 (2012).
Davila et al., "CD19 CAR-Targeted T Cells Induce Long-Term Remission and B Cell Aplasia in an Immunocompetent Mouse Model of B cell Acute Lymphoblastic Leukemia," PLoS One 8(4):e61338 (2013).
Davila et al., "Efficacy and Toxicity Management of 19-28z CAR T Cell Therapy in B Cell Acute Lymphoblastic Leukemia," Sci Transl Med 6:224ra25 (2014).
Dimopoulos et al., "Daratumumab, Lenalidomide, and Dexamethasone for Multiple Myeloma," N Engl. J Med 375(14):1319-1331 (2016).
Downing et al., "Solution Structure of a Pair of Calcium-Binding Epidermal Growth Factor-like Domains: Implications for the Marfan Syndrome and Other Genetic Disorders," Cell 85:597-605 (1996).

Drent et al., "A Rational Strategy for Reducing On-Target Off-Tumor Effects of CD38-Chimeric Antigen Receptors by Affinity Optimization," Mol Ther 25(8):1946-1958 (2017).
Duong et al., "Enhancing the specificity of T-cell cultures for adoptive immunotherapy of cancer," Immunotherapy 3(1):33-48 (2011).
Durinck et al., "Mapping Identifiers for the Integration of Genomic Datasets with the R/Bioconductor package biomaRt," Nat Protoc 4(8):1184-1191 (2009).
Estey et al., "A stratification system for evaluating and selecting therapies in patients with relapsed or primary refractory acute myelogenous leukemia," Blood 88:756 (1996), 3 pages.
Gardner et al., "Acquisition of a CD19-negative myeloid phenotype allows immune escape of MLL-rearranged B-ALL from CD19 CAR-T-cell therapy," Blood 127(20) 2406-2410 (2016).
Gill et al., "Preclinical targeting of human acute myeloid leukemia and myeloablation using chimeric antigen receptor-modified T cells," Blood 123(15):2343-2354 (2014).
Goodwin et al., "Molecular and Biological Characterization of a Ligand for CD27 Defines a New Family of Cytokines with Homology to Tumor Necrosis Factor," Cell 73:447-456 (1993).
Hack, "Integrated transcriptome and proteome data: The challenges ahead," Brief Funct Genomic Proteomic 3(3):212-219 (2004).
Haider et al., "Integrated Analysis of Transcriptomic and Proteomic Data," Curr Genomics 14:91-110 (2013).
Heider et al., "CD44v6: a target for antibody-based cancer therapy," Cancer Immunol Immunother 53:567-579 (2004).
Hills et al., "Addition of gemtuzumab ozogamicin to induction chemotherapy in adult patients with acute myeloid leukaemia: a meta-analysis of individual patient data from randomised controlled trials," Lancet Oncol 15:986-996 (2014).
Hosen et al., "CD96 is a leukemic stem cell-specific marker in human acute myeloid leukemia," PNAS USA 104(26):11008-11013 (2007).
International Search Report mailed Oct. 27, 2017 in International Application No. PCT/US2017/045632.
Jacoby et al., "CD19 CAR immune pressure induces B-precursor acute lymphoblastic leukaemia lineage switch exposing inherent leukaemic plasticity," Nat Commun 7:12320 (2016), 10 pages.
Jensen et al., "Designing chimeric antigen receptors to effectively and safely target tumors," Curr Opin Immunol 33:9-15 (2015).
Jin et al., "Targeting of CD44 eradicates human acute myeloid leukemic stem cells," Nat Med 12(10):1167-1174 (2006).
Jordan et al., "The interleukin-3 receptor alpha chain is a unique marker for human acute myelogenous leukemia stem cells," Leukemia 14:1777-1784 (2000).
Kenderian et al., "CD33-specific chimeric antigen receptor T cells exhibit potent preclinical activity against human acute myeloid leukemia," Leukemia 29(8):1637-1647 (2015).
Kikushige et al., "TIM-3 Is a Promising Target to Selectively Kill Acute Myeloid Leukemia Stem Cells," Cell Stem Cell 7:708-717 (2010).
Kim et al., "A draft map of the human proteome," Nature 509(7502):575-581 (2014).
Kloss et al., "Combinatorial antigen recognition with balanced signaling promotes selective tumor eradication by engineered T cells," Nat Biotechnol 31:71-75 (2013).
Kochenderfer et al., "Donor-derived CD19-targeted T cells cause regression of malignancy persisting after allogeneic hematopoietic stem cell transplantation," Blood 122(25):4129-4139 (2013).
Kochenderfer et al., "Chemotherapy-Refractory Diffuse Large B-Cell Lymphoma and Indolent B-cell Malignancies can be Effectively Treated with Autologous T Cells Expressing an Anti-CD19 Chimeric Antigen Receptor," J Clin. Oncol 33(6):540-549 (2015).
Kong et al., "CD34+CD38+CD19+ as well as CD34+CD38−CD19+ cells are leukemia-initiating cells with self-renewal capacity in human B-precursor ALL," Leukemia 22:1207-1213 (2008).
Lamers et al., "Treatment of Metastatic Renal Cell Carcinoma with CAIX CAR-engineered T cells: Clinical Evaluation and Management of On-Target Toxicity," Mol Ther 21(4):904-912 (2013).

(56) References Cited

OTHER PUBLICATIONS

Lamers et al., "Treatment of Metastatic Renal Cell Carcinoma with Autologous T-Lymphocytes Genetically Retargeted against Carbonic Anhydrase IX: First Clinical Experience," J Clin Oncol 24(13):e20-22 (2006).
Law et al., "Lymphocyte Activation Antigen CD70 Expressed by Renal Cell Carcinoma is a Potential Therapeutic Target for Anti-CD70 Antibody-Drug Conjugates," Cancer Res 66(4):2328-2337 (2006).
Le et al., "PD-1 Blockade in Tumors with Mismatch-Repair Deficiency," N Engl. J Med 372:2509-2520 (2015).
LeBien et al., "B lymphocytes: how they develop and function," Blood 112(5):1570-1580 (2008).
Lee et al., "T cells expressing CD19 chimeric antigen receptors for acute lymphoblastic leukaemia in children and young adults: a phase 1 dose-escalation trial," Lancet 385:517-528 (2015).
Legras et al., "A Strong Expression of CD44-6v Correlates with Shorter Survival of Patients with Acute Myeloid Leukemia," Blood 91(9):3401-3413 (1998).
Lin et al., "Human EMR2, a Novel EGF-TM7 Molecule on Chromosome 19p13.1, is Closely Related to CD97," Genomics 67:188-200 (2000).
Lin et al., Identification and Characterization of a Seven Transmembrane Hormone Receptor using Differential Display, Genomics 41:301-308 (1997).
Lonial et al., "Daratumumab monotherapy in patients with treatment-refractory multiple myeloma (SIRIUS): an open-label, randomised, phase 2 trial," Lancet 387:1551-1560 (2016).
Lynn et al., "High-affinity FRβ-specific CAR T cells eradicate AML and normal myeloid lineage without HSC toxicity," Leukemia 30:1355-1364 (2016).
Lynn et al., "Targeting of folate receptor β on acute myeloid leukemia blasts with chimeric antigen receptor-expressing T cells," Blood 125(22):3466-3476 (2015).
Maiga et al., "Transcriptome analysis of G protein-coupled receptors in distinct genetic subgroups of acute myeloid leukemia: identification of potential disease-specific targets," Blood Cancer Journal, 6:1-9 (2016).
Majeti et al., "CD47 is an Adverse Prognostic Factor and Therapeutic Antibody Target on Human Acute Myeloid Leukemia Stem Cells," Cell 138:286-299 (2009).
Maude et al., "Chimeric Antigen Receptor T cells for Sustained Remissions in Leukemia," N Engl. J Med 371:1507-1517 (2014).
Maude et al., "Chimeric antigen receptor T-cell therapy for ALL," Hematology Am Soc Hematol Educ Program, pp. 559-564 (2014).
McEarchern et al., "Engineered anti-CD70 antibody with multiple effector functions exhibits in vitro and in vivo antitumor activities," Blood 109:1185-1192 (2007).
McEarchern et al., "Preclinical Characterization of SGN-70, a Humanized Antibody Directed against CD70," Clin Cancer Res 14(23):7763-7772 (2008).
McGranahan et al., "Clonal neoantigens elicit T cell immunoreactivity and sensitivity to immune checkpoint blockade," Science 351(6280):1463-1469 (2016).
Morgan et al., "Case Report of a Serious Adverse Event Following the Administration of T cells Transduced with a Chimeric Antigen Receptor Recognizing ERBB2," Mol Ther 18(4):843-851 (2010).
Parkhurst et al., "T cells Targeting Carcinoembryonic Antigen Can Mediate Regression of Metastatic Colorectal Cancer but Induce Severe Transient Colitis," Mol Ther 19(3):620-626 (2011).
Paszkiewicz et al., "Targeted antibody-mediated depletion of murine CD19 CAR T cells permanently reverses B cell aplasia," J Clin Invest 126(11):4262-4272 (2016).
Pegram et al., "Tumor-targeted T cells modified to secrete IL-12 eradicate systemic tumors without need for prior conditioning," Blood 119(18):4133-4141 (2012).
Perna et al., "Myeloid leukemia switch as immune escape from CD19 chimeric antigen receptor (CAR) therapy," Transl Cancer Res 5(Suppl 2):S221-S225 (2016).
Pizzitola et al., "Chimeric antigen receptors against CD33/CD123 antigens efficiently target primary acute myeloid leukemia cells in vivo," Leukemia 28:1596-1605 (2014).
Pulte et al., "Improvements in survival of adults diagnosed with acute myeloblastic leukemia in the early 21st century," Haematologica 93(4):594-600 (2008).
Qasim et al., "Molecular remission of infant B-ALL after infusion of universal TALEN gene-edited CAR T cells," Sci Transl Med 9:8 pages (2017).
Rafiq et al., "CD33-Directed Chimeric Antigen Receptor (CAR) T Cells for the Treatment of Acute Myeloid Leukemia (AML)," Blood 128(22):2825 (2016).
Ravandi et al., "Gemtuzumab Ozogamicin: Time to Resurrect?" J Clin Oncol 30(32):3921-3923 (2012).
Ritchie et al., "Persistence and Efficacy of Second Generation CAR T cell Against the LeY Antigen in Acute Myeloid Leukemia," Mol Ther 21(11):2122-2129 (2013).
Riviere et al., "Chimeric Antigen Receptors: A Cell and Gene Therapy Perspective," Mol Ther 25(5):1117-1124 (2017).
Rizvi et al., "Cancer Immunology. Mutational landscape determines sensitivity to PD-1 blockade in non-small cell lung cancer," Science 348(6230):124-128 (2015).
Ryan et al., "Targeting pancreatic and ovarian carcinomas using the auristatin-based anti-CD70 antibody-drug conjugate SGN-75," Br J Cancer 103:676-684 (2010).
Sadelain et al., "Chimeric antigen receptors: driving immunology towards synthetic biology," Curr Opin Immunol 41:68-76 (2016).
Sadelain et al., "Therapeutic T cell engineering," Nature 545:423-431 (2017).
Sadelain, "CAR therapy: the CD19 paradigm," J Clin Invest 125(9):3392-3400 (2015).
Saito et al., "Identification of Therapeutic Targets for Quiescent, Chemotherapy-Resistant Human Leukemia Stem Cells," Sci Transl Med 2:17ra9 (2010).
Shaffer et al., "T cells redirected against CD70 for the immunotherapy of CD70-positive malignancies," Blood 117(16):4304-4314 (2011).
Snyder et al., "Genetic Basis for Clinical Response to CTLA-4 Blockade in Melanoma," N Engl. J Med 371:2189-2199 (2014).
Sotillo et al., "Convergence of Acquired Mutations and Alternative Splicing of CD19 Enables Resistance to CART-19 Immunotherapy," Cancer Discov 5(12):1282-1295 (2015).
Strassberger et al., "A comprehensive surface proteome analysis of myeloid leukemia cell lines for therapeutic antibody development," J Proteomics 99:138-151 (2014).
Sun et al., "Expression of Ig-Like Transcript 4 Inhibitory Receptor in Human Non-small Cell Lung Cancer," Chest 134:783-788 (2008).
Sun et al., "The quest for spatio-temporal control of CAR T cells," Cell Res 25:1281-1282 (2015).
Supplementary Partial European Search Report dated Apr. 12, 2019 in Application No. EP 17837803.
Tashiro et al., "Treatment of Acute Myeloid Leukemia with T Cells Expressing Chimeric Antigen Receptors Directed to C-type Lectin-like Molecule 1," Mol Therapy 25(9):2202-2213 (2017).
Taussig et al., "Hematopoietic stem cells express multiple myeloid markers: implications for the origin and targeted therapy of acute myeloid leukemia," Blood 106:4086-4092 (2005).
Turatti et al., "Redirected Activity of Human Antitumor Chimeric Immune Receptors is Governed by Antigen and Receptor Expression Levels and Affinity of Interaction," J Immunother 30(7):684-693 (2007).
Turtle et al., "CD19 CAR-T cells of defined CD4+:CD8+ composition in adult B cell ALL patients," J Clin Invest 126(6):2123-2138 (2016).
Turtle et al., "Immunotherapy of non-Hodgkin's lymphoma with a defined ratio of CD8+ and CD4+ CD19-specific chimeric antigen receptor-modified T cells," Sci Transl Med 8:355ra116 (2016).
Uhlen et al., "Proteomics. Tissue-based map of the human proteome," Science 347(6220):11 pages (2015).
Van Allen et al., "Genomic correlates of response to CTLA-4 blockade in metastatic melanoma," Science 350(6257):207-211 (2015).

(56) References Cited

OTHER PUBLICATIONS

Van Rhenen et al., "The novel AML stem cell associated antigen CLL-1 aids in discrimination between normal and leukemic stem cells," Blood 110:2659-2666 (2007).
Walker et al., "Tumor Antigen and Receptor Densities Regulate Efficacy of a Chimeric Antigen Receptor Targeting Anaplastic Lymphoma Kinase," Mol Ther. 25(9):2189-2201 (2017).
Wang et al., "New development in CAR-T cell therapy," J Hematol Oncol 10:53 (2017), 11 pages.
Wang et al., "Treatment of CD33-directed Chimeric Antigen Receptor-modified T cells in One Patient with Relapsed and Refractory Acute Myeloid Leukemia," Mol Ther 23:184-191 (2015).
Weijtens et al., "Functional balance between T cell chimeric receptor density and tumor associated antigen density: CTL mediated cytolysis and lymphokine production," Gene Ther 7:35-42 (2000).
Wilhelm et al., "Mass-spectrometry-based draft of the human proteome," Nature 509:582-587 (2014).
Wilhelm et al., "RNA-seq analysis of 2 closely related leukemia clones that differ in their self-renewal capacity," Blood 117(2):e27-e38 (2011).
Wilkie et al., "Dual Targeting of ErbB2 and MUC1 in Breast Cancer using Chimeric Antigen Receptors Engineered to Provide Complementary Signaling," J Clin Immunol 32:1059-1070 (2012).
Wu et al., "Remote control of therapeutic T cells through a small molecule-gated chimeric receptor," Science 350(6258): 12 pages (2015).
Xin et al., "High-performance web services for querying gene and variant annotation," Genome Biology 17:91 (2016), 7 pages.
Yoshida et al., "All-trans retinoic acid enhances cytotoxic effect of T cells with an anti-CD38 chimeric antigen receptor in acute myeloid leukemia," Clin Transl Immunology 5:e116 (2016), 7 pages.
Yu et al., "Repeated loss of target surface antigen after immunotherapy in primary mediastinal large B cell lymphoma," Am J Hematol 92:E11-E13 (2017).
Zah et al., "T Cells Expressing CD19/CD20 Bispecific Chimeric Antigen Receptors Prevent Antigen Escape by Malignant B Cells," Cancer Immunol Res 4(6):498-508 (2016).
Zheng et al., "Inhibitory receptors bind ANGPTLs and support blood stem cells and leukaemia development," Nature 485:656-660 (2012).
Zhou et al., "Towards Curative Cancer Immunotherapy: Overcoming Posttherapy Tumor Escape," Clin Dev Immunol, Article ID 124187 (2012), 12 pages.

\* cited by examiner

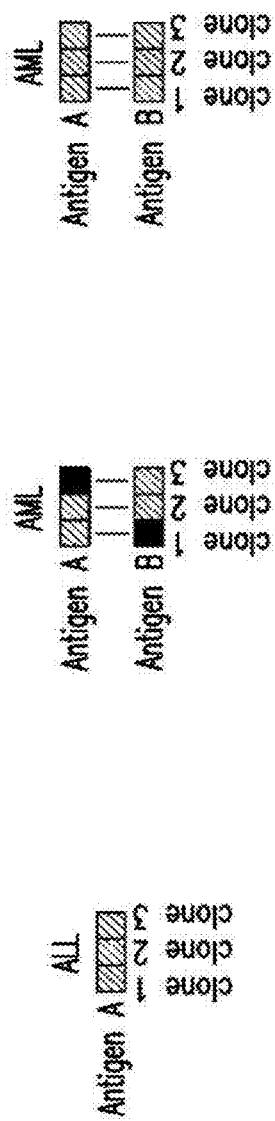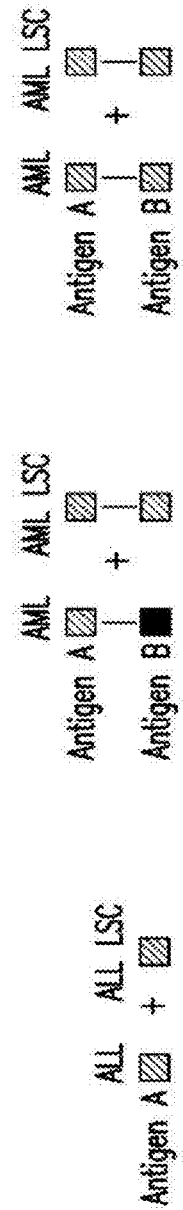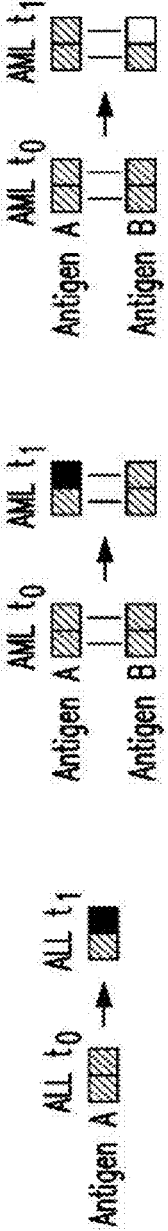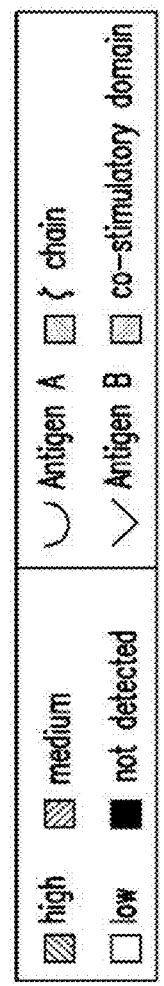
FIG. 9D
FIG. 9E
FIG. 9F

SEQUENCE LISTING

```
<160> NUMBER OF SEQ ID NOS: 25

<210> SEQ ID NO 1
<211> LENGTH: 164
<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80
```

```
Glu Glu Tyr Asp Val Leu Asp Lys Arg Arg Gly Arg Asp Pro Glu Met
                85                  90                  95
Gly Gly Lys Pro Gln Arg Arg Lys Asn Pro Gln Glu Gly Leu Tyr Asn
            100                 105                 110
Glu Leu Gln Lys Asp Lys Met Ala Glu Ala Tyr Ser Glu Ile Gly Met
        115                 120                 125
Lys Gly Glu Arg Arg Arg Gly Lys Gly His Asp Gly Leu Tyr Gln Gly
130                 135                 140
Leu Ser Thr Ala Thr Lys Asp Thr Tyr Asp Ala Leu His Met Gln Ala
145                 150                 155                 160
Leu Pro Pro Arg

<210> SEQ ID NO 2
<211> LENGTH: 220
<212> TYPE: PRT
<213> ORGANISM: Homo sapiens

<400> SEQUENCE: 2

Met Leu Arg Leu Leu Ala Leu Asn Leu Phe Pro Ser Ile Gln Val
1               5                   10                  15
Thr Gly Asn Lys Ile Leu Val Lys Gln Ser Pro Met Leu Val Ala Tyr
            20                  25                  30
Asp Asn Ala Val Asn Leu Ser Cys Lys Tyr Ser Tyr Asn Leu Phe Ser
        35                  40                  45
Arg Glu Phe Arg Ala Ser Leu His Lys Gly Leu Asp Ser Ala Val Glu
    50                  55                  60
Val Cys Val Val Tyr Gly Asn Tyr Ser Gln Gln Leu Gln Val Tyr Ser
65                  70                  75                  80
Lys Thr Gly Phe Asn Cys Asp Gly Lys Leu Gly Asn Glu Ser Val Thr
                85                  90                  95
Phe Tyr Leu Gln Asn Leu Tyr Val Asn Gln Thr Asp Ile Tyr Phe Cys
            100                 105                 110
Lys Ile Glu Val Met Tyr Pro Pro Pro Tyr Leu Asp Asn Glu Lys Ser
        115                 120                 125
Asn Gly Thr Ile Ile His Val Lys Gly Lys His Leu Cys Pro Ser Pro
130                 135                 140
Leu Phe Pro Gly Pro Ser Lys Pro Phe Trp Val Leu Val Val Val Gly
145                 150                 155                 160
Gly Val Leu Ala Cys Tyr Ser Leu Leu Val Thr Val Ala Phe Ile Ile
                165                 170                 175
Phe Trp Val Arg Ser Lys Arg Ser Arg Leu Leu His Ser Asp Tyr Met
            180                 185                 190
Asn Met Thr Pro Arg Arg Pro Gly Pro Thr Arg Lys His Tyr Gln Pro
        195                 200                 205
Tyr Ala Pro Pro Arg Asp Phe Ala Ala Tyr Arg Ser
    210                 215                 220

<210> SEQ ID NO 3
<211> LENGTH: 255
<212> TYPE: PRT
<213> ORGANISM: Homo sapiens

<400> SEQUENCE: 3

Met Gly Asn Ser Cys Tyr Asn Ile Val Ala Thr Leu Leu Leu Val Leu
1               5                   10                  15
```

-continued

Asn Phe Glu Arg Thr Arg Ser Leu Gln Asp Pro Cys Ser Asn Cys Pro
                 20                  25                  30

Ala Gly Thr Phe Cys Asp Asn Asn Arg Asn Gln Ile Cys Ser Pro Cys
             35                  40                  45

Pro Pro Asn Ser Phe Ser Ser Ala Gly Gly Gln Arg Thr Cys Asp Ile
 50                  55                  60

Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
             100                 105                 110

Thr Lys Lys Gly Cys Lys Asp Cys Cys Phe Gly Thr Phe Asn Asp Gln
         115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 4
<211> LENGTH: 183
<212> TYPE: PRT
<213> ORGANISM: Homo sapiens

<400> SEQUENCE: 4

Met Glu Arg Val Gln Pro Leu Glu Glu Asn Val Gly Asn Ala Ala Arg
 1               5                  10                  15

Pro Arg Phe Glu Arg Asn Lys Leu Leu Leu Val Ala Ser Val Ile Gln
             20                  25                  30

Gly Leu Gly Leu Leu Leu Cys Phe Thr Tyr Ile Cys Leu His Phe Ser
         35                  40                  45

Ala Leu Gln Val Ser His Arg Tyr Pro Arg Ile Gln Ser Ile Lys Val
 50                  55                  60

Gln Phe Thr Glu Tyr Lys Lys Glu Lys Gly Phe Ile Leu Thr Ser Gln
 65                  70                  75                  80

Lys Glu Asp Glu Ile Met Lys Val Gln Asn Asn Ser Val Ile Ile Asn
                 85                  90                  95

Cys Asp Gly Phe Tyr Leu Ile Ser Leu Lys Gly Tyr Phe Ser Gln Glu
             100                 105                 110

Val Asn Ile Ser Leu His Tyr Gln Lys Asp Glu Glu Pro Leu Phe Gln
         115                 120                 125

Leu Lys Lys Val Arg Ser Val Asn Ser Leu Met Val Ala Ser Leu Thr
130                 135                 140

```
Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 20
<212> TYPE: PRT
<213> ORGANISM: Homo sapiens

<400> SEQUENCE: 6

Met Glu Thr Pro Ala Gln Leu Leu Phe Leu Leu Leu Leu Trp Leu Pro
1               5                   10                  15

Asp Thr Thr Gly
            20

<210> SEQ ID NO 7
<211> LENGTH: 20
<212> TYPE: PRT
<213> ORGANISM: Mus musculus

<400> SEQUENCE: 7

Met Glu Thr Asp Thr Leu Leu Leu Trp Val Leu Leu Leu Trp Val Pro
1               5                   10                  15

Gly Ser Thr Gly
            20

<210> SEQ ID NO 8
<211> LENGTH: 21
<212> TYPE: PRT
<213> ORGANISM: Homo sapiens

<400> SEQUENCE: 8

Met Ala Leu Pro Val Thr Ala Leu Leu Leu Pro Leu Ala Leu Leu Leu
1               5                   10                  15

His Ala Ala Arg Pro
            20

<210> SEQ ID NO 9
<211> LENGTH: 235
<212> TYPE: PRT
<213> ORGANISM: Homo sapiens

<400> SEQUENCE: 9

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30
```

-continued

```
Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235
```

<210> SEQ ID NO 10
<211> LENGTH: 247
<212> TYPE: PRT
<213> ORGANISM: Mus musculus

<400> SEQUENCE: 10

```
Met Ala Ser Pro Leu Thr Arg Phe Leu Ser Leu Asn Leu Leu Leu Met
 1               5                  10                  15

Gly Glu Ser Ile Ile Leu Gly Ser Gly Glu Ala Lys Pro Gln Ala Pro
            20                  25                  30

Glu Leu Arg Ile Phe Pro Lys Lys Met Asp Ala Glu Leu Gly Gln Lys
        35                  40                  45

Val Asp Leu Val Cys Glu Val Leu Gly Ser Val Ser Gln Gly Cys Ser
 50                  55                  60

Trp Leu Phe Gln Asn Ser Ser Ser Lys Leu Pro Gln Pro Thr Phe Val
 65                  70                  75                  80

Val Tyr Met Ala Ser Ser His Asn Lys Ile Thr Trp Asp Glu Lys Leu
                 85                  90                  95

Asn Ser Ser Lys Leu Phe Ser Ala Val Arg Asp Thr Asn Asn Lys Tyr
            100                 105                 110

Val Leu Thr Leu Asn Lys Phe Ser Lys Glu Asn Glu Gly Tyr Tyr Phe
        115                 120                 125

Cys Ser Val Ile Ser Asn Ser Val Met Tyr Phe Ser Ser Val Val Pro
    130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
```

```
                    165                 170                 175
Asp Cys Arg Pro Arg Gly Ser Val Lys Gly Thr Gly Leu Asp Phe Ala
                180                 185                 190

Cys Asp Ile Tyr Ile Trp Ala Pro Leu Ala Gly Ile Cys Val Ala Pro
            195                 200                 205

Leu Leu Ser Leu Ile Ile Thr Leu Ile Cys Tyr His Arg Ser Arg Lys
        210                 215                 220

Arg Val Cys Lys Cys Pro Arg Pro Leu Val Arg Gln Glu Gly Lys Pro
225                 230                 235                 240

Arg Pro Ser Glu Lys Ile Val
                245

<210> SEQ ID NO 11
<211> LENGTH: 69
<212> TYPE: PRT
<213> ORGANISM: Mus musculus

<400> SEQUENCE: 11

Ser Thr Thr Thr Lys Pro Val Leu Arg Thr Pro Ser Pro Val His Pro
1               5                   10                  15

Thr Gly Thr Ser Gln Pro Gln Arg Pro Glu Asp Cys Arg Pro Arg Gly
            20                  25                  30

Ser Val Lys Gly Thr Gly Leu Asp Phe Ala Cys Asp Ile Tyr Ile Trp
        35                  40                  45

Ala Pro Leu Ala Gly Ile Cys Val Ala Leu Leu Ser Leu Ile Ile
    50                  55                  60

Thr Leu Ile Cys Tyr
65

<210> SEQ ID NO 12
<211> LENGTH: 207
<212> TYPE: DNA
<213> ORGANISM: Mus musculus

<400> SEQUENCE: 12
tctactacta ccaagccagt gctgcgaact ccctcacctg tgcaccctac cgggacatct      60
cagccccaga gaccagaaga ttgtcggccc cgtggctcag tgaagggac cggattggac     120 ttcgcctgtg atatttacat ctgggcaccc ttggccggaa tctgcgtggc ccttctgctg    180
tccttgatca tcactctcat ctgctac                                        207

<210> SEQ ID NO 13
<211> LENGTH: 188
<212> TYPE: PRT
<213> ORGANISM: Mus musculus

<400> SEQUENCE: 13

Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Ile Thr Ala
        35                  40                  45

Leu Tyr Leu Arg Ala Lys Phe Ser Arg Ser Ala Glu Thr Ala Ala Asn
    50                  55                  60

Leu Gln Asp Pro Asn Gln Leu Tyr Asn Glu Leu Asn Leu Gly Arg Arg
65                  70                  75                  80
```

```
Glu Glu Tyr Asp Val Leu Glu Lys Lys Arg Ala Arg Asp Pro Glu Met
            85                  90                  95
Gly Gly Lys Gln Arg Arg Asn Pro Gln Glu Gly Val Tyr Asn Ala
        100                 105                 110
Leu Gln Lys Asp Lys Met Ala Glu Ala Tyr Ser Glu Ile Gly Thr Lys
        115                 120                 125
Gly Glu Arg Arg Arg Gly Lys Gly His Asp Gly Leu Tyr Gln Asp Ser
    130                 135                 140
His Phe Gln Ala Val Gln Phe Gly Asn Arg Glu Arg Glu Gly Ser
145                 150                 155                 160
Glu Leu Thr Arg Thr Leu Gly Leu Arg Ala Arg Pro Lys Ala Cys Arg
            165                 170                 175
His Lys Lys Pro Leu Ser Leu Pro Ala Ala Val Ser
            180                 185

<210> SEQ ID NO 14
<211> LENGTH: 113
<212> TYPE: PRT
<213> ORGANISM: Mus musculus

<400> SEQUENCE: 14

Arg Ala Lys Phe Ser Arg Ser Ala Glu Thr Ala Ala Asn Leu Gln Asp
1               5                   10                  15
Pro Asn Gln Leu Tyr Asn Glu Leu Asn Leu Gly Arg Arg Glu Glu Tyr
            20                  25                  30
Asp Val Leu Glu Lys Lys Arg Ala Arg Asp Pro Glu Met Gly Gly Lys
        35                  40                  45
Gln Gln Arg Arg Asn Pro Gln Glu Gly Val Tyr Asn Ala Leu Gln
    50                  55                  60
Lys Asp Lys Met Ala Glu Ala Tyr Ser Glu Ile Gly Thr Lys Gly Glu
65                  70                  75                  80
Arg Arg Arg Gly Lys Gly His Asp Gly Leu Tyr Gln Gly Leu Ser Thr
                85                  90                  95
Ala Thr Lys Asp Thr Tyr Asp Ala Leu His Met Gln Thr Leu Ala Pro
            100                 105                 110
Arg

<210> SEQ ID NO 15
<211> LENGTH: 342
<212> TYPE: DNA
<213> ORGANISM: Mus musculus

<400> SEQUENCE: 15
agagcaaaat tcagcaggag tgcagagact gctgccaacc tgcaggaccc caaccagctc    60
tacaatgagc tcaatctagg gcgaagagag gaatatgacg tcttggagaa gaagcgggct   120
cgggatccag atgggaggc aaacagcag aggaggagga accccagga aggcgtatac     180
aatgcactgc agaaagacaa gatggcagaa gcctacagtg agatcggcac aaaaggcgag   240
aggcggagag gcaaggggca cgatggcctt taccagggtc tcagcactgc caccaaggac   300
acctatgatg ccctgcatat gcagaccctg gcccctcgct aa                     342

<210> SEQ ID NO 16
<211> LENGTH: 218
<212> TYPE: PRT
<213> ORGANISM: Mus musculus

<400> SEQUENCE: 16
```

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
                20                  25                  30

Asp Ser Asn Glu Val Ser Leu Ser Cys Arg Tyr Ser Tyr Asn Leu Leu
            35                  40                  45

Ala Lys Glu Phe Arg Ala Ser Leu Tyr Lys Gly Val Asn Ser Asp Val
        50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
        195                 200                 205

Pro Ala Arg Asp Phe Ala Ala Tyr Arg Pro
210                 215

<210> SEQ ID NO 17
<211> LENGTH: 123
<212> TYPE: DNA
<213> ORGANISM: Mus musculus

<400> SEQUENCE: 17
aatagtagaa ggaacagact ccttcaaagt gactacatga acatgactcc ccggaggcct      60
gggctcactc gaaagcctta ccagccctac gcccctgcca gagactttgc agcgtaccgc    120
ccc                                                                  123

<210> SEQ ID NO 18
<211> LENGTH: 277
<212> TYPE: PRT
<213> ORGANISM: Homo sapiens

<400> SEQUENCE: 18

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80
```

```
Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 19
<211> LENGTH: 199
<212> TYPE: PRT
<213> ORGANISM: Homo sapiens

<400> SEQUENCE: 19

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
```

-continued

```
                    165                 170                 175
Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 20
<211> LENGTH: 223
<212> TYPE: PRT
<213> ORGANISM: Homo sapiens

<400> SEQUENCE: 20

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 21
<211> LENGTH: 288
<212> TYPE: PRT
<213> ORGANISM: Homo sapiens

<400> SEQUENCE: 21

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
```

```
                65                  70                  75                  80
Ala Phe Pro Glu Asp Arg Ser Gln Pro Gly Gln Asp Cys Arg Phe Arg
                    85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 22
<211> LENGTH: 525
<212> TYPE: PRT
<213> ORGANISM: Homo sapiens

<400> SEQUENCE: 22

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160
```

```
Arg Leu Arg Leu Arg Leu Gly Gln Ala Ser Met Thr Ala Ser Pro Pro
            165                 170                 175

Gly Ser Leu Arg Ala Ser Asp Trp Val Ile Leu Asn Cys Ser Phe Ser
        180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
            515                 520                 525

<210> SEQ ID NO 23
<211> LENGTH: 370
<212> TYPE: PRT
<213> ORGANISM: Homo sapiens

<400> SEQUENCE: 23

Met Leu Gly Gln Val Val Thr Leu Ile Leu Leu Leu Leu Lys Val
1               5                   10                  15
```

Tyr Gln Gly Lys Gly Cys Gln Gly Ser Ala Asp His Val Ser Ile
                20                  25                  30

Ser Gly Val Pro Leu Gln Leu Gln Pro Asn Ser Ile Gln Thr Lys Val
                35                  40                  45

Asp Ser Ile Ala Trp Lys Lys Leu Leu Pro Ser Gln Asn Gly Phe His
 50                  55                  60

His Ile Leu Lys Trp Glu Asn Gly Ser Leu Pro Ser Asn Thr Ser Asn
 65                  70                  75                  80

Asp Arg Phe Ser Phe Ile Val Lys Asn Leu Ser Leu Ile Lys Ala
                 85                  90                  95

Ala Gln Gln Gln Asp Ser Gly Leu Tyr Cys Leu Glu Val Thr Ser Ile
                100                 105                 110

Ser Gly Lys Val Gln Thr Ala Thr Phe Gln Val Phe Val Phe Glu Ser
                115                 120                 125

Leu Leu Pro Asp Lys Val Glu Lys Pro Arg Leu Gln Gly Gln Gly Lys
130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
                180                 185                 190

Gly Thr His Thr Tyr Thr Cys Asn Val Ser Asn Pro Val Ser Trp Glu
                195                 200                 205

Ser His Thr Leu Asn Leu Thr Gln Asp Cys Gln Asn Ala His Gln Glu
                210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
                260                 265                 270

Asp Val Lys Asp Leu Lys Thr Arg Arg Asn His Glu Gln Glu Gln Thr
                275                 280                 285

Phe Pro Gly Gly Gly Ser Thr Ile Tyr Ser Met Ile Gln Ser Gln Ser
290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
                325                 330                 335

Phe Asn Ser Thr Ile Tyr Glu Val Ile Gly Lys Ser Gln Pro Lys Ala
                340                 345                 350

Gln Asn Pro Ala Arg Leu Ser Arg Lys Glu Leu Glu Asn Phe Asp Val
                355                 360                 365

Tyr Ser
    370

<210> SEQ ID NO 24
<211> LENGTH: 289
<212> TYPE: PRT
<213> ORGANISM: Homo sapiens

<400> SEQUENCE: 24

Met Lys Thr Leu Pro Ala Met Leu Gly Thr Gly Lys Leu Phe Trp Val

```
             1               5                  10                 15

Phe Phe Leu Ile Pro Tyr Leu Asp Ile Trp Asn Ile His Gly Lys Glu
                         20                 25                 30

Ser Cys Asp Val Gln Leu Tyr Ile Lys Arg Gln Ser Glu His Ser Ile
                         35                 40                 45

Leu Ala Gly Asp Pro Phe Glu Leu Glu Cys Pro Val Lys Tyr Cys Ala
          50                 55                 60

Asn Arg Pro His Val Thr Trp Cys Lys Leu Asn Gly Thr Thr Cys Val
          65                 70                 75                 80

Lys Leu Glu Asp Arg Gln Thr Ser Trp Lys Glu Lys Asn Ile Ser
                         85                 90                 95

Phe Phe Ile Leu His Phe Glu Pro Val Leu Pro Asn Asp Asn Gly Ser
                        100                105                110

Tyr Arg Cys Ser Ala Asn Phe Gln Ser Asn Leu Ile Glu Ser His Ser
                        115                120                125

Thr Thr Leu Tyr Val Thr Asp Val Lys Ser Ala Ser Glu Arg Pro Ser
                        130                135                140

Lys Asp Glu Met Ala Ser Arg Pro Trp Leu Leu Tyr Arg Leu Leu Pro
         145                150                155                160

Leu Gly Gly Leu Pro Leu Leu Ile Thr Thr Cys Phe Cys Leu Phe Cys
                        165                170                175

Cys Leu Arg Arg His Gln Gly Lys Gln Asn Glu Leu Ser Asp Thr Ala
                        180                185                190

Gly Arg Glu Ile Asn Leu Val Asp Ala His Leu Lys Ser Glu Gln Thr
                        195                200                205

Glu Ala Ser Thr Arg Gln Asn Ser Gln Val Leu Leu Ser Glu Thr Gly
                        210                215                220

Ile Tyr Asp Asn Asp Pro Asp Leu Cys Phe Arg Met Gln Glu Gly Ser
         225                230                235                240

Glu Val Tyr Ser Asn Pro Cys Leu Glu Glu Asn Lys Pro Gly Ile Val
                        245                250                255

Tyr Ala Ser Leu Asn His Ser Val Ile Gly Pro Asn Ser Arg Leu Ala
                        260                265                270

Arg Asn Val Lys Glu Ala Pro Thr Glu Tyr Ala Ser Ile Cys Val Arg
                        275                280                285

Ser

<210> SEQ ID NO 25
<211> LENGTH: 4
<212> TYPE: PRT
<213> ORGANISM: Homo sapiens

<400> SEQUENCE: 25

Tyr Val Lys Met
 1
```

CANCER ANTIGEN TARGETS AND USES THEREOF

CROSS-REFERENCE TO RELATED APPLICATION

This application is a Divisional of U.S. application Ser. No. 15/966,992 filed Apr. 30, 2018, which is a Continuation of International Patent Application No. PCT/US17/045632, filed Aug. 4, 2017, which claims priority to U.S. Provisional Application No. 62/371,199 filed on Aug. 4, 2016, the contents of each of which are hereby incorporated by reference in their entirety herein, and to each of which priority is claimed.

SEQUENCE LISTING

The specification further incorporates by reference the Sequence Listing submitted herewith via EFS on Feb. 19, 2020. Pursuant to 37 C.F.R. § 1.52(e)(5), the Sequence Listing text file, identified as 0727341012SL.txt, is 38,346 bytes and was created on Feb. 19, 2020. The Sequence Listing, electronically filed herewith, does not extend beyond the scope of the specification and thus does not contain new matter.

INTRODUCTION

The presently disclosed subject matter provides methods and compositions for treating cancer (e.g., acute myeloid leukemia (AML)). It relates to immunoresponsive cells comprising antigen recognizing receptors (e.g., chimeric antigen receptors (CARs)) targeting AML-specific antigens.

BACKGROUND OF THE INVENTION

Adoptive T cell therapies using CARs to redirect the specificity and function of T lymphocytes have demonstrated great efficacy in patients with lymphoid malignancies, in particular acute lymphoblastic leukemia (ALL) (Sadelain, 2015). This therapeutic modality induces complete remissions in subjects with $CD19^+$ malignancies for whom chemotherapies have led to drug resistance and tumor progression. "Cancer immunotherapy", including CAR therapy, was proclaimed a scientific breakthrough in 2013 (Couzin-Frankel, 2013). The success of CD19 CAR therapy bodes well for tackling all hematological malignancies, including Acute Myeloid Leukemia (AML), which affects over one quarter million adults annually worldwide.

AML is the most common acute leukemia in adults. The standard induction chemotherapy regimens have not changed substantially over the past 40 years (Pulte et al., 2008) and the overall survival remains very poor. Frequent recurring abnormalities involving genes coding for epigenetic modifiers have been identified. These epigenetic abnormalities include mutations in DNA-methylation related genes (DNMT3A, IDH1/2 in 44% of patients) (Cancer Genome Atlas Research, 2013), which also represent key initiating events in leukemogenesis (Shlush et al., 2014b). Molecularly targeted therapies, such as IDH1/IDH2 and FLT3 inhibitors, are currently in clinical evaluation. The genetic engineering of T cells with CARs mediating antigen recognition, T cell activation, and co-stimulation, is attractive in that it rests on T cell-mediated cytotoxicity, without causing reprogramming or metabolic changes. Unlike the physiological T cell receptor, which engages HLA-peptide complexes, CARs bind to native cell surface molecules and do not require any antigen processing or HLA expression for tumor recognition. CARs therefore can recognize target antigens on any HLA background or even on target tumor cells that have down-regulated HLA expression or proteasomal antigen processing, two mechanisms that contribute to tumor escape from TCR-mediated immunity (Zhou and Levitsky, 2012). The target must, however, be found on the tumor cell surface.

The development of CAR therapy for AML is hampered by the lack of suitable targets. Identifying appropriate CAR targets is important to achieving complete tumor eradication, as is avoiding damage to normal tissues that express the same target antigen ("on-target, off-tumor effect"). So far the search for suitable CAR targets has been limited for several reasons. For example, the major focus of researchers has been restricted to the relative expression of potential targets in cancer cells compared to normal counterparts. While it is true that an ideal CAR target should be expressed in most if not all tumor cells, enabling efficient targeting by $CAR^+$ T cells, it is also very important to consider a whole body picture. For safe discrimination of target cells by $CAR^+$ T cells, an ideal tumor target should not be expressed on any normal tissue/organ of the whole body, including closely related normal counterparts (i.e., $CD34^+$ hematopoietic stem/progenitor cells (HSPCs) and $CD34^+CD38^-$ hematopoietic stem cells (HSCs) in this case) and healthy T cells, which mediate CAR therapy (to avoid fratricide killing). If present on normal cells, the target should be at least restricted to non-vital tissues (as is the case of CD19, which is only found in the normal B cell lineage). CD19 is the poster child of CAR therapy, found on most B lineage lymphomas and leukemias (LeBien and Tedder, 2008). Thus, CD19 CAR therapy is expected to induce a B cell aplasia, as was observed in murine models (Davila et al., 2013; Pegram et al., 2012) and later in leukemia and lymphoma patients. Most targets of CAR T cells have shared expression on normal tissues and some degree of "on-target/off-tumor" toxicity occurred through engagement of target antigen on nonpathogenic tissues (Curran et al., 2012). The severity of reported events has ranged from manageable lineage depletion (B-cell aplasia) to severe toxicity (death). "On-target/off-tumor" recognition is predictably seen in a variety of organ systems, including gastrointestinal, hematologic, and pulmonary. One of the earliest trials utilizing a carboxyanhydrase-IX-specific CAR T cell for renal cell carcinoma resulted in the development of cholestasis due to expression of carboxyanhydrase-IX on bile duct epithelium (Lamers et al., 2013; Lamers et al., 2006). Targeting of carcinoembryonic antigen by CAR T cells in patients with colon cancer resulted in severe, albeit transient, colitis due to antigen recognition of normal colonic tissue (Parkhurst et al., 2011). Finally, in a fatal example of "on-target/off-tumor" recognition, a patient treated with CAR T cells specific for the cancer-associated antigen HER-2/neu developed rapid respiratory failure, multi-organ dysfunction, and subsequent death attributed to reactivity against pulmonary tissue expression of HER-2/neu (Morgan et al., 2010).

In the case of AML, multiple genetic clones exist at diagnosis and contribute to relapse, creating a complex and heterogeneous target prone to conventional and targeted therapies. The ideal CAR target should be expressed on the driver leukemic clones, which survive chemotherapy and persist during remission, to enable AML eradication by $CAR^+$ T cells.

Furthermore, studies have shown that there exists a poor correlation between mRNA expression and protein abundance (Haider and Pal, 2013). So far the search for CAR targets relied mostly on the measurement of transcriptomic profiles through techniques such as microarray and RNA-seq. However, the recent advancement in proteomic studies with Mass-Spectometry and refined techniques in isolation of plasma cell membrane offers additional sources of information to probe the cancer surfaceome and the integration of the two approaches is ideal.

Four CAR targets to AML have been reported in the literature. The first, Lewis (Le)-Y, a difucosylated carbohydrate antigen, was targeted in a phase I study of four patients with relapsed AML. Infusion of second generation CD28-based CARs resulted in stable/transient remission of three patients, who ultimately progressed, despite T cell persistence (Ritchie et al., 2013). Regarding the second, CD123, the high-affinity interleukin-3 receptor α-chain; a partial remission was induced in a patient with FLT3-ITD$^+$ AML treated with a third generation CD123-CD28/CD137/CD27/CD3z/iCaps9 CAR (Yi Luo, 2015). Preclinical studies resulted in significant myeloablation (Gill et al., 2014). The third, CD33, is a myeloid-specific sialic acid-binding receptor which is also targeted by gentuzumab ozogamicin (GO) (Administration, 2010), with demonstrated survival benefit (Hills et al., 2014; Ravandi et al., 2012). Preclinical activity of CD33 CAR$^+$ CIK cells resulted in slowing disease progression (Pizzitola et al., 2014) and CD33 CAR$^+$ T showed significant effector functions in vitro and in vivo with reduction of myeloid progenitors (Kenderian et al., 2015). One AML patient was treated with CD33 CAR T cells at the Chinese PLA General Hospital, showing transient efficacy and mild fluctuations in bilirubin (Wang et al., 2015) and a clinical trial is registered as NCT01864902. The fourth, folate receptor β, is a myeloid-lineage antigen (Lynn et al., 2016; Lynn et al., 2015).

However, none of these meet the criteria of an ideal CAR target. Accordingly, there are needs for novel therapeutic strategies to design CARs targeting antigens that are highly expressed in AML cells and limited expression in normal tissues for treating AML, and for strategies capable of inducing potent cancer eradication with minimal toxicity and immunogenicity.

SUMMARY OF THE INVENTION

The presently disclosed subject matter provides immunoresponsive cells (e.g., T cells, Tumor Infiltrating Lymphocytes, Natural Killer (NK) cells, cytotoxic T lymphocytes (CTLs), Natural Killer T (NKT) cells or regulatory T cells), comprising an antigen recognizing receptor (e.g., CAR or TCR) that binds to an antigen, which is an effective therapeutic agent against a myeloid disorder, for example, AML. In certain non-limiting embodiments, an immunoresponsive cell, such as an immunoresponsive T cell or NK cell, can be engineered to express a combination of two or more CAR, TCR, and/or co-stimulatory receptor ("CCR") that bind to one or more antigen to achieve activation and stimulation of the immunoresponsive T cell or NK cell. In certain non-limiting embodiments, an immunoresponsive T cell can be engineered to express a combination of CAR, TCR, and/or CCR that bind to different antigens to achieve activation and stimulation of the immunoresponsive T cell. In certain non-limiting embodiments, the one or more antigen is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1. In certain embodiments, the one or more antigen is selected from the group consisting of LTB4R, EMR2, CD33, MYADM, PIEZO1, SIRPB1, SLC9A1, KCNN4, ENG, ITGA5, and CD70. In certain embodiments, the one or more antigen is selected from the group consisting of LTB4R, EMR2, MYADM and PIEZO1. In certain embodiments, the one or more antigen is selected from the group consisting of CD82, TNFRSF1B, EMR2, ITGB5, CCR1, CD96, PTPRJ, CD70 and LILRB2. In certain embodiments, the one or more antigen is selected from the group consisting of TNFRSF1B, EMR2, CCR1, CD96, CD70 and LILRB2. In certain embodiments, the one or more antigen is selected from the group consisting of EMR2, CCR1, CD70 and LILRB2. In certain non-limiting embodiments, at least one of the one or more antigen is EMR2.

The presently disclosed subject matter further provides an immunoresponsive cell that comprises (i) an antigen recognizing receptor (e.g. CAR or TCR) that binds to a first antigen, wherein binding of the antigen recognizing receptor to the first antigen is capable of activating the immunoresponsive cell; and (ii) a CCR that binds to a second antigen, wherein binding of the CCR to the second antigen is capable of stimulating the immunoresponsive cell, wherein each of the first antigen and the second antigen is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1, and the first antigen and the second antigen are different. In certain embodiments, the first antigen and the second antigen are a combination selected from the group consisting of LTB4R and EMR2, LTB4R and CD33, LTB4R and ENG, LTB4R and MYADM, LTB4R and PIEZO1, LTB4R and SIRPB1, LTB4R and SLC9A1, LTB4R and ITGA5, LTB4R and CD70, LTB4R and KCNN4. EMR2 and CD33, EMR2 and ENG, EMR2 and MYADM, EMR2 and PIEZO1, EMR2 and SIRPB1, EMR2 and SLC9A1, EMR2 and ITGA5, EMR2 and CD70, EMR2 and KCNN4, CD33 and ENG, CD33 and MYADM, CD33 and PIEZO1, CD33 and SIRPB1, CD33 and SLC9A1, CD33 and ITGA5, CD33 and CD70, CD33 and KCNN4, ENG and MYADM, ENG and PIEZO1, ENG and SIRPB1, ENG and SLC9A1, ENG and ITGA5, ENG and CD70, ENG and KCNN4, MYADM and PIEZO1, MYADM and SIRPB1, MYADM and SLC9A1, MYADM and ITGA5, MYADM and CD70, MYADM and KCNN4, PIEZO1 and SIRPB1, PIEZO1 and SLC9A1, PIEZO1 and ITGA5, PIEZO1 and CD70, PIEZO1 and KCNN4, SIRPB1 and SLC9A1, SIRPB1 and ITGA5, SIRPB1 and CD70, SIRPB1 and KCNN4, SLC9A1 and ITGA5, SLC9A1 and CD70, SLC9A1 and KCNN4, ITGA5 and CD70, ITGA5 and KCNN4, CD70 and KCNN4, EMR2 and CD33, CCR1 and CLEC12A, CD70 and CD33, LILRB2 and CLEC12A, EMR2 and CLEC12A, EMR2 and CD96, CCR1 and CD33, CCR1 and CD96, CD70 and CLEC12A, CD70 and CD96, LILRB2 and CD33, LILRB2 and CD96, EMR2 and CD70. In certain embodiments, the first antigen and the second antigen are a combination selected from the group consisting of EMR2 and CD33, CCR1 and CLEC12A, CD70 and CD33, LILRB2 and CLEC12A, LTB4R1 and CD70, CD70 and EMR2, and LTB4R1 and EMR2. In addition, in non-limiting embodiments, where the antigen recognizing receptor is a TCR, a target antigen can be WT1 or PRAME in addition to the aforementioned target antigens.

The presently disclosed subject matter further provides an immunoresponsive cell that comprises (i) a first antigen recognizing receptor (e.g. CAR or TCR) that binds to a first antigen and (ii) a second antigen recognizing receptor (e.g. CAR or TCR) that binds to a second antigen, wherein the combination of both receptors binding to their targets produces a therapeutic effect. In certain non-limiting embodiments, binding to only one target does not achieve a therapeutic effect. For example, the first and second antigen recognizing receptor can both be CARs; alternatively, the first antigen recognizing receptor can be a CAR and the second antigen binding receptor can be a TCR, or the first antigen recognizing receptor can be a TCR and the second antigen recognizing receptor can be a CAR, or both antigen recognizing receptors can be TCRs. Optionally, said immunoresponsive cell may further comprise a third antigen targeting molecule, which may be a CAR, TCR, or CCR that recognizes a third antigen. In non-limiting embodiments, the first, second, and optional third antigen are different. In non-limiting embodiments, each of the first antigen, second antigen and third antigen is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1, and the first antigen and the second antigen are different. In certain embodiments, the first antigen and the second antigen are a combination selected from the group consisting of LTB4R and EMR2, LTB4R and CD33, LTB4R and ENG, LTB4R and MYADM, LTB4R and PIEZO1, LTB4R and SIRPB1, LTB4R and SLC9A1, LTB4R and ITGA5, LTB4R and CD70, LTB4R and KCNN4. EMR2 and CD33, EMR2 and ENG, EMR2 and MYADM, EMR2 and PIEZO1, EMR2 and SIRPB1, EMR2 and SLC9A1, EMR2 and ITGA5, EMR2 and CD70, EMR2 and KCNN4, CD33 and ENG, CD33 and MYADM, CD33 and PIEZO1, CD33 and SIRPB1, CD33 and SLC9A1, CD33 and ITGA5, CD33 and CD70, CD33 and KCNN4, ENG and MYADM, ENG and PIEZO1, ENG and SIRPB1, ENG and SLC9A1, ENG and ITGA5, ENG and CD70, ENG and KCNN4, MYADM and PIEZO1, MYADM and SIRPB1, MYADM and SLC9A1, MYADM and ITGA5, MYADM and CD70, MYADM and KCNN4, PIEZO1 and SIRPB1, PIEZO1 and SLC9A1, PIEZO1 and ITGA5, PIEZO1 and CD70, PIEZO1 and KCNN4, SIRPB1 and SLC9A1, SIRPB1 and ITGA5, SIRPB1 and CD70, SIRPB1 and KCNN4, SLC9A1 and ITGA5, SLC9A1 and CD70, SLC9A1 and KCNN4, ITGA5 and CD70, ITGA5 and KCNN4, CD70 and KCNN4, EMR2 and CD33, CCR1 and CLEC12A, CD70 and CD33, LILRB2 and CLEC12A, EMR2 and CLEC12A, EMR2 and CD96, CCR1 and CD33, CCR1 and CD96, CD70 and CLEC12A, CD70 and CD96, LILRB2 and CD33, LILRB2 and CD96, EMR2 and CD70. In certain embodiments, the first antigen and the second antigen are a combination selected from the group consisting of EMR2 and CD33, CCR1 and CLEC12A, CD70 and CD33, LILRB2 and CLEC12A, LTB4R1 and CD70, CD70 and EMR2, and LTB4R1 and EMR2 In certain non-limiting embodiments, the first antigen is EMR2. In addition, in non-limiting embodiments, where an antigen recognizing receptor is a TCR, a target antigen can be WT1 or PRAME in addition to the aforementioned target antigens.

In certain embodiments, the aforementioned cell exhibits a greater degree of cytolytic activity against cells that are positive for both the first antigen and the second antigen as compared to against cells that are singly positive for the first antigen.

In certain embodiments, the antigen recognizing receptor binds to the first antigen with a low binding affinity. In certain embodiments, the antigen recognizing receptor binds to the first antigen with a dissociation constant ($K_d$) of $1\times10^{-8}$ M or more. In certain embodiments, the antigen recognizing receptor binds to the first antigen with a $K_d$ of $5\times10^{-8}$ M or more. In certain embodiments, the antigen recognizing receptor binds to the first antigen with a $K_d$ of $1\times10^{-7}$ M or more. In certain embodiments, the antigen recognizing receptor binds to the first antigen with a $K_d$ of $1\times10^{-6}$ M or more. In certain embodiments, the antigen recognizing receptor (e.g. CAR or TCR) binds to the first antigen with a binding affinity that is lower compared to the binding affinity with which the second antigen recognizing receptor or CCR that binds to the second antigen. In certain embodiments, the antigen recognizing receptor (e.g. CAR or TCR) binds to the first antigen with a low binding avidity. In certain embodiments, the antigen recognizing receptor (e.g. CAR or TCR) binds to the first antigen at an epitope of low accessibility.

In certain embodiments, the CCR is recombinantly expressed. In certain embodiments, the CCR is expressed from a vector, or a selected locus from the genome of the immunoresponsive cell. In certain embodiments, the antigen recognizing receptor is a CAR. In certain embodiments, the CAR has a dissociation constant ($K_d$) of about $1\times10^{-8}$ M to about $1\times10^{-6}$ M. In certain embodiments, the CCR has a $K_d$ of about $1\times10^{-9}$M to about $1\times10^{-7}$M.

Furthermore, the presently disclosed subject matter provides methods for treating and/or preventing a myeloid disorder in a subject comprising administering an effective amount of aforementioned immunoresponsive cells. Non-limiting examples of myeloid disorder include myelodysplastic syndromes, myeloproliferative neoplasms, chronic myelomonocytic leukemia, and acute myeloid leukemia (AML), acute myeloblastic leukemia, acute promyelocytic leukemia, acute myelomonocytic leukemia, chronic myelocytic leukemia, and polycythemia vera. In certain embodiments, the myeloid disorder is AML. In certain embodiments, the method reduces or eradicates tumor burden in the subject and/or prolongs remission and/or prolongs survival.

The presently disclosed subject matter also provides methods of reducing tumor burden in a subject comprising administering an effective amount of presently disclosed immunoresponsive cells. In certain embodiments, the method reduces the number of tumor cells (e.g. leukemic cells). In certain embodiments, the method prolongs survival of the subject.

The presently disclosed subject matter further provides methods for producing an antigen-specific immunoresponsive cell. In certain embodiments, the method comprises introducing into the immunoresponsive cell a nucleic acid sequence encoding an antigen recognizing receptor that binds to an antigen, wherein the antigen is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1 and SLC19A1. In certain embodiments, the antigen is selected from the group consisting of LTB4R, EMR2, CD33, MYADM, PIEZO1, SIRPB1, SLC9A1, KCNN4, ENG, ITGA5, and CD70. In certain embodiments, the antigen is selected from the group consisting of LTB4R, EMR2, MYADM and PIEZO1.

In certain embodiments, the method for producing an antigen-specific immunoresponsive cell comprises introducing into the immunoresponsive cell (a) a first nucleic acid sequence encoding an antigen recognizing receptor (e.g., CAR or TCR) that binds to a first antigen, wherein binding of the antigen recognizing receptor to the first antigen is capable of activating the immunoresponsive cell, and (b) a second nucleic acid sequence encoding a CCR that binds to a second antigen, wherein binding of the CCR to the second antigen is capable of stimulating the immunoresponsive cell, wherein each of the first antigen and the second antigen is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1, and the first antigen and the second antigen are different. In certain embodiments, the first antigen and the second antigen are a combination selected from the group consisting of LTB4R and EMR2, LTB4R and CD33, LTB4R and ENG, LTB4R and MYADM, LTB4R and PIEZO1, LTB4R and SIRPB1, LTB4R and SLC9A1, LTB4R and ITGA5, LTB4R and CD70, LTB4R and KCNN4. EMR2 and CD33, EMR2 and ENG, EMR2 and MYADM, EMR2 and PIEZO1, EMR2 and SIRPB1, EMR2 and SLC9A1, EMR2 and ITGA5, EMR2 and CD70, EMR2 and KCNN4, CD33 and ENG, CD33 and MYADM, CD33 and PIEZO1, CD33 and SIRPB1, CD33 and SLC9A1, CD33 and ITGA5, CD33 and CD70, CD33 and KCNN4, ENG and MYADM, ENG and PIEZO1, ENG and SIRPB1, ENG and SLC9A1, ENG and ITGA5, ENG and CD70, ENG and KCNN4, MYADM and PIEZO1, MYADM and SIRPB1, MYADM and SLC9A1, MYADM and ITGA5, MYADM and CD70, MYADM and KCNN4, PIEZO1 and SIRPB1, PIEZO1 and SLC9A1, PIEZO1 and ITGA5, PIEZO1 and CD70, PIEZO1 and KCNN4, SIRPB1 and SLC9A1, SIRPB1 and ITGA5, SIRPB1 and CD70, SIRPB1 and KCNN4, SLC9A1 and ITGA5, SLC9A1 and CD70, SLC9A1 and KCNN4, ITGA5 and CD70, ITGA5 and KCNN4, CD70 and KCNN4, EMR2 and CD33, CCR1 and CLEC12A, CD70 and CD33, LILRB2 and CLEC12A, EMR2 and CLEC12A, EMR2 and CD96, CCR1 and CD33, CCR1 and CD96, CD70 and CLEC12A, CD70 and CD96, LILRB2 and CD33, LILRB2 and CD96, and EMR2 and CD70. In certain embodiments, the combination is selected from the group consisting of EMR2 and CD33, CCR1 and CLEC12A, CD70 and CD33, LILRB2 and CLEC12A, LTB4R1 and CD70, CD70 and EMR2, and LTB4R1 and EMR2.

In certain non-limiting embodiments, the presently disclosed subject matter provides a nucleic acid encoding an antigen recognizing receptor that binds to an antigen. In certain embodiments, the antigen is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1 and SLC19A1. The presently disclosed subject matter further provides a vector comprising such nucleic acid. In certain non-limiting embodiments, the antigen recognizing receptor is a CAR. In certain embodiments, the vector is a retroviral vector.

The presently disclosed subject matter further provides pharmaceutical compositions comprising an effective amount of the presently disclosed immunoresponsive cells and a pharmaceutically acceptable excipient. In certain embodiments, the pharmaceutical composition is for treat or preventing a myeloid disorder (e.g., AML).

Furthermore, the presently disclosed subject matter provides kits for treating or preventing a myeloid disorder (e.g., AML), comprising one or more presently disclosed immunoresponsive cells, or a presently disclosed nucleic acid. In certain embodiments, the kit further comprises written instructions for using the cell for treating and/or preventing a myeloid disorder in a subject. The nucleic acid may encode more than one antigen recognizing receptor, each may be operably linked to a promoter which may be the same or different promoters. In certain embodiments, the kit further comprises written instructions for using the nucleic acids to produce a cell for treating and/or preventing a myeloid disorder in a subject.

The presently disclosed subject matter further provides an isolated immunoresponsive cell comprising an antigen recognizing receptor (e.g., CAR or TCR) that binds to an antigen, wherein binding of the antigen recognizing receptor to the antigen is capable of activating the immunoreponsive cell, and wherein the antigen is selected from the group consisting of TMEM40, GNAZ, SLC6A16, PPP2R5B, TEX29, FKBP1B, KCNJ5, CAPN3, TNFRSF14, SPAG17, MMP25, NGFR, CLEC1A, OTOA, LRRN2, RHBDL3, HEPHL1, TSPEAR, TAS1R3, MBOAT1, MT-ND1, DARC, SH3PXD2A, BEST4, STON2, ACKR6, LRRTM2, STC1, SLC16A6, CDHR1, MYADML2, PNPLA3, PSD2, SLC25A41, SUSD2, KCND1, HILPDA, TMEM145, DFNB31, PPFIA4, NLGN3, FAM186B, KCNV2, SCN11A, ABCG2, ANO9, GAS2, ASIC3, B3GNT4, TMEM59L, SLC25A36, FRMD5, COL15A1, ZDHHC11, ITGA8, PEAR1, ASPRV1, LOXL4, TRIMS 5, KIF19, LPAR2, CNIH2, FLRT1, RNF183, RDH16, CADM3, C3orf35, GDPD3, TMPRSS5, SEC31B, AGER, ADAMTS13, IL20RB, WNT4, LRRC37A3, SCNN1D, TMEM89, EXOC3L4, ATP6V0A4, CHST3, NPAS2, IGFBP3, ADRA1D, RNF173, CEACAM6, MANSC1, ELOVL6, LEPR, SUN3, HOOK1, CCDC155, TMEM27, GABRB2, EPHA4, CDH13, AQP2, KCNK13, KIF26B, HTR2A, SLC44A3, ILDR1, CYP4F11, SLC8A3, GPR153, SLCO2B1, SCIN, SCN2A, IL23R, ALS2, GNA14, TMEFF2, EXTL3, PDE3A, MFAP3L, SLC34A3, TACSTD2, ITGB8, LAX1, SLC45A3, SYNC, PLXNA4, ADORA3, SIGLEC11, RYR2, LRRC8E, DGKI, COLEC12, and CX3CR1.

The presently disclosed subject matter further provides an isolated immunoresponsive cell comprising: (a) an antigen recognizing receptor that binds to a first antigen, wherein binding of the antigen recognizing receptor to the first antigen is capable of activating the immunoresponsive cell, and (b) a chimeric co-stimulating receptor (CCR) that binds to a second antigen, wherein binding of the CCR to the second antigen is capable of stimulating the immunoresponsive cell, wherein each of the first antigen and the second antigen is selected from the group consisting of TMEM40, GNAZ, SLC6A16, PPP2R5B, TEX29, FKBP1B, KCNJ5, CAPN3, TNFRSF14, SPAG17, MMP25, NGFR, CLEC1A, OTOA, LRRN2, RHBDL3, HEPHL1, TSPEAR, TAS1R3, MBOAT1, MT-ND1, DARC, SH3PXD2A, BEST4, STON2, ACKR6, LRRTM2, STC1, SLC16A6, CDHR1, MYADML2, PNPLA3, PSD2, SLC25A41, SUSD2, KCND1, HILPDA, TMEM145, DFNB31, PPFIA4, NLGN3, FAM186B, KCNV2, SCN11A, ABCG2, ANO9, GAS2, ASIC3, B3GNT4, TMEM59L, SLC25A36, FRMD5, COL15A1, ZDHHC11, ITGA8, PEAR1, ASPRV1, LOXL4, TRIM55, KIF19, LPAR2, CNIH2, FLRT1, RNF183, RDH16, CADM3, C3orf35, GDPD3, TMPRSS5, SEC31B, AGER, ADAMTS13, IL20RB, WNT4, LRRC37A3, SCNN1D, TMEM89, EXOC3L4, ATP6V0A4, CHST3, NPAS2, IGFBP3, ADRA1D, RNF173, CEACAM6, MANSC1, ELOVL6, LEPR, SUN3, HOOK1, CCDC155, TMEM27, GABRB2, EPHA4, CDH13, AQP2, KCNK13, KIF26B, HTR2A, SLC44A3, ILDR1, CYP4F11, SLC8A3, GPR153, SLCO2B1, SCIN, SCN2A, IL23R, ALS2, GNA14, TMEFF2, EXTL3, PDE3A, MFAP3L, SLC34A3, TACSTD2, ITGB8, LAX1, SLC45A3, SYNC, PLXNA4, ADORA3, SIGLEC11, RYR2, LRRC8E, DGKI, COLEC12, and CX3CR1, and the first antigen and the second antigen are different.

In various embodiments of any of the aspects delineated herein, the antigen recognizing receptor is a T cell receptor (TCR) or chimeric antigen receptor (CAR). In various embodiments of any of the aspects delineated herein, the antigen recognizing receptor is exogenous or endogenous. In various embodiments of any of the aspects delineated herein, the antigen recognizing receptor is recombinantly expressed. In various embodiments of any of the aspects delineated herein, the antigen recognizing receptor is expressed from a vector. The CAR can comprise an intracellular signaling domain. In various embodiments of any of the aspects delineated herein, the intracellular signaling domain is the CD3ζ-chain, CD97, CD11a-CD18, CD2, ICOS, CD27, CD154, CD8, OX40, 4-1BB, CD28 signaling domain, a portion thereof, or combinations thereof. In certain non-limiting embodiments, the antigen recognizing receptor is a CAR comprising at least a portion of CD28, 4-1BB, and/or CD3ζ-chain, together with an antigen binding portion. In certain non-limiting embodiments, the antigen recognizing receptor is a CAR described in Kohn et al., 2011, Molecular Ther. 19(3):432-438, optionally where the antigen binding portion is substituted with amino acid sequence that binds to another tumor or pathogen antigen. In various embodiments, the cell expresses a recombinant or an endogenous antigen receptor that is 1928z or 4H1128z.

In an additional aspect, the invention provides a method for treating or preventing a myeloid disorder, comprising administering an effective amount of at least one antibody that binds to an antigen selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1. In certain embodiments, the antigen is selected from the group consisting of LTB4R, EMR2, CD33, MYADM, PIEZO1, SIRPB1, SLC9A1, KCNN4, ENG, ITGA5, and CD70. In certain embodiments, the antigen is selected from the group consisting of LTB4R, EMR2, MYADM and PIEZO1.

BRIEF DESCRIPTION OF THE FIGURES

The following Detailed Description, given by way of example but not intended to limit the invention to specific embodiments described, may be understood in conjunction with the accompanying drawings.

FIG. 1A depicts the screening strategy and databases involved in study. FIG. 1B depicts the algorithm to identify suitable CAR targets in AML. FIG. 1C depicts the 32 "Rank Selection" proteins from step #3 of FIG. 1B. FIG. 1D depicts the 11 top candidates from step #4 of FIG. 1B. FIG. 1E depicts the combinatorial targeting strategy with immunoresponsive cells expressing both a suboptimal CAR and a chimeric co-stimulatory receptor (CCR) recognizing a second antigen.

FIG. 2A shows expression of 9 candidates: LTB4R, EMR2, SLC9A1, MYADM, CD33, SLC6A6, KCNN4, PIEZO1, and SIRPB1. FIG. 2B shows 3 candidates, CD70, ENG, and ITGA5 with high expression in T cells. FIG. 2C shows 13 candidates, CCR1, SLC22A5, TFR2, LILRB4, GYPA, FCGR1A, IL10RB, PLXNC1, CD300LF, MBOAT7, MRP1, SLC43A3, and SLC44A1, which have a non-homogenous expression in all AML cells. FIG. 2D shows 6 candidates, CPM, TTYH3, ITGA4, SLC19A1, CD38, ICAM1, which have high expression in normal HSCs. FIG. 2E is a summary of FIGS. 2A-2D.

FIG. 3A depicts the algorithm that identifies the 55 pairs of CAR targets. FIG. 3B depicts the flow cytometry results verifying expression of LTB4R1 and EMR2 in normal and malignant cells.

FIGS. 9A-9F depict the principles of pairwise analysis. A) An ideal pair should not present overlapping expression in normal tissues. In the CAR/CAR approach, some low or moderate expression in normal tissues, albeit not optimal, may be tolerable depending on the tissues in question. In the CAR/CCR, T cells are more restricted to dual-antigen positive tumor cells, thus relaxing the expression criteria for at least one of the paired antigens. B) The expression of target pairs should be very low in CD34+CD38- HSCs. C) The expression of two targets in a pair should be very low in normal resting and activated (r/a) T cells. D) Each antigen in a pair may be differentially expressed in different clones. The CAR/CCR approach requires expression of the CAR target. E) The pair should be expressed in leukemic stem cells. The CAR/CAR approach may pair an antigen expressed on most cells but not on LSCs. F) Co-targeting may prevent the emergence of clones that may downregulate the expression of one antigen at a later time (t1).

DETAILED DESCRIPTION OF THE INVENTION

Figure 1A:
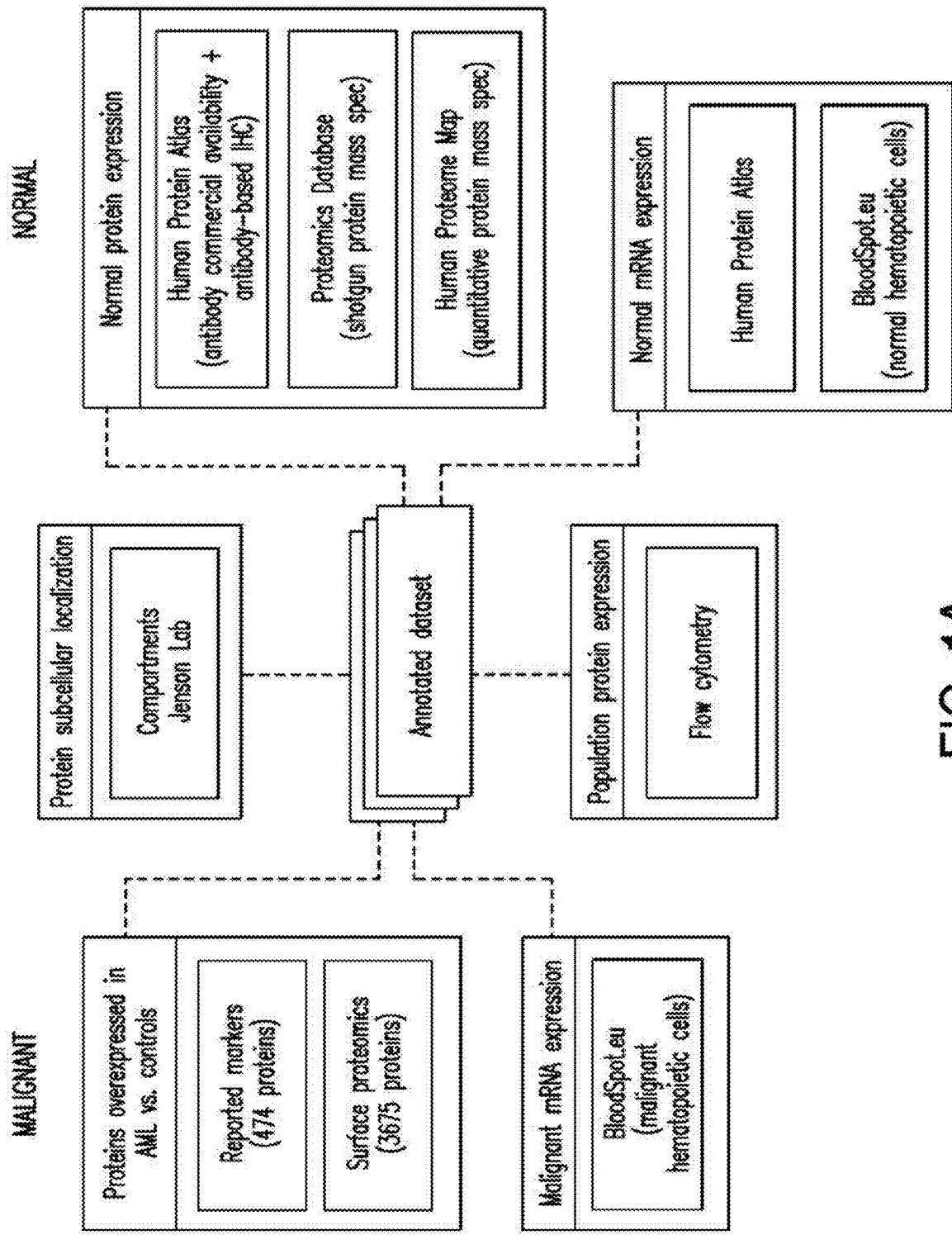
FIGS. 1A-1E depict strategy and results of the study to identify CAR targets in AML.

The presently disclosed subject matter provides cells, including genetically modified immunoresponsive cells (e.g., T cells, Natural Killer (NK) cells, cytotoxic T lymphocytes (CTL) cells and regulatory T cells) comprising one or more antigen recognizing receptor (e.g., TCR or CAR) that binds to an antigen of interest and can optionally further comprise a co-stimulatory receptor (CCR), and methods of using such cells for treating and/or preventing myeloid disorders and other pathologies where an antigen-specific immune response is desired. The presently disclosed subject matter is based, at least in part, on the discovery of antigens specific to AML cells.

Malignant cells have developed a series of mechanisms to protect themselves from immune recognition and elimination. The present approach provides immunogenicity within the tumor microenvironment for tumor eradication, and represents a significant advance over conventional adoptive T cell therapy. In certain non-limiting embodiments, it provides an option of foregoing some or all ancillary treatments such as prior conditioning of the host with total body irradiation, high-dose chemotherapy, and/or postinfusion cytokine support.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds antigen, a formation of an immunological synapse occurs that includes clustering of many molecules near the bound receptor (e.g. CD4 or CD8, CD3γ/δ/ε/ζ, etc.) This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response.

By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Without being bound to a particular theory, receiving multiple stimulatory signals is important to mount a robust and long-term T cell mediated immune response. Without receiving these stimulatory signals, T cells quickly become inhibited and unresponsive to antigen. While the effects of these co-stimulatory signals vary and remain partially understood, they generally result in increasing gene expression in order to generate long lived, proliferative, and anti-apoptotic T cells that robustly respond to antigen for complete and sustained eradication.

The term "antigen recognizing receptor" as used herein refers to a receptor that is capable of activating an immune cell (e.g., a T-cell) in response to antigen binding. Exemplary antigen recognizing receptors may be native or endogenous T cell receptors or chimeric antigen receptors in which an antigen-binding domain is fused to an intracellular signaling domain capable of activating an immune cell (e.g., a T-cell).

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fe fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

As used herein, the term "single-chain variable fragment" or "scFv" is a fusion protein of the variable regions of the heavy (VH) and light chains (VL) of an immunoglobulin covalently linked to form a VH::VL heterodimer. The heavy (VH) and light chains (VL) are either joined directly or joined by a peptide-encoding linker (e.g., 10, 15, 20, 25 amino acids), which connects the N-terminus of the VH with the C terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, the term "affinity" refers to a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, including use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

The term "chimeric antigen receptor" or "CAR" as used herein refers to an antigen-binding domain that is fused to an intracellular signaling domain capable of activating or stimulating an immune cell, and in certain embodiments, the CAR also comprises a transmembrane domain. In certain embodiments, the CAR's antigen-binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries). In various embodiments, the scFv is fused to the transmembrane domain and then to the intracellular signaling domain. "First generation" CARs include those that solely provide CD3ζ signals upon antigen binding, "Second-generation" CARs include those that provide both co-stimulation (e.g., CD28 or CD137) and activation (CD3ζ). "Third-generation" CARs include those that provide multiple co-stimulation (e.g. CD28 and CD137) and activation (CD3ζ). In various embodiments, the CAR is selected to have high affinity or avidity for the antigen.

The term "chimeric co-stimulating receptor" or "CCR" refers to a chimeric receptor that binds to an antigen and provides co-stimulatory signals, but does not provide a T-cell activation signal. CCR is described in Krause, et al., J. Exp. Med. (1998); 188(4):619-626, and US20020018783, the contents of which are incorporated by reference in their entireties. CCRs mimic co-stimulatory signals, but unlike, CARs, do not provide a T-cell activation signal, e.g., CCRs lack a CD3ζ polypeptide.

The term "immunosuppressive activity" is meant induction of signal transduction or changes in protein expression in a cell (e.g., an activated immunoresponsive cell) resulting in a decrease in an immune response. Polypeptides known to suppress or decrease an immune response via their binding include CD47, PD-1, CTLA-4, and their corresponding ligands, including SIRPa, PD-L1, PD-L2, B7-1, and B7-2. Such polypeptides are present in the tumor microenvironment and inhibit immune responses to neoplastic cells. In various embodiments, inhibiting, blocking, or antagonizing the interaction of immunosuppressive polypeptides and/or their ligands enhances the immune response of the immunoresponsive cell.

The term "immunostimulatory activity" is meant induction of signal transduction or changes in protein expression in a cell (e.g., an activated immunoresponsive cell) resulting in an increase in an immune response. Immunostimulatory activity may include pro-inflammatory activity. Polypeptides known to stimulate or increase an immune response via their binding include CD28, OX-40, 4-1BB, and their corresponding ligands, including B7-1, B7-2, OX-40L, and 4-1BBL. Such polypeptides are present in the tumor microenvironment and activate immune responses to neoplastic cells. In various embodiments, promoting, stimulating, or agonizing pro-inflammatory polypeptides and/or their ligands enhances the immune response of the immunoreponsive cell.

By "OX40L polypeptide" is meant a polypeptide having at least about 85%, about 90 about, about 95%, about 96%, about 97%, about 98%, about 99% or about 100% homologous to NCBI Reference No: BAB18304 or NP_003317 (SEQ ID NO: 4) or fragments thereof, and/or may optionally comprise up to one or up to two or up to three conservative amino acid substitutions. SEQ ID NO: 4 is provided below By "OX40L nucleic acid molecule" is meant a polynucleotide encoding a OX40L polypeptide.

Nucleic acid molecules useful in the methods of the invention include any nucleic acid molecule that encodes a polypeptide of the invention or a fragment thereof. Such nucleic acid molecules need not be 100% homolgous or identical with an endogenous nucleic acid sequence, but will typically exhibit substantial identity. Polynucleotides having "substantial identity" or "substantial homology" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about

[SEQ ID NO: 4]
```
  1 MERVQPLEEN VGNAARPRFE RNKLLLVASV IQGLGLLLCF TYICLHFSAL QVSHRYPRIQ

61 SIKVQFTEYK KEKGFILTSQ KEDEIMKVQN NSVIINCDGF YLISLKGYFS QEVNISLHYQ

121 KDEEPLFQLK KVRSVNSLMV ASLTYKDKVY LNVTTDNTSL DDFHVNGGEL ILIHQNPGEF

181 CVL
```

68° C. In a preferred embodiment, wash steps will occur at 25° C. in 30 mM NaCl, 3 mM trisodium citrate, and 0.1% SDS. In certain embodiments, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" or "substantially homologous" is meant a polypeptide or nucleic acid molecule exhibiting at least about 50% homolougs or identical to a reference amino acid sequence (for example, any one of the amino acid sequences described herein) or nucleic acid sequence (for example, any one of the nucleic acid sequences described herein). Preferably, such a sequence is at least about 60%, about 80%, about 85%, about 90%, about 95%, about 99%, or about 100% homolgous or identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "analog" is meant a structurally related polypeptide or nucleic acid molecule having the function of a reference polypeptide or nucleic acid molecule.

The term "ligand" as used herein refers to a molecule that binds to a receptor. In particular, the ligand binds a receptor on another cell, allowing for cell-to-cell recognition and/or interaction.

The term "constitutive expression" as used herein refers to expression under all physiological conditions.

By "disease" is meant any condition or disorder that damages or interferes with the normal function of a cell, tissue, or organ. Examples of diseases include neoplasia or pathogen infection of cell.

By "effective amount" is meant an amount sufficient to have a therapeutic effect. In certain embodiments, an "effective amount" is an amount sufficient to arrest, ameliorate, or inhibit the continued proliferation, growth, or metastasis (e.g., invasion, or migration) of disease or disorder of interest, e.g., a myeloid disorder.

By "endogenous" is meant a nucleic acid molecule or polypeptide that is normally expressed in a cell or tissue.

By "enforcing tolerance" is meant preventing the activity of self-reactive cells or immunoresponsive cells that target transplanted organs or tissues.

By "exogenous" is meant a nucleic acid molecule or polypeptide that is not endogenously present in the cell. The term "exogenous" would therefore encompass any recombinant nucleic acid molecule or polypeptide expressed in a cell, such as foreign, heterologous, and over-expressed nucleic acid molecules and polypeptides. By "exogenous" nucleic acid is meant a nucleic acid not present in a native wild type cell; for example an exogenous nucleic acid may vary from an endogenous counterpart by sequence, by position/location, or both. For clarity, an exogenous nucleic acid may have the same or different sequence relative to its native endogenous counterpart; it may be introduced by genetic engineering into the cell itself or a progenitor thereof, and may optionally be linked to alternative control sequences, such as a non-native promoter or secretory sequence.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "immunoresponsive cell" is meant a cell that functions in an immune response or a progenitor, or progeny thereof.

By "increase" is meant to alter positively by at least 5%. An alteration may be by about 5%, about 10%, about 25%, about 30%, about 50%, about 75%, about 100% or more.

By "isolated cell" is meant a cell that is separated from the molecular and/or cellular components that naturally accompany the cell.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "obtaining" as in "obtaining the agent" is intended to include purchasing, synthesizing or otherwise acquiring the agent (or indicated substance or material).

"Linker", as used herein, shall mean a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). An exemplary linker sequence used in the invention is GGGGSGGGGSGGGGS [SEQ ID NO: 5].

By "modulate" is meant positively or negatively alter. Exemplary modulations include a about 1%, about 2%, about 5%, about 10%, about 25%, about 50%, about 75%, or about 100% change.

By "reduce" is meant to alter negatively by at least about 5%. An alteration may be by about 5%, about 10%, about 25%, about 30%, about 50%, about 75%, or even by about 100%.

By "recognize" is meant selectively binds a target. A T cell that recognizes an antigen typically comprises or expresses a receptor that binds to that antigen.

By "signal sequence" or "leader sequence" is meant a peptide sequence (e.g., 5, 10, 15, 20, 25 or 30 amino acids) present at the N-terminus of newly synthesized proteins that directs their entry to the secretory pathway. Exemplary leader sequences include, but is not limited to, the kappa leader sequence: METPAQLLFLLLLWLPDTTG [SEQ ID NO:6] (human), METDTLLLWVLLLWVPGSTG [SEQ ID NO:7] (mouse); and the CD8 leader sequence: MALPVTALLLPLALLLHAARP [SEQ ID NO:8] (human).

By "soluble" is meant a polypeptide that is freely diffusible in an aqueous environment (e.g., not membrane bound).

By "specifically binds" is meant a polypeptide or fragment thereof that recognizes and binds a biological molecule of interest (e.g., a polypeptide), but which does not substantially recognize and bind other molecules in a sample, for example, a biological sample, which naturally includes a polypeptide of the invention. In certain embodiments, "specifically binds" refers to binding of, for example, an antibody to an epitope or antigen or antigenic determinant in such a manner that binding can be displaced or competed with a second preparation of identical or similar epitope, antigen or antigenic determinant.

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, reducing or preventing metastases, decreasing the rate of disease progression, amelioration or palliation of the disease state, and remission or improved prognosis. By preventing progression of a disease or disorder, a treatment can reduce or prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

The term "subject" as used herein refers to a vertebrate, preferably a mammal, more preferably a human. Non-human subjects include non-human primates, dogs, cats, horses, rodents, etc.

The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

Other aspects of the invention are described in the following disclosure and are within the ambit of the invention.

Antibodies

The present disclosure provides antibodies or antigen-binding portions thereof that bind to a myeloid/AML antigen.

Antibodies for use in the presently disclosed subject matter include any antibody, whether natural or synthetic, full length or a fragment thereof, monoclonal or polyclonal, that binds sufficiently strongly and specifically to a myeloid/AML antigen. An antibody can have a $K_d$ of at most about about $10^{-6}$M, about $10^{-7}$M, about $10^{-8}$M, about $10^{-9}$M, about $10^{-10}$ M, about $10^{-11}$M and about $10^{-12}$M.

Antibodies and derivatives thereof that can be used encompasses polyclonal or monoclonal antibodies, chimeric, human, humanized, primatized (CDR-grafted), veneered or single-chain antibodies, phase produced antibodies (e.g., from phage display libraries), as well as functional binding fragments, of antibodies. For example, antibody fragments capable of binding to a myeloid/AML antigen, or portions thereof, including, but not limited to Fv, Fab, Fab' and F(ab')2 fragments can be used. Such fragments can be produced by enzymatic cleavage or by recombinant techniques. For example, and not by way of limitation, papain or pepsin cleavage can generate Fab or F(ab')2 fragments, respectively. Other proteases with the requisite substrate specificity can also be used to generate Fab or F(ab')2 fragments. Antibodies can also be produced in a variety of truncated forms using antibody genes in which one or more stop codons have been introduced upstream of the natural stop site. For example, a chimeric gene encoding a F(ab')2 heavy chain portion can be designed to include DNA sequences encoding the CH, domain and hinge region of the heavy chain.

Methods of raising an antibody targeting a specific antigen are generally known in the art. Synthetic and engineered antibodies are described in, e.g., Cabilly et al., U.S. Pat. No. 4,816,567 Cabilly et al., European Patent No. 0125023 B1; Boss et al., U.S. Pat. No. 4,816,397; Boss et al., European Patent No. 0,120,694 B1; Neuberger, M. S. et al., WO 86/01533; Neuberger et al., European Patent No. 0,194,276 B1; Winter, U.S. Pat. No. 5,225,539; Winter, European Patent No. 0,239,400 B1; Queen et al., European Patent No. 0451216 B1; and Padlan et al., EP 0519596 A1. See also, Newman et al., BioTechnology, 10: 1455-1460 (1992), regarding primatized antibody, and Ladner et al., U.S. Pat. No. 4,946,778 and Bird et al., Science, 242: 423-426 (1988)) regarding single-chain antibodies. The contents of those publications are incorporated by reference in their entireties.

In certain embodiments, one or more of the flowing commercially available antibodies can be used for binding to a myeloid/AML antigen: CD70-PE cat. 355104 (Biolegend); EMR2-FITC cat. 130-104-654; EMR2-APC cat. 130-104-656 (Miltenty); LTB4R1-AF700 cat. FAB099N; LTB4R1-AF405 cat. FAB099V; LTB4R1-FITC cat. NB100-64832 (Novus Biologicals); LTB4R1-PE cat. FAB099P (R&D); PIEZO1-AF488 cat. NBP11-78537; CD33-APC cat. 551378 (BD Pharmingen); ENG-APC cat. MHCD10505 (Invitrogen); MYADM cat. NBP2-24494SS (Novus); ITGA5 (CD49e)-APC cat. 328011 (Biolegend); SLC19A1-APC cat. FAB8450A (R&D); ILT3-APC (LILRB4) cat. FAB24251A (R&D); CCR1-PE cat. 130-100-368 (Miltenty); ITGA4-APC cat. FAB2450A (R&D); CD49d-PE cat. 130-099-691 (Miltenyi); ICAM1-PE cat. 130-103-909 (Miltenyi); SIRPB1-PE cat. 130-105-310 (Miltenyi); CD64-APC (FCGR1A) cat. 561189 (BD); CD300f (IREM-1)-PE cat. 130-098-472; CD300f (IREM-1)-FITC cat. 130-098-443 (Miltenyi); IL10RB-APC cat. FAB874A (R&D); MRP1-PE cat. IC19291P (R&D); CD38-APC cat. MHCD3805; CD38-

PE cat. MHCD3804 (Invitrogen); CD34-APC cat. 340667 (BD); CPM cat. DDX0520P (Dendritics); TTYH3 cat. NBP1-91350 (Novus); SLC NHE1 (SLC9A1) ab58304 (abcam); SLC22A5 bs-8149R (Bioss); KCNN4 PA5-33875 (Thermo Scientific); ITFG3 PA5-31403 (Thermo Scientific); SLC6A6 LS-C179237 (LSBio); SLC43A3 NBP1-85026 (Novus); TFR2 TA504592 (Origene); MBOAT7 NBP1-69610 (Novus); CD235a-APC (GYPA) cat. 551336 (BD Pharmigen); and PLXNC1 cat. AF3887-SP (R&D Systems).

The CDRs of the commercially available antibodies are readily accessible by one skilled in the art using conventional sequencing technology. Further, one skilled in the art is able to construct nucleic acids encoding scFvs and antigen recognizing receptors (e.g., CARs and TCRs) based on the CDRs of those antibodies.

T-Cell Receptor (TCR)

The present disclosure provides antigen binding receptors that bind to a myeloid/AML antigen. In certain embodiments, the antigen recognizing receptor is a TCR. A TCR is a disulfide-linked heterodimeric protein consisting of two variable chains expressed as part of a complex with the invariant CD3 chain molecules. A TCR is found on the surface of T cells, and is responsible for recognizing antigens as peptides bound to major histocompatibility complex (MHC) molecules. In certain embodiments, a TCR comprises an alpha chain and a beta chain (encoded by TRA and TRB, respectively). In certain embodiments, a TCR comprises a gamma chain and a delta chain (encoded by TRG and TRD, respectively).

Each chain of a TCR is composed of two extracellular domains: Variable (V) region and a Constant (C) region. The Constant region is proximal to the cell membrane, followed by a transmembrane region and a short cytoplasmic tail. The Variable region binds to the peptide/MHC complex. The variable domain of both chains each has three complementarity determining regions (CDRs).

In certain embodiments, a TCR can form a receptor complex with three dimeric signaling modules CD3δ/ε, CD3γ/ε and CD247ζ/ζ or ζ/η. When a TCR complex engages with its antigen and MHC (peptide/MHC), the T cell expressing the TCR complex is activated.

In certain embodiments, the presently disclosed subject matter provides a recombinant TCR. In certain embodiments, the TCR is a non-naturally occurring TCR. In certain embodiments, the TCR differs from any naturally occurring TCR by at least one amino acid residue. In certain embodiments, the TCR differs from any naturally occurring TCR by at least 2, 3, 4, 5, 6, 7, 8, 9, 10, 11, 12, 13, 14, 15, 20, 25, 30, 40, 50, 60, 70, 80, 90, 100 or more amino acid residues. In certain embodiments, the TCR is modified from a naturally occurring TCR by at least one amino acid residue. In certain embodiments, the TCR is modified from a naturally occurring TCR by at least 2, 3, 4, 5, 6, 7, 8, 9, 10, 11, 12, 13, 14, 15, 20, 25, 30, 40, 50, 60, 70, 80, 90, 100 or more amino acid residues.

Chimeric Antigen Receptor (CAR)

The present disclosure further provides chimeric antigen receptors (CARs) that target a myeloid/AML antigen.

CARs are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen binding domain (e.g., a single-chain variable fragments (scFv)) fused to a transmembrane domain, fused to cytoplasmic/intracellular signaling domain of the T cell receptor chain. "First generation" CARs typically have the intracellular signaling domain from the CD3-chain, which is the primary transmitter of signals from endogenous TCRs. "First generation" CARs can provide de novo antigen recognition and cause activation of both CD4$^+$ and CD8$^+$ T cells through their CD3ζ chain signaling domain in a single fusion molecule, independent of HLA-mediated antigen presentation. "Second generation" CARs add intracellular signaling domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3). Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL). "Third generation" CARs comprise those that provide multiple co-stimulation (e.g., CD28 and 4-1BB) and activation (CD3).

In certain non-limiting embodiments, the extracellular antigen-binding domain of the CAR (embodied, for example, an scFv or an analog thereof) binds to an AML antigen with a dissociation constant ($K_d$) of about $2 \times 10^{-7}$ M or less. In certain embodiments, the $K_d$ is about $2 \times 10^{-7}$ M or less, about $1 \times 10^{-7}$ M or less, about $9 \times 10^{-8}$ M or less, about $1 \times 10^{-7}$ M or less, about $9 \times 10^{-9}$ M or less, about $5 \times 10^{-9}$ M or less, about $4 \times 10^{-9}$ M or less, about $3 \times 10^{-9}$ or less, about $2 \times 10^{-9}$ M or less, or about $1 \times 10^{-9}$ M or less. In certain non-limiting embodiments, the $K_d$ is about $3 \times 10^{-9}$ M or less. In certain non-limiting embodiments, the $K_d$ is from about $1 \times 10^{-9}$ M to about $3 \times 10^{-7}$ M. In certain non-limiting embodiments, the $K_d$ is from about $1.5 \times 10^{-9}$ M to about $3 \times 10^{-7}$ M. In certain non-limiting embodiments, the $K_d$ is from about $1.5 \times 10^{-9}$ M to about $2.7 \times 10^{-7}$ M.

Binding of the extracellular antigen-binding domain (for example, in an scFv or an analog thereof) of a presently disclosed AML-targeted CAR can be confirmed by, for example, enzyme-linked immunosorbant assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the extracellular antigen-binding domain of the AML antigen-targeted CAR is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet). In one embodiment, the scFv of a presently disclosed AML antigen-targeted CAR is labeled with GFP.

In accordance with the presently disclosed subject matter, the CARs comprise an extracellular antigen-binding domain, a transmembrane domain and an intracellular signaling domain, wherein the extracellular antigen-binding domain specifically binds to an AML antigen. In certain embodiments, the extracellular antigen-binding domain is an scFv. In certain embodiments, the extracellular antigen-binding domain is a Fab, which is optionally crosslinked. In a certain embodiments, the extracellular binding domain is a F(ab)$_2$. In certain embodiments, any of the foregoing molecules may be comprised in a fusion protein with a heterologous sequence to form the extracellular antigen-binding domain. In certain embodiments, the scFv is identified by screening scFv phage library with an AML antigen-Fc fusion protein.

Extracellular Antigen Binding Domain of A CAR

In certain embodiments, the extracellular antigen-binding domain specifically binds to an AML antigen. In certain embodiments, the AML antigen is a human polypeptide. In certain embodiments, the extracellular antigen-binding domain is an scFv. In certain embodiments, the scFv is a human scFv. In certain embodiments, the scFv is a humanized scFv.

Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof.

In certain embodiments, the transmembrane domain comprises a CD8 polypeptide. In certain embodiments, the CD8 polypeptide has an amino acid sequence that is at least about 85%, about 90%, about 95%, about 96%, about 97%, about 98%, about 99% or about 100% homologous to the sequence having a NCBI Reference No: NP_001139345.1 (SEQ ID NO: 9) (homology herein may be determined using standard software such as BLAST or FASTA) as provided below, or fragments thereof, and/or may optionally comprise up to one or up to two or up to three conservative amino acid substitutions. In certain embodiments, the CD8 polypeptide can have an amino acid sequence that is a consecutive portion of SEQ ID NO: 9 which is at least 20, or at least 30, or at least 40, or at least 50, and up to 235 amino acids in length. Alternatively or additionally, in non-limiting various embodiments, the CD8 polypeptide comprises or has an amino acid sequence of amino acids 1 to 235, 1 to 50, 50 to 100, 100 to 150, 150 to 200, or 200 to 235 of SEQ ID NO: 9. In certain embodiments, the CAR of the presently disclosed comprises a transmembrane domain comprising a CD8 polypeptide that comprises an amino acid sequence of amino acids 137 to 209 of SEQ ID NO: 9.

[SEQ ID NO: 9]
MALPVTALLLPLALLLHAARPSQFRVSPLDRTWNLGETVELKCQVLLSNPT

SGCSWLFQPRGAAASPTFLLYLSQNKPKAAEGLDTQRFSGKRLGDTFVLTL

SDFRRENEGYYFCSALSNSIMYFSHFVPVFLPAKPTTTPAPRPPTPAPTIA

SQPLSLRPEACRPAAGGAVHTRGLDFACDIYIWAPLAGTCGVLLLSLVITL

YCNHRNRRRVCKCPRPVVKSGDKPSLSARYV

In certain embodiments, the CD8 polypeptide has an amino acid sequence that is at least about 85%, about 90%, about 95%, about 96%, about 97%, about 98%, about 99% or about 100% homologous to the sequence having a NCBI Reference No: AAA92533.1 (SEQ ID NO: 10) (homology herein may be determined using standard software such as BLAST or FASTA) as provided below, or fragments thereof, and/or may optionally comprise up to one or up to two or up to three conservative amino acid substitutions. In certain embodiments, the CD8 polypeptide can have an amino acid sequence that is a consecutive portion of SEQ ID NO: 10 which is at least about 20, or at least about 30, or at least about 40, or at least about 50, or at least about 60, or at least about 70, or at least about 100, or at least about 200, and up to 247 amino acids in length. Alternatively or additionally, in non-limiting various embodiments, the CD8 polypeptide comprises or has an amino acid sequence of amino acids 1 to 247, 1 to 50, 50 to 100, 100 to 150, 150 to 200, 151 to 219, or 200 to 247 of SEQ ID NO: 10. In certain embodiments, the CAR of the presently disclosed comprises a transmembrane domain comprising a CD8 polypeptide that comprises an amino acid sequence of amino acids 151 to 219 of SEQ ID NO: 10.

[SEQ ID NO: 10]
1 MASPLTRELS LNLLLMGESI ILGSGEAKPQ APELRIFPKK MDAELGQKVD LVCEVLGSVS

61 QGCSWLFQNS SSKLPQPTFV VYMASSHNKI TWDEKLNSSK LFSAVRDTNN KYVLTLNKFS

121 KENEGYYFCS VISNSVMYFS SVVPVLQKVN STTTKPVLRT PSPVHPTGTS QPQRPEDCRP

181 RGSVKGTGLD FACDIYIWAP LAGICVAPLL SLIITLICYH RSRKRVCKCP RPLVRQEGKP

241 RPSEKIV

In certain embodiments, the CD8 polypeptide comprises or has the amino acid sequence set forth in SEQ ID NO: 11, which is provided below:

[SEQ ID NO: 11]
STTTKPVLRTPSPVHPTGTSQPQRPEDCRPRGSVKGTGLDFACDIYIWAPL

AGICVALLLSLIITLICY

In accordance with the presently disclosed subject matter, a "CD8 nucleic acid molecule" refers to a polynucleotide encoding a CD8 polypeptide.

In certain embodiments, the CD8 nucleic acid molecule encoding the CD8 polypeptide comprised in the transmembrane domain of the presently disclosed CAR (SEQ ID NO: 11) comprises nucleic acids having the sequence set forth in SEQ ID NO: 12 as provided below.

```
                                                           [SEQ ID NO: 12]
TCTACTACTACCAAGCCAGTGCTGCGAACTCCCTCACCTGTGCACCCTACC

GGGACATCTCAGCCCCAGAGACCAGAAGATTGTCGGCCCCGTGGCTCAGTG

AAGGGGACCGGATTGGACTTCGCCTGTGATATTTACATCTGGGCACCCTTG

GCCGGAATCTGCGTGGCCCTTCTGCTGTCCTTGATCATCACTCTCATCTGC

TAC
```

In certain embodiments, the transmembrane domain of a presently disclosed CAR comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: P10747 or NP_006130 (SEQ ID No: 2), or fragments thereof, and/or may optionally comprise up to one or up to two or up to three conservative amino acid substitutions. In non-limiting certain embodiments, the CD28 polypeptide can have an amino acid sequence that is a consecutive portion of SEQ ID NO: 2 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 114 to 220, 150 to 200, or 200 to 220 of SEQ ID NO: 2. In certain embodiments, the CD28 polypeptide comprised in the transmembrane domain of a presently disclosed CAR has an amino acid sequence of amino acids 153 to 179 of SEQ ID NO: 2.

SEQ ID NO: 2 is provided below:

```
                                                                [SEQ ID NO: 2]
  1 MLRLLLALNL FPSIQVTGNK ILVKQSPMLV AYDNAVNLSC KYSYNLFSRE FRASLHKGLD

61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS
```

In accordance with the presently disclosed subject matter, a "CD28 nucleic acid molecule" refers to a polynucleotide encoding a CD28 polypeptide.

In certain non-limiting embodiments, a CAR can also comprise a spacer region that links the extracellular antigen-binding domain to the transmembrane domain. The spacer region can be flexible enough to allow the antigen binding domain to orient in different directions to facilitate antigen recognition. The spacer region can be the hinge region from IgG1, or the $CH_2CH_3$ region of immunoglobulin and portions of CD3.

Intracellular Signaling Domain of a CAR

In certain non-limiting embodiments, an intracellular signaling domain of the CAR can comprise a CD3ζ polypeptide, which can activate or stimulate a cell (e.g., a cell of the lymphoid lineage, e.g., a T cell). CD3ζ comprises 3 ITAMs, and transmits an activation signal to the cell (e.g., a cell of the lymphoid lineage, e.g., a T cell) after antigen is bound. In certain embodiments, the CD3ζ polypeptide has an amino acid sequence that is at least about 85%, about 90%, about 95%, about 96%, about 97%, about 98%, about 99% or about 100% homologous to the sequence having a NCBI Reference No: NP_932170 (SEQ ID No: 1), or fragments thereof, and/or may optionally comprise up to one or up to two or up to three conservative amino acid substitutions. In certain non-limiting embodiments, the CD3ζ polypeptide can have an amino acid sequence that is a consecutive portion of SEQ ID NO: 1 which is at least 20, or at least 30, or at least 40, or at least 50, and up to 164 amino acids in length. Alternatively or additionally, in non-limiting various embodiments, the CD3ζ polypeptide has an amino acid sequence of amino acids 1 to 164, 1 to 50, 50 to 100, 100 to 150, or 150 to 164 of SEQ ID NO: 1. In certain embodiments, the CD3ζ polypeptide comprises or has an amino acid sequence of amino acids 52 to 164 of SEQ ID NO: 1.

SEQ ID NO: 1 is provided below:

```
                                                                [SEQ ID NO: 1]
  1 MKWKALFTAA ILQAQLPITE AQSFGLLDPK LCYLLDGILF IYGVILTALF LRVKFSRSAD

61 APAYQQGQNQ LYNELNLGRR EEYDVLDKRR GRDPEMGGKP QRRKNPQEGL YNELQKDKMA

121 EAYSEIGMKG ERRRGKGHDG LYQGLSTATK DTYDALHMQA LPPR
```

In certain embodiments, the CD3ζ polypeptide has an amino acid sequence that is at least about 85%, about 90%, about 95%, about 96%, about 97%, about 98%, about 99% or about 100% homologous to the sequence having a NCBI Reference No: NP_001106864.2 (SEQ ID No: 13), or fragments thereof, and/or may optionally comprise up to one or up to two or up to three conservative amino acid substitutions. In certain non-limiting embodiments, the CD3ζ polypeptide can have an amino acid sequence that is a consecutive portion of SEQ ID NO: 13 which is at least about 20, or at least about 30, or at least about 40, or at least about 50, or at least about 90, or at least about 100, and up to 188 amino acids in length. Alternatively or additionally, in non-limiting various embodiments, the CD3ζ polypeptide has an amino acid sequence of amino acids 1 to 164, 1 to 50, 50 to 100, 52 to 142, 100 to 150, or 150 to 188 of SEQ ID NO: 13. In certain embodiments, the CD3ζ polypeptide comprises or has an amino acid sequence of amino acids 52 to 142 of SEQ ID NO: 13.

SEQ ID NO: 13 is provided below:

[SEQ ID NO: 13]

```
  1 MKWKVSVLAC ILHVRFPGAE AQSFGLLDPK LCYLLDGILF IYGVIITALY LRAKFSRSAE

61 TAANLQDPNQ LYNELNLGRR EEYDVLEKKR ARDPEMGGKQ RRRNPQEGVY NALQKDKMAE

121 AYSEIGTKGE RRRGKGHDGL YQDSHFQAVQ FGNRREREGS ELTRTLGLRA RPKACRHKKP

181 LSLPAAVS
```

In certain embodiments, the CD3ζ polypeptide comprises or has the amino acid sequence set forth in SEQ ID NO: 14, which is provided below:

[SEQ ID NO: 14]
```
RAKFSRSAETAANLQDPNQLYNELNLGRREEYDVLEKKRARDPEMGGK

QQRRRNPQEGVYNALQKDKMAEAYSEIGTKGERRRGKGHDGLYQGLST

ATKDTYDALHMQTLAPR
```

In accordance with the presently disclosed subject matter, a "CD3ζ nucleic acid molecule" refers to a polynucleotide encoding a CD3ζ polypeptide. In certain embodiments, the CD3ζ nucleic acid molecule encoding the CD3ζ polypeptide comprised in the intracellular domain of a presently disclosed CAR (SEQ ID NO: 14) comprises the nucleotide sequence set forth in SEQ ID NO: 15 as provided below.

[SEQ ID NO: 15]
```
AGAGCAAAATTCAGCAGGAGTGCAGAGACTGCTGCCAACCTGCAGGAC

CCCAACCAGCTCTACAATGAGCTCAATCTAGGGCGAAGAGAGGAATAT

GACGTCTTGGAGAAGAAGCGGGCTCGGGATCCAGAGATGGGAGGCAAA

CAGCAGAGGAGGAGGAACCCCCAGGAAGGCGTATACAATGCACTGCAG

AAAGACAAGATGGCAGAAGCCTACAGTGAGATCGGCACAAAAGGCGAG

AGGCGGAGAGGCAAGGGGCACGATGGCCTTTACCAGGGTCTCAGCACT

GCCACCAAGGACACCTATGATGCCCTGCATATGCAGACCCTGGCCCCT

CGCTAA
```

In certain non-limiting embodiments, an intracellular signaling domain of the CAR further comprises at least one signaling region. The at least one signaling region can include a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof.

In certain embodiments, the signaling region is a co-stimulatory signaling region. In certain embodiments, the co-stimulatory region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule.

Co-stimulatory ligands, include, but are not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD137") for providing an intracellular signal that in combination with a CAR signal induces an effector cell function of the CAR' T cell. CARs comprising an intracellular domain that comprises a co-stimulatory signaling region comprising 4-1BB, ICOS or DAP-10 are disclosed in U.S. Pat. No. 7,446,190 (e.g., the nucleotide sequence encoding 4-1BB is set forth in SEQ ID NO:15, the nucleotide sequence encoding ICOS is set forth in SEQ ID NO:16, and the nucleotide sequence encoding DAP-10 is set forth in SEQ ID NO:17 in U.S. Pat. No. 7,446,190), which is herein incorporated by reference in its entirety.

In certain embodiments, the intracellular signaling domain of the CAR comprises a co-stimulatory signaling region that comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: P10747 or NP_006130 (SEQ ID No: 2), or fragments thereof, and/or may optionally comprise up to one or up to two or up to three conservative amino acid substitutions. In non-limiting certain embodiments, the CD28 polypeptide has an amino acid sequence that is a consecutive portion of SEQ ID NO: 2 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 114 to 220, 150 to 200, or 200 to 220 of SEQ ID NO: 2. In certain embodiments, the intracellular signaling domain of the CAR comprises a co-stimulatory signaling region that comprises a CD28 polypeptide having an amino acid sequence of amino acids 180 to 220 of SEQ ID NO: 2.

In certain embodiments, the CD28 polypeptide has an amino acid sequence that is at least about 85%, about 90%, about 95%, about 96%, about 97%, about 98%, about 99% or about 100% homologous to the sequence having a NCBI Reference No: NP_031668.3 (SEQ ID No: 16), or fragments thereof, and/or may optionally comprise up to one or up to two or up to three conservative amino acid substitutions. In non-limiting certain embodiments, the CD28 polypeptide has an amino acid sequence that is a consecutive portion of SEQ ID NO: 16 which is at least about 20, or at least about 30, or at least about 40, or at least about 50, and up to 218 amino acids in length. Alternatively or additionally, in non-limiting various embodiments, the CD28 polypeptide has an amino acid sequence of amino acids 1 to 218, 1 to 50, 50 to 100, 100 to 150, 114 to 220, 150 to 200, 178 to 218, or 200 to 220 of SEQ ID NO: 16. In certain embodiments, the co-stimulatory signaling region of a presently disclosed CAR comprises a CD28 polypeptide that comprises or has the amino acids 178 to 218 of SEQ ID NO: 16.

SEQ ID NO: 16 is provided below:

[SEQ ID NO: 16]
```
  1 MTLRLLFLAL NFFSVQVTEN KILVKQSPLL VVDSNEVSLS CRYSYNLLAK EFRASLYKGV
 61 NSDVEVCVGN GNFTYQPQFR SNAEFNCDGD FDNETVTFRL WNLHVNHTDI YFCKIEFMYP
121 PPYLDNERSN GTIIHIKEKH LCHTQSSPKL FWALVVVAGV LFCYGLLVTV ALCVIWTNSR
181 RNRLLQSDYM NMTPRRPGLT RKPYQPYAPA RDFAAYRP
```

In accordance with the presently disclosed subject matter, a "CD28 nucleic acid molecule" refers to a polynucleotide encoding a CD28 polypeptide. In certain embodiments, a CD28 nucleic acid molecule that encodes a CD28 polypeptide comprised in the co-stimulatory signaling region of a presently disclosed CAR (e.g., amino acids 178 to 218 of SEQ ID NO: 16) comprises or has a nucleotide sequence set forth in SEQ ID NO: 17, which is provided below.

[SEQ ID NO: 17]
```
AATAGTAGAAGGAACAGACTCCTTCAAAGTGACTACATGAACATGACT
CCCCGGAGGCCTGGGCTCACTCGAAAGCCTTACCAGCCCTACGCCCCT
GCCAGAGACTTTGCAGCGTACCGCCCC
```

In certain embodiments, the intracellular domain of the CAR comprises a co-stimulatory signaling region that comprises two co-stimulatory molecules: CD28 and 4-1BB or CD28 and OX40.

4-1BB can act as a tumor necrosis factor (TNF) ligand and have stimulatory activity. The 4-1BB polypeptide can have an amino acid sequence that is at least about 85%, about 90%, about 95%, about 96%, about 97%, about 98%, about 99% or about 100% homologous to the sequence having a NCBI Reference No: P41273 or NP_001552 (SEQ ID NO: 3) or fragments thereof, and/or may optionally comprise up to one or up to two or up to three conservative amino acid substitutions.

SEQ ID NO: 3 is provided below:

[SEQ ID NO: 3]
```
  1 MGNSCYNIVA TLLLVLNFER TRSLQDPCSN CPAGTFCDNN RNQICSPCPP NSFSSAGGQR
 61 TCDICRQCKG VFRTRKECSS TSNAECDCTP GFHCLGAGCS MCEQDCKQGQ ELTKKGCKDC
121 CFGTFNDQKR GICRPWTNCS LDGKSVLVNG TKERDVVCGP SPADLSPGAS SVTPPAPARE
181 PGHSPQIISF FLALTSTALL FLLFFLTLRF SVVKRGRKKL LYIFKQPFMR PVQTTQEEDG
241 CSCRFPEEEE GGCEL
```

In accordance with the presently disclosed subject matter, a "4-1BB nucleic acid molecule" refers to a polynucleotide encoding a 4-1BB polypeptide.

An OX40 polypeptide can have an amino acid sequence that is at least about 85%, about 90%, about 95%, about 96%, about 97%, about 98%, about 99% or about 100% homologous to the sequence having a NCBI Reference No: P43489 or NP_003318 (SEQ ID NO: 18), or fragments thereof, and/or may optionally comprise up to one or up to two or up to three conservative amino acid substitutions.

SEQ ID NO: 18 is provided below:

```
                                                              [SEQ ID NO: 18]
  1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK

121 PGVDCAPCPP GHFSPGDNQA CKPWTNCTLA GKHTLQPASN SSDAICEDRD PPATQPQETQ

181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI
```

In accordance with the presently disclosed subject matter, an "OX40 nucleic acid molecule" refers to a polynucleotide encoding an OX40 polypeptide.

An ICOS polypeptide can have an amino acid sequence that is at least about 85%, about 90%, about 95%, about 96%, about 97%, about 98%, about 99% or about 100% homologous to the sequence having a NCBI Reference No: NP_036224 (SEQ ID NO: 19) or fragments thereof, and/or may optionally comprise up to one or up to two or up to three conservative amino acid substitutions.

SEQ ID NO: 19 is provided below:

```
                                                              [SEQ ID NO: 19]
  1 MKSGLWYFFL FCLRIKVLTG EINGSANYEM FIFHNGGVQI LCKYPDIVQQ FKMQLLKGGQ

61 ILCDLIKTKG SGNTVSIKSL KFCHSQLSNN SVSFFLYNLD HSHANYYFCN LSIFDPPPFK

121 VTLIGGYLHI YESQLCCQLK FWLPIGCAAF VVVCILGCIL ICWLTKKKYS SSVHDPNGEY

181 MFMRAVNTAK KSRLTDVTL
```

In accordance with the presently disclosed subject matter, an "ICOS nucleic acid molecule" refers to a polynucleotide encoding an ICOS polypeptide.

CTLA-4 is an inhibitory receptor expressed by activated T cells, which when engaged by its corresponding ligands (CD80 and CD86; B7-1 and B7-2, respectively),mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif (SEQ ID NO: 25) able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

In accordance with the presently disclosed subject matter, a CTLA-4 polypeptide can have an amino acid sequence that is at least about 85%, about 90%, about 95%, about 96%, about 97%, about 98%, about 99% or about 100% homologous to UniProtKB/Swiss-Prot Ref. No.: P16410.3 (SEQ ID NO: 20) (homology herein may be determined using standard software such as BLAST or FASTA) or fragments thereof, and/or may optionally comprise up to one or up to two or up to three conservative amino acid substitutions.

SEQ ID NO: 20 is provided below:

```
                                                         [SEQ ID NO: 20]
  1 MACLGFQRHK AQLNLATRTW PCTLLFFLLF IPVFCKAMHV AQPAVVLASS RGIASFVCEY

61 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN
```

In accordance with the presently disclosed subject matter, a "CTLA-4 nucleic acid molecule" refers to a polynucleotide encoding a CTLA-4 polypeptide.

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-I and SHP-2 phosphatases bind to the cytoplasmic tail of PD-1 upon ligand binding. Upregulation of PD-L1 is one mechanism tumor cells may evade the host immune system. In pre-clinical and clinical trials, PD-1 blockade by antagonistic antibodies induced anti-tumor responses mediated through the host endogenous immune system.

In accordance with the presently disclosed subject matter, a PD-1 polypeptide can have an amino acid sequence that is at least about 85%, about 90%, about 95%, about 96%, about 97%, about 98%, about 99% or about 100% homologous to NCBI Reference No: NP_005009.2 (SEQ ID NO: 21) or fragments thereof, and/or may optionally comprise up to one or up to two or up to three conservative amino acid substitutions.

SEQ ID NO: 21 is provided below:

```
                                                         [SEQ ID NO: 21]
  1 MQIPQAPWPV VWAVLQLGWR PGWFLDSPDR PWNPPTFSPA LLVVTEGDNA TFTCSFSNTS

61 ESFVLNWYRM SPSNQTDKLA AFPEDRSQPG QDCRFRVTQL PNGRDFHMSV VRARRNDSGT

121 YLCGAISLAP KAQIKESLRA ELRVTERRAE VPTAHPSPSP RPAGQFQTLV VGVVGGLLGS

181 LVLLVWVLAV ICSRAARGTI GARRTGQPLK EDPSAVPVFS VDYGELDFQW REKTPEPPVP

241 CVPEQTEYAT IVFPSGMGTS SPARRGSADG PRSAQPLRPE DGHCSWPL
```

In accordance with the presently disclosed subject matter, a "PD-1 nucleic acid molecule" refers to a polynucleotide encoding a PD-1 polypeptide.

Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

In accordance with the presently disclosed subject matter, a LAG-3 polypeptide can have an amino acid sequence that is at least about 85%, about 90%, about 95%, about 96%, about 97%, about 98%, about 99% or about 100% homologous to UniProtKB/Swiss-Prot Ref. No.: P18627.5 (SEQ ID NO: 22) or fragments thereof, and/or may optionally comprise up to one or up to two or up to three conservative amino acid substitutions.

SEQ ID NO: 22 is provided below:

```
                                                               [SEQ ID NO: 22]
  1 MWEAQFLGLL FLQPLWVAPV KPLQPGAEVP VVWAQEGAPA QLPCSPTIPL QDLSLLRRAG

61 VTWQHQPDSG PPAAAPGHPL APGPHPAAPS SWGPRPRRYT VLSVGPGGLR SGRLPLQPRV

121 QLDERGRQRG DFSLWLRPAR RADAGEYRAA VHLRDRALSC RLRLRLGQAS MTASPPGSLR

181 ASDWVILNCS FSRPDRPASV HWFRNRGQGR VPVRESPHHH LAESFLFLPQ VSPMDSGPWG

241 CILTYRDGFN VSIMYNLTVL GLEPPTPLTV YAGAGSRVGL PCRLPAGVGT RSFLTAKWTP

301 PGGGPDLLVT GDNGDFTLRL EDVSQAQAGT YTCHIHLQEQ QLNATVTLAI ITVTPKSFGS

361 PGSLGKLLCE VTPVSGQERF VWSSLDTPSQ RSFSGPWLEA QEAQLLSQPW QCQLYQGERL

421 LGAAVYFTEL SSPGAQRSGR APGALPAGHL LLFLILGVLS LLLLVTGAFG FHLWRRQWRP

481 RRFSALEQGI HPPQAQSKIE ELEQEPEPEP EPEPEPEPEP EPEQL
```

In accordance with the presently disclosed subject matter, a "LAG-3 nucleic acid molecule" refers to a polynucleotide encoding a LAG-3 polypeptide.

Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

In accordance with the presently disclosed subject matter, a 2B4 polypeptide can have an amino acid sequence that is at least about 85%, about 90%, about 95%, about 96%, about 97%, about 98%, about 99% or about 100% homologous to UniProtKB/Swiss-Prot Ref. No.: Q9BZW8.2 (SEQ ID NO: 23) or fragments thereof, and/or may optionally comprise up to one or up to two or up to three conservative amino acid substitutions.

SEQ ID NO: 23 is provided below:

```
                                                               [SEQ ID NO: 23]
  1 MLGQVVTLIL LLLLKVYQGK GCQGSADHVV SISGVPLQLQ PNSIQTKVDS IAWKKLLPSQ

61 NGFHHILKWE NGSLPSNTSN DRFSFIVKNL SLLIKAAQQQ DSGLYCLEVT SISGKVQTAT

121 FQVFVFESLL PDKVEKPRLQ GQGKILDRGR CQVALSCLVS RDGNVSYAWY RGSKLIQTAG

181 NLTYLDEEVD INGTHTYTCN VSNPVSWESH TLNLTQDCQN AHQEFRFWPF LVIIVILSAL

241 FLGTLACFCV WRRKRKEKQS ETSPKEFLTI YEDVKDLKTR RNHEQEQTFP GGGSTIYSMI

301 QSQSSAPTSQ EPAYTLYSLI QPSRKSGSRK RNHSPSFNST IYEVIGKSQP KAQNPARLSR

361 KELENFDVYS
```

In accordance with the presently disclosed subject matter, a "2B4 nucleic acid molecule" refers to a polynucleotide encoding a 2B4 polypeptide.

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human $CD8^+$ cancer-specific T cells. BTLA has also been designated as CD272 (cluster of differentiation 272).

In accordance with the presently disclosed subject matter, a BTLA polypeptide can have an amino acid sequence that is at least about 85%, about 90%, about 95%, about 96%, about 97%, about 98%, about 99% or about 100% homologous to UniProtKB/Swiss-Prot Ref. No.: Q7Z6A9.3 (SEQ ID NO: 24) or fragments thereof, and/or may optionally comprise up to one or up to two or up to three conservative amino acid substitutions.

SEQ ID NO: 24 is provided below:

```
                                                        [SEQ ID NO: 24]
  1 MKTLPAMLGT GKLFWVFFLI PYLDIWNIHG KESCDVQLYI KRQSEHSILA GDPFELECPV

61 KYCANRPHVT WCKLNGTTCV KLEDRQTSWK EEKNISFFIL HFEPVLPNDN GSYRCSANFQ

121 SNLIESHSTT LYVTDVKSAS ERPSKDEMAS RPWLLYRLLP LGGLPLLITT CFCLFCCLRR

181 HQGKQNELSD TAGREINLVD AHLKSEQTEA STRQNSQVLL SETGIYDNDP DLCFRMQEGS

241 EVYSNPCLEE NKPGIVYASL NHSVIGPNSR LARNVKEAPT EYASICVRS
```

In accordance with the presently disclosed subject matter, a "BTLA nucleic acid molecule" refers to a polynucleotide encoding a BTLA polypeptide.

In certain embodiments, the CAR of the presently disclosed subject matter can further comprise an inducible promoter, for expressing nucleic acid sequences in human cells. Promoters for use in expressing CAR genes can be a constitutive promoter, such as ubiquitin C (UbiC) promoter.

The presently disclosed subject matter also provides isolated nucleic acid molecule encoding an AML antigen-targeted CAR described herein or a functional portion thereof. In certain embodiments, the isolated nucleic acid molecule encodes a presently disclosed an AML antigen-targeted CAR comprising an scFv that specifically binds to an AML antigen, a transmembrane domain comprising a CD8 polypeptide, and an intracellular domain comprising a co-stimulatory signaling region comprising a CD28 polypeptide and a CD3ζ polypeptide.

In certain embodiments, the isolated nucleic acid molecule encodes a functional portion of a presently disclosed an AML antigen-targeted CAR. As used herein, the term "functional portion" refers to any portion, part or fragment of a presently disclosed an AML antigen-targeted CAR, which portion, part or fragment retains the biological activity of an AML antigen-targeted CAR (the parent CAR). For example, functional portions encompass the portions, parts or fragments of a presently disclosed an AML antigen-targeted CAR that retains the ability to recognize a target cell, to treat a disease, e.g., myeloid disorder, to a similar, same, or even a higher extent as the parent CAR. In certain embodiments, an isolated nucleic acid molecule encoding a functional portion of a presently disclosed an AML antigen-targeted CAR can encode a protein comprising, e.g., about 10%, about 20%, about 25%, about 30%, about 35%, about 40%, about 45%, about 50%, about 55%, about 60%, about 65%, about 70%, about 75%, about 80%, about 85%, about 90%, and about 95%, or more of the parent CAR.

Chimeric Co-Stimulatory Receptor (CCR)

As used herein, the term "chimeric co-stimulatory receptor" or "CCR" refers to a chimeric receptor that binds to an antigen and provides co-stimulatory signals, but does not provide a T-cell activation signal. CCR is described in Krause, et al., J. Exp. Med. (1998); 188(4):619-626, and US20020018783, the contents of which are incorporated by reference in their entireties. CCRs mimic co-stimulatory signals, but unlike, CARs, do not provide a T-cell activation signal, e.g., CCRs lack a CD3ζ polypeptide. CCRs provide co-stimulation, e.g., a CD28-like signal, in the absence of the natural co-stimulatory ligand on the antigen-presenting cell. A combinatorial antigen recognition, i.e., use of a CCR in combination with a CAR, can augment T-cell reactivity against the dual-antigen expressing T cells, thereby improving selective tumor targeting. Kloss et al., describe a strategy that integrates combinatorial antigen recognition, split signaling, and, critically, balanced strength of T-cell activation and costimulation to generate T cells that eliminate target cells that express a combination of antigens while sparing cells that express each antigen individually (Kloss et al., Nature Biotechnology (2013); 31(1):71-75, the content of which is incorporated by reference in its entirety). With this approach, T-cell activation requires CAR-mediated recognition of one antigen, whereas costimulation is independently mediated by a CCR specific for a second antigen. To achieve tumor selectivity, the combinatorial antigen recognition approach diminishes the efficiency of T-cell activation to a level where it is ineffective without rescue provided by simultaneous CCR recognition of the second antigen.

In certain embodiments, the CCR comprises an extracellular antigen-binding domain that binds to a second antigen, a transmembrane domain, and a co-stimulatory signaling region that comprises at least one co-stimulatory molecule. In certain embodiments, the CCR does not alone deliver an activation signal to the cell. Non-limiting examples of co-stimulatory molecules include CD28, 4-1BB, OX40ICOS, and DAP-10. In certain embodiments, the co-stimulatory signaling region of the CCR comprises one co-stimulatory signaling molecule. In certain embodiments, the one co-stimulatory signaling molecule is CD28. In certain embodiments, the one co-stimulatory signaling molecule is 4-1BB. In certain embodiments, the co-stimulatory signaling region of the CCR comprises two co-stimulatory signaling molecules. In certain embodiments, the two co-stimulatory signaling molecules are CD28 and 4-1BB. A second antigen is selected so that expression of both the first antigen and the second antigen is restricted to the targeted cells (e.g., cancerous tissue or cancerous cells). Similar to a CAR, the extracellular antigen-binding domain can be a scFv, a Fab, a F(ab)2, or a fusion protein with a heterologous sequence to form the extracellular antigen-binding domain.

In certain embodiments, the CCR is co-expressed with an antigen recognizing receptor (e.g. CAR or TCR) binding to an antigen that is different from the antigen to which the CCR binds, e.g., the antigen recognizing receptor binds to a first antigen and the CCR binds to a second antigen. In certain embodiments, the antigen recognizing receptor is a CAR. In certain embodiments, the immunoresponsive cell expressing the antigen recognizing receptor (e.g., CAR) and the CCR exhibits a greater degree of cytolytic activity against cells that are positive for both the first antigen and the second antigen as compared to against cells that are singly positive for the first antigen. In certain embodiments, the immunoresponsive cell expressing the antigen recognizing receptor (e.g., CAR) and the CCR exhibits substantially no or negligible cytolytic activity against cells that are singly positive for the first antigen.

In certain embodiments, the antigen recognizing receptor (e.g., CAR) is not potent or efficient, e.g., an antigen recognizing receptor (e.g., a CAR) that exhibits substantially no or negligible cytolytic activity against cells that are singly positive for the antigen to which the antigen recognizing receptor binds. In certain embodiments, the antigen recognizing receptor (e.g., CAR) binds to the first antigen with a low binding affinity, e.g., a dissociation constant ($K_d$) of about $1\times10^{-8}$ M or more, about $5\times10^{-7}$ M or more, about $1\times10^{-7}$ M or more, about $5\times10^{-7}$ M or more, or about $1\times10^{-7}$ M or more, or from about $1\times10^{-8}$ M to about $1\times10^{-7}$ M. In certain embodiments, the binding affinity of a CAR refers to the binding affinity of the extracellular antigen-binding domain (e.g., scFv) of the CAR to the antigen. In certain embodiments, the antigen recognizing receptor (e.g., CAR) binds to the first antigen with a low binding avidity. In certain embodiments, the antigen recognizing receptor (e.g., CAR) binds to the first antigen at an epitope of low accessibility. In certain embodiments, the antigen recognizing receptor (e.g., CAR) binds to the first antigen with a binding affinity that is lower compared to the binding affinity with which the CCR binds to the second antigen. In certain embodiments, the CCR binds to the second antigen with a binding affinity $K_d$ of from about $1\times10^{-9}$ M to about $1\times10^{-7}$ M, e.g., about $1\times10^{-7}$ M or less, about $1\times10^{-8}$ M or less, or about $1\times10^{-9}$ M or less.

Tumor Microenvironment

Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory $CD4^+$ T cells (Tregs), myeloid derived suppressor cells (MDSCs), tumor associated macrophages (TAMs), immune suppressive cytokines including IL-10 and TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

Myeloid malignancies and Acute Myeloid Leukemia (AML)

Myeloid malignancies are clonal diseases caused by dysfunction of hematopoietic stem cells or progenitor cells, resulting from genetic and epigenetic alterations that disrupt key processes such as cell proliferation and differentiation. Myeloid malignancies can be chronic or acute. Chronic diseases include myeloproliferative neoplasms (MPN), myelodysplastic syndromes (MDS) and chronic myelomonocytic leukemia (CMML). MPNs include chronic myeloid leukemia (CML) and non-CML MPNs such as polycythemia vera (PV), essential thrombocythemia (ET) and primary myelofibrosis (PMF). Acute diseases include acute myeloid leukemia (AML).

AML is characterized by the rapid growth of abnormal leukocytes which accumulate in the bone marrow and disrupt the production of normal blood cells. Symptoms of AML include fatigue, shortness of breath, increased susceptibility of infection, and easy bruising and bleeding. The majority of AML cases occur de novo, but some cases can be secondary to a chronic disease. There are eight different subtypes of AML: myeloblastic—undifferentiated (M0), myeloblastic—minimal maturation (M1), myeloblastic—full maturation (M2), promyeloctic (M3), myelomonocytic (M4), monocytic (M5), erythroleukemia (M6), and megakaryocytic (M7). The classification is based on the type of cell from which the leukemia is originated and how mature the cells are.

AML Antigens

Antigens suitable for CAR targets to AML have been reported: 1) Lewis (Le)-Y, a difucosylated carbohydrate antigen, targeted in a phase I study of four patients with relapsed AML. Infusion of second generation CD28-based CARs resulted in stable/transient remission of three patients, who ultimately progressed, despite T cell persistence (Ritchie et al., 2013); 2) CD123, the high-affinity interleukin-3 receptor α-chain; a partial remission was induced in a patient with FLT3-ITD+ AML treated with a third generation CD123-CD28/CD137/CD27/CD3z/iCaps9 CAR(Yi Luo, 2015). Preclinical studies resulted in significant myeloablation (Gill et al., 2014); 3) CD33 is a myeloid-specific sialic acid-binding receptor, also targeted by gentuzumab ozogamicin (GO)(Administration, 2010), with demonstrated survival benefit (Hills et al., 2014; Ravandi et al., 2012). Preclinical activity of CD33 $CAR^+$ CIK cells resulted in slowing disease progression (Pizzitola et al., 2014) and CD33 $CAR^+$ T showed significant effector functions in vitro and in vivo with reduction of myeloid progenitors (Kenderian et al., 2015). One AML patient was treated with CD33 CAR T cells at the Chinese PLA General Hospital, showing transient efficacy and mild fluctuations in bilirubin (Wang et al., 2015) and a clinical trial is registered as NCT01864902; 4). Folate receptor β is a myeloid-lineage antigen (Lynn et al., 2016; Lynn et al., 2015). However, none of these meet the criteria of an ideal CAR target.

The present disclosure provides new AML antigens suitable for CAR targets, which include EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1.

ADGRE2/EMR2

EGF-like module-containing mucin-like hormone receptor-like 2 (EMR2) (official name: adhesion G protein-coupled receptor E2 gene (ADGRE2), GenBank ID: 30817, also known as VBU and CD312) is a gene encoding a member of G-protein coupled receptors, and is expressed mainly in myeloid cells where it promotes cell-cell adhesion through interaction with chondroitin sulfate chains.

CD33

CD33 (GenBank ID: 945, also known as Siglec-3, sialic acid binding Ig-like lectin 3, SIGLEC3, SIGLEC-3, gp67, p67) is a transmembrane receptor expressed on cells of myeloid lineage. It is mainly expressed in myeloid cells.

IL10RB

Interleukin 10 receptor subunit beta (GenBank ID: 3588, also known as CRFB4; CRF2-4; D21S58; D21S66; CDW210B; and IL-10R2) is a gene encoding a cytokine receptor, which is an accessory chain essential for the active interleukin 10 receptor complex.

PLXNC1

Plexin C1 (GenBank ID: 10154, also known as CD232; VESPR; and PLXN-C1) is a gene encoding a member of the plexin family, which are transmembrane receptors for semaphorins.

PIEZO1

Piezo type mechanosensitive ion channel component 1 (GenBank ID: 9780, also known as DHS; Mib; LMPH3; and FAM38A) is a gene encoding a mechanically-activated ion channel that links mechanical forces to biological signals.

CD300LF

CD300 molecule like family member f (GenBank ID: 146722, also known as CLM1; NKIR; CLM-1; IREM1; LMIR3; CD300f; IREM-1; and IgSF13) is a gene encoding a member of the CD300 protein family, which are cell surface glycoproteins with a single IgV-like extracellular domain.

CPM carboxypeptidase M (GenBank ID: 1368) is a gene encoding a membrane-bound arginine/lysine carboxypeptidase.

ITFG3

Integrin alpha FG-GAP repeat containing 3 (official name: family with sequence similarity 234 member A (FAM234A), GenBank ID: 83986, also known as gs19, and C16orf9) is a gene encoding a member of proteins containing integrin alpha FG-GAP repeat.

TTYH3

Tweety family member 3 (GenBank ID: 80727) is a gene encoding a member of the chloride anion channels.

ITGA4

Integrin subunit alpha 4 (GenBank ID: 3676, also known as IA4 and CD49D) is a gene encoding a member of the integrin alpha chain family of proteins.

SLC9A1

Solute carrier family 9 member A1 (GenBank ID: 6548, also known as APNH; NHE1; LIKNS; NHE-1; and PPP1R143) is a gene encoding a Na+/H+ antiporter.

MBOAT7

Membrane bound O-acyltransferase domain containing 7 (GenBank ID: 79143, also known as BB1; LRC4; LENG4; LPIAT; MBOA7; OACT7; and hMBOA-7) is a gene encoding a member of the membrane-bound O-acyltransferases family of integral membrane proteins that have acyltransferase activity.

CD38

CD38 (GenBank ID: 952, also known as ADPRC1 and ADPRC 1) is a gene encoding a non-lineage-restricted, type II transmembrane glycoprotein that synthesizes and hydrolyzes cyclic adenosine 5'-diphosphate-ribose, an intracellular calcium ion mobilizing messenger.

SLC6A6

Solute carrier family 6 member 6 (GenBank ID: 6533, also known as TAUT) is a gene encoding a member of a family of sodium and chloride-ion dependent transporters.

ENG

Endoglin (GenBank ID: 2022, also known as END; HHT1; and ORW1) is a gene encoding a homodimeric transmembrane protein which is a major glycoprotein of the vascular endothelium.

SIRPB1

Signal regulatory protein beta 1 (GenBank ID: 10326, also known as CD172b and SIRP-BETA-1) is a gene encoding a member of the signal-regulatory-protein (SIRP) family, and also belongs to the immunoglobulin superfamily.

MRP1

Multidrug resistance-associated protein 1 (MRP1) (official name: ATP binding cassette subfamily C member 1 (ABCC1), GenBank ID: 4363, also known as MRP; ABCC; GS-X; and ABC29) is a gene encoding a member of the superfamily of ATP-binding cassette (ABC) transporters.

ITGA5

Integrin subunit alpha 5 (GenBank ID: 3678, also known as FNRA; CD49e; VLA-5; and VLA5A) is a gene encoding a member of the integrin alpha chain family of proteins.

SLC43A3

Solute carrier family 43 member 3 (GenBank ID: 29015, also known as EEG1; FOAP-13; PRO1659; and SEEEG-1) is a gene encoding an equilibrative nucleobase transporter.

MYADM

Myeloid associated differentiation marker (GenBank ID: 91663, also known as SB135) is a gene encoding a protein highly up-regulated as multipotent progenitor cells differentiate into myeloid cells. The protein is predicted to be a membrane protein.

ICAM1

Intercellular adhesion molecule 1 (GenBank ID: 3383, also known as BB2; CD54; and P3.58) is a gene encoding a cell surface glycoprotein.

SLC44A1

Solute carrier family 44 member 1 (GenBank ID: 23446, also known as CD92; CTL1; CDW92; and CHTL1) is a gene encoding a choline transporter with an intermediate affinity for choline.

CCR1

C—C motif chemokine receptor 1 (GenBank ID: 1230, also known as CKR1; CD191; CKR-1; HM145; CMKBR1; MIP1aR; and SCYAR1) is a gene encoding a member of the beta chemokine receptor family, which is predicted to be a seven transmembrane protein similar to G protein-coupled receptors.

SLC22A5

Solute carrier family 22 member 5 (GenBank ID: 6584, also known as CDSP and OCTN2) is a gene encoding a plasma integral membrane protein that functions as an organic cation transporter. The protein also functions as a sodium-dependent high affinity carnitine transporter, which is involved in active cellular uptake of carnitine.

TFR2

Transferrin receptor 2 (GenBank ID: 7036, also known as HFE3; and TFRC2) is a gene encoding a single-pass type II membrane protein, which is a member of the transferrin receptor-like family.

KCNN4

Potassium calcium-activated channel subfamily N member 4 (GenBank ID: 3783, also known as IK; IK1; SK4;

DHS2; KCA4; hSK4; IKCA1; hKCa4; KCa3.1; and hIKCa1) is a gene encoding a part of a potentially heterotetrameric voltage-independent potassium channel that is activated by intracellular calcium.

LILRB4

Leukocyte immunoglobulin like receptor B4 (GenBank ID: 11006, also known as ILT3; LIR5; CD85K; ILT-3; and LIR-5) is a gene encoding a member of the leukocyte immunoglobulin-like receptor (LIR) family.

LTB4R

Leukotriene B4 receptor (GenBank ID: 1241, also known as BLT1; BLTR; P2Y7; GPR16; LTBR1; P2RY7; CMKRL1; and LTB4R1) is a gene encoding a member of leukotriene receptors, which are G protein-coupled receptors that bind and are activated by the leukotrienes.

CD70

CD70 (GenBank ID: 970, also known as CD27L; CD27LG; TNFSF7; and TNLG8A) is a gene encoding a cytokine that belongs to the tumor necrosis factor (TNF) ligand family.

GYPA

Glycophorin A (MNS blood group) (GenBank ID: 2993, also known as MN; GPA; MNS; GPSAT; PA5-2; CD235a; GPErik; HGpMiV; HGpMiXI; and HGpSta(C)) is a gene encoding a major sialoglycoprotein of the human erythrocyte membrane which bear the antigenic determinants for the MN and Ss blood groups.

FCGR1A

Fc fragment of IgG receptor Ia (GenBank ID: 2209, also known as CD64; FCRI; CD64A; and IGFR1) is a gene encoding a high-affinity Fc-gamma receptor.

LILRB2

Leukocyte immunoglobulin like receptor B2 (GenBank ID: 10288, also known as CD85d; ILT4; LIR2; CD85D; ILT-4; LIR-2; MIR10; and MIR-10) is a gene encoding a member of the leukocyte immunoglobulin-like receptor (LIR) family. The encoded protein is expressed on myeloid and B cells, acting to suppress the immune response. It is also expressed on NSCLC cells (Sun et al., 2008).

CLEC12A

C-type lectin domain family 12 member A (GenBank ID: 160364, also known as CLL1; MICL; CD371; CLL-1; and DCAL-2) is a gene encoding a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response.

CD123

Interleukin 3 receptor subunit alpha (GenBank ID: 3563, also known as IL3R; CD123; IL3RX; IL3RY; IL3RAY; and hIL-3Ra) is a gene encoding an interleukin 3 specific subunit of a heterodimeric cytokine receptor. The receptor is comprised of a ligand specific alpha subunit and a signal transducing beta subunit shared by the receptors for interleukin 3 (IL3), colony stimulating factor 2 (CSF2/GM-CSF), and interleukin 5 (IL5).

ITGB5

Integrin subunit beta 5 (GenBank ID: 3693) is a gene encoding a member of the integrin beta chain family of proteins.

PTPRJ

Protein tyrosine phosphatase, receptor type J (GenBank ID: 5795, also known as DEP1; SCC1; CD148; HPTPeta; and R-PTP-ETA) is a gene encoding a member of the protein tyrosine phosphatase (PTP) family. PTPs are known to be signaling molecules that regulate a variety of cellular processes, including cell growth, differentiation, mitotic cycle, and oncogenic transformation.

SLC30A1

Solute carrier family 30 member 1 (GenBank ID: 7779, also known as ZNT1 and ZRC1) is a gene encoding a zinc transporter.

EMC10

ER membrane protein complex subunit 10 (GenBank ID: 284361, also known as HSM1; HSS1; and C19orf63) is a gene encoding a component of the ER membrane protein complex (EMC) in mammals.

TNFRSF1B

TNF receptor superfamily member 1B (GenBank ID: 7133, also known as p75; TBPII; TNFBR; TNFR2; CD120b; TNFR1B; TNFR80; TNF-R75; p75TNFR; and TNF-R-II) is a gene encoding a member of the TNF-receptor superfamily. This protein and TNF-receptor 1 form a heterocomplex that mediates the recruitment of two anti-apoptotic proteins, c-IAP1 and c-IAP2, which possess E3 ubiquitin ligase activity.

CD82

CD82 molecule (GenBank ID: 3732, also known as R2; 4F9; C33; IA4; ST6; GR15; KAI1; SAR2; and TSPAN27) is a gene encoding a membrane glycoprotein that is a member of the transmembrane 4 superfamily.

ITGAX

Integrin subunit alpha X (GenBank ID: 3687, also known as CD11C and SLEB6) is a gene encoding a member of the integrin alpha chain family of proteins. This protein combines with the beta 2 chain (ITGB2) to form a leukocyte-specific integrin referred to as inactivated-C3b (iC3b) receptor 4 (CR4).

CR1

Complement C3b/C4b receptor 1 (GenBank ID: 1378, also known as KN; C3BR; C4BR; and CD35) is a gene encoding a member of the receptors of complement activation (RCA) family and is located in the 'cluster RCA' region of chromosome 1, which is a monomeric single-pass type I membrane glycoprotein found on erythrocytes, leukocytes, glomerular podocytes, and splenic follicular dendritic cells.

DAGLB

Diacylglycerol lipase beta (GenBank ID: 221955, also known as KCCR13L and DAGLBETA) is a gene encoding an enzyme in the biosynthesis of the endocannabinoid 2-arachidonoylglycerol, which catalyzes the hydrolysis of diacylglycerol.

SEMA4A

Semaphorin 4A (GenBank ID: 64218, also known as RP35; SEMB; SEMAB; and CORD10) is a gene encoding a member of the semaphorin family of soluble and transmembrane proteins, which is a single-pass type I membrane protein containing an immunoglobulin-like C2-type domain, a PSI domain and a sema domain.

TLR2

Toll like receptor 2 (GenBank ID: 7097, also known as TIL4 and CD282) is a gene encoding a member of the Toll-like receptor (TLR) family which plays a fundamental role in pathogen recognition and activation of innate immunity. This protein is a cell-surface protein that can form heterodimers with other TLR family members to recognize conserved molecules derived from microorganisms known as pathogen-associated molecular patterns (PAMPs).

P2RY13

Purinergic receptor P2Y13 (GenBank ID: 53829, also known as GPCR1; GPR86; GPR94; P2Y13; SP174; and FKSG77) is a gene encoding a member of the family of G-protein coupled receptors. This receptor is activated by ADP.

EMB

Embigin (GenBank ID: 133418, also known as GP70) is a gene encoding a transmembrane glycoprotein that is a member of the immunoglobulin superfamily.

CD96

CD96 molecule (GenBank ID: 10225) is a gene encoding a member of the immunoglobulin superfamily.

LILRB3

Leukocyte immunoglobulin like receptor B3 (GenBank ID: 11025, also known as HL9; ILT5; LIR3; PIRB; CD85A; ILT-5; LIR-3; PIR-B; and LILRA6) is a gene encoding a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs).

LILRA6

Leukocyte immunoglobulin like receptor A6 (GenBank ID: 79168, also known as ILT5; ILT8; CD85b; ILT-8; LILRB3; and LILRB6) is a gene encoding a member of a family of immunoreceptors that are expressed predominantly on monocytes and B cells, and at lower levels on dendritic cells and natural killer cells.

LILRA2

Leukocyte immunoglobulin like receptor A2 (GenBank ID: 11027, also known as ILT1; LIR7; CD85H; LIR-7) is a gene encoding a member of a family of immunoreceptors that are expressed predominantly on monocytes and B cells, and at lower levels on dendritic cells and natural killer cells.

In certain embodiments, the antigen suitable for antigen recognizing receptor (CAR or TCR) and/or CCR targets for treating AML is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1.

Immunoresponsive Cells

The presently disclosed subject matter provides cells comprising an antigen recognizing receptor (e.g., CAR or TCR) targeting an antigen of interest, e.g., an AML antigen, and methods of using such cells for treating myeloid disorders. For example, a T cell comprising a chimeric antigen receptor that recognizes EMR2. Such cells are administered to a human subject in need thereof for treating and/or preventing myeloid disorders.

The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells. A patient's own T cells may be genetically modified to target specific antigens through the introduction of an antigen recognizing receptor, e.g., a CAR or a TCR.

Natural killer (NK) cells can be lymphocytes that are part of cell-mediated immunity and act during the innate immune response. NK cells do not require prior activation in order to perform their cytotoxic effect on target cells.

Types of human lymphocytes of the presently disclosed subject matter include, without limitation, peripheral donor lymphocytes genetically modified to express CARs (Sadelain, M., et al. 2003 *Nat Rev Cancer* 3:35-45), peripheral donor lymphocytes genetically modified to express a full-length antigen-recognizing T cell receptor complex comprising the α and β heterodimer (Morgan, R. A., et al. 2006 *Science* 314:126-129), lymphocyte cultures derived from tumor infiltrating lymphocytes (TILs) in tumor biopsies (Panelli, M. C., et al. 2000 *J Immunol* 164:495-504; Panelli, M. C., et al. 2000 *J Immunol* 164:4382-4392), and selectively in vitro-expanded antigen-specific peripheral blood leukocytes employing artificial antigen-presenting cells (AAPCs) or pulsed dendritic cells (Dupont, J., et al. 2005 *Cancer Res* 65:5417-5427; Papanicolaou, G. A., et al. 2003 *Blood* 102:2498-2505). The T cells may be autologous, allogeneic, or derived in vitro from engineered progenitor or stem cells.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

In certain embodiments, an allogenic immunoresponsive cell (e.g., an allogenic T cell) is used. In certain embodiments, a universal T cell with deficient TCRαβ is used. The methods of developing universal T cells are described in the art, for example, in Valton et al., Molecular Therapy (2015); 23 9, 1507-1518, and Torikai et al., Blood 2012 119:5697-5705, which are incorporated by reference in their entireties.

In certain embodiments, the presently disclosed subject matter provides an isolated immunoresponsive cell comprising an antigen recognizing receptor (e.g. CAR or TCR) that binds to an antigen selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1. In certain embodiments, the antigen is selected from the group consisting of LTB4R, EMR2, CD33, MYADM, PIEZO1, SIRPB1, SLC9A1, KCNN4, ENG, ITGA5, and CD70. In certain embodiments, the antigen is selected from the group consisting of LTB4R, EMR2, MYADM and PIEZO1. In certain embodiments, the antigen is selected from the group consisting of CD82, TNFRSF1B, EMR2, ITGB5, CCR1, CD96, PTPRJ, CD70 and LILRB2. In certain embodiments, the antigen is selected from the group consisting of TNFRSF1B, EMR2, CCR1, CD96, CD70 and LILRB2. In certain embodiments, the antigen is selected from the group consisting of EMR2, CCR1, CD70 and LILRB2. In certain non-limiting embodiments, the antigen is EMR2. In certain embodiments, the binding of the antigen recognizing receptor to the antigen is capable of activating the immunoresponsive cell.

In certain embodiments, the presently disclosed subject matter provides an isolated immunoresponsive cell comprising: (a) an antigen recognizing receptor (e.g. CAR or TCR) that binds to a first antigen, wherein binding of the receptor to the first antigen is capable of activating the immunoresponsive cell, and (b) a chimeric co-stimulating receptor (CCR) that binds to a second antigen, wherein binding of the CCR to the second antigen is capable of stimulating the immunoresponsive cell, wherein each of the first and second antigens is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1, and wherein the first antigen and the second antigen are different. In certain embodiments, the first antigen and the second antigen are a combination selected from the group consisting of LTB4R and EMR2, LTB4R and CD33, LTB4R and ENG, LTB4R and MYADM, LTB4R and PIEZO1, LTB4R and SIRPB1, LTB4R and SLC9A1, LTB4R and ITGA5, LTB4R and CD70, LTB4R and KCNN4. EMR2 and CD33, EMR2 and ENG, EMR2 and MYADM, EMR2 and PIEZO1, EMR2 and SIRPB1, EMR2 and SLC9A1, EMR2 and ITGA5, EMR2 and CD70, EMR2 and KCNN4, CD33 and ENG, CD33 and MYADM, CD33 and PIEZO1, CD33 and SIRPB1, CD33 and SLC9A1, CD33 and ITGA5, CD33 and CD70, CD33 and KCNN4, ENG and MYADM, ENG and PIEZO1, ENG and SIRPB1, ENG and SLC9A1, ENG and ITGA5, ENG and CD70, ENG and KCNN4, MYADM and PIEZO1, MYADM and SIRPB1, MYADM and SLC9A1, MYADM and ITGA5, MYADM and CD70, MYADM and KCNN4, PIEZO1 and SIRPB1, PIEZO1 and SLC9A1, PIEZO1 and ITGA5, PIEZO1 and CD70, PIEZO1 and KCNN4, SIRPB1 and SLC9A1, SIRPB1 and ITGA5; SIRPB1 and CD70; SIRPB1 and KCNN4, SLC9A1 and ITGA5, SLC9A1 and CD70, SLC9A1 and KCNN4, ITGA5 and CD70, ITGA5 and KCNN4, CD70 and KCNN4, EMR2 and CD33, CCR1 and CLEC12A, CD70 and CD33, LILRB2 and CLEC12A, EMR2 and CLEC12A, EMR2 and CD96, CCR1 and CD33, CCR1 and CD96, CD70 and CLEC12A, CD70 and CD96, LILRB2 and CD33, LILRB2 and CD96, and EMR2 and CD70. In certain embodiments, the first antigen and the second antigen are a combination selected from the group consisting of EMR2 and CD33, CCR1 and CLEC12A, CD70 and CD33, LILRB2 and CLEC12A, LTB4R1 and CD70, CD70 and EMR2, and LTB4R1 and EMR2.

In certain embodiments, the immunoresponsive cell exhibits a greater degree of cytolytic activity against cells that are positive for both the first antigen and the second antigen as compared to against cells that are singly positive for the first antigen. In certain embodiments, the antigen recognizing receptor comprises an antigen recognizing receptor (e.g. CAR or TCR) that binds to a first antigen with a low binding affinity or a low binding avidity. In certain embodiments, the antigen recognizing receptor (e.g. CAR or TCR) binds to the first antigen at an epitope of low accessibility. In certain embodiments, the antigen recognizing receptor (e.g. CAR or TCR) binds to the first antigen with a binding affinity that is lower compared to the binding affinity with which the CCR binds to the second antigen. In non-limiting embodiments herein, for example certain embodiments that employ a CAR/CCR combination, the CCR-recognized antigen is used to direct costimulation to enhance or rescue suboptimal function of a CAR or TCR targeting a second antigen. Using this approach, the immunoresponsive T cells are more restricted to dual-antigen positive tumor cells, thus relaxing the expression criteria for at least one of the paired antigens; however the presence of the CAR or TCR antigen becomes more important to avert antigen escape. In contrast, immunoresponsive cells expressing a CAR/CAR or CAR/TCR combination would engage tissues expressing either antigen alone and depending on choice of antigen, binding affinity, and functionality, could avoid undesirable off-target effects. Thus, with regards to increasing therapeutic efficacy, the first principle for choosing target antigen is to maximize the number of targetable tumor cells, addressing the challenge of clonal heterogeneity. Another priority is to target leukemia stem cells ("LSCs") to achieve satisfactory therapeutic benefit. Finally, pairing choices should favor redundant expression of the two targets in the tumor in order to minimize the risk of antigen escape. Accordingly, in non-limiting embodiments, provided herein are an immunoresponsive cell that comprises (i) a first antigen recognizing receptor (e.g. CAR or TCR) that binds to a first antigen and (ii) a second antigen recognizing receptor (e.g. CAR or TCR) that binds to a second antigen, wherein the combination of both receptors binding to their targets produces a therapeutic effect. In certain non-limiting embodiments, binding to only one target does not achieve a therapeutic effect. For example, the first and second antigen recognizing receptor can both be CARs; alternatively, the first antigen recognizing receptor can be a CAR and the second antigen binding receptor can be a TCR, or the first antigen recognizing receptor can be a TCR and the second antigen recognizing receptor can be a CAR, or both antigen recognizing receptors can be TCRs. Optionally, said immunoresponsive cell may further comprise a third antigen targeting molecule, which may be a CAR, TCR, or CCR that recognizes a third antigen. In non-limiting embodiments, the first, second, and optional third antigen are different. In non-limiting embodiments, each of the first antigen, second antigen and third antigen is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1, and the first antigen and the second antigen are different. In certain embodiments, the first antigen and the second antigen are a combination selected from the group consisting of LTB4R and EMR2, LTB4R and CD33, LTB4R and ENG, LTB4R and MYADM, LTB4R and PIEZO1, LTB4R and SIRPB1, LTB4R and SLC9A1, LTB4R and ITGA5, LTB4R and CD70, LTB4R and KCNN4. EMR2 and CD33, EMR2 and ENG, EMR2 and MYADM, EMR2 and PIEZO1, EMR2 and SIRPB1, EMR2 and SLC9A1, EMR2 and ITGA5, EMR2 and CD70, EMR2 and KCNN4, CD33 and ENG, CD33 and MYADM, CD33 and PIEZO1, CD33 and SIRPB1, CD33 and SLC9A1, CD33 and ITGA5, CD33 and CD70, CD33 and KCNN4, ENG and MYADM, ENG and PIEZO1, ENG and SIRPB1, ENG and SLC9A1, ENG and ITGA5, ENG and CD70, ENG and KCNN4, MYADM and PIEZO1, MYADM and SIRPB1, MYADM and SLC9A1, MYADM and ITGA5, MYADM and CD70, MYADM and KCNN4, PIEZO1 and SIRPB1, PIEZO1 and SLC9A1, PIEZO1 and ITGA5, PIEZO1 and CD70, PIEZO1 and KCNN4, SIRPB1 and SLC9A1, SIRPB1 and ITGA5, SIRPB1 and CD70, SIRPB1 and KCNN4, SLC9A1 and ITGA5, SLC9A1 and CD70, SLC9A1 and KCNN4, ITGA5 and CD70, ITGA5 and KCNN4, CD70 and KCNN4, EMR2 and CD33, CCR1 and CLEC12A, CD70 and CD33, LILRB2 and CLEC12A, EMR2 and CLEC12A, EMR2 and CD96, CCR1 and CD33, CCR1 and CD96, CD70 and CLEC12A, CD70 and CD96, LILRB2 and CD33, LILRB2 and CD96, EMR2 and CD70. In certain embodiments, the first antigen and the second antigen are a combination selected from the group consisting of EMR2 and CD33, CCR1 and CLEC12A, CD70 and CD33, LILRB2 and CLEC12A, LTB4R1 and CD70, CD70 and EMR2, and LTB4R1 and EMR2 In addition, in non-limiting embodiments, where an antigen recognizing receptor is a TCR, a target antigen can be WT1 or PRAME. In certain non-limiting embodiments, the first antigen is EMR2. In certain embodiments, the immunoresponsive cell exhibits a greater degree of cytolytic activity against cells that are positive for both the first antigen and the second antigen as compared to against cells that are singly positive for the first antigen. In certain embodiments, the first antigen recognizing receptor comprises an antigen recognizing receptor (e.g. CAR or TCR) that binds to a first antigen with a low binding affinity or a low binding avidity. In certain embodiments, the first antigen recognizing receptor (e.g. CAR or TCR) binds to the first antigen at an epitope of low accessibility. In certain embodiments, the first antigen recognizing receptor (e.g. CAR or TCR) binds to the first antigen with a binding affinity that is lower compared to the binding affinity with which the second antigen recognizing receptor binds to the second antigen. In certain embodiments, the first antigen recognizing receptor (e.g. CAR or TCR) binds to the first antigen with a binding affinity that is at least 5 fold lower compared to the binding affinity with which the second antigen recognizing receptor binds to the second antigen. In certain embodiments, the first antigen recognizing receptor (e.g. CAR or TCR) binds to the first antigen with a binding affinity that is at least 10 fold, 20 fold, 30 fold, 40 fold, 50 fold, 60 fold, 70 fold, 80 fold, 90 fold, 100 fold, 200 fold, 5000 fold, 1000 fold, 5000 fold, or 10000 fold lower compared to the binding affinity with which the second antigen recognizing receptor binds to the second antigen.

In certain non-limiting embodiments, an immunoresponsive cell comprises two CAR constructs. In certain embodiments, the cell comprises a first CAR comprising a first intracellular signaling domain, and a second CAR comprising a second introcellular signalling domain, wherein the first intracellular signaling domain and the second intracellular signaling domain are different. In certain embodiments, each of the first intracellular signaling domain and the second intracellular signaling domain is selected from the group consisting of CD3Cζ-chain, CD97, CD11a-CD18, CD2, ICOS, CD27, CD154, CD8, OX40, 4-1BB, CD28 signaling domain, or combinations thereof, wherein the first intracellular signaling domain and the second intracellular signaling domain are different. In certain embodiments, each of the first intracellular signaling domain and the second intracellular signaling domain comprises a CD3Cζ-chain, and optionally further comprise a signaling domain selected from the group consisting of CD97, CD11a-CD18, CD2, ICOS, CD27, CD154, CD8, OX40, 4-1BB, CD28 signaling domain, or combinations thereof, wherein the first intracellular signaling domain and the second intracellular signaling domain are different. In certain embodiments, the first intracellular signaling domain comprises a CD3Cζ-chain and a CD28 signaling domain, and the second intracellular signaling domain comprises a CD3Cζ-chain. In certain embodiments, the first intracellular signaling domain comprises a CD3Cζ-chain and a CD28 signaling domain, and the second intracellular signaling domain comprises a CD3Cζ-chain and a 4-1BB signaling domain. In certain embodiments, the first intracellular signaling domain comprises a CD3Cζ-chain and a 4-1BB signaling domain, and the second intracellular signaling domain comprises a CD3Cζ-chain.

In certain non-limiting embodiments, an immunoresponsive cell may comprise three elements; for example three species of CAR, or two species of CAR and one CCR; or two species of CAR and one TCR; or one CAR, one TCR, and one CCR. Still further combinations adding additional CAR, CCR, and/or TCR are provided.

In particular non-limiting embodiments, an immunoresponsive cell, such as a T cell or NK cell, may comprise a CAR that specifically binds to CLEC12A, a CAR that specifically binds to CD70, and a CCR that specifically binds to ADGRE2.

In particular non-limiting embodiments, an immunoresponsive cell, such as a T cell or NK cell, may comprise a CAR that specifically binds to CLEC12A, a CAR that specifically binds to CD70, and a CCR that specifically binds to CD33.

In particular non-limiting embodiments, an immunoresponsive cell, such as a T cell or NK cell, may comprise a CAR that specifically binds to CLEC12A, a CCR that specifically binds to CD70, and a CAR that specifically binds to TIM3. A presently disclosed immunoresponsive cell can further include at least one recombinant or exogenous co-stimulatory ligand. For example, a presently disclosed immunoresponsive cell can be further transduced with at least one co-stimulatory ligand, such that the immunoresponsive cell co-expresses or is induced to co-express the AML antigen-targeted CAR or TCR and the at least one co-stimulatory ligand. The interaction between the CAR and at least one co-stimulatory ligand provides a non-antigen-specific signal important for full activation of an immunoresponsive cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD154, CD137L/4-1BBL, TNF-α, CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28, PD-L1/(B7-H1) that ligands for PD-1. In certain embodiments, the at least one co-stimulatory ligand is selected from the group consisting of 4-1BBL, CD80, CD86, CD70, OX40L, CD48, TNFRSF14, PD-L1, and combinations thereof. In certain embodiments, the immunoresponsive cell comprises one recombinant co-stimulatory ligand that is 4-1BBL. In certain embodiments, the immunoresponsive cell comprises two recombinant co-stimulatory ligands that are 4-1BBL and CD80. CARs comprising at least one co-stimulatory ligand are described in U.S. Pat. No. 8,389,282, which is incorporated by reference in its entirety.

Vectors

Genetic modification of immunoresponsive cells (e.g., T cells, CTL cells, NK cells) can be accomplished by transducing a substantially homogeneous cell composition with a recombinant DNA construct. Preferably, a retroviral vector (either gamma-retroviral or lentiviral) is employed for the introduction of the DNA construct into the cell. For example, a polynucleotide encoding a receptor that binds an antigen (e.g., a tumor antigen, or a variant, or a fragment thereof), can be cloned into a retroviral vector and expression can be driven from its endogenous promoter, from the retrovirallong terminal repeat, or from a promoter specific for a target cell type of interest. Non-viral vectors may be used as well.

For initial genetic modification of the cells to provide antigen receptors, a retroviral vector is generally employed for transduction, however any other suitable viral vector or non-viral delivery system can be used. For genetic modification of the cells to provide cells comprising a CAR and a CCR, retroviral gene transfer (transduction) likewise proves effective. The CAR and CCR can be constructed in a single, multicistronic expression cassette, in multiple expression cassettes of a single vector, or in multiple vectors. Examples of elements which create polycistronic expression cassette include, but is not limited to, various Internal Ribosome Entry Sites (IRES, e.g., poliovirus IRES and encephalomyocarditis virus IRES) and 2A peptides (e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci.* USA 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Other transducing viral vectors can be used to express a antigen receptor, a CAR, a CCR, and/or other components of the invention in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

Polypeptides and Analogs

Also included in the presently disclosed subject matter are a CD8, CD28, CD3Cζ, 4-1BB, EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1 polypeptides or fragments thereof that are modified in ways that enhance their activity when expressed in an immunoresponsive cell. The presently disclosed subject matter provides methods for optimizing an amino acid sequence or nucleic acid sequence by producing an alteration in the sequence. Such alterations may include certain mutations, deletions, insertions, or post-translational modifications. The presently disclosed subject matter further includes analogs of any naturally-occurring polypeptide of the invention. Analogs can differ from a naturally occurring polypeptide of the invention by amino acid sequence differences, by post-translational modifications, or by both. Analogs of the invention will generally exhibit at least about 85%, about 90%, about 91%, about 92%, about 93%, about 94%, about 95%, about 96%, about 97%, about 98%, about 99% or more identity with all or part of a naturally-occurring amino, acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., .beta. or .gamma. amino acids.

In addition to full-length polypeptides, the presently disclosed subject matter also provides fragments of any one of the polypeptides or peptide domains of the presently disclosed subject matter. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80, 100, 200, 300 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. In certain embodiments, the protein analogs are relatively resistant to in vivo degradation, resulting in a more prolonged therapeutic effect upon administration. Assays for measuring functional activity include, but are not limited to, those described in the Examples below.

Pre-Leukemic Stem Cell Model

Pre-leukemic stem cells are genetically defined by the expression of initiating mutations including, but are not limited to, DNMT3a (Shlush et al., 2014b) and fusion protein MLLAF9.

The DNA (cytosine-5)-methyltransferase 3A (DNMT3A) is a member of the DNA methyltransferase family and one of the most frequently mutated genes in AML, occurring in up to 36% of cytogenetically normal AML (CN-AML) patients (Marcucci et al., 2012). A recurrent heterozygous mutation at residue Arginine 882 accounts for 40% to 60% of DNMT3A mutations (Ley et al., 2010; Yan et al., 2011). In AML cells, R882 mutations always occur with retention of the wild-type allele and it was showed that the R882 mutant serves as a dominant-negative regulator of wild-type DNMT3A (Russler-Germain et al., 2014).

The most common fusion protein MLLAF9 induces the inappropriate expression of homeotic (Hox) genes, which, during normal hematopoiesis, are maintained by wild-type MLL. Studies in mice have demonstrated that MLL-fusions can confer self-renewal activity to committed myeloid progenitors (Cozzio et al., 2003; So et al., 2003).

Targeting Myeloid/AML Antigens with Genetically Modified T Cells

In certain non-limiting embodiments, an immunoresponsive cell (e.g., a T cell, Tumor Infiltrating Lymphocyte, Natural Killer (NK) cell, cytotoxic T lymphocyte (CTL), Natural Killer T (NKT) cells or regulatory T cell), which comprises an antigen binding receptor (e.g., CAR or TCR) directed toward a myeloid/AML antigen, is used to treat and/or prevent a myeloid disorder (e.g., AML). In certain non-limiting embodiments, the antigen is selected from the group consisting of EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, and SLC19A1. In certain embodiments, the antigen is selected from the group consisting of LTB4R, EMR2, CD33, MYADM, PIEZO1, SIRPB1, SLC9A1, KCNN4, ENG, ITGA5, and CD70. In certain embodiments, the antigen is selected from the group consisting of LTB4R, EMR2, MYADM and PIEZO1. In certain embodiments, the antigen is selected from the group consisting of CD82, TNFRSF1B, EMR2, ITGB5, CCR1, CD96, PTPRJ, CD70 and LILRB2. In certain embodiments, the antigen is selected from the group consisting of TNFRSF1B, EMR2, CCR1, CD96, CD70 and LILRB2. In certain embodiments, the antigen is selected from the group consisting of EMR2, CCR1, CD70 and LILRB2.

In certain non-limiting embodiments, the antigen is a cell surface gene having increased expression level in DNMT3a mutant cells or in MLLAF9 mutant cells. In certain non-limiting embodiments, the antigen is selected from the group consisting of genes in Table 2.

In certain embodiment, a T cell is engineered to express a CAR targeting a Myeloid/AML antigen (e.g., LTB4R, EMR2, MYADM, and PIEZO1).

In certain embodiment, a T cells is engineered to comprise (e.g., express) (a) a CAR targeting a Myeloid/AML antigen, and (b) a CCR targeting a different Myeloid/AML antigen. The combination of the targeted antigens can be any one selected from Table 1. In certain embodiment the combination can be any one of the following pairs of targets: LTB4R and EMR2, LTB4R and CD33, LTB4R and ENG, LTB4R and MYADM, LTB4R and PIEZO1, LTB4R and SIRPB1, LTB4R and SLC9A1, LTB4R and ITGA5, LTB4R and CD70, LTB4R and KCNN4. EMR2 and CD33, EMR2 and ENG, EMR2 and MYADM, EMR2 and PIEZO1, EMR2 and SIRPB1, EMR2 and SLC9A1, EMR2 and ITGA5, EMR2 and CD70, EMR2 and KCNN4, CD33 and ENG, CD33 and MYADM, CD33 and PIEZO1, CD33 and SIRPB1, CD33 and SLC9A1, CD33 and ITGA5, CD33 and CD70, CD33 and KCNN4, ENG and MYADM, ENG and PIEZO1, ENG and SIRPB1, ENG and SLC9A1, ENG and ITGA5, ENG and CD70, ENG and KCNN4, MYADM and PIEZO1, MYADM and SIRPB1, MYADM and SLC9A1, MYADM and ITGA5, MYADM and CD70, MYADM and KCNN4, PIEZO1 and SIRPB1, PIEZO1 and SLC9A1, PIEZO1 and ITGA5, PIEZO1 and CD70, PIEZO1 and KCNN4, SIRPB1 and SLC9A1, SIRPB1 and ITGA5, SIRPB1 and CD70, SIRPB1 and KCNN4, SLC9A1 and ITGA5, SLC9A1 and CD70, SLC9A1 and KCNN4, ITGA5 and CD70, ITGA5 and KCNN4, CD70 and KCNN4, EMR2 and CD33, CCR1 and CLEC12A, CD70 and CD33, LILRB2 and CLEC12A, EMR2 and CLEC12A, EMR2 and CD96, CCR1 and CD33, CCR1 and CD96, CD70 and CLEC12A, CD70 and CD96, LILRB2 and CD33, LILRB2 and CD96, and EMR2 and CD70. In certain embodiments, the combination is EMR2 and CD33, CCR1 and CLEC12A, CD70 and CD33, LILRB2 and CLEC12A, LTB4R1 and CD70, CD70 and EMR2, or LTB4R1 and EMR2.

In certain embodiments, the combination is selected from the group consisting of EMR2 and CD33, CCR1 and CLEC12A, CD70 and CD33, and LILRB2 and CLEC12A.

In certain embodiment, the CAR is a second generation CAR, comprising an scFv targeting an antigen of interest, a co-stimulatory domain from CD3ζ-chain, CD97, CD11a-CD18, CD2, ICOS, CD27, CD154, CD8, OX40, 4-1BB, or CD28 signaling domain. In certain embodiment, the CAR is recombinantly expressed (e.g., via a vector, e.g., a retroviral vector). In certain embodiment, the vector is 28z retroviral vector (see detailed description of 28z vector in WO 2014165707 A2, WO 2014134165 A1, and WO 2016042461 A1, which are incorporated by reference in their entireties). In certain embodiment, the CCR is recombinantly expressed (e.g., via a vector, e.g., a retroviral vector). In certain embodiment, the vector comprises an scFv targeting an antigen of interest, a CD28 transmembrane and signaling domain, fused to a 4-1 BB (aka CD137) cytosoiic signaling domain (e.g., 28BB CCR, see detailed description in WO2014055668 A1, which is incorporated by reference in its entirety). In certain embodiment, the T cell is autologous.

TABLE 1

| | | | |
|---|---|---|---|
| [CRR1 + SLC22A5] | [SLC19A1 + CD300LF] | [LILRB4 + CD33] | [CD300LF + SLC43A3] |
| [CRR1 + TFR2] | [SLC19A1 + CPM] | [LILRB4 + IL10RB] | [CD300LF + MYADM] |
| [CRR1 + KCNN4] | [SLC19A1 + ITFG3] | [LILRB4 + PLNXC1] | [CD300LF + ICAM1] |
| [CRR1 + LILRB4] | [SLC19A1 + TTYH3] | [LILRB4 + PIEZO1] | [CD300LF + SLC44A1] |
| [CRR1 + LTB4R] | [SLC19A1 + ITGA4] | [LILRB4 + CD300LF] | [CPM + ITFG3] |
| [CRR1 + CD70] | [SLC19A1 + SLC9A1] | [LILRB4 + CPM] | [CPM + TTYH3] |
| [CRR1 + GYPA] | [SLC19A1 + MBOAT7] | [LILRB4 + ITFG3] | [CPM + ITGA4] |
| [CRR1 + FCGR1A] | [SLC19A1 + CD38] | [LILRB4 + TTYH3] | [CPM + SLC9A1] |
| [CRR1 + SLC19A1] | [SLC19A1 + SLC6A6] | [LILRB4 + ITGA4] | [CPM + MBOAT7] |
| [CRR1 + EMR2] | [SLC19A1 + ENG] | [LILRB4 + SLC9A1] | [CPM + CD38] |
| [CRR1 + CD33] | [SLC19A1 + SIRPB1] | [LILRB4 + MBOAT7] | [CPM + SLC6A6] |
| [CRR1 + IL10RB] | [SLC19A1 + MRP1] | [LILRB4 + CD38] | [CPM + ENG] |
| [CRR1 + PLNXC1] | [SLC19A1 + ITGA5] | [LILRB4 + SLC6A6] | [CPM + SIRPB1] |
| [CRR1 + PIEZO1] | [SLC19A1 + SLC43A3] | [LILRB4 + ENG] | [CPM + MRP1] |
| [CRR1 + CD300LF] | [SLC19A1 + MYADM] | [LILRB4 + SIRPB1] | [CPM + ITGA5] |
| [CRR1 + CPM] | [SLC19A1 + ICAM1] | [LILRB4 + MRP1] | [CPM + SLC43A3] |
| [CRR1 + ITFG3] | [SLC19A1 + SLC44A1] | [LILRB4 + ITGA5] | [CPM + MYADM] |
| [CRR1 + TTYH3] | [EMR2 + CD33] | [LILRB4 + SLC43A3] | [CPM + ICAM1] |

TABLE 1-continued

| | | | | |
|---|---|---|---|---|
| [CRR1 + ITGA4] | [EMR2 + IL10RB] | [LILRB4 + MYADM] | [CPM + SLC44A1] | |
| [CRR1 + SLC9A1] | [EMR2 + PLNXC1] | [LILRB4 + ICAM1] | [ITFG3 + TTYH3] | |
| [CRR1 + MBOAT7] | [EMR2 + PIEZO1] | [LILRB4 + SLC44A1] | [ITFG3 + ITGA4] | |
| [CRR1 + CD38] | [EMR2 + CD300LF] | [LTB4R + CD70] | [ITFG3 + SLC9A1] | |
| [CRR1 + SLC6A6] | [EMR2 + CPM] | [LTB4R + GYPA] | [ITFG3 + MBOAT7] | |
| [CRR1 + ENG] | [EMR2 + ITFG3] | [LTB4R + FCGR1A] | [ITFG3 + CD38] | |
| [CRR1 + SIRPB1] | [EMR2 + TTYH3] | [LTB4R + SLC19A1] | [ITFG3 + SLC6A6] | |
| [CRR1 + MRP1] | [EMR2 + ITGA4] | [LTB4R + EMR2] | [ITFG3 + ENG] | |
| [CRR1 + ITGA5] | [EMR2 + SLC9A1] | [LTB4R + CD33] | [ITFG3 + SIRPB1] | |
| [CRR1 + SLC43A3] | [EMR2 + MBOAT7] | [LTB4R + IL10RB] | [ITFG3 + MRP1] | |
| [CRR1 + MYADM] | [EMR2 + CD38] | [LTB4R + PLNXC1] | [ITFG3 + ITGA5] | |
| [CRR1 + ICAM1] | [EMR2 + SLC6A6] | [LTB4R + PIEZO1] | [ITFG3 + SLC43A3] | |
| [CRR1 + SLC44A1] | [EMR2 + ENG] | [LTB4R + CD300LF] | [ITFG3 + MYADM] | |
| [SLC22A5 + TFR2] | [EMR2 + SIRPB1] | [LTB4R + CPM] | [ITFG3 + ICAM1] | |
| [SLC22A5 + KCNN4] | [EMR2 + MRP1] | [LTB4R + ITFG3] | [ITFG3 + SLC44A1] | |
| [SLC22A5 + LILRB4] | [EMR2 + ITGA5] | [LTB4R + TTYH3] | [TTYH3 + ITGA4] | |
| [SLC22A5 + LTB4R] | [EMR2 + SLC43A3] | [LTB4R + ITGA4] | [TTYH3 + SLC9A1] | |
| [SLC22A5 + CD70] | [EMR2 + MYADM] | [LTB4R + SLC9A1] | [TTYH3 + MBOAT7] | |
| [SLC22A5 + GYPA] | [EMR2 + ICAM1] | [LTB4R + MBOAT7] | [TTYH3 + CD38] | |
| [SLC22A5 + FCGR1A] | [EMR2 + SLC44A1] | [LTB4R + CD38] | [TTYH3 + SLC6A6] | |
| [SLC22A5 + SLC19A1] | [CD33 + IL10RB] | [LTB4R + SLC6A6] | [TTYH3 + ENG] | |
| [SLC22A5 + EMR2] | [CD33 + PLNXC1] | [LTB4R + ENG] | [TTYH3 + SIRPB1] | |
| [SLC22A5 + CD33] | [CD33 + PIEZO1] | [LTB4R + SIRPB1] | [TTYH3 + MRP1] | |
| [SLC22A5 + IL10RB] | [CD33 + CD300LF] | [LTB4R + MRP1] | [TTYH3 + ITGA5] | |
| [SLC22A5 + PLNXC1] | [CD33 + CPM] | [LTB4R + ITGA5] | [TTYH3 + SLC43A3] | |
| [SLC22A5 + PIEZO1] | [CD33 + ITFG3] | [LTB4R + SLC43A3] | [TTYH3 + MYADM] | |
| [SLC22A5 + CD300LF] | [CD33 + TTYH3] | [LTB4R + MYADM] | [TTYH3 + ICAM1] | |
| [SLC22A5 + CPM] | [CD33 + ITGA4] | [LTB4R + ICAM1] | [TTYH3 + SLC44A1] | |
| [SLC22A5 + ITFG3] | [CD33 + SLC9A1] | [LTB4R + SLC44A1] | [ITGA4 + SLC9A1] | |
| [SLC22A5 + TTYH3] | [CD33 + MBOAT7] | [CD70 + GYPA] | [ITGA4 + MBOAT7] | |
| [SLC22A5 + ITGA4] | [CD33 + CD38] | [CD70 + FCGR1A] | [ITGA4 + CD38] | |
| [SLC22A5 + SLC9A1] | [CD33 + SLC6A6] | [CD70 + SLC19A1] | [ITGA4 + SLC6A6] | |
| [SLC22A5 + MBOAT7] | [CD33 + ENG] | [CD70 + EMR2] | [ITGA4 + ENG] | |
| [SLC22A5 + CD38] | [CD33 + SIRPB1] | [CD70 + CD33] | [ITGA4 + SIRPB1] | |
| [SLC22A5 + SLC6A6] | [CD33 + MRP1] | [CD70 + IL10RB] | [ITGA4 + MRP1] | |
| [SLC22A5 + ENG] | [CD33 + ITGA5] | [CD70 + PLNXC1] | [ITGA4 + ITGA5] | |
| [SLC22A5 + SIRPB1] | [CD33 + SLC43A3] | [CD70 + PIEZO1] | [ITGA4 + SLC43A3] | |
| [SLC22A5 + MRP1] | [CD33 + MYADM] | [CD70 + CD300LF] | [ITGA4 + MYADM] | |
| [SLC22A5 + ITGA5] | [CD33 + ICAM1] | [CD70 + CPM] | [ITGA4 + ICAM1] | |
| [SLC22A5 + SLC43A3] | [CD33 + SLC44A1] | [CD70 + ITFG3] | [ITGA4 + SLC44A1] | |
| [SLC22A5 + MYADM] | [IL10RB + PLNXC1] | [CD70 + TTYH3] | [SLC9A1 + MBOAT7] | |
| [SLC22A5 + ICAM1] | [IL10RB + PIEZO1] | [CD70 + ITGA4] | [SLC9A1 + CD38] | |
| [SLC22A5 + SLC44A1] | [IL10RB + CD300LF] | [CD70 + SLC9A1] | [SLC9A1 + SLC6A6] | |
| [TFR2 + KCNN4] | [IL10RB + CPM] | [CD70 + MBOAT7] | [SLC9A1 + ENG] | |
| [TFR2 + LILRB4] | [IL10RB + ITFG3] | [CD70 + CD38] | [SLC9A1 + SIRPB1] | |
| [TFR2 + LTB4R] | [IL10RB + TTYH3] | [CD70 + SLC6A6] | [SLC9A1 + MRP1] | |
| [TFR2 + CD70] | [IL10RB + ITGA4] | [CD70 + ENG] | [SLC9A1 + ITGA5] | |
| [TFR2 + GYPA] | [IL10RB + SLC9A1] | [CD70 + SIRPB1] | [SLC9A1 + SLC43A3] | |
| [TFR2 + FCGR1A] | [IL10RB + MBOAT7] | [CD70 + MRP1] | [SLC9A1 + MYADM] | |
| [TFR2 + SLC19A1] | [IL10RB + CD38] | [CD70 + ITGA5] | [SLC9A1 + ICAM1] | |
| [TFR2 + EMR2] | [IL10RB + SLC6A6] | [CD70 + SLC43A3] | [SLC9A1 + SLC44A1] | |
| [TFR2 + CD33] | [IL10RB + ENG] | [CD70 + MYADM] | [MBOAT7 + CD38] | |
| [TFR2 + IL10RB] | [IL10RB + SIRPB1] | [CD70 + ICAM1] | [MBOAT7 + SLC6A6] | |
| [TFR2 + PLNXC1] | [IL10RB + MRP1] | [CD70 + SLC44A1] | [MBOAT7 + ENG] | |
| [TFR2 + PIEZO1] | [IL10RB + ITGA5] | [GYPA + FCGR1A] | [MBOAT7 + SIRPB1] | |
| [TFR2 + CD300LF] | [IL10RB + SLC43A3] | [GYPA + SLC19A1] | [MBOAT7 + MRP1] | |
| [TFR2 + CPM] | [IL10RB + MYADM] | [GYPA + EMR2] | [MBOAT7 + ITGA5] | |
| [TFR2 + ITFG3] | [IL10RB + ICAM1] | [GYPA + CD33] | [MBOAT7 + SLC43A3] | |
| [TFR2 + TIYH3] | [IL10RB + SLC44A1] | [GYPA + IL10RB] | [MBOAT7 + MYADM] | |
| [TFR2 + ITGA4] | [PLNXC1 + PIEZO1] | [GYPA + PLNXC1] | [MBOAT7 + ICAM1] | |
| [TFR2 + SLC9A1] | [PLNXC1 + CD300LF] | [GYPA + PIEZO1] | [MBOAT7 + SLC44A1] | |
| [TFR2 + MBOAT7] | [PLNXC1 + CPM] | [GYPA + CD300LF] | [CD38 + SLC6A6] | |
| [TFR2 + CD38] | [PLNXC1 + ITFG3] | [GYPA + CPM] | [CD38 + ENG] | |
| [TFR2 + SLC6A6] | [PLNXC1 + TTYH3] | [GYPA + ITFG3] | [CD38 + SIRPB1] | |
| [TFR2 + ENG] | [PLNXC1 + ITGA4] | [GYPA + TTYH3] | [CD38 + MRP1] | |
| [TFR2 + SIRPB1] | [PLNXC1 + SLC9A1] | [GYPA + ITGA4] | [CD38 + ITGA5] | |
| [TFR2 + MRP1] | [PLNXC1 + MBOAT7] | [GYPA + SLC9A1] | [CD38 + SLC43A3] | |
| [TFR2 + ITGA5] | [PLNXC1 + CD38] | [GYPA + MBOAT7] | [CD38 + MYADM] | |
| [TFR2 + SLC43A3] | [PLNXC1 + SLC6A6] | [GYPA + CD38] | [CD38 + ICAM1] | |
| [TFR2 + MYADM] | [PLNXC1 + ENG] | [GYPA + SLC6A6] | [CD38 + SLC44A1] | |
| [TFR2 + ICAM1] | [PLNXC1 + SIRPB1] | [GYPA + ENG] | [SLC6A6 + ENG] | |
| [TFR2 + SLC44A1] | [PLNXC1 + MRP1] | [GYPA + SIRPB1] | [SLC6A6 + SIRPB1] | |
| [KCNN4 + LILRB4] | [PLNXC1 + ITGA5] | [GYPA + MRP1] | [SLC6A6 + MRP1] | |
| [KCNN4 + LTB4R] | [PLNXC1 + SLC43A3] | [GYPA + ITGA5] | [SLC6A6 + ITGA5] | |
| [KCNN4 + CD70] | [PLNXC1 + MYADM] | [GYPA + SLC43A3] | [SLC6A6 + SLC43A3] | |
| [KCNN4 + GYPA] | [PLNXC1 + ICAM1] | [GYPA + MYADM] | [SLC6A6 + MYADM] | |
| [KCNN4 + FCGR1A] | [PLNXC1 + SLC44A1] | [GYPA + ICAM1] | [SLC6A6 + ICAM1] | |
| [KCNN4 + SLC19A1] | [PIEZO1 + CD300LF] | [GYPA + SLC44A1] | [SLC6A6 + SLC44A1] | |
| [KCNN4 + EMR2] | [PIEZO1 + CPM] | [FCGR1A + SLC19A1] | [ENG + SIRPB1] | |
| [KCNN4 + CD33] | [PIEZO1 + ITFG3] | [FCGR1A + EMR2] | [ENG + MRP1] | |

TABLE 1-continued

| | | | |
|---|---|---|---|
| [KCNN4 + IL10RB] | [PIEZO1 + TTYH3] | [FCGR1A + CD33] | [ENG + ITGA5] |
| [KCNN4 + PLNXC1] | [PIEZO1 + ITGA4] | [FCGR1A + IL10RB] | [ENG + SLC43A3] |
| [KCNN4 + PIEZO1] | [PIEZO1 + SLC9A1] | [FCGR1A + PLNXC1] | [ENG + MYADM] |
| [KCNN4 + CD300LF] | [PIEZO1 + MBOAT7] | [FCGR1A + PIEZO1] | [ENG + ICAM1] |
| [KCNN4 + CPM] | [PIEZO1 + CD38] | [FCGR1A + CD300LF] | [ENG + SLC44A1] |
| [KCNN4 + ITFG3] | [PIEZO1 + SLC6A6] | [FCGR1A + CPM] | [SIRPB1 + MRP1] |
| [KCNN4 + TTYH3] | [PIEZO1 + ENG] | [FCGR1A + ITFG3] | [SIRPB1 + ITGA5] |
| [KCNN4 + ITGA4] | [PIEZO1 + SIRPB1] | [FCGR1A + TTYH3] | [SIRPB1 + SLC43A3] |
| [KCNN4 + SLC9A1] | [PIEZO1 + MRP1] | [FCGR1A + ITGA4] | [SIRPB1 + MYADM] |
| [KCNN4 + MBOAT7] | [PIEZO1 + ITGA5] | [FCGR1A + SLC9A1] | [SIRPB1 + ICAM1] |
| [KCNN4 + CD38] | [PIEZO1 + SLC43A3] | [FCGR1A + MBOAT7] | [SIRPB1 + SLC44A1] |
| [KCNN4 + SLC6A6] | [PIEZO1 + MYADM] | [FCGR1A + CD38] | [MRP1 + ITGA5] |
| [KCNN4 + ENG] | [PIEZO1 + ICAM1] | [FCGR1A + SLC6A6] | [MRP1 + SLC43A3] |
| [KCNN4 + SIRPB1] | [PIEZO1 + SLC44A1] | [FCGR1A + ENG] | [MRP1 + MYADM] |
| [KCNN4 + MRP1] | [CD300LF + CPM] | [FCGR1A + SIRPB1] | [MRP1 + ICAM1] |
| [KCNN4 + ITGA5] | [CD300LF + ITFG3] | [FCGR1A + MRP1] | [MRP1 + SLC44A1] |
| [KCNN4 + SLC43A3] | [CD300LF + TTYH3] | [FCGR1A + ITGA5] | [ITGA5 + 5LC43A3] |
| [KCNN4 + MYADM] | [CD300LF + ITGA4] | [FCGR1A + 5LC43A3] | [ITGA5 + MYADM] |
| [KCNN4 + ICAM1] | [CD300LF + SLC9A1] | [FCGR1A + MYADM] | [ITGA5 + ICAM1] |
| [KCNN4 + SLC44A1] | [CD300LF + MBOAT7] | [FCGR1A + ICAM1] | [ITGA5 + SLC44A1] |
| [LILRB4 + LTB4R] | [CD300LF + CD38] | [FCGR1A + SLC44A1] | [SLC43A3 + MYADM] |
| [LILRB4 + CD70] | [CD300LF + SLC6A6] | [SLC19A1 + EMR2] | [SLC43A3 + ICAM1] |
| [LILRB4 + GYPA] | [CD300LF + ENG] | [SLC19A1 + CD33] | [SLC43A3 + SLC44A1] |
| [LILRB4 + FCGR1A] | [CD300LF + SIRPB1] | [SLC19A1 + IL10RB] | [MYADM + ICAM1] |
| [LILRB4 + SLC19A1] | [CD300LF + MRP1] | [SLC19A1 + PLNXC1] | [MYADM + SLC44A1] |
| [LILRB4 + EMR2] | [CD300LF + ITGA5] | [SLC19A1 + PIEZO1] | [ICAM1 + SLC44A1] |

TABLE 2

| DNMT3a Mutant | | MLLAF9 mutant |
|---|---|---|
| TMEM40 | ABCG2 | CEACAM6 |
| GNAZ | ANO9 | MANSC1 |
| SLC6A16 | GAS2 | ELOVL6 |
| PPP2R5B | ASIC3 | LEPR |
| TEX29 | B3GNT4 | SUN3 |
| FKBP1B | TMEM59L | HOOK1 |
| KCNJ5 | SLC25A36 | CCDC155 |
| CAPN3 | FRMD5 | TMEM27 |
| TNFRSF14 | COL15A1 | GABRB2 |
| SPAG17 | ZDHHC11 | EPHA4 |
| MMP25 | ITGA8 | CDH13 |
| NGFR | PEAR1 | AQP2 |
| CLEC1A | ASPRV1 | KCNK13 |
| OTOA | LOXL4 | KIF26B |
| LRRN2 | TRIM55 | HTR2A |
| RHBDL3 | KIF19 | SLC44A3 |
| HEPHL1 | LPAR2 | ILDR1 |
| TSPEAR | CNIH2 | CYP4F11 |
| TAS1R3 | FLRT1 | SLC8A3 |
| MBOAT1 | RNF183 | GPR153 |
| MT-ND1 | RDH16 | SLCO2B1 |
| DARC | CADM3 | SCIN |
| SH3PXD2A | C3orf35 | SCN2A |
| BEST4 | GDPD3 | IL23R |
| STON2 | TMPRSS5 | ALS2 |
| ACKR6 | SEC31B | GNA14 |
| LRRTM2 | AGER | TMEFF2 |
| STC1 | ADAMTS13 | EXTL3 |
| SLC16A6 | IL20RB | PDE3A |
| CDHR1 | WNT4 | MFAP3L |
| MYADML2 | LRRC37A3 | SLC34A3 |
| PNPLA3 | SCNN1D | TACSTD2 |
| PSD2 | TMEM89 | ITGB8 |
| SLC25A41 | EXOC3L4 | LAX1 |
| SUSD2 | ATP6V0A4 | SLC45A3 |
| KCND1 | CHST3 | SYNC |
| HILPDA | NPAS2 | PLXNA4 |
| TMEM145 | IGFBP3 | ADORA3 |
| DFNB31 | ADRA1D | SIGLEC11 |
| PPFIA4 | RNF173 | RYR2 |
| NLGN3 | | LRRC8E |
| FAM186B | | DGKI |
| KCNV2 | | COLEC12 |
| SCN11A | | CX3CR1 |

Gnomic Integration into Immunoresponsive Cell

In certain embodiments, an antigen recognizing receptor (e.g., a CAR or a TCR) can be integrated into a selected locus of the genome of an immunoresponsive cell. Any targeted genome editing methods can be used to integrate the antigen recognizing receptor (e.g., CAR or TCR) in selected loci of the genome of an immunoresponsive cell. In certain embodiments, the expression of the antigen recognizing receptor (e.g., CAR or TCR) is driven by an endogenous promoter/enhancer within or near the locus. In certain embodiments, the expression of the antigen recognizing receptor (e.g., CAR or TCR) is driven by an exogenous promoter integrated into the locus. The locus where the antigen recognizing receptor (e.g., CAR or TCR) is integrated is selected based on the expression level of the genes within the locus, and timing of the gene expression of the genes within the locus. The expression level and timing can vary under different stages of cell differentiation and mitogen/cytokine microenvironment, which are among the factors to be considered when making the selection.

In certain embodiments, the CRISPR system is used to integrate the antigen recognizing receptor (e.g., CAR or TCR) in selected loci of the genome of an immunoresponsive cell. Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying CAR expression cassette need also be designed for each application, as it must overlap with the sequences on either side of the cut and code for the insertion sequence. Multiple crRNA's and the tracrRNA can be packaged together to form a single-guide RNA (sgRNA). This sgRNA can be joined together with the Cas9 gene and made into a plasmid in order to be transfected into cells. Methods of using the CRISPR system are described, for example, in WO 2014093661 A2, WO 2015123339 A1 and WO 2015089354 A1, which are incorporated by reference in their entireties.

In certain embodiments, zinc-finger nucleases are used to integrate the antigen recognizing receptor (e.g., CAR or TCR) in selected loci of the genome of an immunoresponsive cell. A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of basepairs. The most common method to generate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying CAR expression cassette, ZFNs can be used to insert the CAR expression cassette into genome. When the targeted sequence is cleaved by ZFNs, the HR machinery searches for homology between the damaged chromosome and the homologous DNA template, and then copies the sequence of the template between the two broken ends of the chromosome, whereby the homologous DNA template is integrated into the genome. Methods of using the ZFN system are described, for example, in WO 2009146179 A1, WO 2008060510 A2 and CN 102174576 A, which are incorporated by reference in their entireties.

In certain embodiments, the TALEN system is used to integrate the antigen recognizing receptor (e.g., CAR or TCR) in selected loci of the genome of an immunoresponsive cell. Transcription activator-like effector nucleases (TALEN) are restriction enzymes that can be engineered to cut specific sequences of DNA. TALEN system operates on almost the same principle as ZFNs. They are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome. Methods of using the TALEN system are described, for example, in WO 2014134412 A1, WO 2013163628 A2 and WO 2014040370 A1, which are incorporated by reference in their entireties.

Methods for delivering the genome editing agents can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

Modification can be made anywhere within the selected locus, or anywhere that can influence gene expression of the integrated antigen recognizing receptor (e.g., CAR or TCR). In certain embodiments, the modification is introduced upstream of the transcriptional start site of the integrated antigen recognizing receptor (e.g., CAR or TCR). In certain embodiments, the modification is introduced between the transcriptional start site and the protein coding region of the integrated antigen recognizing receptor (e.g., CAR or TCR). In certain embodiments, the modification is introduced downstream of the protein coding region of the integrated antigen recognizing receptor (e.g., CAR or TCR).

Administration

Compositions comprising genetically modified immunoresponsive cells of the invention (e.g., T cells, NK cells, CTL cells, or their progenitors) can be provided systemically or directly to a subject for the treatment of a myeloid disorder. In certain embodiments, the presently disclosed cells are directly injected into an organ of interest (e.g., an organ affected by a myeloid disorder). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T cells, NK cells, or CTL cells in vitro or in vivo.

The modified cells can be administered in any physiologically acceptable vehicle, normally intravascularly, although they may also be introduced into bone or other convenient site where the cells may find an appropriate site for regeneration and differentiation (e.g., thymus). Usually, at least $1\times10^5$ cells will be administered, eventually reaching $1\times10^{10}$ or more. Genetically modified immunoresponsive cells of the invention can comprise a purified population of cells. Those skilled in the art can readily determine the percentage of genetically modified immunoresponsive cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Dosages can be readily adjusted by those skilled in the art (e.g., a decrease in purity may require an increase in dosage). The cells can be introduced by injection, catheter, or the like. If desired, factors can also be included, including, but not limited to, interleukins, e.g. IL-2, IL-3, IL-6, IL-11, IL7, IL12, IL1S, IL21, as well as the other interleukins, the colony stimulating factors, such as G-, M- and GM-CSF, interferons, e.g. .gamma.-interferon and erythropoietin.

In certain embodiments, the compositions are pharmaceutical compositions comprising genetically modified immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a presently disclosed therapeutic composition (e.g., a pharmaceutical composition containing a genetically modified immunoresponsive cell), it will generally be formulated in a unit dosage injectable form (solution, suspension, emulsion).

Formulations

Presently disclosed compositions comprising genetically modified immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified immunoresponsive cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the genetically modified immunoresponsive cells or their progenitors.

The compositions can be isotonic, i.e., they can have the same osmotic pressure as blood and lacrimal fluid. The desired isotonicity of the presently disclosed compositions may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the genetically modified immunoresponsive cells as described in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the presently disclosed immunoresponsive cells is the quantity of cells necessary to achieve an optimal effect. The quantity of cells to be administered will vary for the subject being treated. In certain embodiments, between $10^4$ to $10^{10}$ between $10^5$ to $10^9$, or between $10^6$ and $10^8$ genetically presently disclosed cells are administered to a human subject. More effective cells may be administered in even smaller numbers. In some embodiments, at least about $1\times10^8$, $2\times10^8$, $3\times10^8$, $4\times10^8$, and $5\times10^8$ presently disclosed cells are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Methods of Treatment

Provided herein are methods for treating a myeloid disorder in a subject. Also contemplated herein are methods for treating a pathogen infection or other infectious disease in a subject, such as an immunocompromised human subject. The methods comprise administering the presently disclosed cells in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific T cells, cell doses in the range of about $10^6$-$10^{10}$ (e.g., about $10^9$) are typically infused. Upon administration of the presently disclosed cells into the host and subsequent differentiation, T cells are induced that are specifically directed against the specific antigen. "Induction" of T cells can include inactivation of antigen-specific T cells such as by deletion or anergy. Inactivation is particularly useful to establish or reestablish tolerance such as in autoimmune disorders. The modified cells can be administered by any method known in the art including, but not limited to, intravenous, subcutaneous, intranodal, intratumoral, intrathecal, intrapleural, intraperitoneal and directly to the thymus.

Therapeutic Methods

The presently disclosed subject matter provides methods for increasing an immune response in a subject in need thereof. The presently disclosed subject matter provides methods for treating and/or preventing a myeloid disorder in a subject. Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., based on percentage of leukemic cells, by palpation, CAT scan, sonogram, mammogram or X-ray; positive biochemical or histopathologic markers on their own are insufficient to identify this population). A pharmaceutical composition embodied in this invention is administered to these subjects to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of a myeloid disorder, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different myeloid disorder. Features typical of high-risk subgroups are those in which the tumor has invaded neighboring tissues, or who show involvement of lymph nodes.

Another group have a genetic predisposition to a myeloid disorder but have not yet evidenced clinical signs of the myeloid disorder. For instance, women testing positive for a genetic mutation associated with AML, but still of childbearing age, can wish to receive one or more of the immunoresponsive cells described herein in treatment prophylactically to prevent the occurrence of AML until it is suitable to perform preventive surgery.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Accordingly, the presently disclosed subject matter provides a method of treating and/or preventing a myeloid disorder in a subject, the method comprising administering an effective amount of the presently disclosed immunoresponsive cells.

As a consequence of surface expression of a receptor that binds to a myeloid disorder associated antigen and activates the immunoresponsive cell that enhances the anti-myeloid cell effect of the immunoresponsive cell, adoptively transferred human T or NK cells are endowed with augmented and selective cytolytic activity at the treatment site. Furthermore, subsequent to their localization to treatment site and their proliferation, the T cells turn the site into a highly conductive environment for a wide range of immune cells involved in the physiological immune response (tumor infiltrating lymphocytes, NK-, NKT-cells, dendritic cells, and macrophages).

Kits

The invention provides kits for the treatment and/or prevention of a myeloid disorder. In certain embodiments, the kit includes a therapeutic or prophylactic composition comprising an effective amount of the presently disclosed immunoresponsive cells. In some embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In certain embodiments, the kit includes an isolated nucleic acid encoding an antigen recognizing receptor (e.g., a CAR or a TCR) directed toward an antigen of interest in expessible (and secretable) form, which may optionally be comprised in the same or different vectors.

If desired, the immunoresponsive cell and/or nucleic acid is provided together with instructions for administering the cell or nucleic acid to a subject having or at risk of developing a myeloid disorder. The instructions will generally include information about the use of the composition for the treatment and/or prevention of myeloid disorder. In certain embodiments, the instructions include at least one of the following: description of the therapeutic agent; dosage schedule and administration for treatment or prevention of a myeloid disorder or a symptom thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the compositions, and assay, screening, and therapeutic methods of the invention, and are not intended to limit the scope of what the inventors regard as their invention.

Example 1—Integrated Analysis of the AML Cell Surfaceome Identifies CAR Targets

Summary

Adoptive T cell therapies using chimeric antigen receptors (CARs) to redirect the specificity and function of T lymphocytes have demonstrated efficacy in patients with lymphoid malignancies, in particular acute lymphoblastic leukemia (ALL) (Sadelain, 2015). This therapeutic modality induces complete remissions in subjects with CD19+ malignancies for whom chemotherapies have led to drug resistance and tumor progression. "Cancer immunotherapy", including CAR therapy, was proclaimed a scientific breakthrough in 2013 (Couzin-Frankel, 2013). The success of CD19 CAR therapy bodes well for tackling all hematological malignancies, including Acute Myeloid Leukemia (AML), which affects over one quarter million adults annually worldwide. However, the development of CAR therapy for AML is hampered by the lack of suitable targets.

The search for suitable CAR targets has been limited so far to comparisons of antigen expression levels between cancer cells and normal counterparts, without comprehensively considering antigen expression in normal organs/tissues across the whole body. Such searches have mostly relied on the analysis of the transcriptome, under the assumption that there exists a direct correspondence between mRNA transcripts and generated protein expressions. Alternatively, advanced proteomic technologies combined to enrichment strategies to identify plasma cell membrane proteins offer direct measurements of the surface proteome. Recent studies have however shown that the correlation between mRNA and protein expressions is complex and sometimes unreliable due to various factors including different half lives and post transcription machinery. Therefore, an integrated and comprehensive analysis of both transcriptomic and proteomic data is best positioned to capture useful information that may not be deciphered from individual or limited analysis of mRNA or protein expression (Haider and Pal, 2013). Moreover, defined criteria of a suitable CAR target have never been set and besides the CD19 paradigm. There is thus an unmet need to define analytical tools to select proper candidate targets for CAR therapy.

A multi-tiered approach was developed, integrating transcriptomic and proteomic data from several malignant and normal cell subsets in search for CAR targets. Starting from multiple annotation data sources, multi-step ranking criteria was defined to identify suitable CAR targets. This allowed to annotate, filter and validate thousands of surface potential targets, which were found overexpressed in AML cells compared to normal controls. Eleven suitable candidate antigens were identified that can be targeted by single and/or combinatorial CAR T cell strategies for patients with AML. These do not overlap with the four molecules that have been pursued to date as CAR targets: Lewis (Le)-Y(Ritchie et al., 2013); CD123 (Al-Hussaini et al., 2016; Gill et al., 2014; Jordan et al., 2000; Yi Luo, 2015); CD33 (Kenderian et al., 2015; Pizzitola et al., 2014) and folate receptor-B (Lynn et al., 2016; Lynn et al., 2015). None of these 4 meet stringent efficacy and safety criteria for an ideal CAR target or represent the equivalent of CD19 for ALL. Furthermore, genetically-defined models of leukemic stem cells are generated, which were used to further validate the candidates and pairs of candidates and also to identify mutation-specific surface signatures, which may be used to design patient-tailored CAR strategies, based on the genetic mutational profile.

Generating a Comprehensive Annotated Dataset of Surface AML Targets to Identify Suitable CAR Targets In order to generate a comprehensive dataset of surface AML targets, from which suitable CAR targets could be selected, previously reported markers (474 proteins) were first collected, and additional surface-specific proteomic studies were performed (3675 proteins) (FIG. 1A).

Reported markers include CD44 (Jin et al., 2006), TIM-3 (Kikushige et al., 2010), CD123 (Jordan et al., 2000), CD47 (Majeti et al., 2009), CD32 and CD25 (Saito et al., 2010), CLL-1 (Bakker et al., 2004), CD96 (Hosen et al., 2007), CD33 (Taussig et al., 2005) for instance, and also the results of surface-specific proteomic studies in five human myeloid leukemia (NB4, HL60, THP1, PLB985, K562) cell lines and normal human granulocytes (Strassberger et al., 2014). Also performed was cell surface biotinylation of additional four (Kasumi, Monomac, Molm13, 09AML, THP1, K562) human AML cell lines, which was used for mass-spectrometric analysis. These eight cell lines bear different genetic background and therefore including additional lines expanded the cohort of potential candidate targets given the complex heterogenicity of AML. For instance, THP1 line bears MLL-AF9 translocation, deletion of p16, p53, UTX and rearrangement of RB1; Kasumi line bears AML1-ETO translocation; Molm13 FLT3-ITD; NB4 and HL60 PML-RAR.

The expression of each candidate was annotated through multiple data sources, including the Human Protein Atlas (HPA)(Uhlen et al., 2015), the Human Proteome Map (HPM)(Kim et al., 2014) and the Proteomics Database (PD)(Wilhelm et al., 2014), which provide information on protein expression in several (>60) normal tissues/organs, including liver, gallbladder, pancreas, stomach, duodenum, colon, rectum, testis, epididymis, prostate, breast, vagina, uterus, ovary, skin, skeletal and smooth muscle, cerebral cortex, hippocampus, lateral ventricle, cerebellum, thyroid, bronchus, lung, heart, retina, vitreous humor, bone marrow, lymphocytes, lymph nodes, tonsil, synovial fluid, bile, saliva, through different means such as antibody-based immunohistochemistry (HPA) and protein mass spectrometry (HPM and PD) (FIG. 1A). By converting and integrating these data, the expression profile of each AML target was defined in any of those normal organ systems and tissue types that signify different vital and non-vital organ structures and functions. Through the subcellular localization database (aka Compartments), the proteins localized at the cell membrane was annotated (FIG. 1A).

HPA also provided mRNA data enabling calculation of correlation between protein and mRNA expression of each candidate in any normal tissue. the mRNA expression of each candidate was also studied in multiple normal hematopoietic cells, such as HSCs, myeloid progenitors, monocytes etc and primary AML patient samples bearing specific chromosomal abnormalities such as t(15;17), t(8;21), t(11q23)/MLL, inv(16)/t(16;16) etc (Bagger et al., 2016) (FIG. 1A). Also, upon purchasing specific antibodies of a subset of 32 selected antigens, additional information of their expression was obtained in multiple primary cell subsets such as healthy CAR+ T cells or oncogene-expressing CD34+ cells by flow-cytometry (FIG. 1A). All these information contributed in generating a comprehensive annotated dataset of AML surface targets, which is not-previously reported (FIG. 1A).

The Algorithm to Identify Suitable CAR Targets in AML

Described here is the algorithm and the criteria applied to the annotated dataset of potential AML candidates, described above in FIG. 1. This multi-step approach enabled identification of a limited number of suitable CAR targets, starting from a much larger number.

Figure 1B:
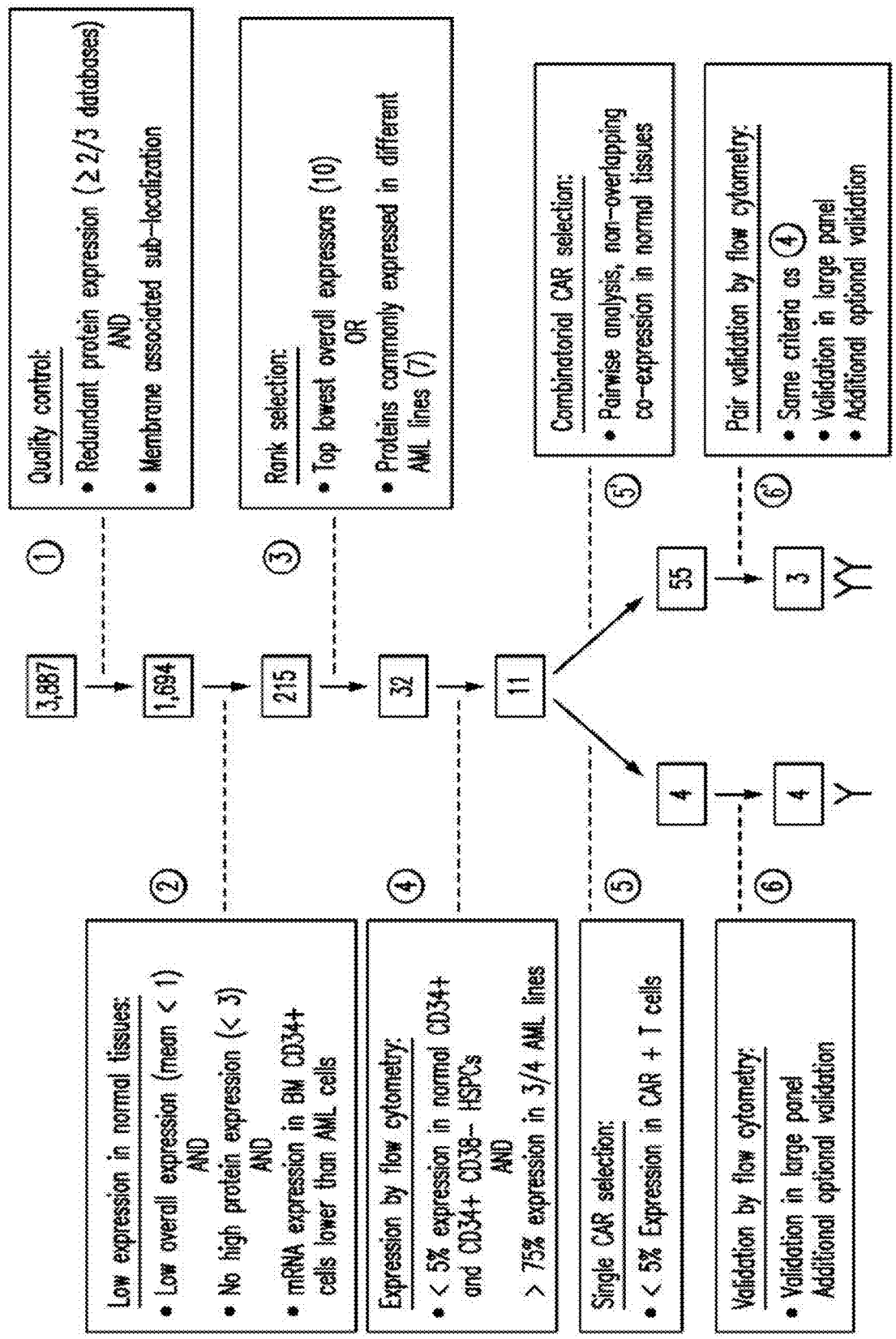

Starting from a dataset of 3,887 molecules, priority was first given to antigens with redundant protein expression data in at least 2 out the 3 databases, which provide information on the antigen expression in normal tissues and organs (HPA, HPM and PD). This assured high level of confidence in the analysis. Additionally, antigens with a membrane associated sub-localization were prioritized. This first step is termed "Quality control", which resulted in 1,694 candidates (FIG. 1B—step #1).

Secondly, the antigens with less chance of expression by normal tissues was selected. three selection criteria which would prefer the candidates with were defined: a) low average expression in 64 normal tissues/organs (using 1 as cut-off value) b) no high expression in any tissue (using a scale 0 to 3 where 0, 1, 2 and 3 indicate zero, low, medium and high expression respectively) c) low mRNA expression in HSCs compared to primary AML samples. This was called the second step "Low expression in normal tissues" resulting in 215 candidates (FIG. 1B—step #2).

Figure 1C:
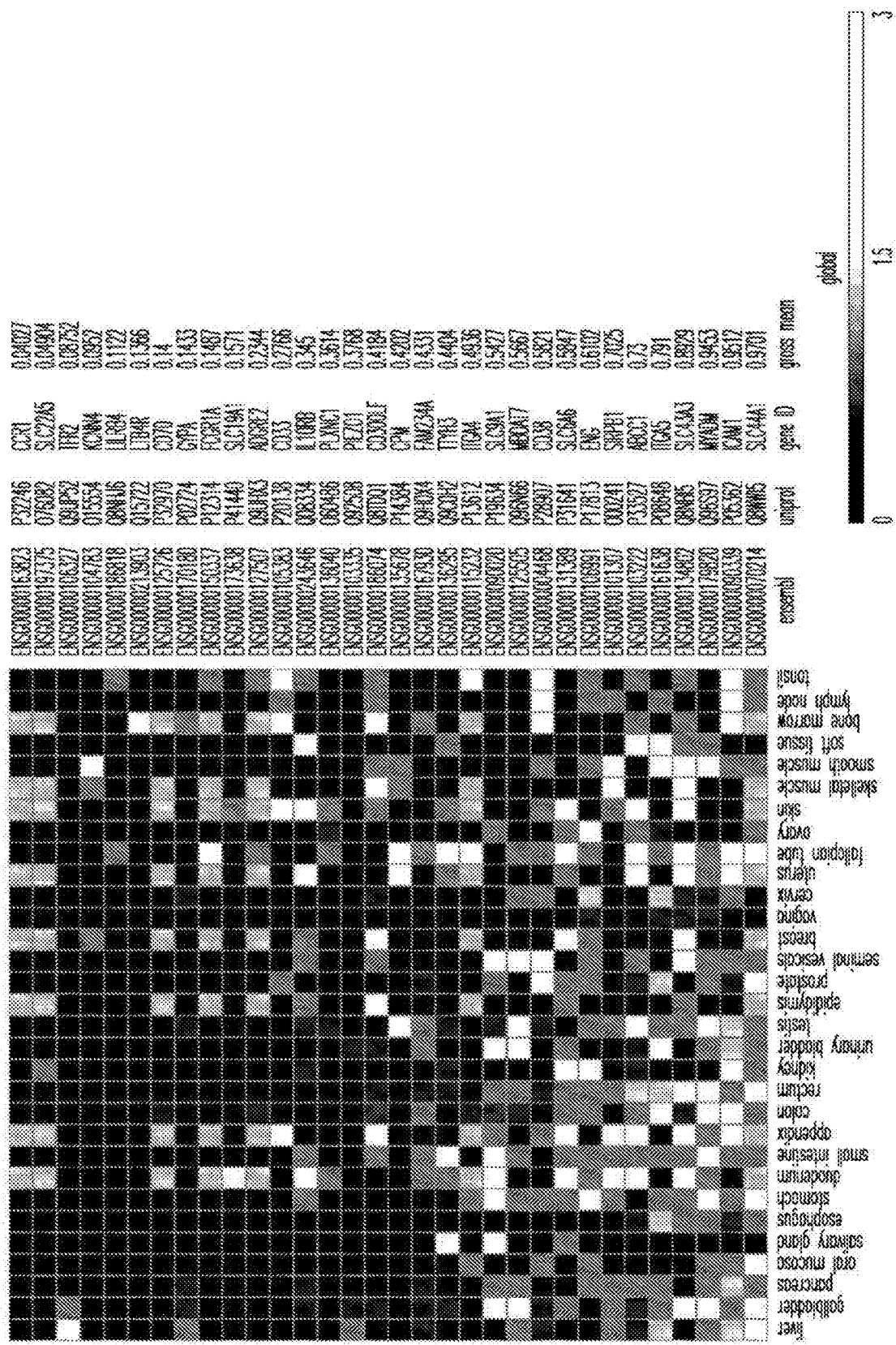
Figure 1C:
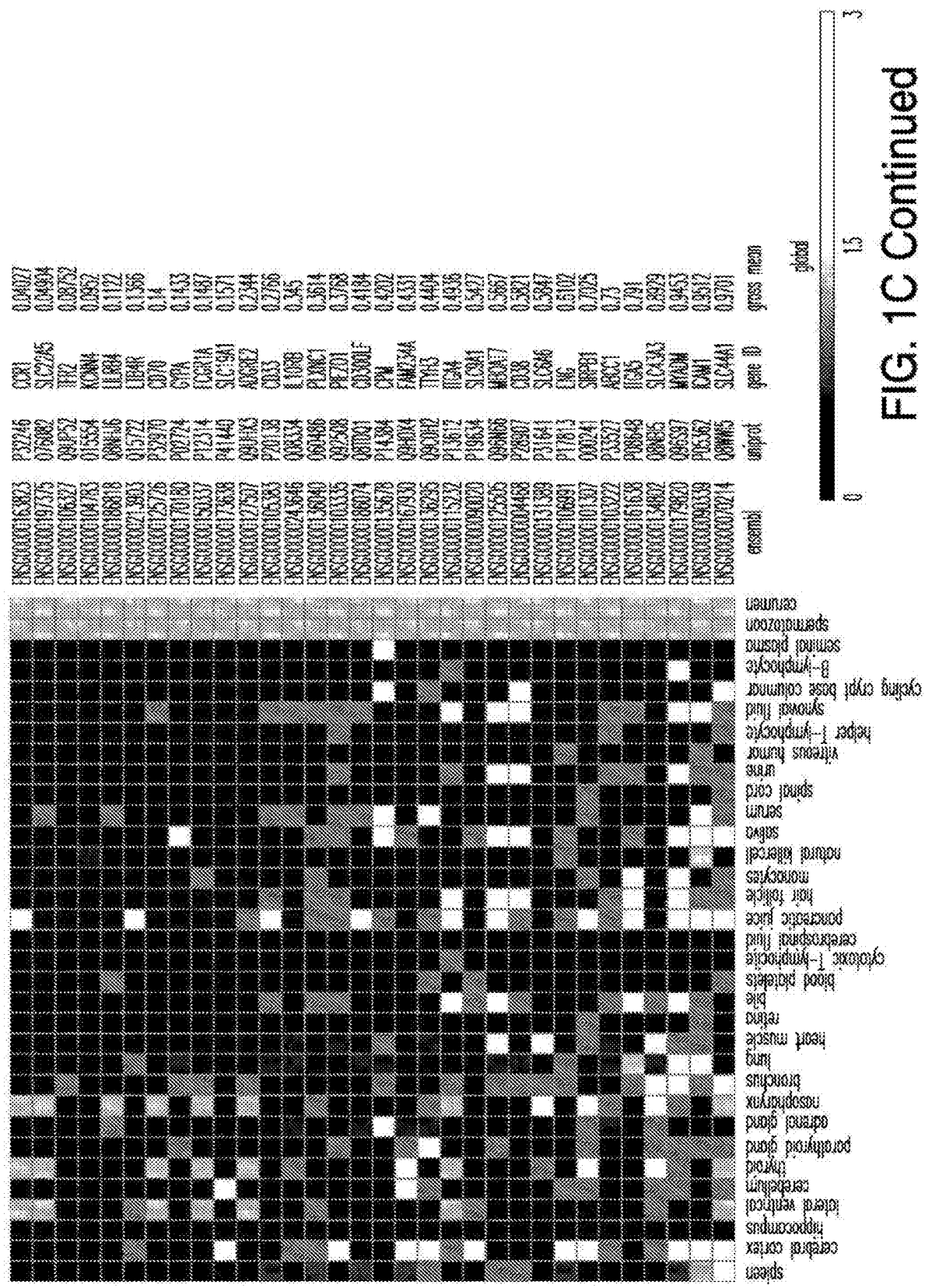

The top lowest overall expressors were selected (10) based on mean value (in increasing order): CCR1, SLC22A5, TFR2, KCNN4, LILRB4, LTB4R, CD70, GYPA, FCGR1A and SLC19A1. Also selected are the candidates that are commonly expressed between the group of reported molecules and the results of the proteomics studies in additional AML cell lines (FIG. 1A—blue boxes). This assured broad distribution of candidate expression across multiple AML models, thus extended application in targeting those candidates. They are 29 in total and the molecules are listed below, not including the 10 lowest overall expressors: EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1. This third step was termed "Rank selection", resulting in 32 proteins (FIG. 1B—step #3 and FIG. 1C).

Figure 1D:
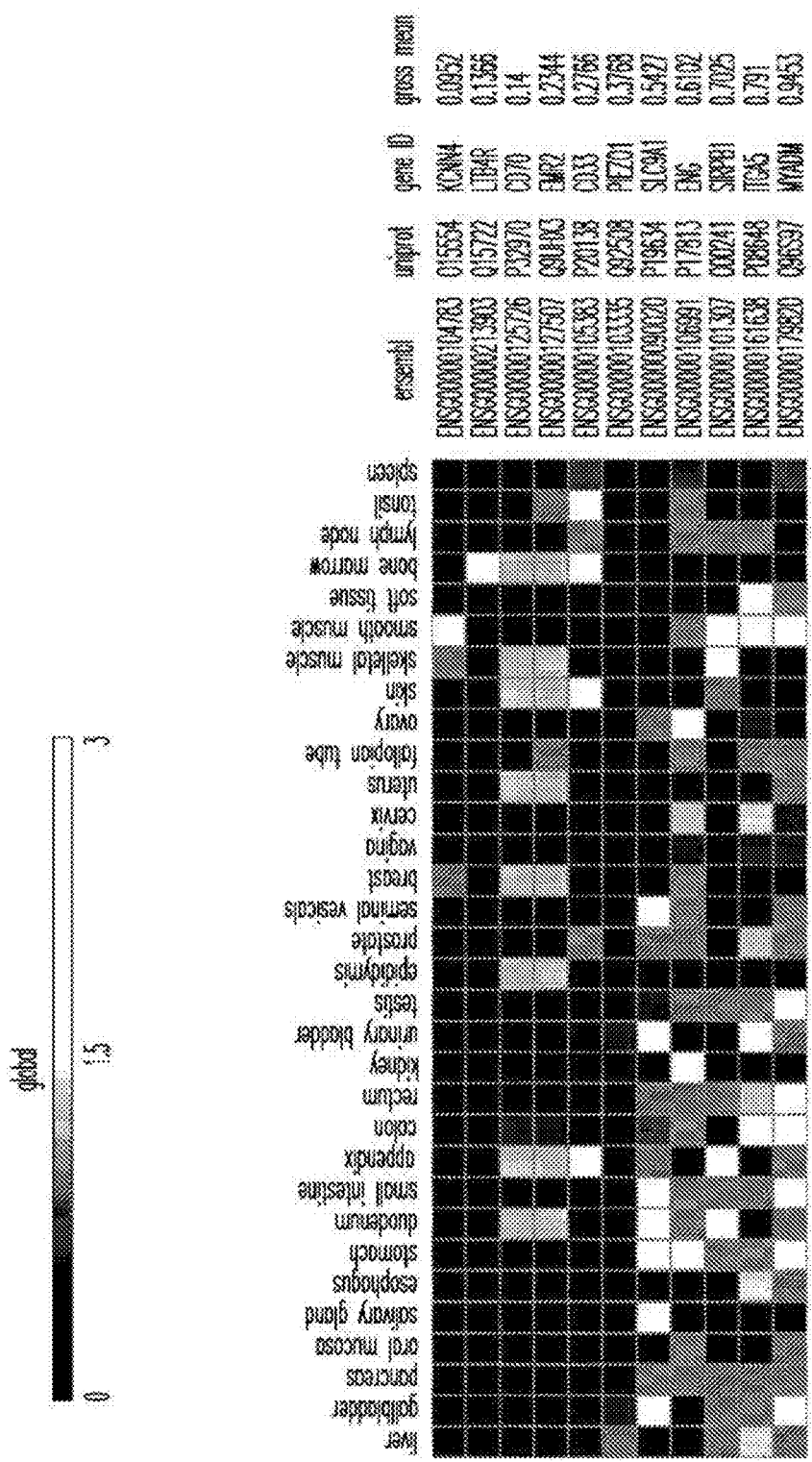
Figure 1D:
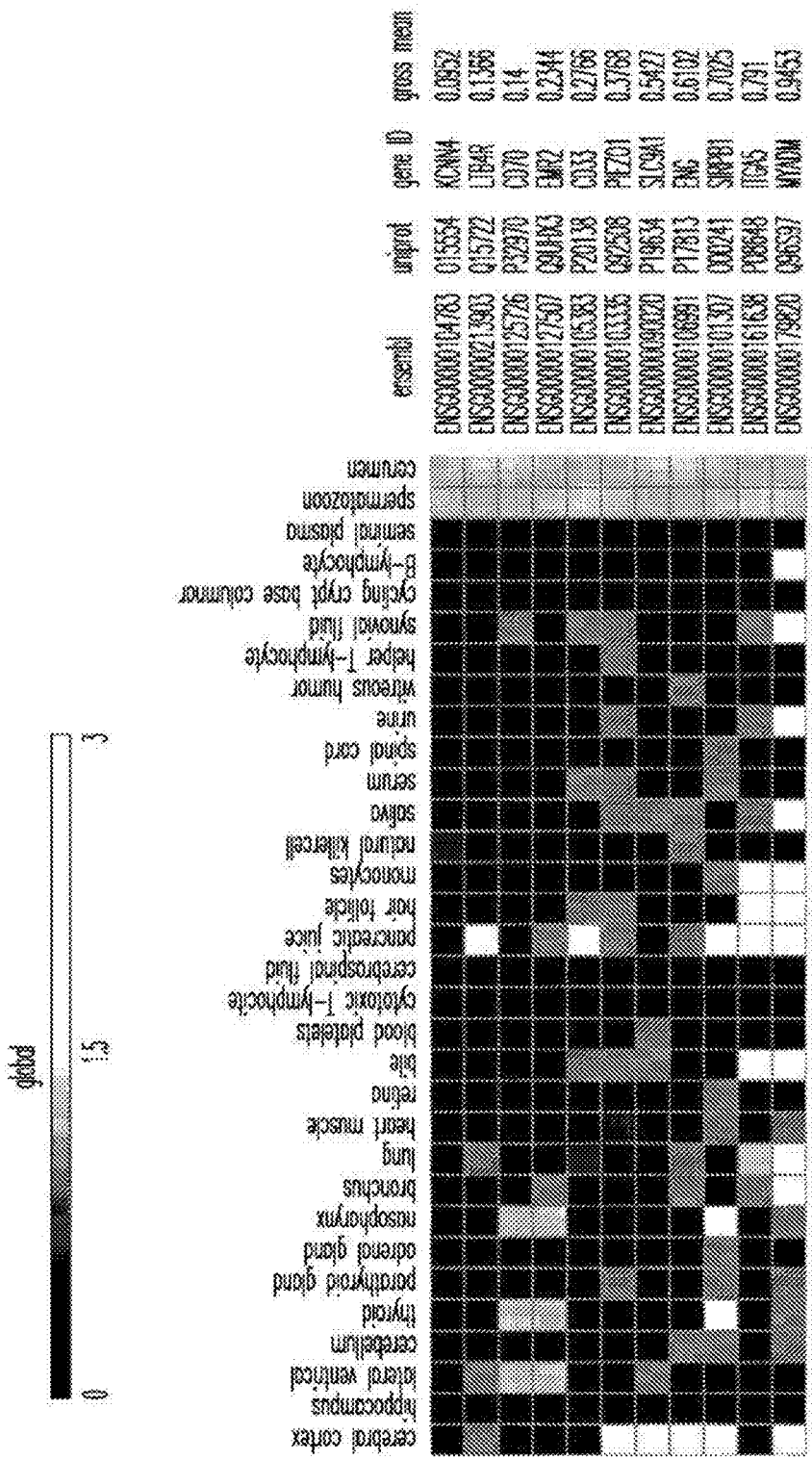
Figure 1E:
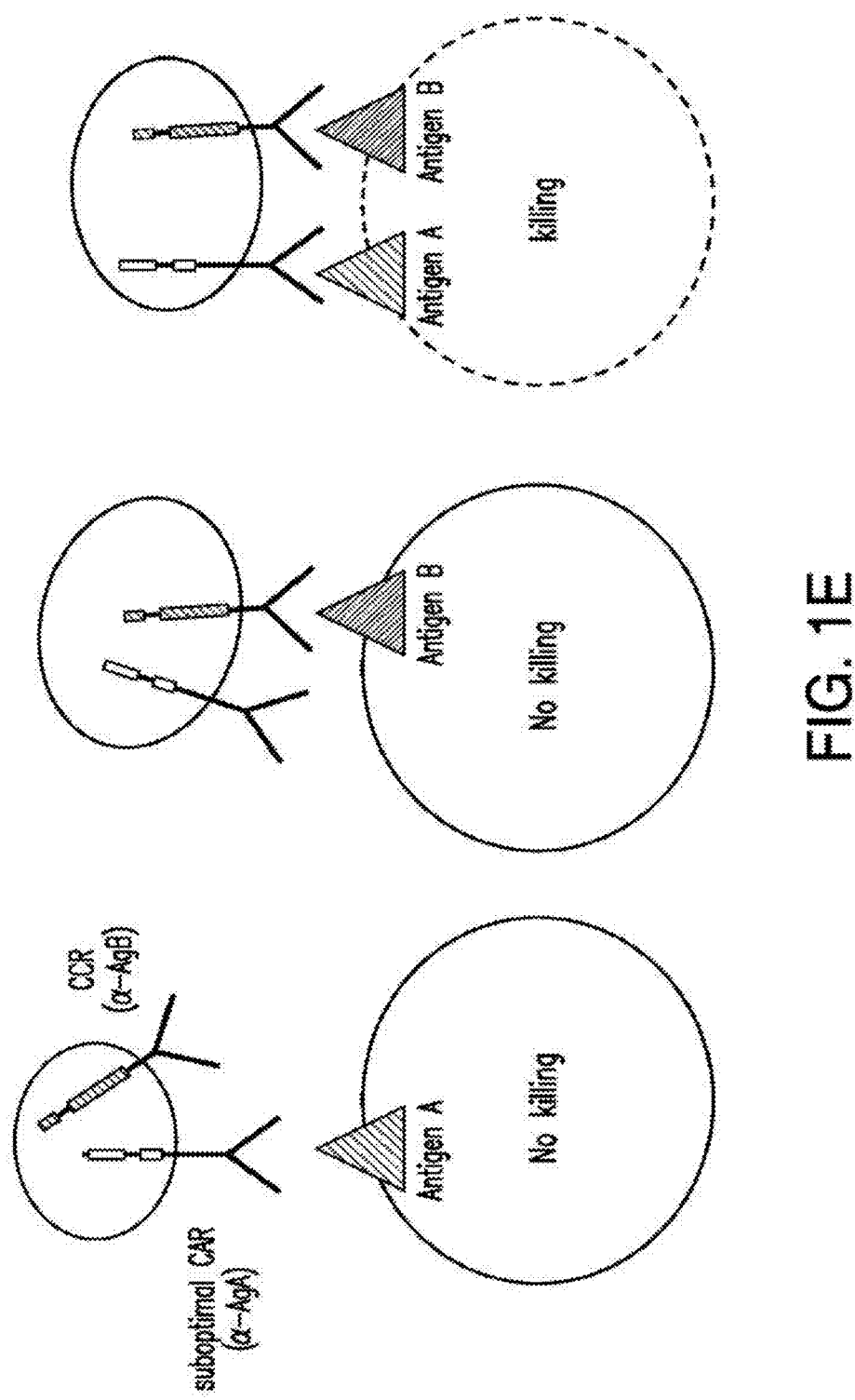

Upon purchasing specific antibodies, the expression of these selected candidates were systematically defined in primary CD34$^+$, CD34$^+$CD38" HSCs which were purified from cord blood, and in five AML cell lines by flow-cytometry. This fourth step was termed "Expression by flow-cytometry", which selected the candidates with <5% expression in normal CD34+ and CD34+CD38-HSCs and >75% expression in 4/5 AML cells (FIG. 1B—step #4). This resulted in 11 top candidates that can be targeted by CAR T cells safely and efficiently: LTB4R, EMR2, CD33, MYADM, PIEZO1, SIRPB1, SLC9A1, KCNN4, ENG, ITGA5, CD70 (FIG. 1D).

Figure 3A:
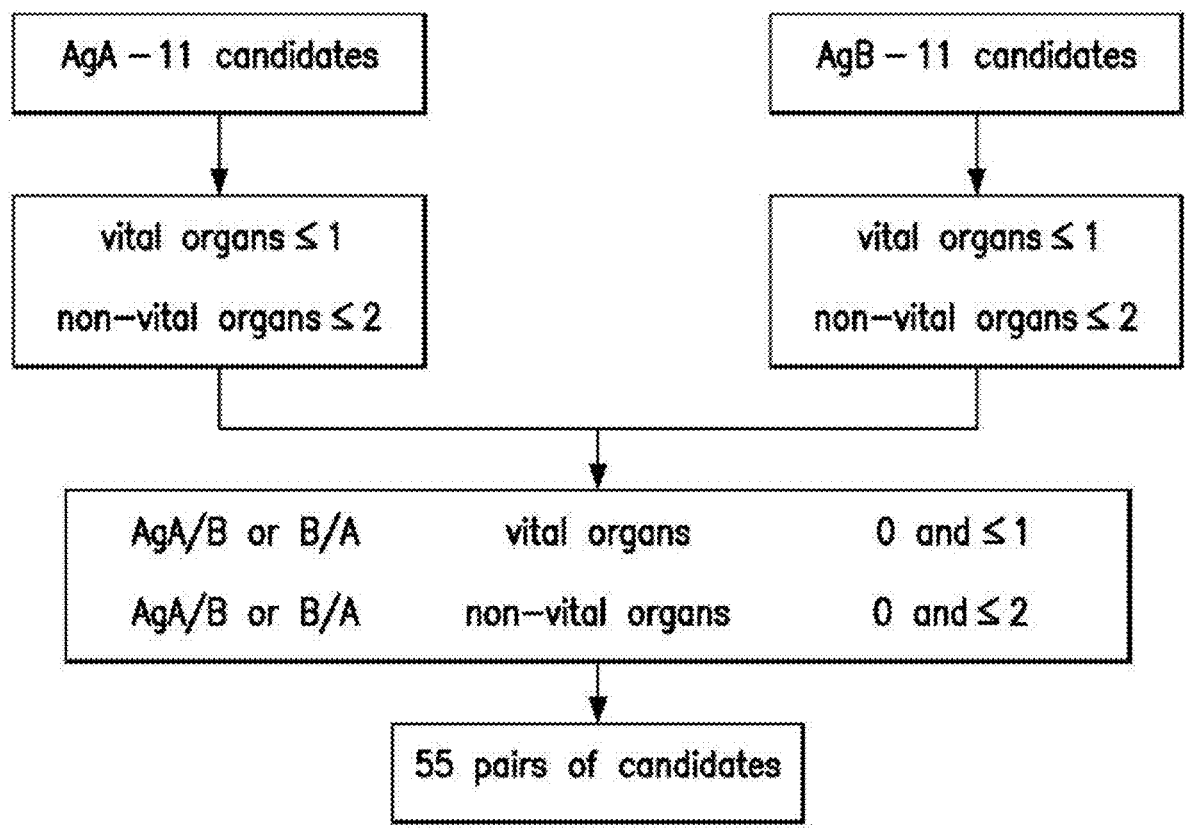
FIGS. 3A-3B depict the results of further screening of CAR targets in AML.

A further step was taken to consider T cells mediate CAR therapy, the expression of each of those 11 molecules were defined in healthy PHA-stimulated CD19+CAR T cells before and after stimulation on CD19$^{+3}$ T3 cells, mimicking therapeutic cells. the candidates with <5% expression in T cells: LTB4R, EMR2, MYADM and PIEZO1 were selected (FIG. 1B—step #5). This fifth step was termed "Single CAR selection." Targeting AML with any of those can result in efficient and safe CAR T cell therapies. The 11 top targets were paired for non-overlapping expression in normal organs/tissues and 55 pairs of antigens were obtained from the step termed "Combinatorial CAR selection" (FIG. 1B—step #5'; FIG. 3A).

[LTB4R+EMR2]; [LTB4R+CD33]; [LTB4R+ENG]; [LTB4R+MYADM]; [LTB4R+PIEZO1]; [LTB4R+SIRPB1];
[LTB4R+SLC9A1]; [LTB4R+ITGA5]; [LTB4R+CD70]; [LTB4R+KCNN4];
[EMR2+CD33]; [EMR2+ENG]; [EMR2+MYADM]; [EMR2+PIEZO1]; [EMR2+SIRPB1]; [EMR2+SLC9A1]; [EMR2+ITGA5]; [EMR2+CD70]; [EMR2+KCNN4];
[CD33+ENG]; [CD33+MYADM]; [CD33+PIEZO1]; [CD33+SIRPB1]; [CD33+SLC9A1]; [CD33+ITGA5]; [CD33+CD70]; [CD33+KCNN4];
[ENG+MYADM]; [ENG+PIEZO1]; [ENG+SIRPB1]; [ENG+SLC9A1]; [ENG+ITGA5]; [ENG+CD70]; [ENG+KCNN4];
[MYADM+PIEZO1]; [MYADM+SIRPB1]; [MYADM+SLC9A1]; [MYADM+ITGA5]; [MYADM+CD70]; [MYADM+KCNN4];
[PIEZO1+SIRPB1]; [PIEZO1+SLC9A1]; [PIEZO1+ITGA5]; [PIEZO1+CD70]; [PIEZO1+KCNN4];
[SIRPB1+SLC9A1]; [SIRPB1+ITGA5]; [SIRPB1+CD70]; [SIRPB1+KCNN4];
[SLC9A1+ITGA5]; [SLC9A1+CD70]; [SLC9A1+KCNN4];
[ITGA5+CD70]; [ITGA5+KCNN4] and
[CD70+KCNN4].

The 32 rank selections yielded total 496 pairs of targets, which are show in Table 1.

A combinatorial targeting and recognition strategy was previously developed with T cells transduced with both a suboptimal CAR and a chimeric co-stimulatory receptor (CCR) recognizing a second antigen. Co-transduced T cells destroy cells expressing both antigens but do not affect cells expressing either antigen alone (Kloss et al., 2013). This strategy are to be employed to assess and compare the efficacy and specificity of the pairs of CARs in AML (FIG.

1E). Exemplary combination can be: LTB4R1+CD70; CD70+EMR2; and LTB4R1+EMR2.

Further validation by flow-cytometry in large panel of AML cells and additional optional validation (in genetically-defined subsets of AML cells) refined the choice of the top target or pair of targets and/or indicate the best CAR treatment option based on the specific mutational profile of AML (FIG. 1B—step #6 and #6').

2. Antigen Expression Levels in Normal and Malignant Cells by Flow-Cytometry

The expression levels of top 11 antigens were accessed in normal CD34+, CD34+CD38-HSCs, CAR+ T cells (before and after activation) and in four malignant AML (THP1, Monomac, Molm13 and 09AML) cells.

Figure 2A:
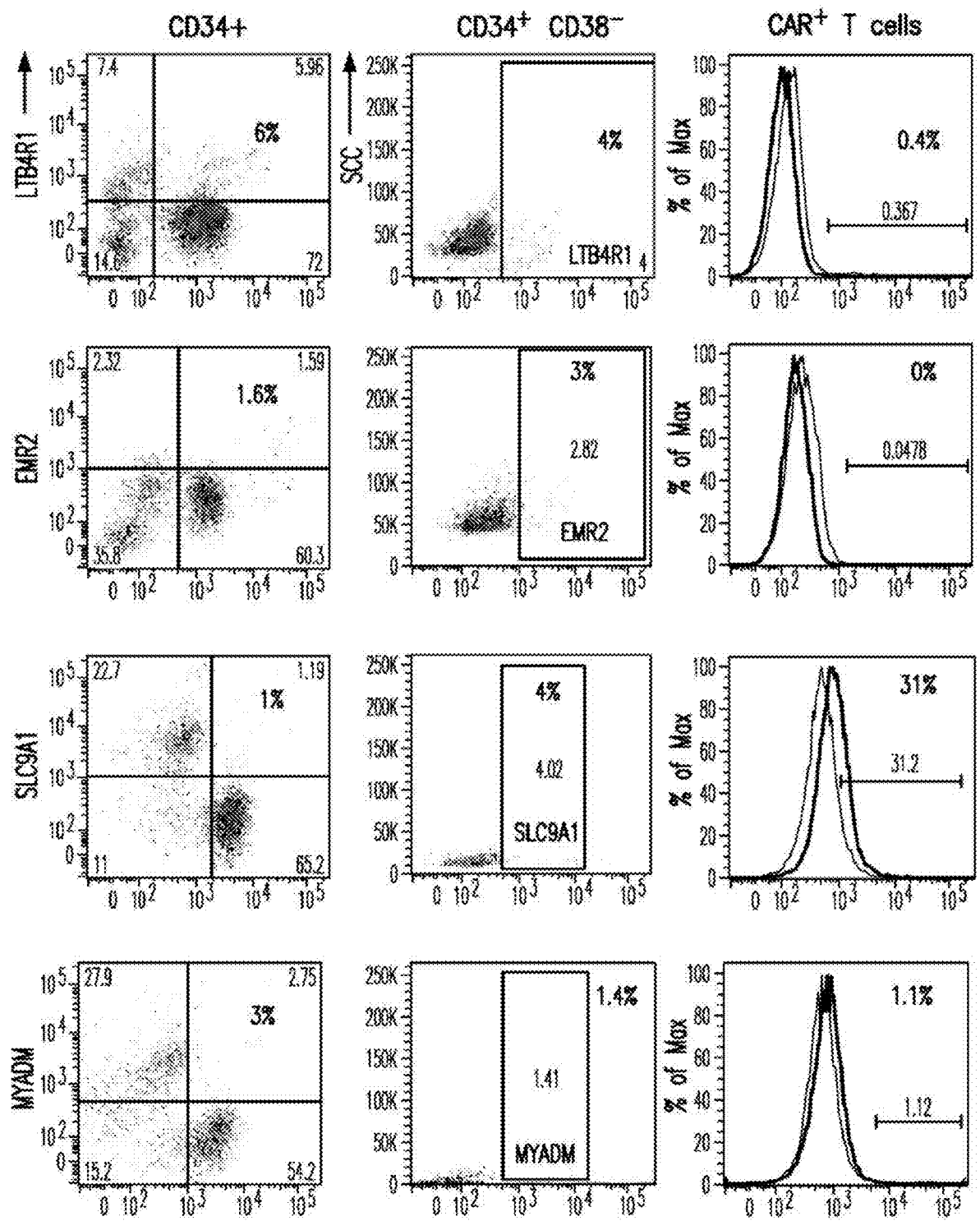
FIGS. 2A-2E depict the results of antigen expression analyses in normal and malignant cells by flow-cytometry.
Figure 2A:
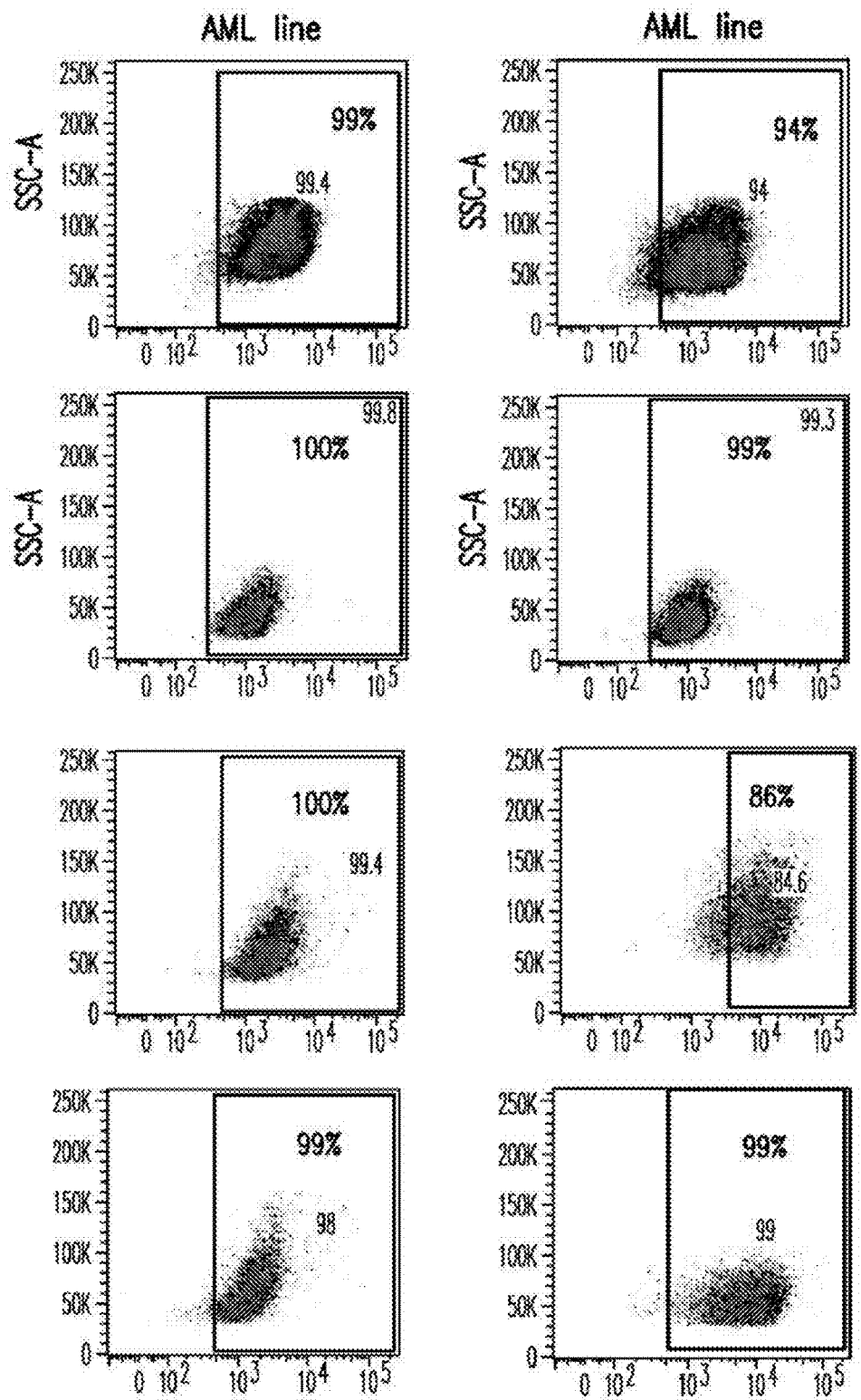
Figure 2A:
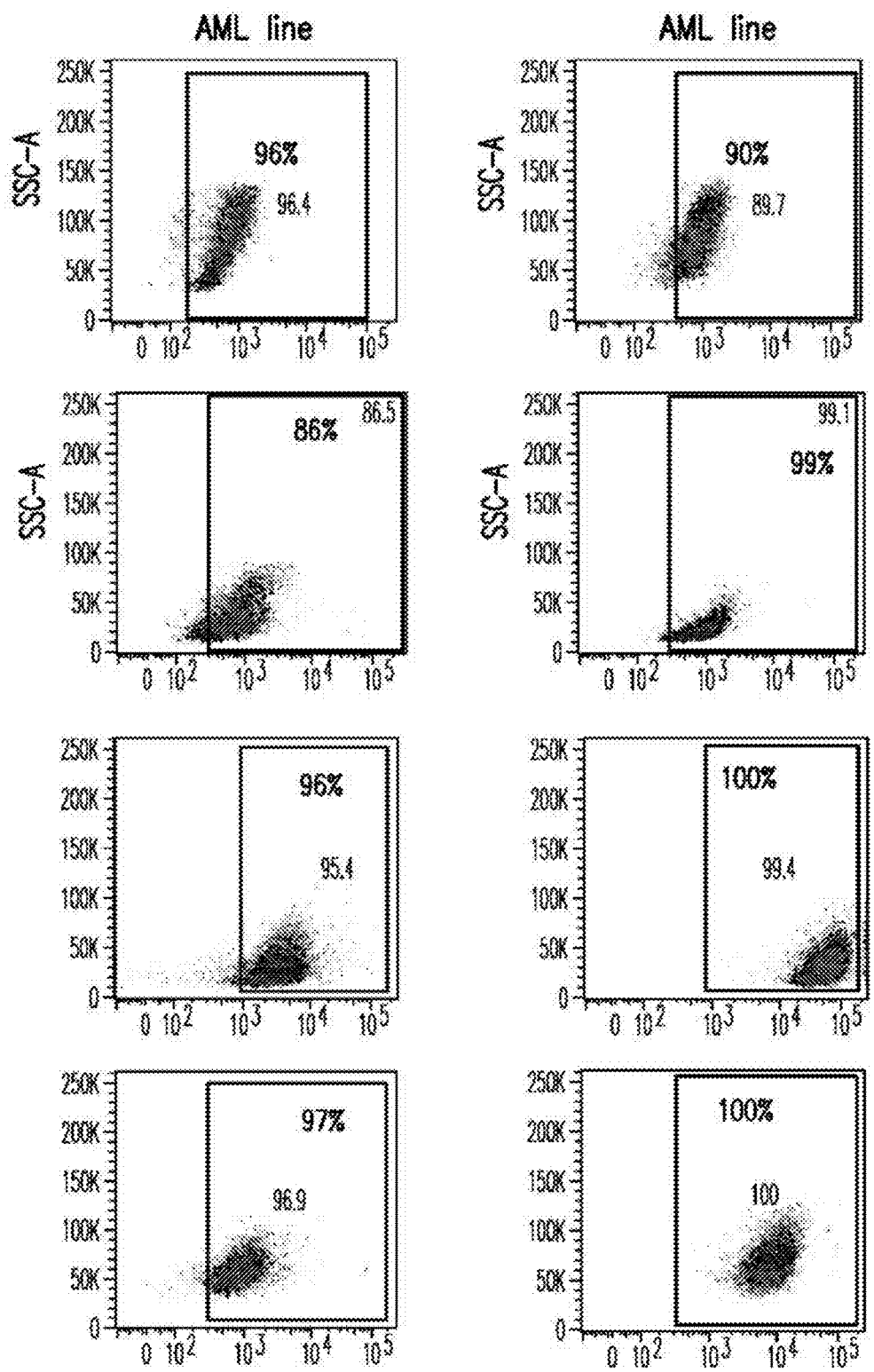
Figure 2A:
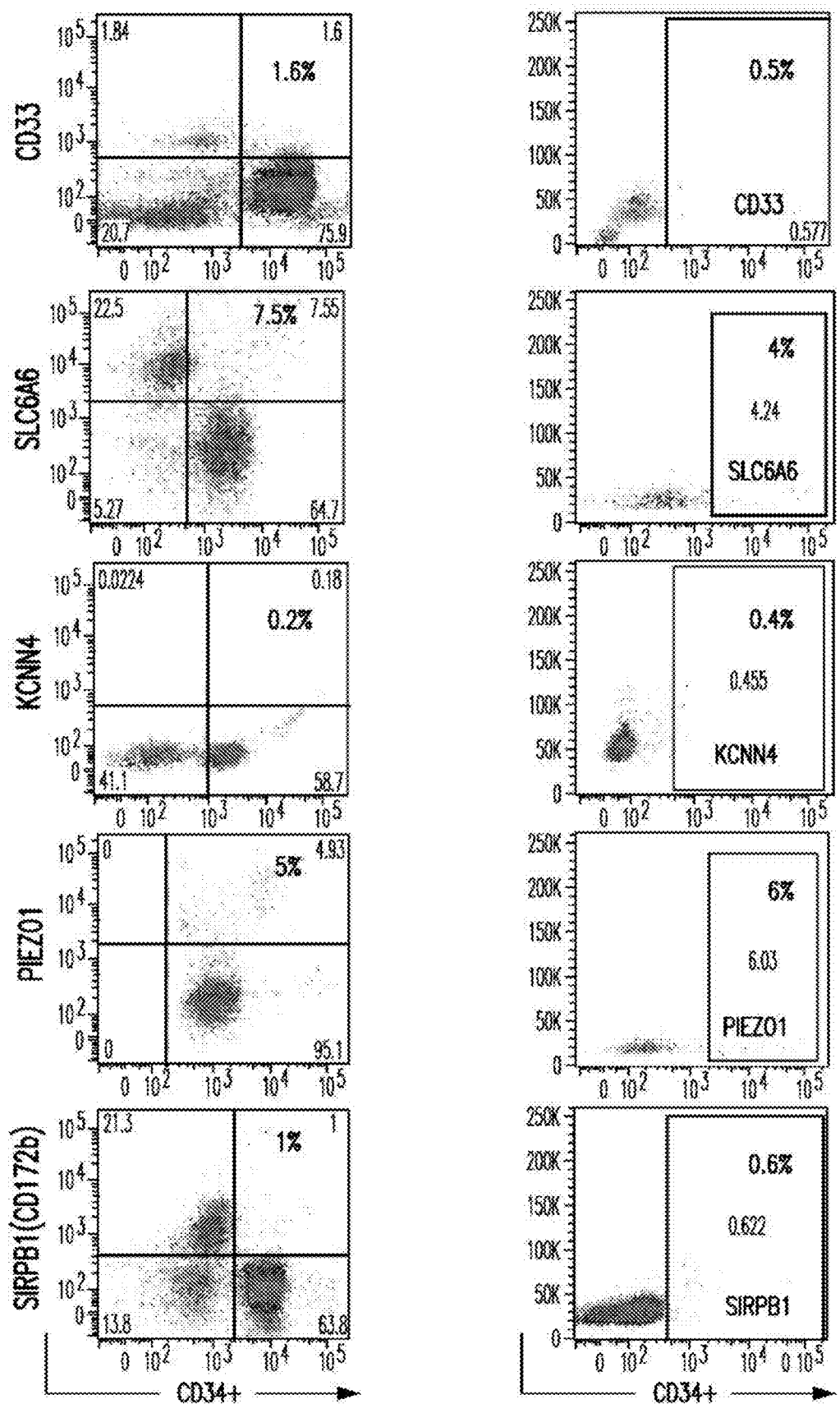
Figure 2A:
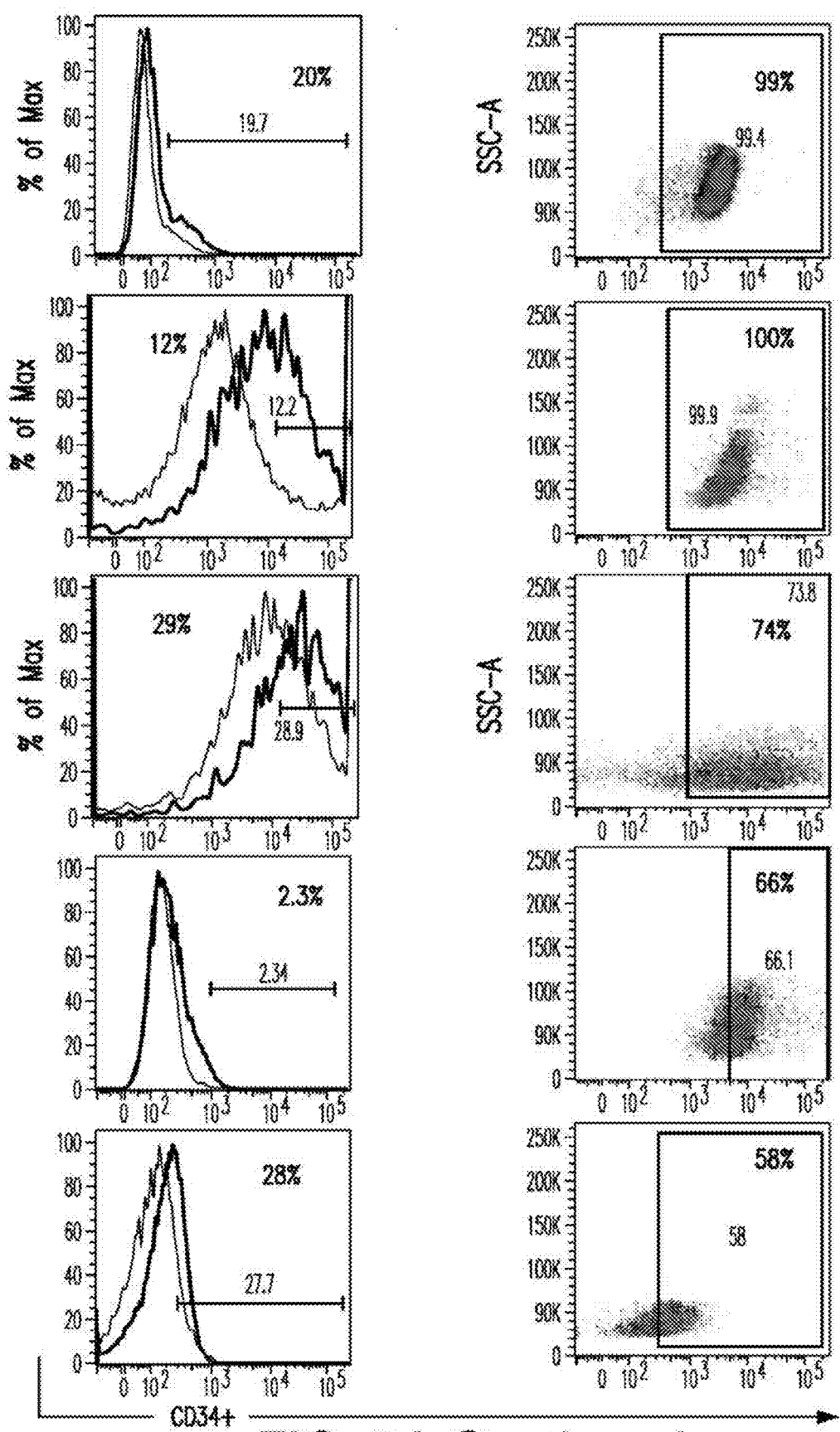
Figure 2A:
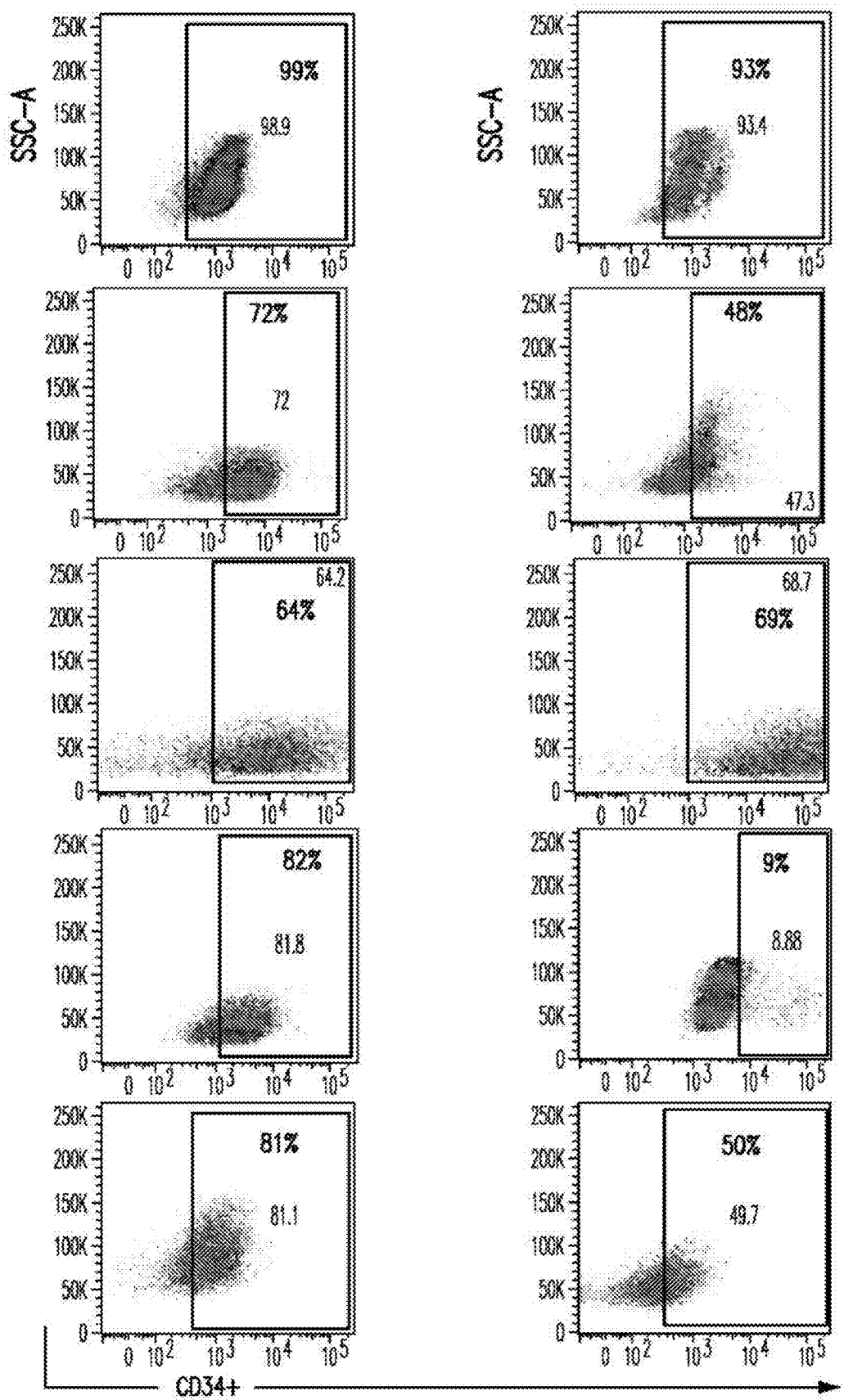
Figure 2A:
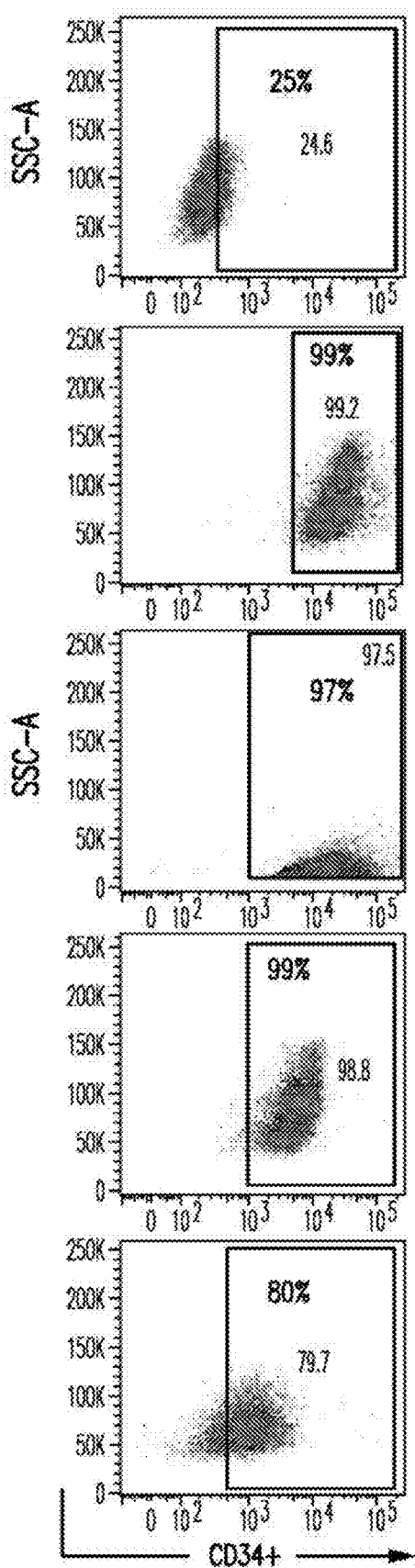

FIG. 2A shows 9 candidates: LTB4R, EMR2, SLC9A1, MYADM, CD33, SLC6A6, KCNN4, PIEZO1, SIRPB1. LTB4R and EMR2 present the best expression profile compared to the whole panel in FIG. 2.

Figure 2B:
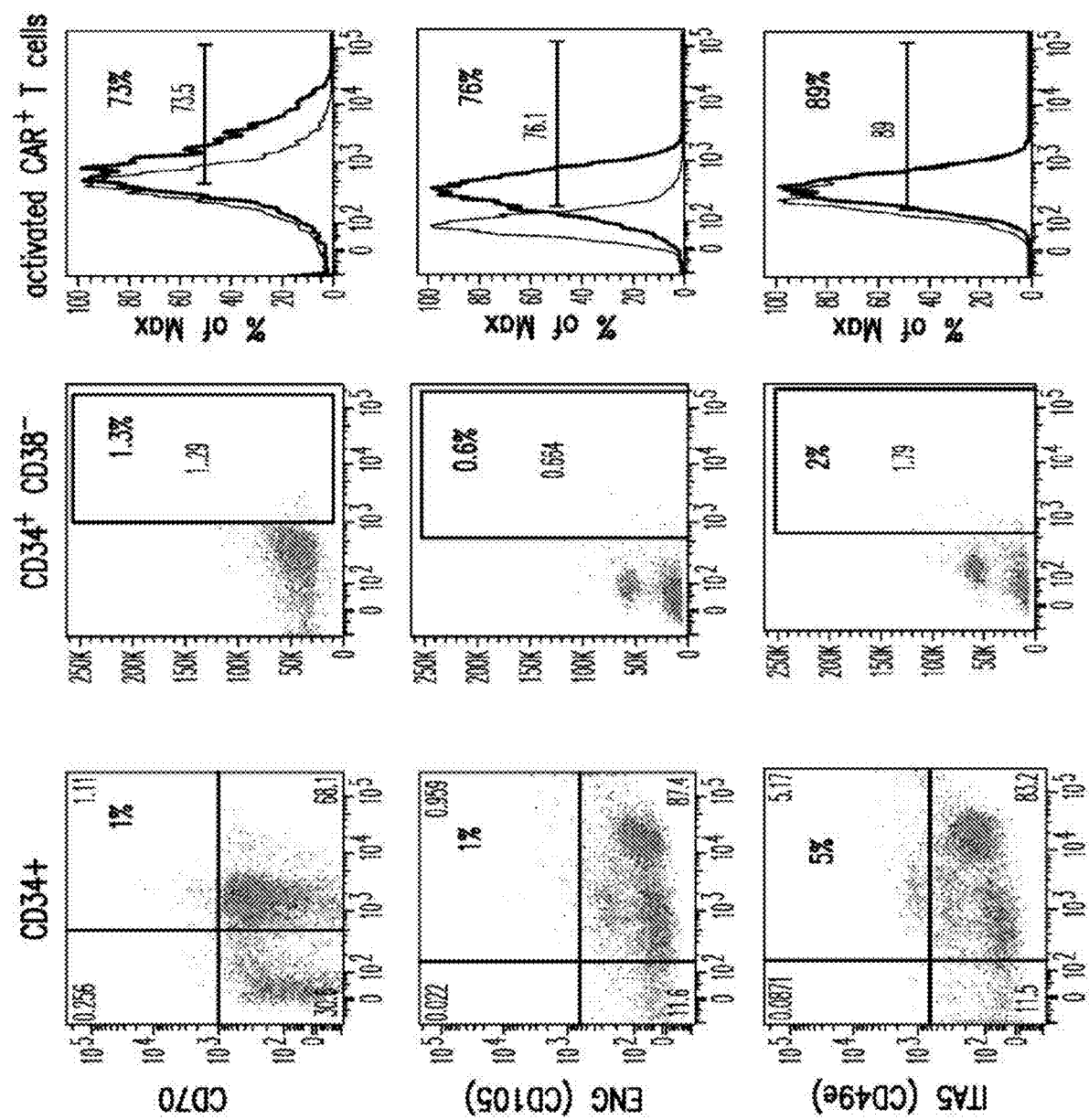
Figure 2B:
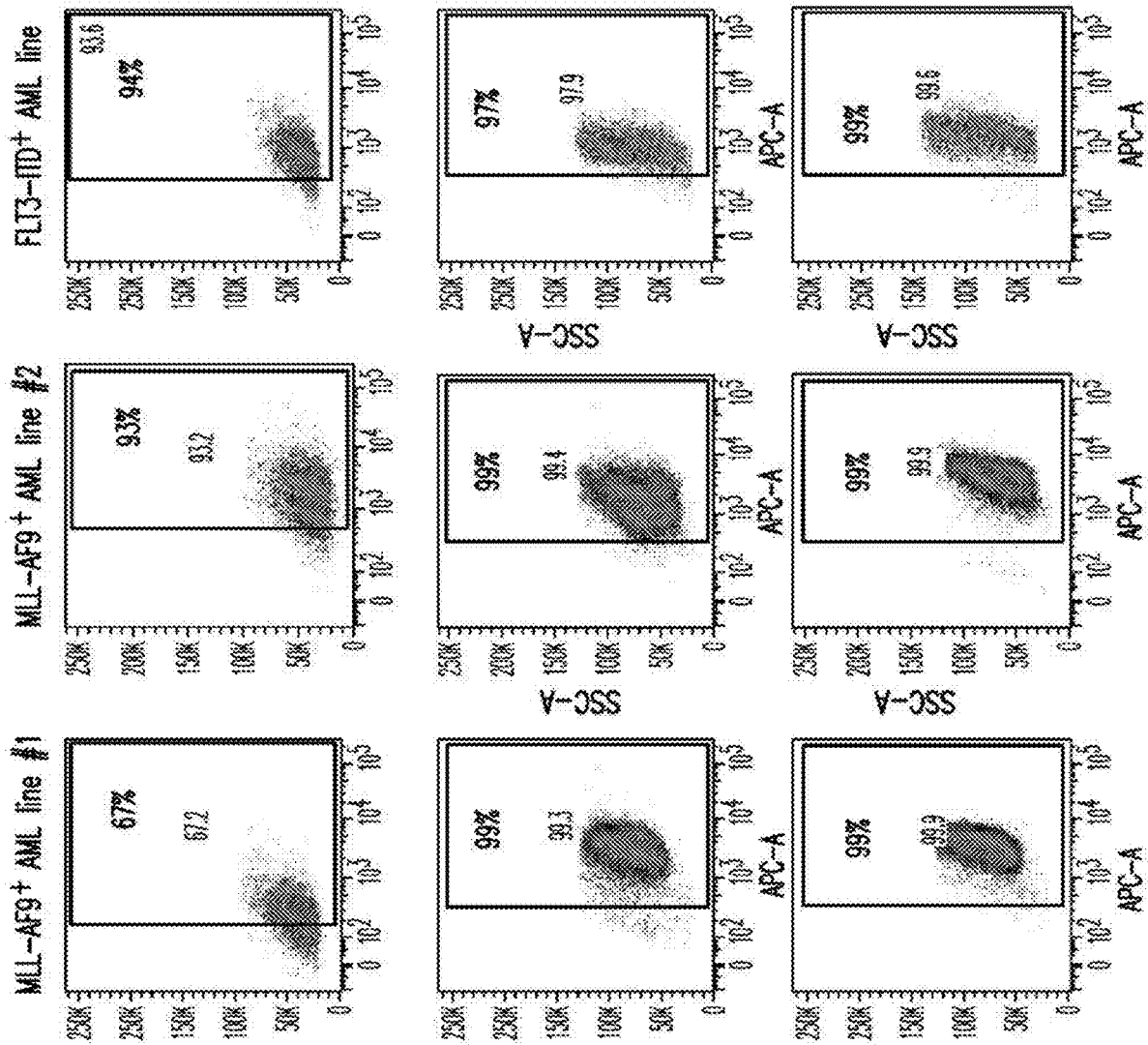
Figure 2B:
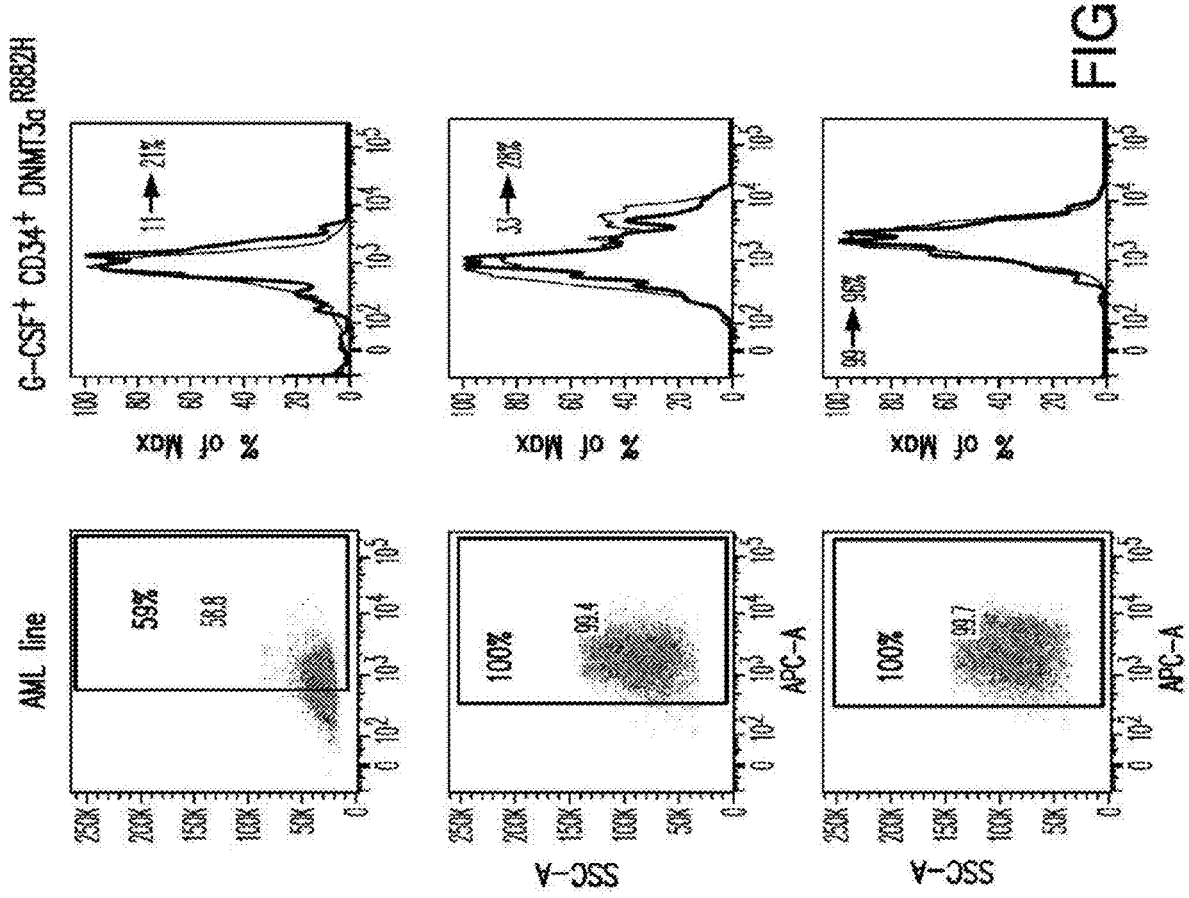
Figure 2B:
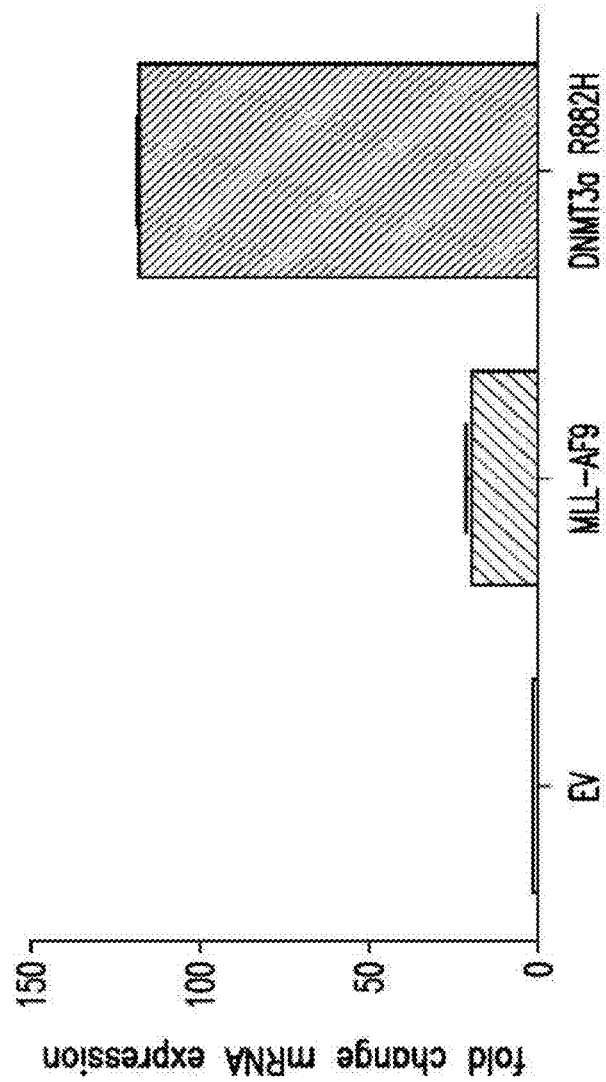

FIG. 2B shows 3 candidates: CD70, ENG, ITGA5. These antigens share high expression in T cells.

Figure 2C:
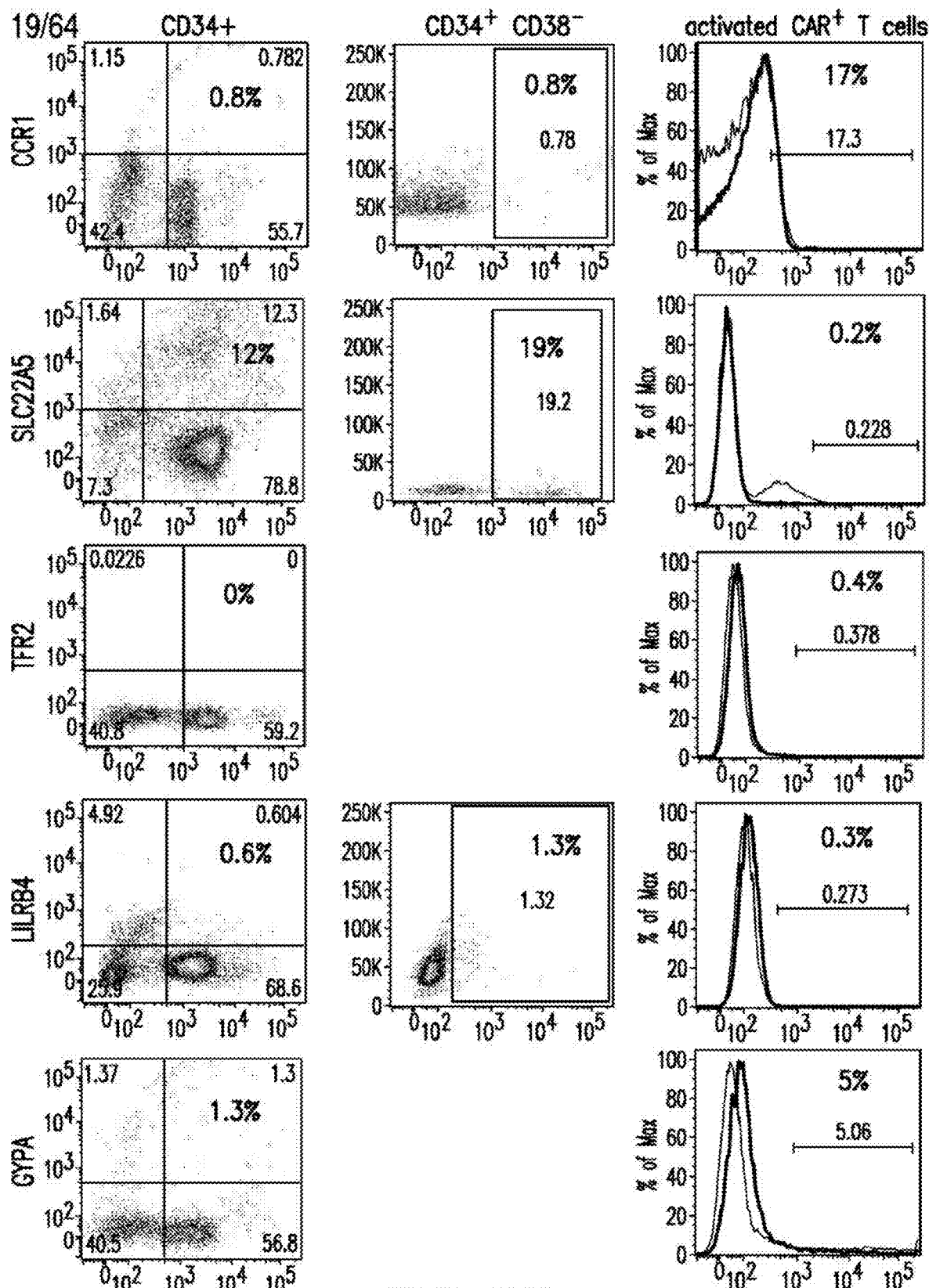
Figure 2C:
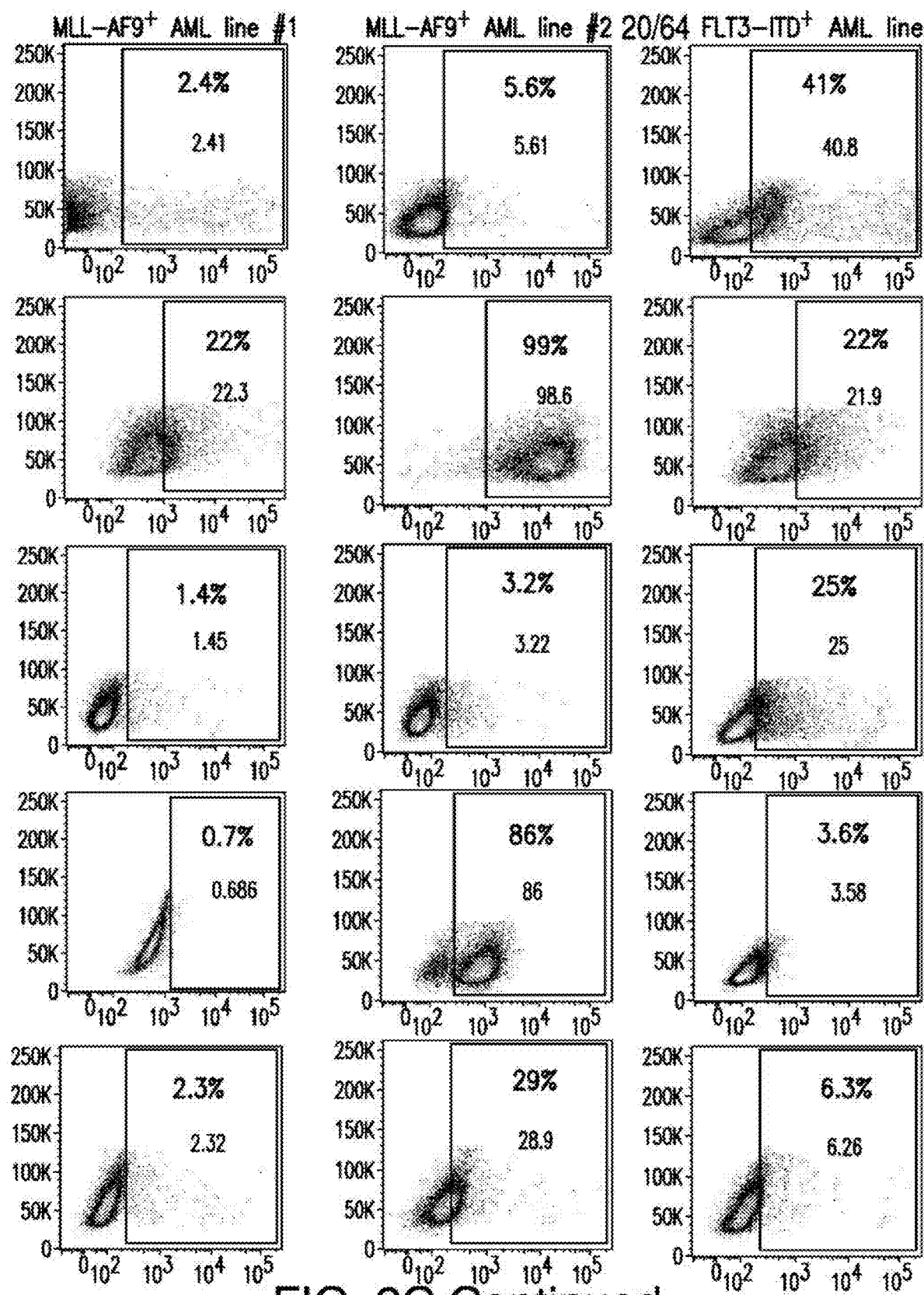
Figure 2C:
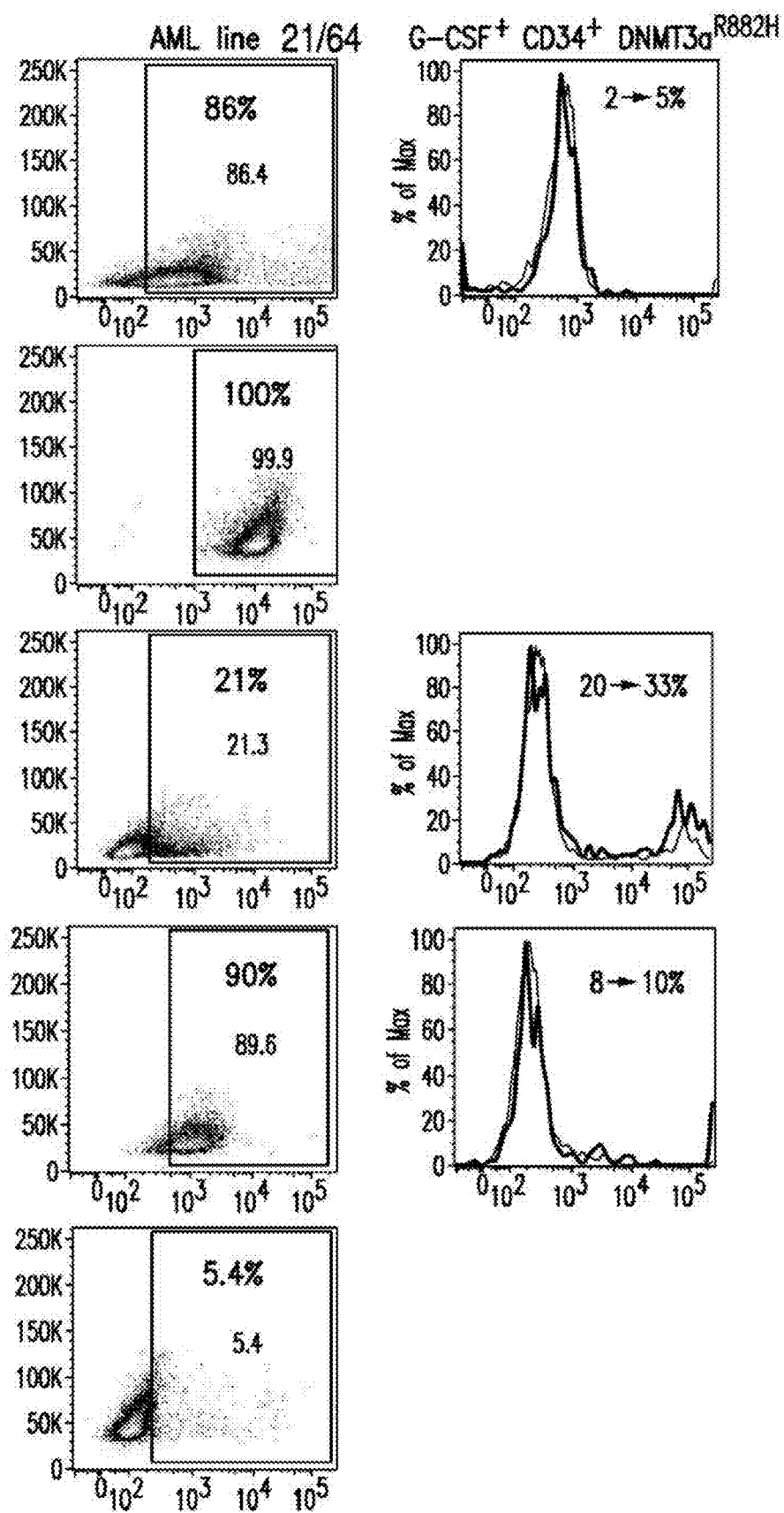
Figure 2C:
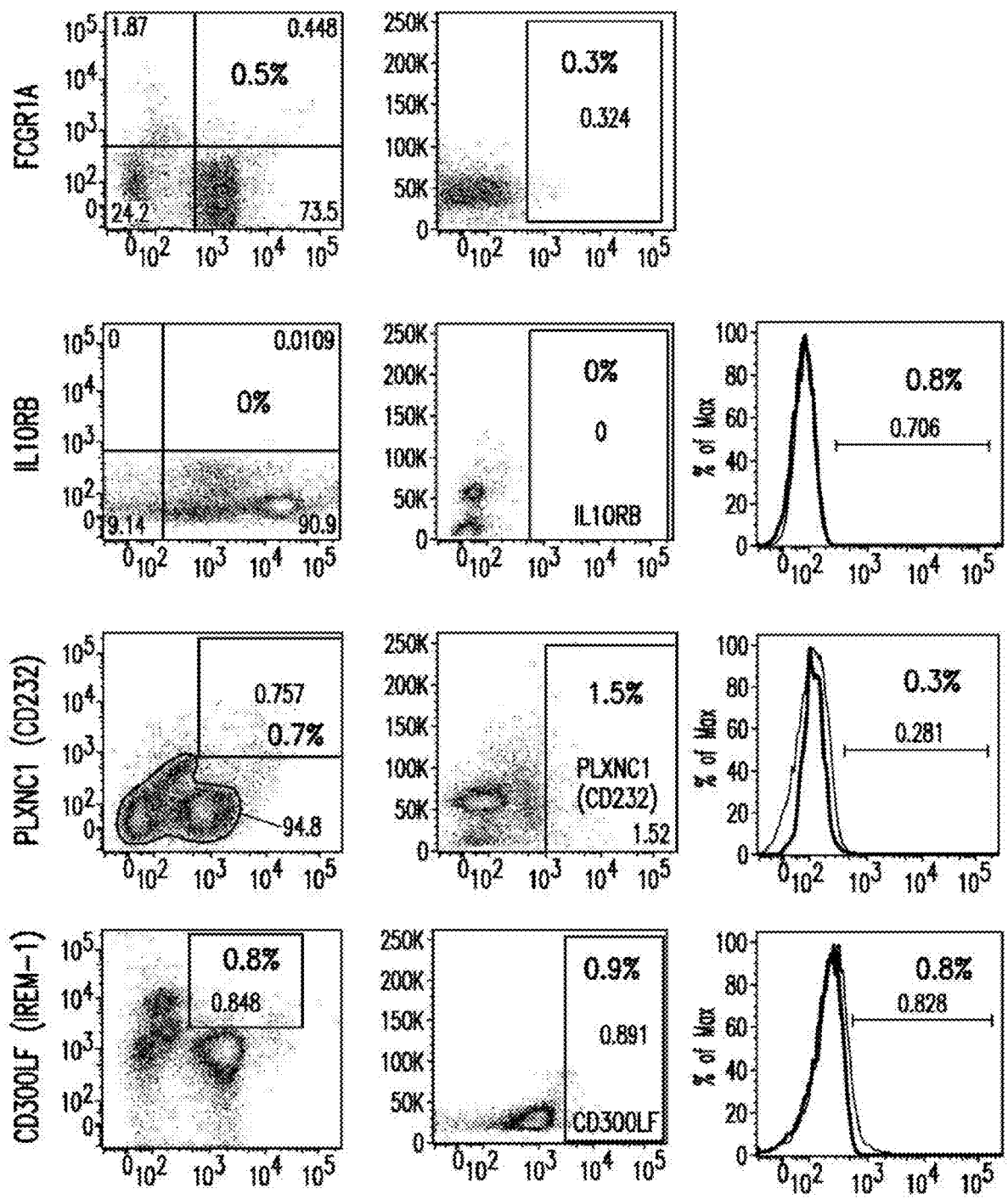
Figure 2C:
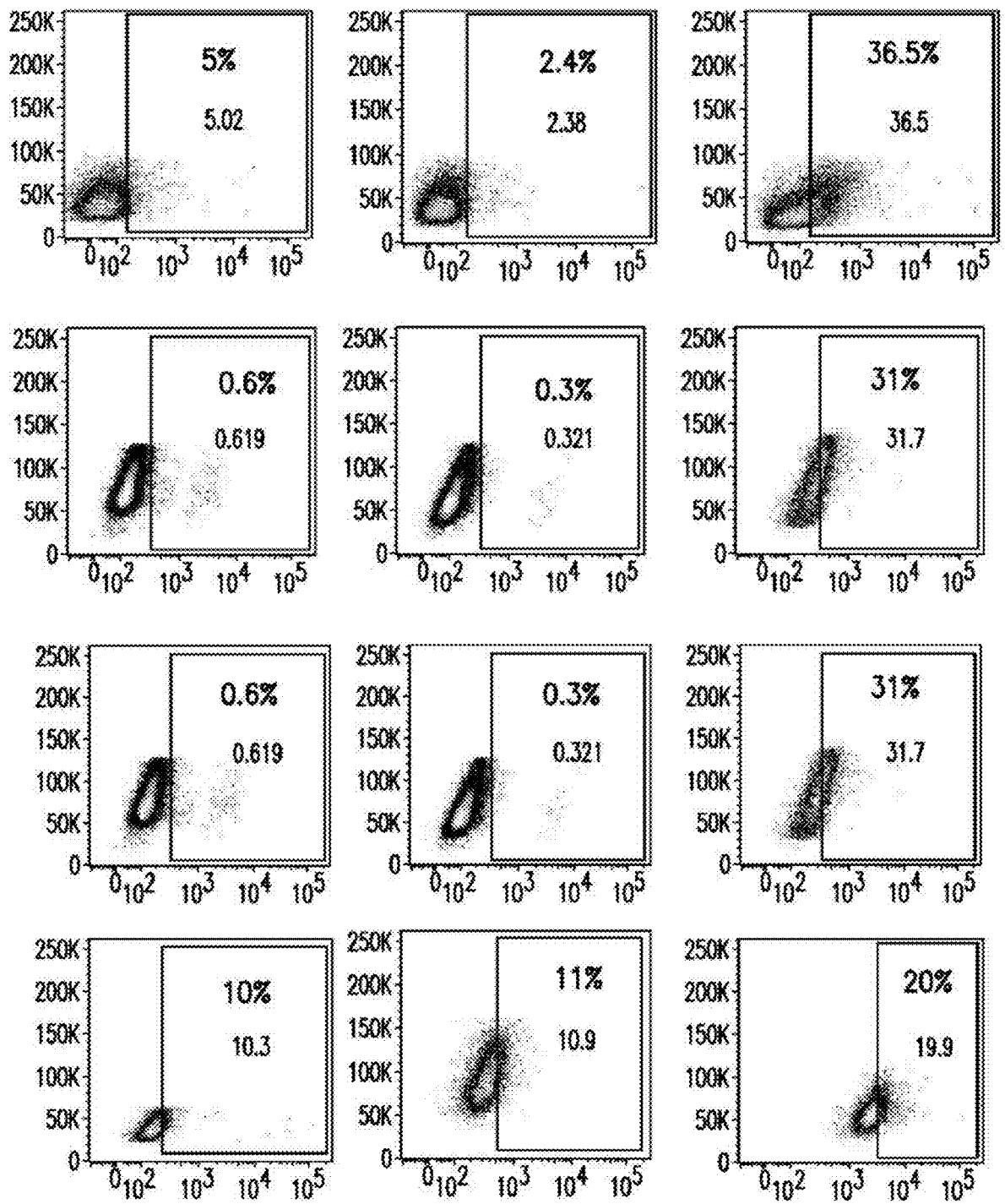
Figure 2C:
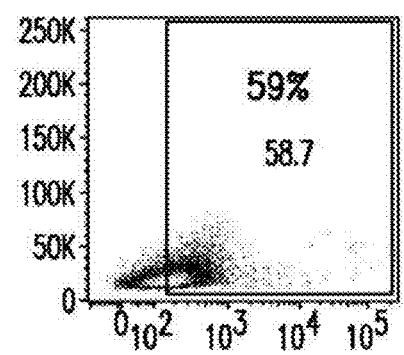
Figure 2C:
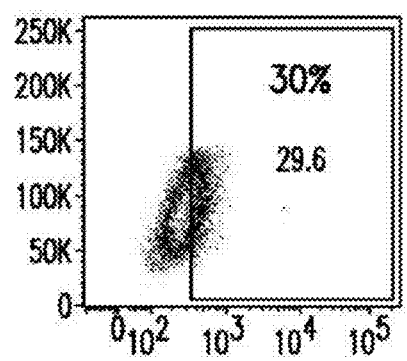
Figure 2C:
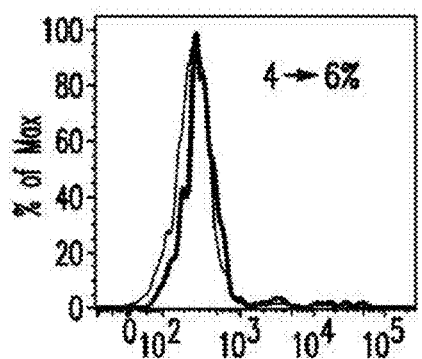
Figure 2C:
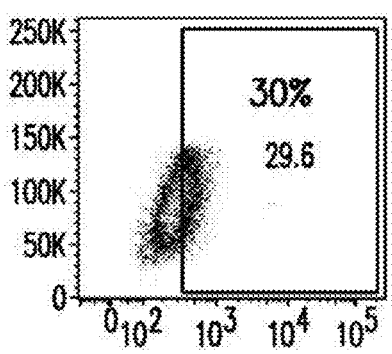
Figure 2C:
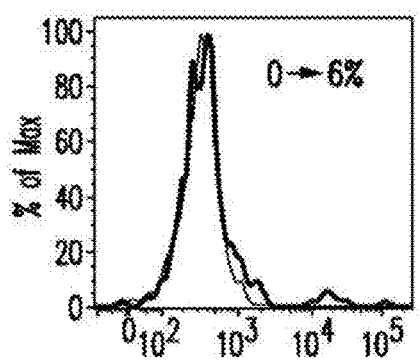
Figure 2C:
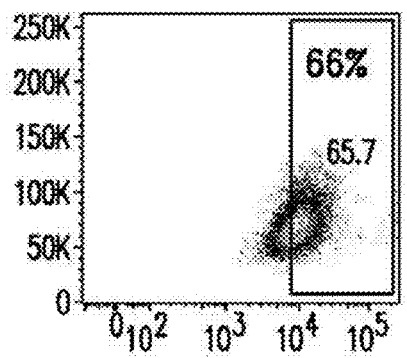
Figure 2C:
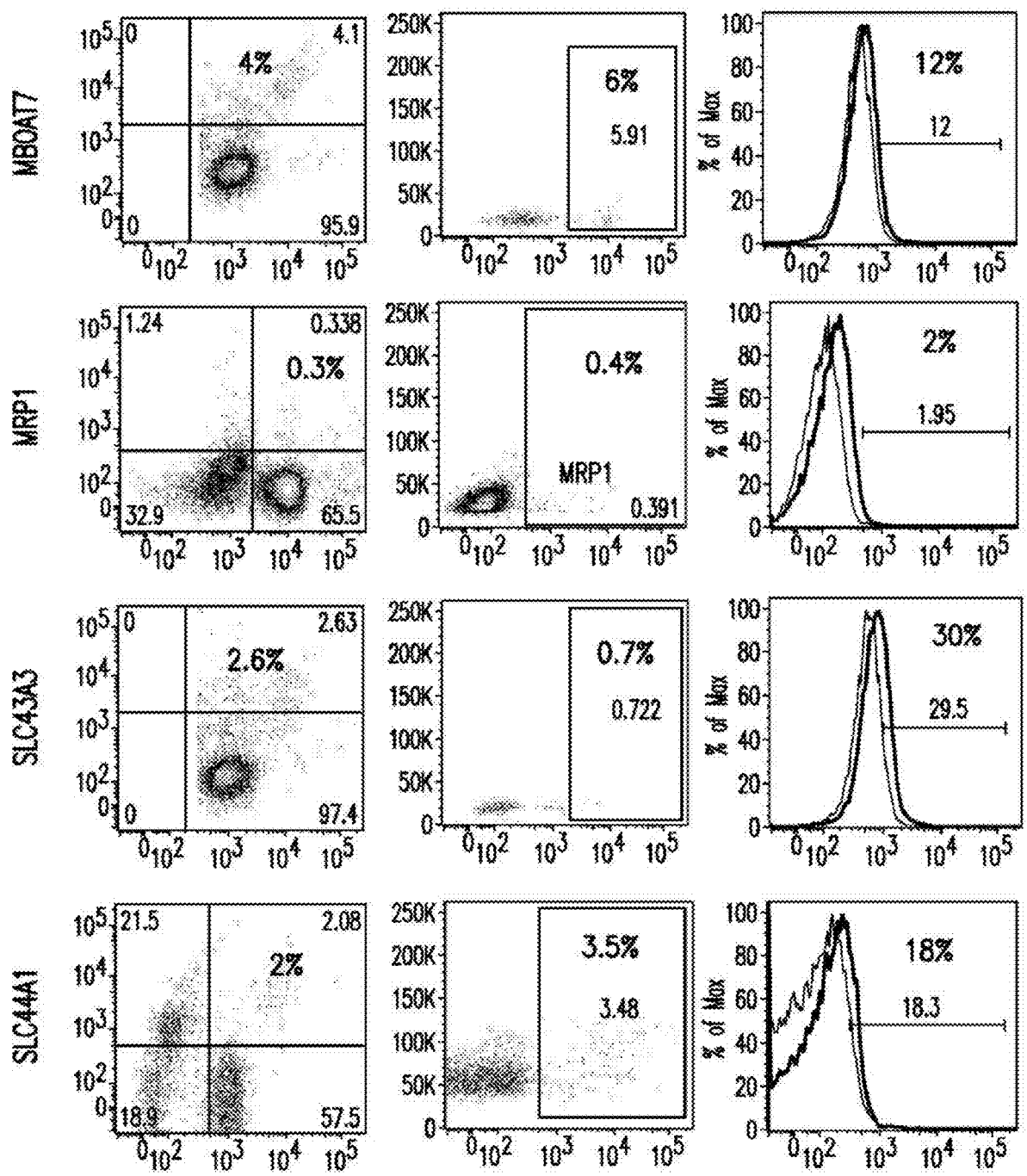
Figure 2C:
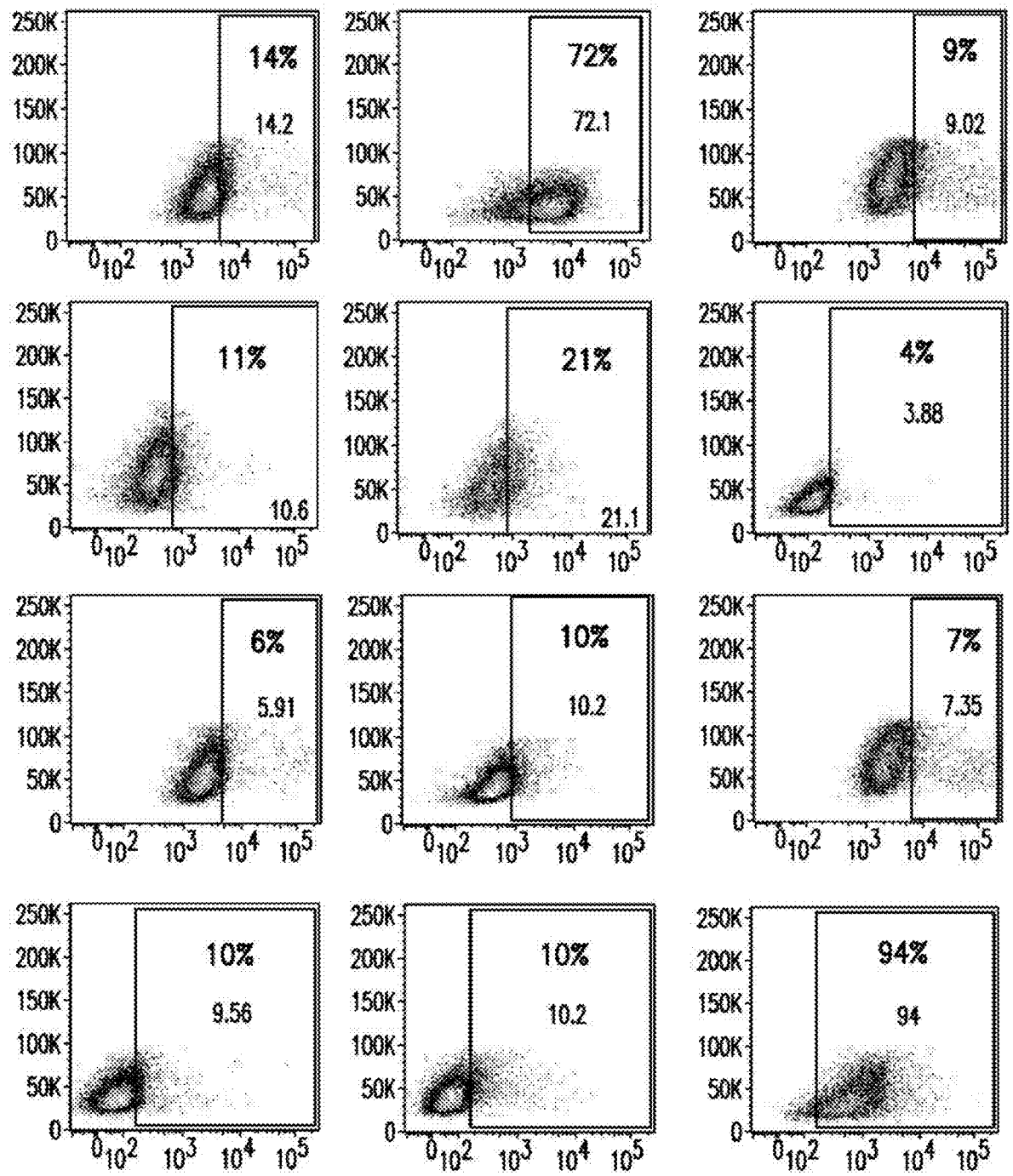
Figure 2C:
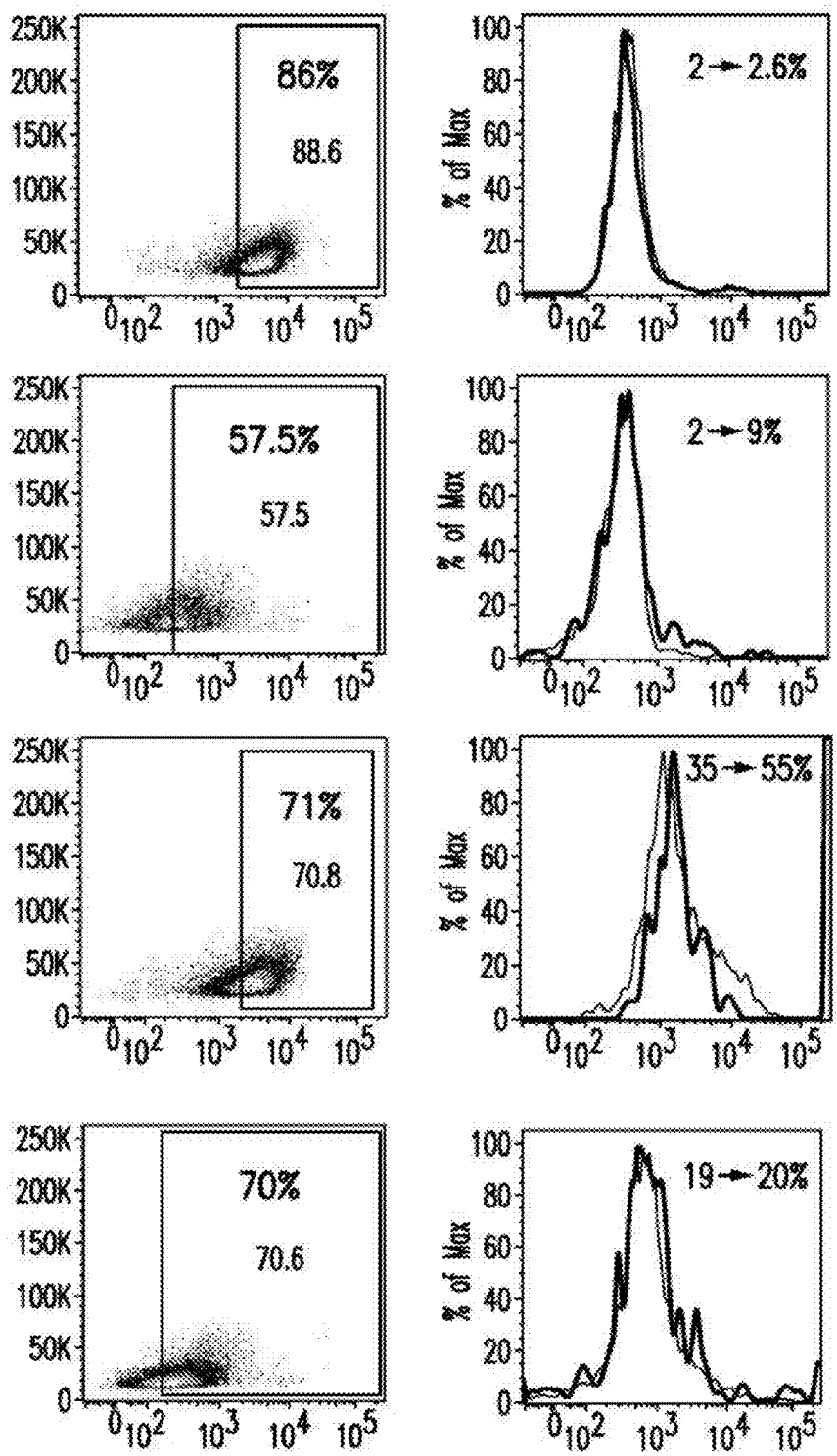

FIG. 2C shows 13 candidates: CCR1, SLC22A5, TFR2, LILRB4, GYPA, FCGR1A, IL10RB, PLXNC1, CD300LF, MBOAT7, MRP1, SLC43A3, SLC44A1. These antigens share a non-homogenous expression in all AML cells.

Figure 2D:
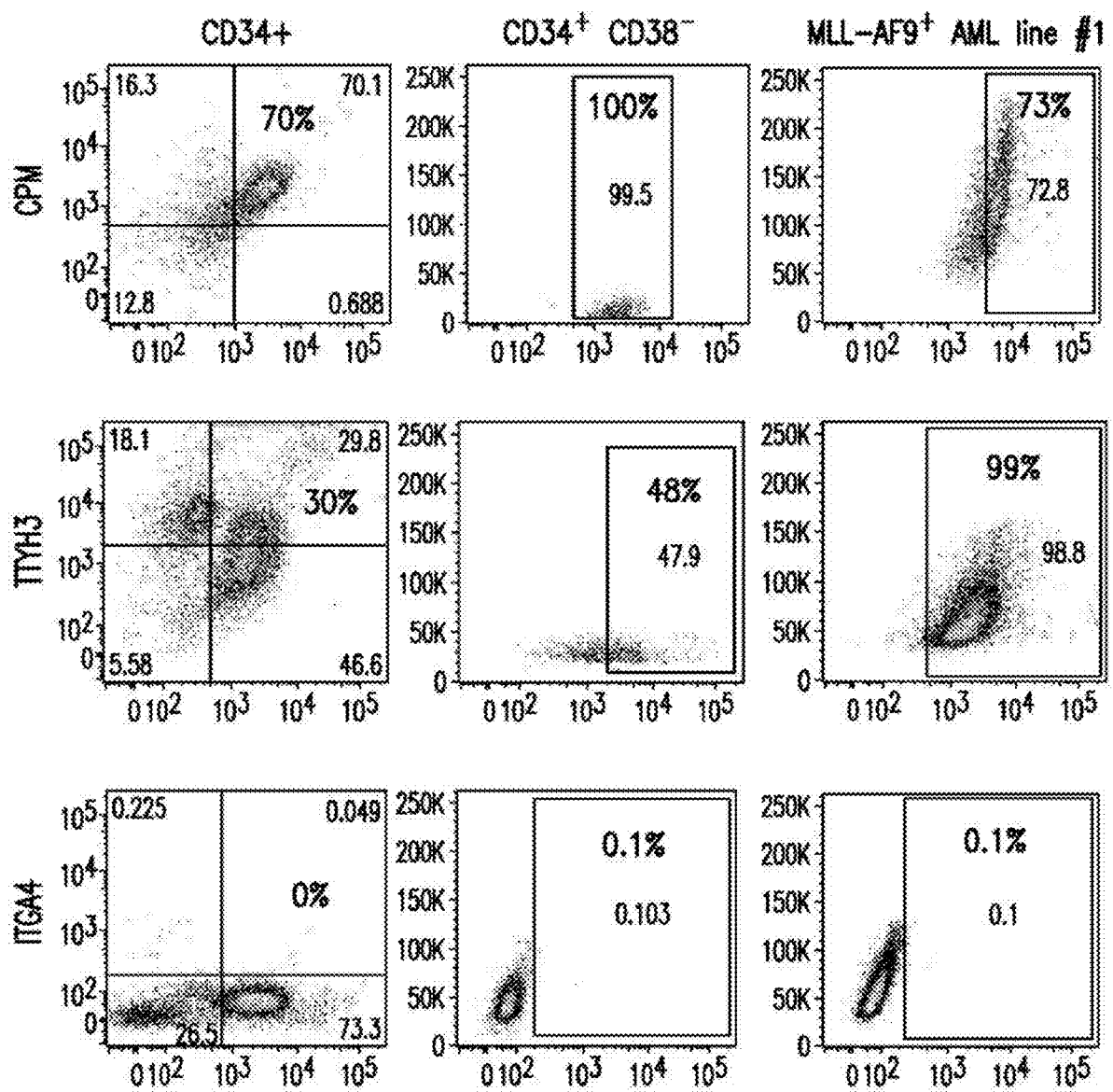
Figure 2D:
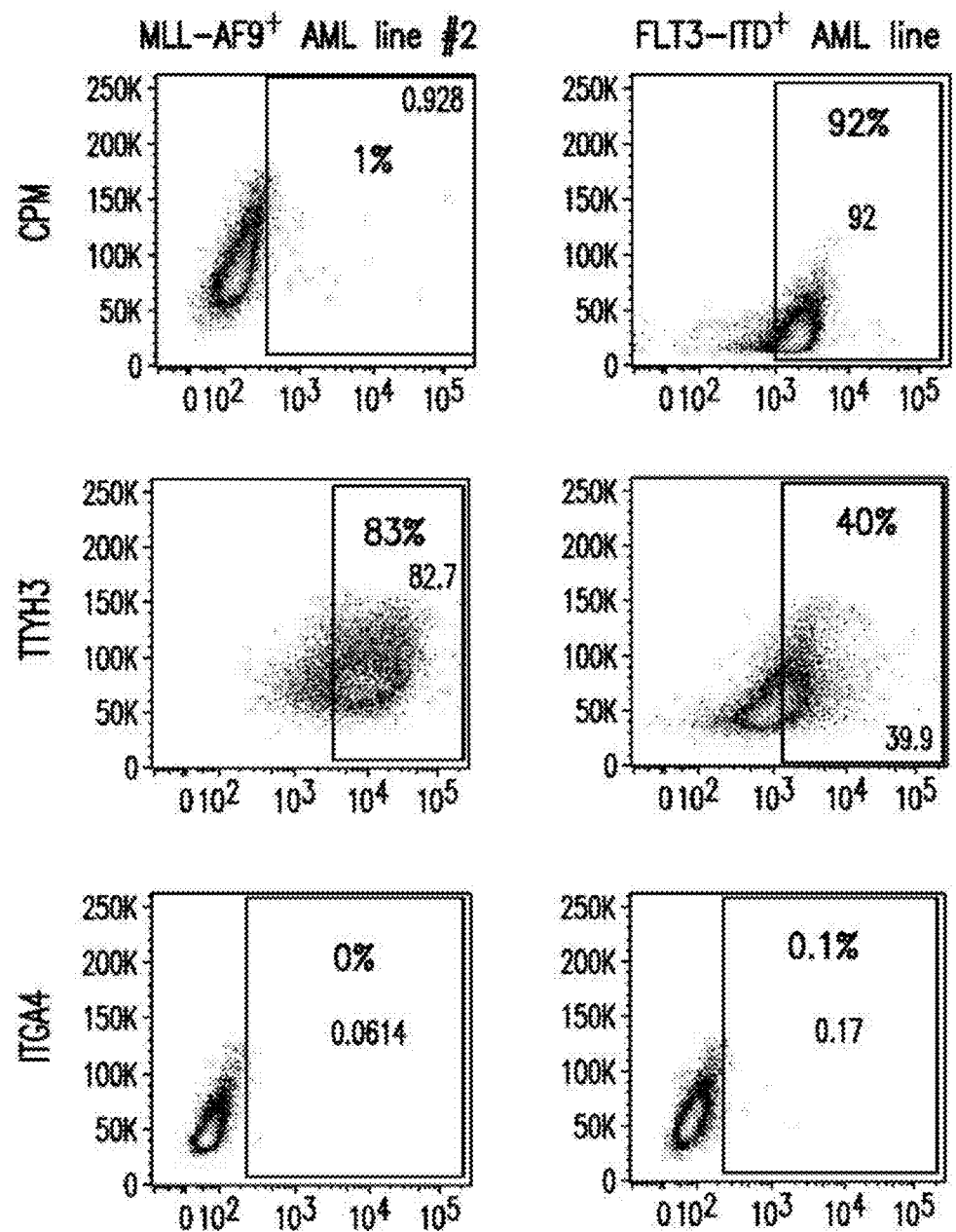
Figure 2D:
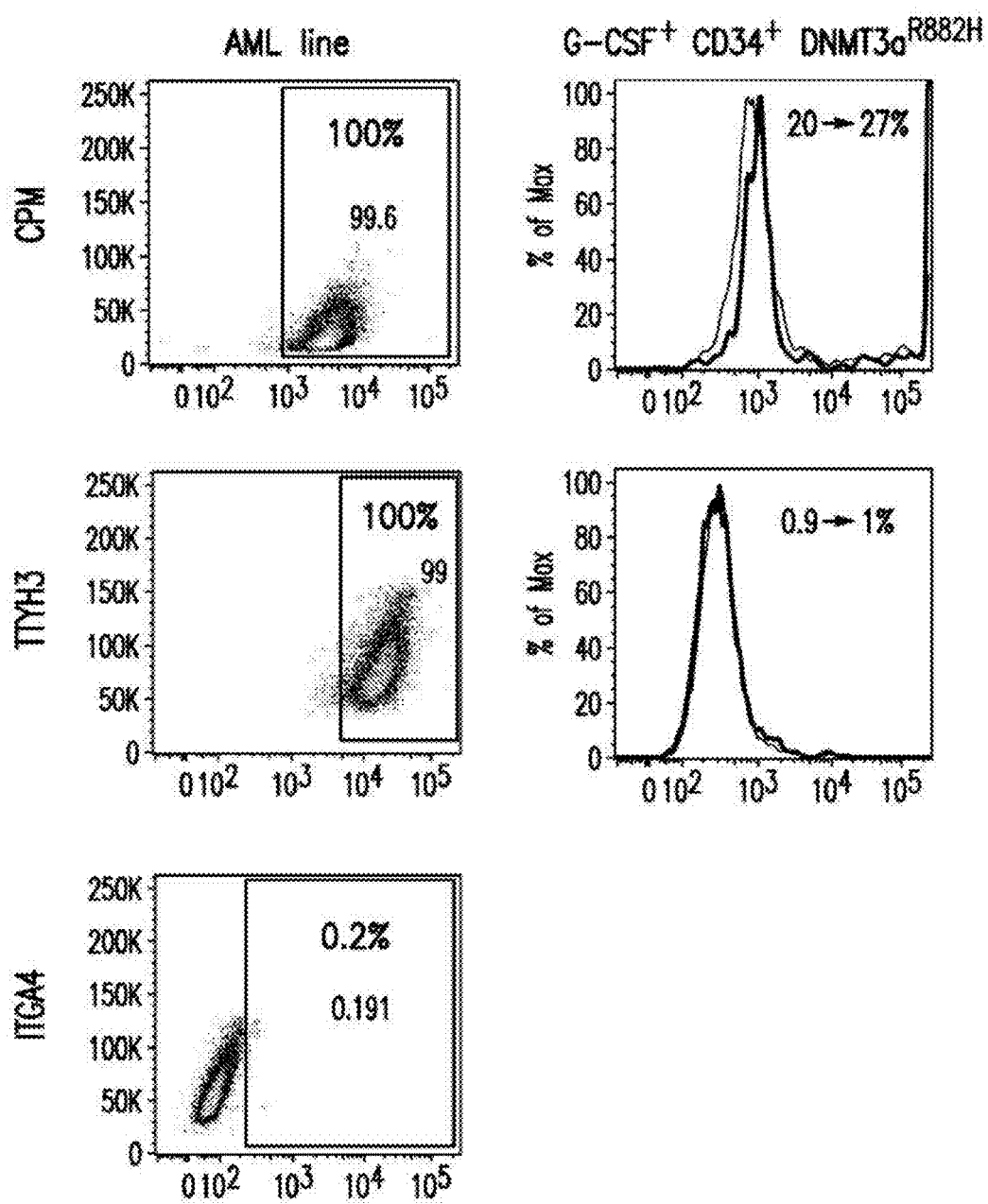
Figure 2D:
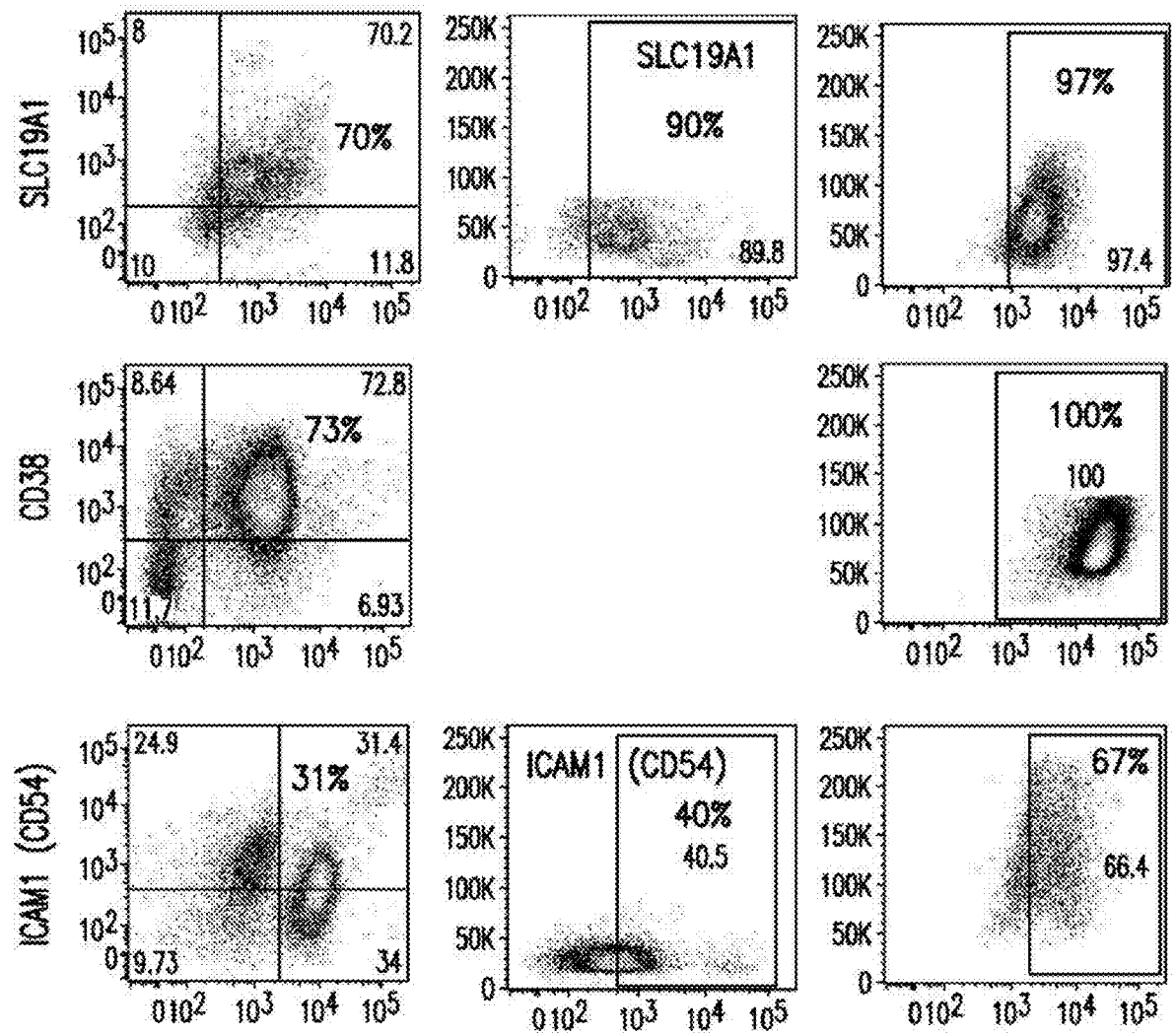
Figure 2D:
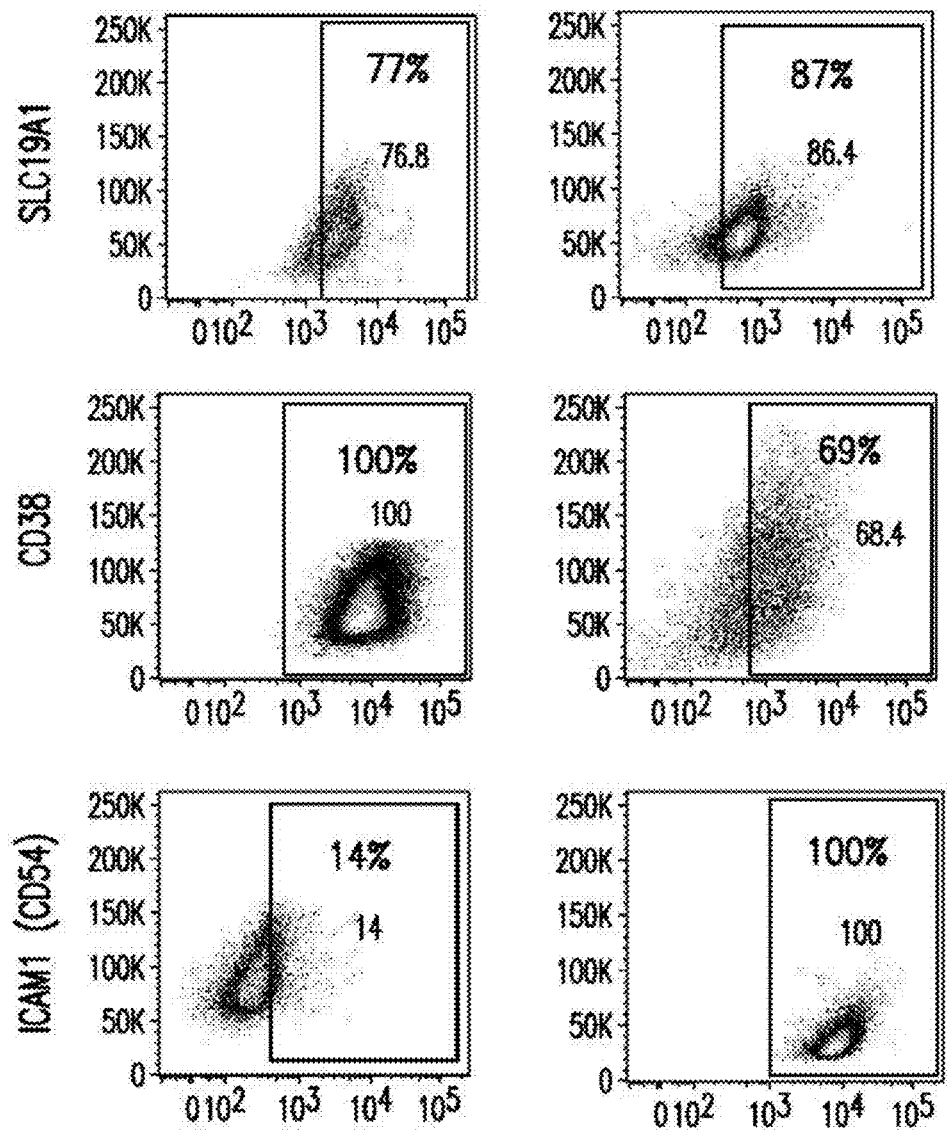
Figure 2D:
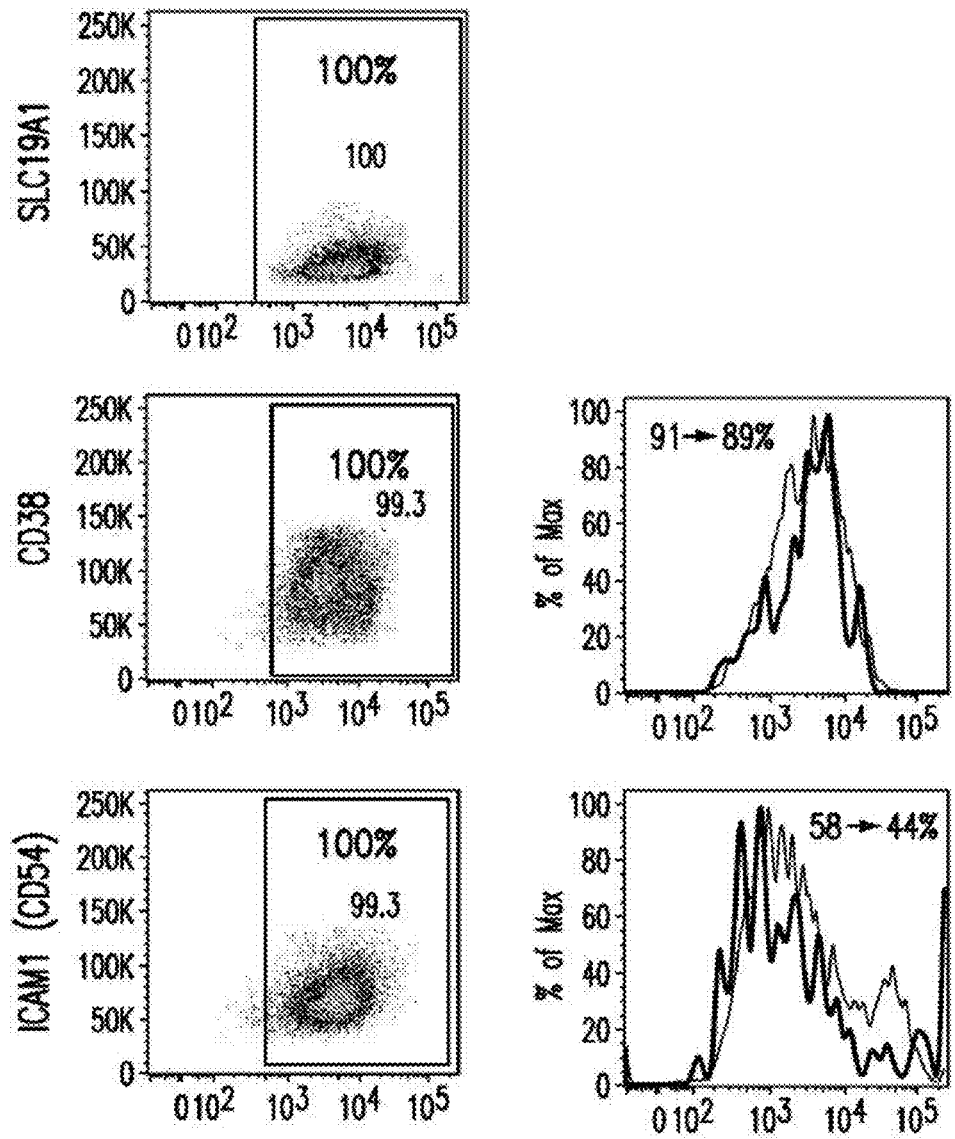
Figure 2E:
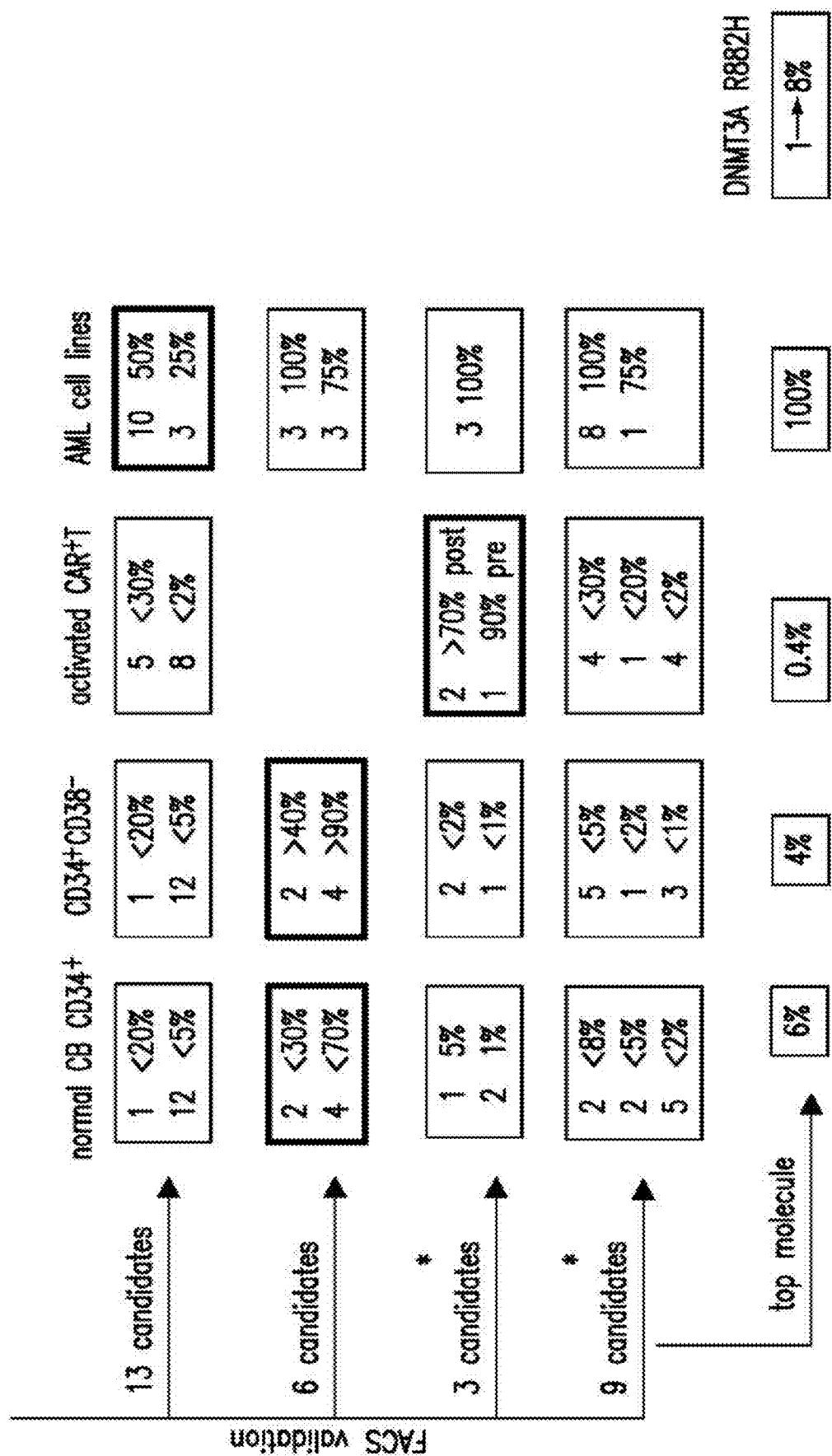

FIG. 2D shows 6 candidates: CPM, TTYH3, ITGA4, SLC19A1, CD38, ICAM1. These antigens share high expression in normal HSCs.

Figure 3B:
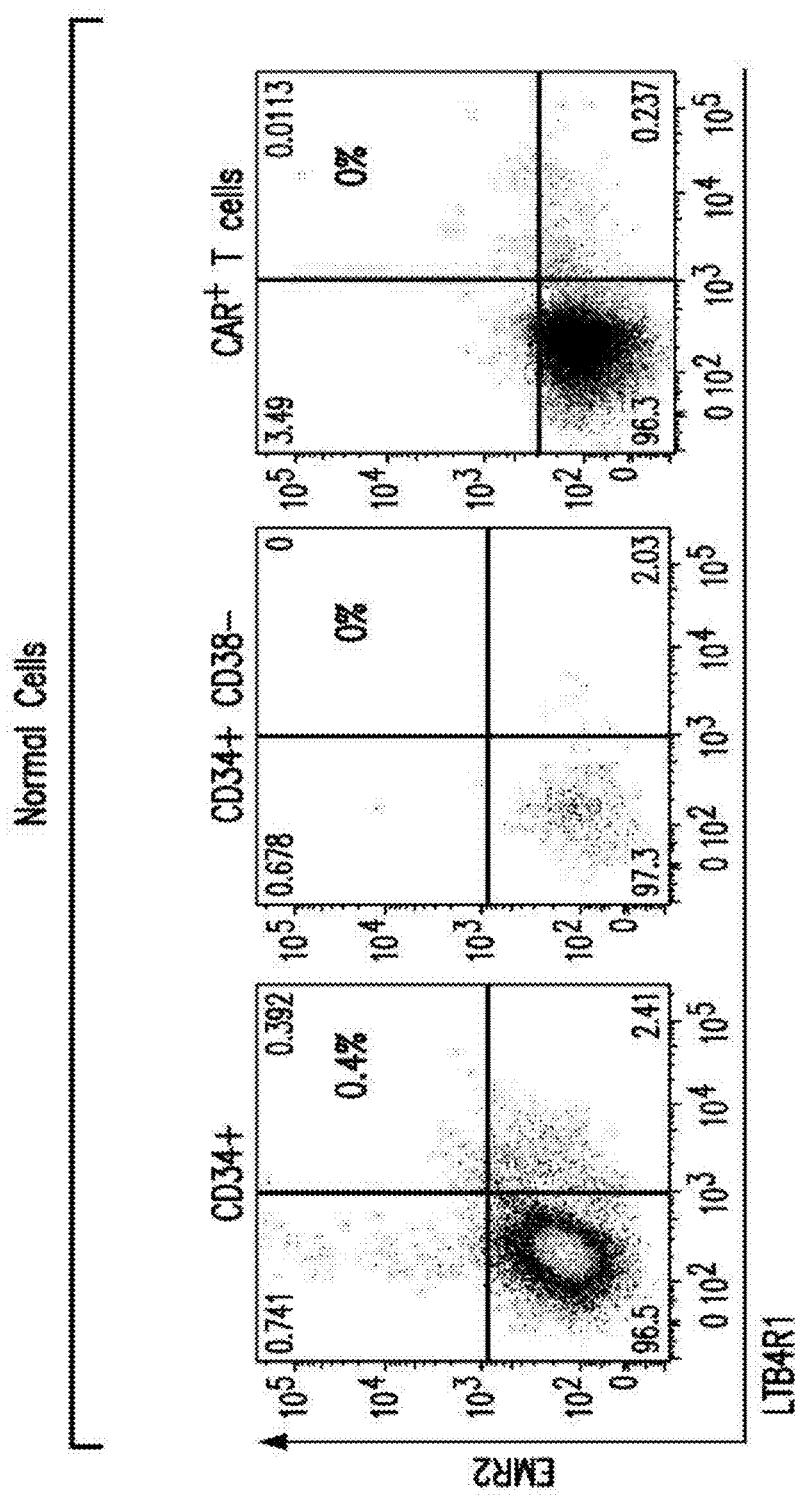
Figure 3B:
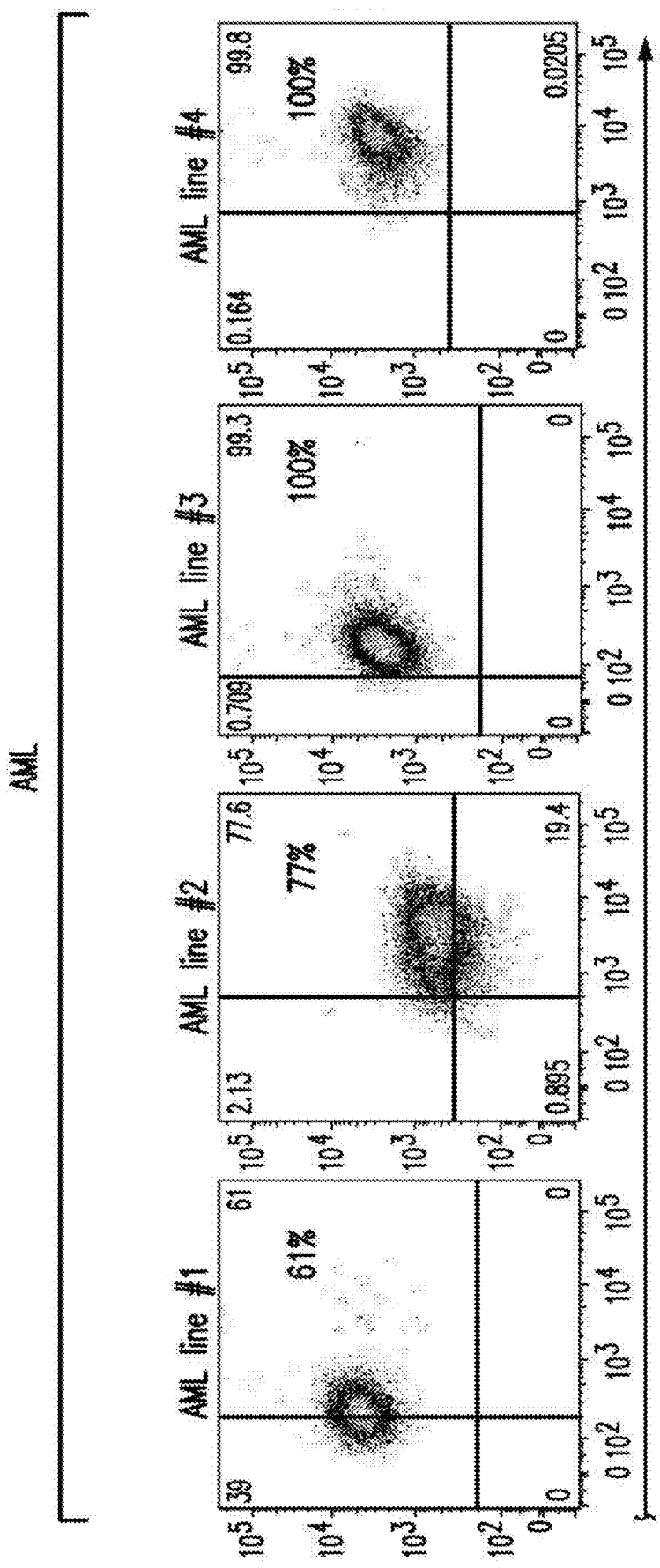
Figure 4:
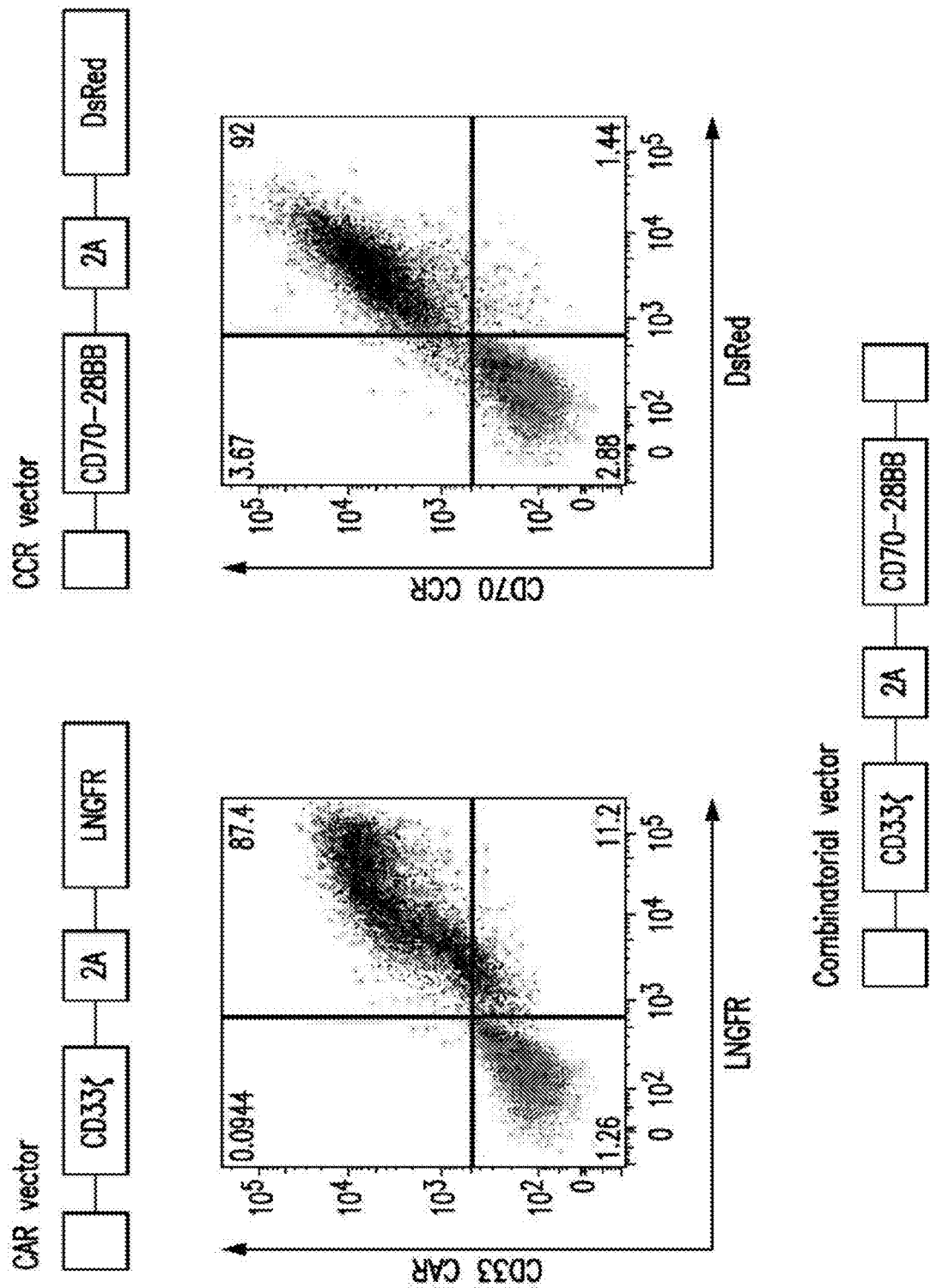
FIG. 4 depicts the combinatorial approach. Using CD70-CCR and CD33-CAR as example, the figure illustrates the vector design, the expression in T cells by flow-cytometry and the preliminary data on AML cells by the cytotoxic T lymphocyte (CTL) assay.

The top 11 antigens were used to screen for combanatorial CAR targets as discussed above, which yeilded 55 pairs of suitable targets (FIG. 3A). FIG. 3B shows the flow cytometry results verifying expression of LTB4R1 and EMR2, one pair of the 55 pairs of targets, in normal and malignant cells. FIG. 4 depict the combinatorial approach. Using CD70-CCR and CD33-CAR as example, the CAR and CCR can be constructed in separate vector/cassette (the upper two schematics), or in a bicistronic cassette (the bottom schematic, with CD33 CAR and CD70 CCR linked by a 2A peptide). The expression of the CD33 CAR and CD70 CCR in T cells and the cytotoxic T lymphocyte (CTL) assay in AML cells are also shown in FIG. 4.

Information on top single targets (also included in the combinatorial study) is provided below. They both belong to the family of G protein-coupled receptors (GPCRs). GPCRs represent the largest family of membrane receptors with an estimated number of 800 members in human. Several GPCRs are critical for cell proliferation and survival and can be aberrantly expressed in cancer cells (O'Hayre et al., 2014). In AML, for instance CXCR4 overexpression has been associated with poor outcome (Konoplev et al., 2007). RNA-seq analysis of GPCRs in 148 AML samples vs normal hematopoietic cells demonstrated that the most highly expressed GPCRs in AML cells are in decreasing order: CXCR4, CD97, PTGER4, GPR183, PTGER2, S1PR4, FPR1, EMR2, C3AR1, LTB4R, TPRA1, C5AR1, LPAR2, LTB4R2 and GPR107 (Maiga et al., 2016). Chemokine receptors found to be overexpressed in AML specimens such as CCR1 have a crucial role in the pathogenesis of myeloma-associated bone disease and CCX721, a selective CCR1 inhibitor, improves osteolytic bone lesions in a preclinical mouse model of this disease (Dairaghi et al., 2012). This suggests that these surface receptors are potential novel therapeutic targets in AML.

Leukotriene B4 (LTB4), an eicosanoid derivative of arachidonic acid metabolism produced by the sequential action of 5-lipoxygenase and leukotriene A4-hydrolase, is a leukocyte chemoattractant (Samuelsson et al., 1987). LTB4 signals through two G protein-coupled seven-transmembrane domain receptors, LTB4 receptor (BLT1) and BLT2, the high- and low-affinity receptors, respectively (Yokomizo et al., 1997; Yokomizo et al., 2000). BLT1 is a mediator of inflammation (Kim et al., 2006). In sharp contrast to BLT2, which is expressed ubiquitously, BLT1 is predominantly expressed in granulocytes. Yokota et al. used a GM-CSF-based tumor vaccine setting in BALB/c leukemia model and showed better primary and recall immune responses in the BLT1−/− mice (Yokota et al., 2012). In human promyelocytic leukemia cell lines (HL60), the expression of BLT1 during neutrophilic differentiation is markedly increased by stimulation with retinoic acid (RA) (Obinata et al., 2003). An enhancer element, termed AE-Blex, is involved in the facilitation of BLT1 expression in leukocytes. AE-BLex contains 2 recognition sites for AML1 (aka Runx1), both of which are required for the enhancer function. The histone acetylation and chromatin remodeling of this region are facilitated during the neutrophilic differentiation of leukemia cells, providing access for AML1 and other transcription factors (Hashidate et al., 2010). Sp1 site is the essential element of the BLT1 promoter (Kato et al., 2000). Ohler et al identified LTB4R as a top gene (out of 2612 differentially expressed genes) able to discriminate blastic crisis from chronic phase CML by applying a probabilistic method called Bayesian model averaging (BMA) to a large CML patient microarray dataset (Oehler et al., 2009).

In addition to mediating the chemotactic responses to LTB4 in leukocytes, the LTB4 receptor has been shown to act as a co-receptor mediating entry of HIV-1 into CD4-positive cells (Martin et al., 1999; Owman et al., 1998). Thus, a CAR targeting this receptor may be utilized also for this purpose. LTB4R was detected on peripheral blood monocytes, lymphocytes and granulocytes by flow-cytometry (Dasari et al., 2000). Human BLT1 protein expression has been confirmed by flow cytometry using anti-BLT1 monoclonal antibodies on CD15+ peripheral blood granulocytes, and on HL-60 cells when differentiated into neutrophil-like cells by treatment with DMSO (Pettersson et al., 2000). The human high-affinity LTB4 receptor was cloned by Yokomizo et al in 1997 from retinoic acid-differentiated HL-60 cells using a subtraction strategy (Yokomizo et al., 1997). BLT1 binds to LTB4 with significantly greater specificity than BLT2. Multiple LTB4 receptor anatgonists have been developed, including CP-105,696 (Showell et al., 1995), CP-195,543 (Showell et al., 1998), U-75302 (Lawson et al., 1989), ZK158252 and ONO-4057 (Kishikawa et al., 1992). Some of these agents selectively antagonize BLT1, whereas others antagonize both receptors. Leukocyte BLT1 expression is upregulated in inflammation. Specific inflammatory stimuli responsible for the induction of BLT1 expression have not yet been fully characterized, but to date both IFNgamma and glucocorticoids have been shown to induce BLT1 expression.

EMR2 is a member of the epidermal growth factor (EGF)-TM7 family of proteins. EMR2, EMR1 (EGF-like molecule containing mucin-like hormone receptor 1) (Baud et al., 1995), F4/80 (the probable mouse homologue of human EMR1) (Lin et al., 1997) and CD97 (Hamann et al., 1995) constitute the class B GPCR subfamily and are predominantly expressed on leukocytes, suggesting a role in the immune system by interacting with either cell surface proteins or extracellular matrix proteins, possibly leading to signal transduction via the 7TM domain. These molecules possess N-terminal EGF-like domains coupled to a seven-span transmembrane (7TM) moiety via a mucin-like spacer domain. EMR2 shares strikingly similar molecular characteristics with CD97. It maps closely to CD97 on human chromosome 19p13.1 region (contains 20 exons), and contains a total of five tandem highly homologous EGF-like domains, indicating that both genes are the products of a gene duplication event. The EGF domains of EMR2 are almost identical to those of CD97 with the sequence identity ranging from 95 to 100% in corresponding EGF domains. Of 236 amino acid residues in the five EGF domains of EMR2 and CD97, only 2 residues in domain 1, 1 residue in domain 2, and 3 residues in domain 3 are different. The high degree of identity in the EGF domains conserves the consensus amino acid sequences for the EGF domain calcium-binding site and for posttranslational beta-hydroxylation of aspartate/asparagine, which were identified in EGF domains 2-5 (Gray et al., 1996; Hamann et al., 1995). Such calcium-binding EGF domains, found in a broad spectrum of extracellular proteins have been shown to play an important role in protein-protein interactions involving cell adhesion, blood coagulation and receptor-ligand binding (Downing et al., 1996), including the interaction of CD97 and its cellular ligand CD55 (Hamann et al., 1998). Significant amino acid sequence homology between EMR2 and CD97 also extends to the spacer region (46% identity) and the 7TM region (45% identity). Multiple potential N- and O-glycosylation sites within the extracellular domain are found conserved as well. Monoclonal antibodies (mAbs) raised against the extracellular spacer domain of CD97 are able to differentiate these two proteins. Within the spacer region, a cysteine-rich motif of approximately 55 amino acids located immediately before the first TM segment was also recognized; this motif is characterized by four invariant cysteine residues and two conserved tryptophan residues and is found in other members of the EGF-TM7 family and family B GPCR-related proteins. The cysteine-rich motif, named GPS for GPCR proteolytic site, is believed to be involved in the proteolytic cleavage. In addition four consensus sequences for protein kinase C-mediated phosphorylation in intracellular loops 2 and 3 and the cytoplasmic tail were identified. Unlike CD97, which is ubiquitously expressed in most cell types, EMR2 expression is restricted to monocytes/macrophages and granulocytes. In addition, CD97 is rapidly up-regulated in activated T and B cells but similar up-regulation is not observed for EMR2 (Lin et al., 2000). EMR2 fails to interact with CD55, the cellular ligand for CD97 (Hamann et al., 1998) and may therefore have a unique function in the myeloid lineage (Lin et al., 2000). EMR2 protein is a cell surface molecule containing a long N-terminal extracellular region of 511 amino acids, a 7TM region of 248 amino acids and a cytoplasmic tail of 41 amino acids.

Alternative splicing has been found to occur predominantly at the 5'-end of the transcripts, potentially resulting in multiple protein isoforms that contain different numbers and/or combinations of EGF-like domains (Gray et al., 1996; Lin et al., 1997; McKnight and Gordon, 1996). Putative EMR2 protein isoforms containing five EGF domains (EGF 1-5), four EGF domains (EGF 1,2,3,5), three EGF domains (EGF 1,2,5), and two EGF domains (EGF 1,2) are predicted. A splice variant resulting from the by-pass of exon 12 predicted to encode a soluble EMR2 molecule. Possible ligand candidates include the regulators of complement activation, such as CD46, CD35, CD21 and C4-binding protein, all of which contain short consensus repeats similar to those found in CD55 (Liszewski et al., 1996).

CD70 is the membrane-bound ligand of the CD27 receptor, which belongs to the tumor necrosis factor receptor superfamily (Bowman et al., 1994; Hintzen et al., 1994). CD70 is expressed by DLBCL, follicular lymphoma, Hodgkin lymphoma (Lens et al., 1999), Waldenstrom macroglobulinemia, multiple myeloma, human T-lymphotropic virus type 1- (Baba et al., 2008), EBV-associated malignancies (Agathanggelou et al., 1995), renal cell carcinoma (Junker et al., 2005) and glioblastoma (Chahlavi et al., 2005). Physiologically, CD70 expression is transient and restricted to a subset of highly activated T, B, and dendritic cells. Targeting CD70-positive malignancies with CD70-specific monoclonal antibodies has shown promise in pre-clinical animal models (McEarchern et al., 2007; McEarchern et al., 2008) and Shaffer et al have targeted CD70 generating CD70-specific CAR, consisting of full-length CD27 as the antigen recognition domain fused to the intracellular domain of the CD3-zeta chain (Shaffer et al., 2011).

Generation of Human Genetic Models of Pre-Leukemic Stem Cells

In order to design a curative therapeutic strategy with CAR T cells, the top candidates in leukemic initiating cells are to be further validated. To this purpose, key epigenetic mutations in $CD34^+$ HSPCs, that were purified from cord blood, were retrovirally expressed (Perna et al., 2010). Pre-leukemic stem cells are genetically defined by the expression of initiating mutations such as DNMT3a (Shlush et al., 2014b). Several mutant oncogenes including DNMT3aR882H were cloned into MSCV retroviral vectors carrying GFP that served as selection marker of the transduced cells. Most of the oncogenic mutations used herein also characterize specific phenotypic subsets of AML, behave as dominant-negative on the wild type allele and associate with poor prognostic outcome, thus representing the types of patients that will most likely benefit from immune mediated therapies.

The DNA (cytosine-5)-methyltransferase 3A (DNMT3A) is a member of the DNA methyltransferase family and one of the most frequently mutated genes in AML, occurring in up to 36% of cytogenetically normal AML (CN-AML) patients (Marcucci et al., 2012). Despite the high frequency of mutations in DNMT3A in AML and their consistent association with adverse prognosis, the targets of DNMT3A mutations, which might contribute to leukemogenesis have not been definitively delineated. A recurrent heterozygous mutation at residue Arginine 882 accounts for 40% to 60% of DNMT3A mutations (Ley et al., 2010; Yan et al., 2011). In AML cells, R882 mutations always occur with retention of the wild-type allele and it was showed that the R882 mutant serves as a dominant-negative regulator of wild-type DNMT3A (Russler-Germain et al., 2014). Methylation studies using the HELP (HpaII tiny fragment enrichment by ligation-mediated polymerase chain reaction) assay have not thus far resolved a methylation-specific signature characteristic of DNMT3A mutant AML samples compared with DNMT3A wild-type samples. DNMT3a mutation is an early event in leukemogenesis. In fact, purified HSCs, progenitor and mature cell fractions from the blood of AML patients contain recurrent DNMT3A mutations at high allele frequency and DNMT3Amut-bearing HSCs show a multilineage repopulation advantage over non-mutated HSCs in xenografts. These finding established the DNMT3amut-expressing HSCs are pre-leukemic HSCs. Pre-leukemic HSCs were found in remission samples, indicating that they survive chemotherapy, leading to a clonally expanded pool of pre-leukemic HSCs from which AML evolves (Shlush et al., 2014a). Currently, no specific therapies targeted toward DNMT3A have been developed to date.

Rearrangements of the Mixed-Lineage Leukemia (MLL) gene are found in >70% of infant leukemia, ~10% of adult AML, and many cases of secondary acute leukemias. The presence of an MLL rearrangement generally confers a poor prognosis. The most common fusion protein MLLAF9 induces the inappropriate expression of homeotic (Hox) genes, which, during normal hematopoiesis, are maintained by wild-type MLL. Studies in mice have demonstrated that MLL-fusions can confer self-renewal activity to committed myeloid progenitors (Cozzio et al., 2003; So et al., 2003).

The AML1-ETO fusion transcription factor is generated by the t(8;21) translocation, which is present in approximately 4%-12% of adult and 12%-30% of pediatric AML patients. Both human and mouse models of AML have demonstrated that AML1-ETO is insufficient for leukemogenesis in the absence of secondary events. Although AML patients harboring the t(8;21) translocation are generally given a good prognosis and the majority achieve complete remission, the 5-year survival is only ~50%, and the presence of a c-kit mutation decreases the prognosis significantly. The identification of novel therapeutic targets in t(8;21) positive AML may lead to treatment options that improve patient survival.

The t(15;17)(q24;q21), generating a PML-RARA fusion gene, is the hallmark of acute promyelocytic leukemia (APL). The resulting fusion protein retains domains of the RARA protein allowing binding to retinoic acid response elements (RARE) and dimerization with the retinoid X receptor protein (RXRA). They participate in protein-protein interactions, associating with RXRA to form hetero-oligomeric complexes that can bind to RARE. They have a dominant-negative effect on wild-type RARA/RXRA transcriptional activity. Moreover, RARA fusion proteins can homodimerize, conferring the ability to regulate an expanded repertoire of genes normally not affected by RARA. RARA fusion proteins behave as potent transcriptional repressors of retinoic acid signaling, inducing a differentiation blockage at the promyelocyte stage, which can be overcome with therapeutic doses of ATRA or arsenic trioxide. However, resistance to these two drugs is a major problem, which necessitates development of new therapies.

Figure 5A:
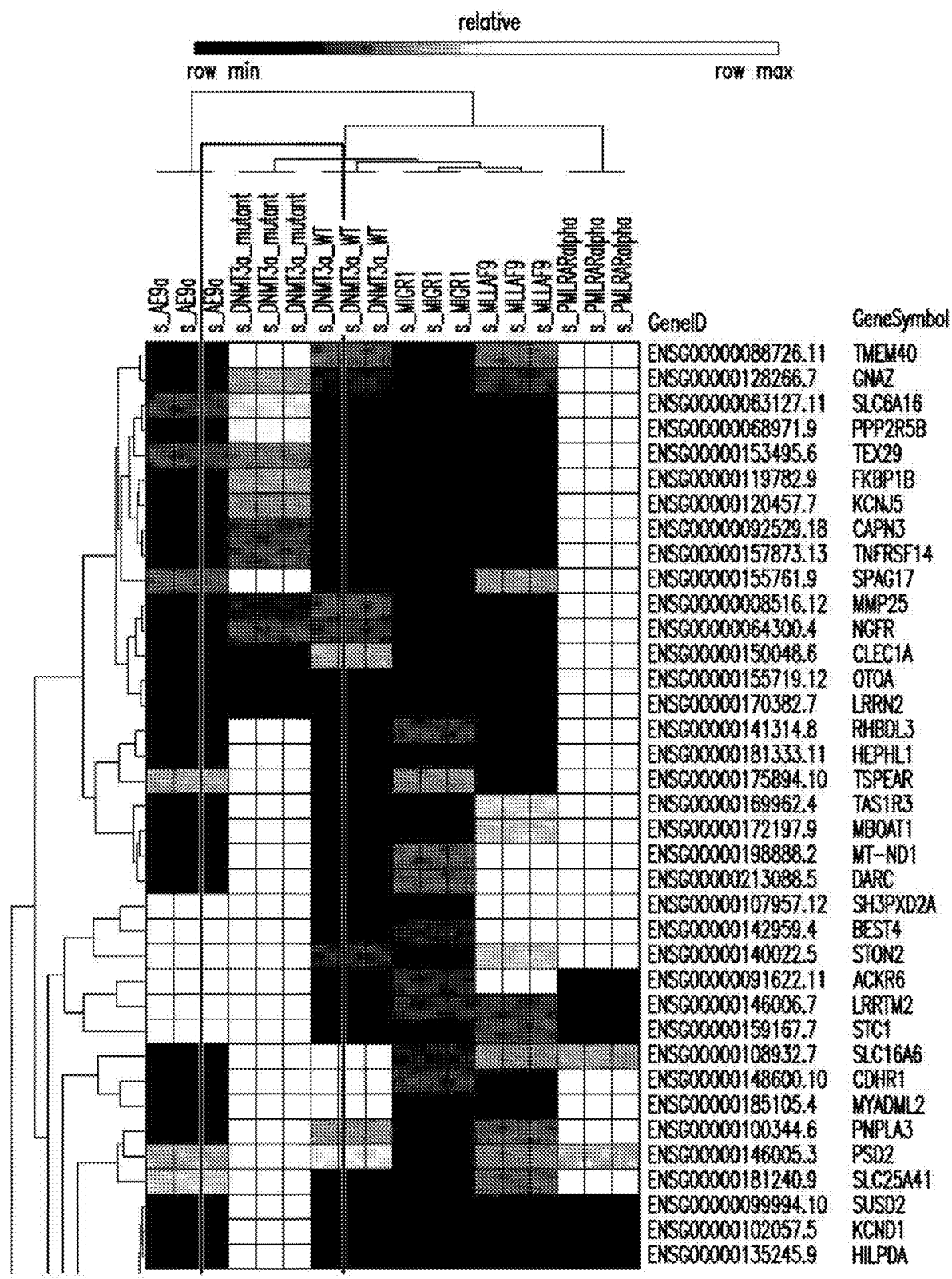
FIGS. 5A-5B depict the RNA-sequencing results from pre-leukemic stem cells expressing indicated mutant genes and wildtype controls.

Primary CD34+ HSCs isolated from cord blood were retrovirally infected, and a "myeloid priming" was provided in liquid cultures supporting the myeloid differentiation. The GFP+ cells were sorted by FACS and used for flow-cytometry, Mass-Spect and RNA-seq analyses. Cell surface genes listed in FIG. 5A have at least 2-fold increase in the DNMT3a R882H mutant cells compared to control cells (MIGR1). Cell surface genes listed in FIG. 5B have at least 2-fold increase in the MLLAF9 mutant cells compared to control cells (MIGR1). Those genes (also listed in Table 2) can be considered for CAR target in AML therapy.

Conclusions

CAR therapy is a novel approach to cancer immunotherapy that has demonstrated great potential against B-cell malignancies and may soon be approved for relapsed, chemo-refractory ALL. One may anticipate a similar outcome for AML if suitable targets are identified.

Through an innovative multi-tiered platform integrating surface-specific proteomics and transcriptomics in several malignant and normal cell subsets, 32 candidates, 11 top candidates, 4 candidates for single CAR strategies and 55 pairs, 3 top pairs of targets for combinatorial strategies were identified. Furthermore, pre-leukemic stem cells model indicated an additional set of surface genes suitable for CAR therapy Materials and Methods Flow-Cytometry We used the following antibodies to define antigen expression by flow-cytometry:
  CD70-PE cat. 355104 (Biolegend);
  EMR2-FITC cat. 130-104-654; EMR2-APC cat. 130-104-656 (Milteny);
  LTB4R1-AF700 cat. FAB099N; LTB4R1-AF405 cat. FAB099V; LTB4R1-FITC cat. NB100-64832 (Novus Biologicals); LTB4R1-PE cat. FAB099P (R&D)
  PIEZO1-AF488 cat. NBP11-78537;
  CD33-APC cat. 551378 (BD Pharmingen);
  ENG-APC cat. MHCD10505 (Invitrogen);
  MYADM cat. NBP2-24494SS (Novus)
  ITGA5 (CD49e)-APC cat. 328011 (Biolegend)
  SLC19A1-APC cat. FAB8450A (R&D)
  ILT3-APC (LILRB4) cat. FAB24251A (R&D)
  CCR1-PE cat. 130-100-368 (Milteniy)
  ITGA4-APC cat. FAB2450A (R&D); CD49d-PE cat. 130-099-691 (Miltenyi)
  ICAM1-PE cat. 130-103-909 (Miltenyi)
  SIRPB1-PE cat. 130-105-310 (Miltenyi)
  CD64-APC (FCGR1A) cat. 561189 (BD)
  CD300f (IREM-1)-PE cat. 130-098-472; CD300f (IREM-1)-FITC cat. 130-098-443 (Miltenyi);
  IL10RB-APC cat. FAB874A (R&D)
  MRP1-PE cat. IC19291P (R&D)
  CD38-APC cat. MHCD3805; CD38-PE cat. MHCD3804 (Invitrogen);
  CD34-APC cat. 340667 (BD)
  CPM cat. DDX0520P (Dendritics)
  TTYH3 cat. NBP1-91350 (Novus)
  SLC NHE1 (SLC9A1) ab58304 (abeam)
  SLC22A5 bs-8149R (Bioss)
  KCNN4 PA5-33875 (Thermo Scientific)
  ITFG3 PA5-31403 (Thermo Scientific)
  SLC6A6 LS-C179237 (LSBio)
  SLC43A3 NBP1-85026 (Novus)
  TFR2 TA504592 (Origene)
  MBOAT7 NBP1-69610 (Novus)
  CD235a-APC (GYPA) cat. 551336 (BD Pharmigen)
  PLXNC1 cat. AF3887-SP (R&D Systems)

Vectors Cloning

Figure 5A:
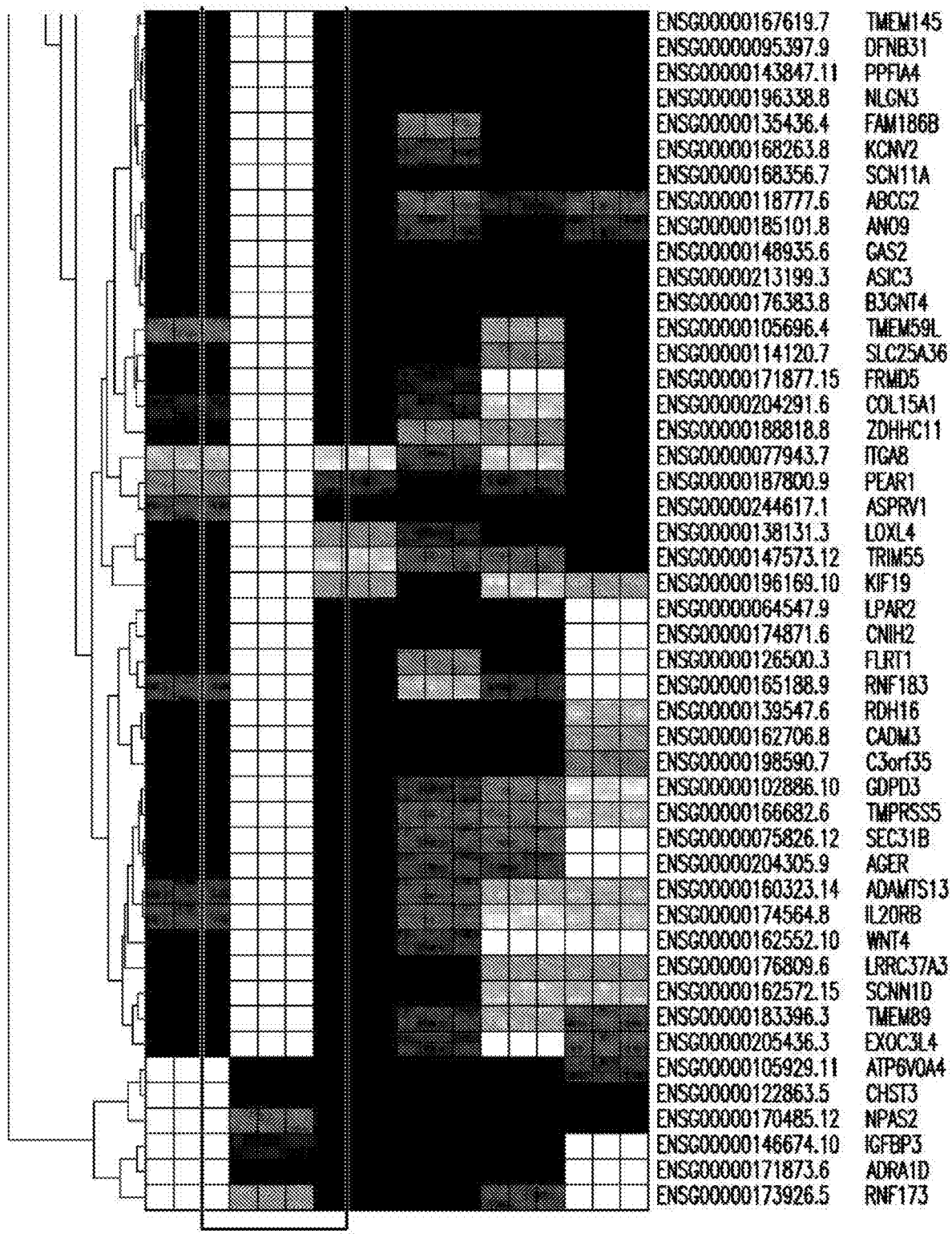
Figure 5B:
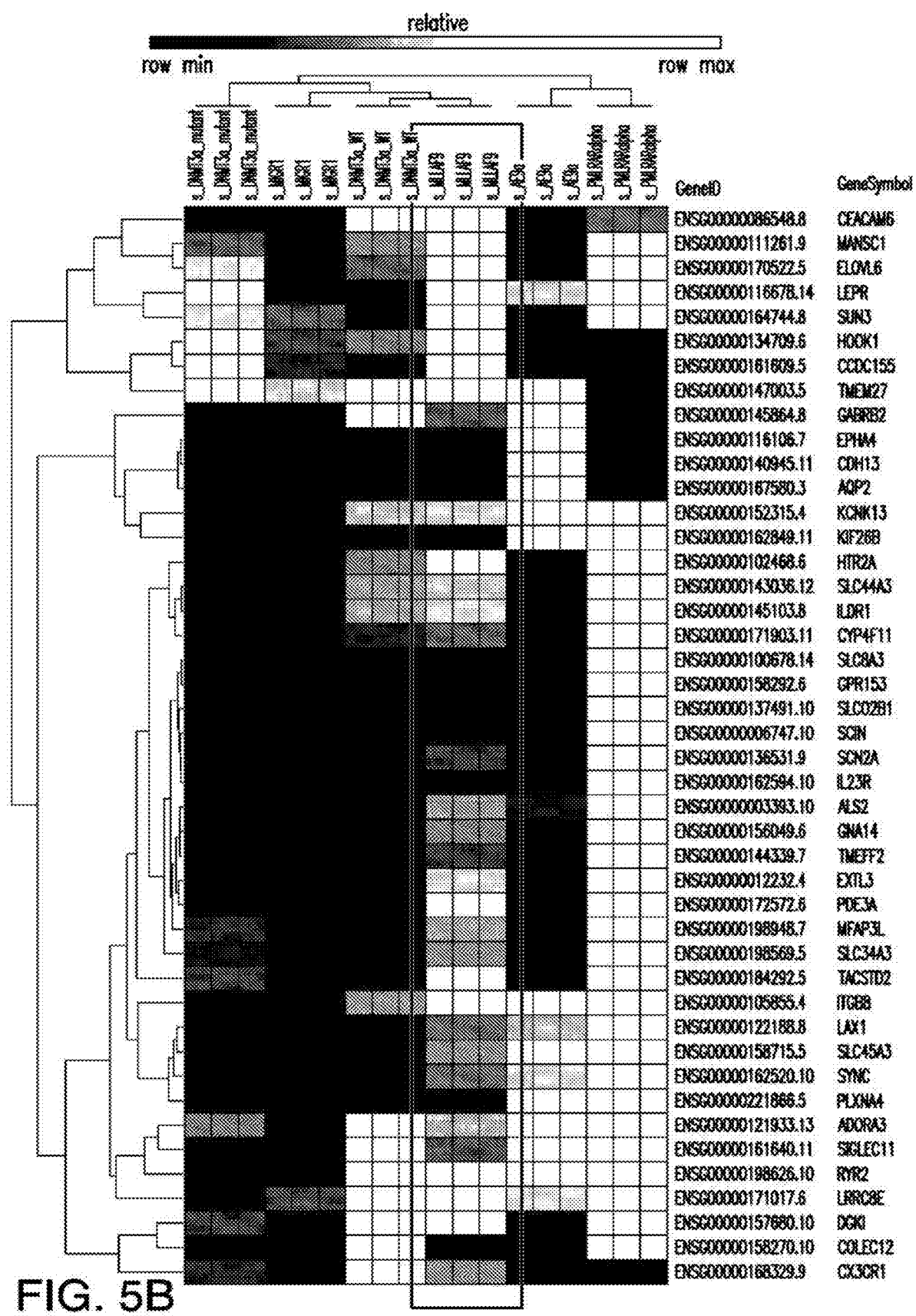

DNMT3a WT, DNMT3a R882H, IDH2 WT, IDH2 R172K, IDH1 WT, IDH1 R132C, IDH1 R132H, IDH2 R140Q, IDH1 R140H were cloned into MIGR1 MSCV GFP vectors. Design in CD70 CAR and CD33 CAR are shown in FIG. 5.

CD34+ Cells Purification and Culture Conditions

Mononuclear cells are isolated by centrifugation on a gradient of Ficoll-Hypaque Plus density. CD34+ HPCs are purified by positive selection using Midi MACS (magnetic-activated cell sorting) LS+ separation columns and isolation Kit according to the manufacturer's protocol (Miltenyi). Cells may be frozen in DMEM supplemented with 10% DMSO and stored in liquid nitrogen.

One day before the transduction, CD34+ cells are thawed and cultured in Iscove's modified Dulbecco's medium (IMDM) containing 20% BIT medium supplemented with SCF (100 ng/ml), FLT-3 (10 ng/ml), IL-6 (20 ng/ml) and TPO (100 ng/ml). Cytokines may be purchased purchased from Peprotech and R&D. After a 24 hours-recover CD34+ cells are infected with high-titer retroviral suspensions in presence of polybrene (8 μg/ml).

Generation and Concentration of Retroviruses

Retroviral vectors are produced by transfection of H29 packaging cells according to standard protocols. Briefly H29 cells may be cultured in Dulbecco modified Eagle medium (DMEM), supplemented with 10% fetal bovine serum (FBS) and when subconfluent, transfected with plasmids. The transfection is performed by calcium-phosphate precipitation. Vectors supernatants are harvested 6 and 7 days later and used to infect RD114 cells.

REFERENCES

1. Administration, U. S. F. a. D. (2010). Myelotarg (gentuzumab ozogamicin): market withdrawal
2. Agathanggelou, A., Niedobitek, G., Chen, R., Nicholls, J., Yin, W., and Young, L. S. (1995). Expression of immune regulatory molecules in Epstein-Barr virus-associated nasopharyngeal carcinomas with prominent lymphoid stroma. Evidence for a functional interaction between epithelial tumor cells and infiltrating lymphoid cells. Am J Pathol 147, 1152-1160.
3. Al-Hussaini, M., Rettig, M. P., Ritchey, J. K., Karpova, D., Uy, G. L., Eissenberg, L. G., Gao, F., Eades, W. C., Bonvini, E., Chichili, G. R., et al. (2016). Targeting CD123 in acute myeloid leukemia using a T-cell-directed dual-affinity retargeting platform. Blood 127, 122-131.
4. Baba, M., Okamoto, M., Hamasaki, T., Horai, S., Wang, X., Ito, Y., Suda, Y., and Arima, N. (2008). Highly enhanced expression of CD70 on human T-lymphotropic virus type 1-carrying T-cell lines and adult T-cell leukemia cells. J Virol 82, 3843-3852.
5. Bagger, F. O., Sasivarevic, D., Sohi, S. H., Laursen, L. G., Pundhir, S., Sonderby, C. K., Winther, O., Rapin, N., and Porse, B. T. (2016). BloodSpot: a database of gene expression profiles and transcriptional programs for healthy and malignant haematopoiesis. Nucleic Acids Res 44, D917-924.
6. Bakker, A. B., van den Oudenrijn, S., Bakker, A. Q., Feller, N., van Meijer, M., Bia, J. A., Jongeneelen, M. A., Visser, T. J., Bijl, N., Geuij en, C. A., et al. (2004). C-type lectin-like molecule-1: a novel myeloid cell surface marker associated with acute myeloid leukemia. Cancer Res 64, 8443-8450.
7. Baud, V., Chissoe, S. L., Viegas-Pequignot, E., Diriong, S., N'Guyen, V. C., Roe, B. A., and Lipinski, M. (1995). EMR1, an unusual member in the family of hormone receptors with seven transmembrane segments. Genomics 26, 334-344.
8. Bowman, M. R., Crimmins, M. A., Yetz-Aldape, J., Kriz, R., Kelleher, K., and Herrmann, S. (1994). The cloning of CD70 and its identification as the ligand for CD27. J Immunol 152, 1756-1761.
9. Cancer Genome Atlas Research, N. (2013). Genomic and epigenomic landscapes of adult de novo acute myeloid leukemia. N Engl J Med 368, 2059-2074.
10. Chahlavi, A., Rayman, P., Richmond, A. L., Biswas, K., Zhang, R., Vogelbaum, M., Tannenbaum, C., Barnett, G., and Finke, J. H. (2005). Glioblastomas induce T-lymphocyte death by two distinct pathways involving gangliosides and CD70. Cancer Res 65, 5428-5438.
11. Couzin-Frankel, J. (2013). Breakthrough of the year 2013. Cancer immunotherapy. Science 342, 1432-1433.
12. Cozzio, A., Passegue, E., Ayton, P. M., Karsunky, H., Cleary, M. L., and Weissman, I. L. (2003). Similar MLL-associated leukemias arising from self-renewing stem cells and short-lived myeloid progenitors. Genes Dev 17, 3029-3035.
13. Curran, K. J., Pegram, H. J., and Brentjens, R. J. (2012). Chimeric antigen receptors for T cell immunotherapy: current understanding and future directions. J Gene Med 14, 405-415.
14. Dairaghi, D. J., Oyaj obi, B. O., Gupta, A., McCluskey, B., Miao, S., Powers, J. P., Seitz, L. C., Wang, Y., Zeng, Y., Zhang, P., et al. (2012). CCR1 blockade reduces tumor burden and osteolysis in vivo in a mouse model of myeloma bone disease. Blood 120, 1449-1457.
15. Dasari, V. R., Jin, J., and Kunapuli, S. P. (2000). Distribution of leukotriene B4 receptors in human hematopoietic cells. Immunopharmacology 48, 157-163.
16. Davila, M. L., Kloss, C. C., Gunset, G., and Sadelain, M. (2013). CD19 CAR-targeted T cells induce long-term remission and B Cell Aplasia in an immunocompetent mouse model of B cell acute lymphoblastic leukemia. PLoS One 8, e61338.
17. Downing, A. K., Knott, V., Werner, J. M., Cardy, C. M., Campbell, I. D., and Handford, P. A. (1996). Solution structure of a pair of calcium-binding epidermal growth factor-like domains: implications for the Marfan syndrome and other genetic disorders. Cell 85, 597-605.
18. Gill, S., Tasian, S. K., Ruella, M., Shestova, O., Li, Y., Porter, D. L., Carroll, M., Danet-Desnoyers, G., Scholler, J., Grupp, S. A., et al. (2014). Preclinical targeting of human acute myeloid leukemia and myeloablation using chimeric antigen receptor-modified T cells. Blood 123, 2343-2354.
19. Gray, J. X., Haino, M., Roth, M. J., Maguire, J. E., Jensen, P. N., Yarme, A., Stetler-Stevenson, M. A., Siebenlist, U., and Kelly, K. (1996). CD97 is a processed, seven-transmembrane, heterodimeric receptor associated with inflammation. J Immunol 157, 5438-5447.
20. Haider, S., and Pal, R. (2013). Integrated analysis of transcriptomic and proteomic data. Curr Genomics 14, 91-110.
21. Hamann, J., Eichler, W., Hamann, D., Kerstens, H. M., Poddighe, P. J., Hoovers, J. M., Hartmann, E., Strauss, M., and van Lier, R. A. (1995). Expression cloning and chromosomal mapping of the leukocyte activation antigen CD97, a new seven-span transmembrane molecule of the secretion receptor superfamily with an unusual extracellular domain. J Immunol 155, 1942-1950.
22. Hamann, J., Stortelers, C., Kiss-Toth, E., Vogel, B., Eichler, W., and van Lier, R. A. (1998). Characterization of the CD55 (DAF)-binding site on the seven-span transmembrane receptor CD97. Eur J Immunol 28, 1701-1707.
23. Hashidate, T., Murakami, N., Nakagawa, M., Ichikawa, M., Kurokawa, M., Shimizu, T., and Nakamura, M. (2010). AML1 enhances the expression of leukotriene B4 type-1 receptor in leukocytes. FASEB J 24, 3500-3510.
24. Hills, R. K., Castaigne, S., Appelbaum, F. R., Delaunay, J., Petersdorf, S., Othus, M., Estey, E. H., Dombret, H., Chevret, S., Ifrah, N., et al. (2014). Addition of gemtuzumab ozogamicin to induction chemotherapy in adult patients with acute myeloid leukaemia: a meta-analysis of individual patient data from randomised controlled trials. Lancet Oncol 15, 986-996.
25. Hintzen, R. Q., Lens, S. M., Beckmann, M. P., Goodwin, R. G., Lynch, D., and van Lier, R. A. (1994). Characterization of the human CD27 ligand, a novel member of the TNF gene family. J Immunol 152, 1762-1773.
26. Hosen, N., Park, C. Y., Tatsumi, N., Oji, Y., Sugiyama, H., Gramatzki, M., Krensky, A. M., and Weissman, I. L. (2007). CD96 is a leukemic stem cell-specific marker in human acute myeloid leukemia. Proc Natl Acad Sci USA 104, 11008-11013.

27. Jin, L., Hope, K. J., Zhai, Q., Smadja-Joffe, F., and Dick, J. E. (2006). Targeting of CD44 eradicates human acute myeloid leukemic stem cells. Nat Med 12, 1167-1174.
28. Jordan, C. T., Upchurch, D., Szilvassy, S. J., Guzman, M. L., Howard, D. S., Pettigrew, A. L., Meyerrose, T., Rossi, R., Grimes, B., Rizzieri, D. A., et al. (2000). The interleukin-3 receptor alpha chain is a unique marker for human acute myelogenous leukemia stem cells. Leukemia 14, 1777-1784.
29. Junker, K., Hindermann, W., von Eggeling, F., Diegmann, J., Haessler, K., and Schubert, J. (2005). CD70: a new tumor specific biomarker for renal cell carcinoma. J Urol 173, 2150-2153.
30. Kato, K., Yokomizo, T., Izumi, T., and Shimizu, T. (2000). Cell-specific transcriptional regulation of human leukotriene B (4) receptor gene. J Exp Med 192, 413-420.
31. Kenderian, S. S., Ruella, M., Shestova, O., Klichinsky, M., Aikawa, V., Morrissette, J. J., Scholler, J., Song, D., Porter, D. L., Carroll, M., et al. (2015). CD33-specific chimeric antigen receptor T cells exhibit potent preclinical activity against human acute myeloid leukemia. Leukemia 29, 1637-1647.
32. Kikushige, Y., Shima, T., Takayanagi, S., Urata, S., Miyamoto, T., Iwasaki, H., Takenaka, K., Teshima, T., Tanaka, T., Inagaki, Y., and Akashi, K. (2010). TIM-3 is a promising target to selectively kill acute myeloid leukemia stem cells. Cell Stem Cell 7, 708-717.
33. Kim, M. S., Pinto, S. M., Getnet, D., Nirujogi, R. S., Manda, S. S., Chaerkady, R., Madugundu, A. K., Kelkar, D. S., Isserlin, R., Jain, S., et al. (2014). A draft map of the human proteome. Nature 509, 575-581.
34. Kim, N. D., Chou, R. C., Seung, E., Tager, A. M., and Luster, A. D. (2006). A unique requirement for the leukotriene B4 receptor BLT1 for neutrophil recruitment in inflammatory arthritis. J Exp Med 203, 829-835.
35. Kishikawa, K., Tateishi, N., Maruyama, T., Seo, R., Toda, M., and Miyamoto, T. (1992). ONO-4057, a novel, orally active leukotriene B4 antagonist: effects on LTB4-induced neutrophil functions. Prostaglandins 44, 261-275.
36. Kloss, C. C., Condomines, M., Cartellieri, M., Bachmann, M., and Sadelain, M. (2013). Combinatorial antigen recognition with balanced signaling promotes selective tumor eradication by engineered T cells. Nat Biotechnol 31, 71-75.
37. Konoplev, S., Rassidakis, G. Z., Estey, E., Kantarjian, H., Liakou, C. I., Huang, X., Xiao, L., Andreeff, M., Konopleva, M., and Medeiros, L. J. (2007). Overexpression of CXCR4 predicts adverse overall and event-free survival in patients with unmutated FLT3 acute myeloid leukemia with normal karyotype. Cancer 109, 1152-1156.
38. Lamers, C. H., Sleijfer, S., van Steenbergen, S., van Elzakker, P., van Krimpen, B., Groot, C., Vulto, A., den Bakker, M., Oosterwijk, E., Debets, R., and Gratama, J. W. (2013). Treatment of metastatic renal cell carcinoma with CAIX CAR-engineered T cells: clinical evaluation and management of on-target toxicity. Mol Ther 21, 904-912.
39. Lamers, C. H., Sleijfer, S., Vulto, A. G., Kruit, W. H., Kliffen, M., Debets, R., Gratama, J. W., Stoter, G., and Oosterwijk, E. (2006). Treatment of metastatic renal cell carcinoma with autologous T-lymphocytes genetically retargeted against carbonic anhydrase IX: first clinical experience. J Clin Oncol 24, e20-22.
40. Lawson, C. F., Wishka, D. G., Morris, J., and Fitzpatrick, F. A. (1989). Receptor antagonism of leukotriene B4 myotropic activity by the 2,6 disubstituted pyridine analog U-75302: characterization on lung parenchyma strips. J Lipid Mediat 1, 3-12.
41. LeBien, T. W., and Tedder, T. F. (2008). B lymphocytes: how they develop and function. Blood 112, 1570-1580.
42. Lens, S. M., Drillenburg, P., den Drijver, B. F., van Schijndel, G., Pals, S. T., van Lier, R. A., and van Oers, M. H. (1999). Aberrant expression and reverse signalling of CD70 on malignant B cells. Br J Haematol 106, 491-503.
43. Ley, T. J., Ding, L., Walter, M. J., McLellan, M. D., Lamprecht, T., Larson, D. E., Kandoth, C., Payton, J. E., Baty, J., Welch, J., et al. (2010). DNMT3A mutations in acute myeloid leukemia. The New England journal of medicine 363, 2424-2433.
44. Lin, H. H., Stacey, M., Hamann, J., Gordon, S., and McKnight, A. J. (2000). Human EMR2, a novel EGF-TM7 molecule on chromosome 19p13.1, is closely related to CD97. Genomics 67, 188-200.
45. Lin, H. H., Stubbs, L. J., and Mucenski, M. L. (1997). Identification and characterization of a seven transmembrane hormone receptor using differential display. Genomics 41, 301-308.
46. Liszewski, M. K., Farries, T. C., Lublin, D. M., Rooney, I. A., and Atkinson, J. P. (1996). Control of the complement system. Adv Immunol 61, 201-283.
47. Lynn, R. C., Feng, Y., Schutsky, K., Poussin, M., Kalota, A., Dimitrov, D. S., and Powell, D. J., Jr. (2016). High-affinity FRbeta-specific CAR T cells eradicate AML and normal myeloid lineage without HSC toxicity. Leukemia.
48. Lynn, R. C., Poussin, M., Kalota, A., Feng, Y., Low, P. S., Dimitrov, D. S., and Powell, D. J., Jr. (2015). Targeting of folate receptor beta on acute myeloid leukemia blasts with chimeric antigen receptor-expressing T cells. Blood 125, 3466-3476.
49. Maiga, A., Lemieux, S., Pabst, C., Lavallee, V. P., Bouvier, M., Sauvageau, G., and Hebert, J. (2016). Transcriptome analysis of G protein-coupled receptors in distinct genetic subgroups of acute myeloid leukemia: identification of potential disease-specific targets. Blood Cancer J 6, e431.
50. Majeti, R., Chao, M. P., Alizadeh, A. A., Pang, W. W., Jaiswal, S., Gibbs, K. D., Jr., van Rooijen, N., and Weissman, I. L. (2009). CD47 is an adverse prognostic factor and therapeutic antibody target on human acute myeloid leukemia stem cells. Cell 138, 286-299.
51. Marcucci, G., Metzeler, K. H., Schwind, S., Becker, H., Maharry, K., Mrozek, K., Radmacher, M. D., Kohlschmidt, J., Nicolet, D., Whitman, S. P., et al. (2012). Age-related prognostic impact of different types of DNMT3A mutations in adults with primary cytogenetically normal acute myeloid leukemia. Journal of clinical oncology: official journal of the American Society of Clinical Oncology 30, 742-750.
52. Martin, V., Ronde, P., Unett, D., Wong, A., Hoffman, T. L., Edinger, A. L., Doms, R. W., and Funk, C. D. (1999). Leukotriene binding, signaling, and analysis of HIV coreceptor function in mouse and human leukotriene B4 receptor-transfected cells. J Biol Chem 274, 8597-8603.
53. McEarchern, J. A., Oflazoglu, E., Francisco, L., McDonagh, C. F., Gordon, K. A., Stone, I., Klussman, K., Turcott, E., van Rooij en, N., Carter, P., et al. (2007). Engineered anti-CD70 antibody with multiple effector functions exhibits in vitro and in vivo antitumor activities. Blood 109, 1185-1192.
54. McEarchern, J. A., Smith, L. M., McDonagh, C. F., Klussman, K., Gordon, K. A., Morris-Tilden, C. A., Duniho, S., Ryan, M., Boursalian, T. E., Carter, P. J., et al. (2008). Preclinical characterization of SGN-70, a humanized antibody directed against CD70. Clin Cancer Res 14, 7763-7772.

55. McKnight, A. J., and Gordon, S. (1996). EGF-TM7: a novel subfamily of seven-transmembrane-region leukocyte cell-surface molecules. Immunol Today 17, 283-287.

56. Morgan, R. A., Yang, J. C., Kitano, M., Dudley, M. E., Laurencot, C. M., and Rosenberg, S. A. (2010). Case report of a serious adverse event following the administration of T cells transduced with a chimeric antigen receptor recognizing ERBB2. Mol Ther 18, 843-851.

57. O'Hayre, M., Degese, M. S., and Gutkind, J. S. (2014). Novel insights into G protein and G protein-coupled receptor signaling in cancer. Curr Opin Cell Biol 27, 126-135.

58. Obinata, H., Yokomizo, T., Shimizu, T., and Izumi, T. (2003). Glucocorticoids up-regulate leukotriene B4 receptor-1 expression during neutrophilic differentiation of HL-60 cells. Biochem Biophys Res Commun 309, 114-119.

59. Oehler, V. G., Yeung, K. Y., Choi, Y. E., Bumgarner, R. E., Raftery, A. E., and Radich, J. P. (2009). The derivation of diagnostic markers of chronic myeloid leukemia progression from microarray data. Blood 114, 3292-3298.

60. Owman, C., Garzino-Demo, A., Cocchi, F., Popovic, M., Sabirsh, A., and Gallo, R. C. (1998). The leukotriene B4 receptor functions as a novel type of coreceptor mediating entry of primary HIV-1 isolates into CD4-positive cells. Proc Natl Acad Sci USA 95, 9530-9534.

61. Parkhurst, M. R., Yang, J. C., Langan, R. C., Dudley, M. E., Nathan, D. A., Feldman, S. A., Davis, J. L., Morgan, R. A., Merino, M. J., Sherry, R. M., et al. (2011). T cells targeting carcinoembryonic antigen can mediate regression of metastatic colorectal cancer but induce severe transient colitis. Mol Ther 19, 620-626.

62. Pegram, H. J., Lee, J. C., Hayman, E. G., Imperato, G. H., Tedder, T. F., Sadelain, M., and Brentjens, R. J. (2012). Tumor-targeted T cells modified to secrete IL-12 eradicate systemic tumors without need for prior conditioning. Blood 119, 4133-4141.

63. Perna, F., Gurvich, N., Hoya-Arias, R., Abdel-Wahab, O., Levine, R. L., Asai, T., Voza, F., Menendez, S., Wang, L., Liu, F., et al. (2010). Depletion of L3MBTL1 promotes the erythroid differentiation of human hematopoietic progenitor cells: possible role in 20q-polycythemia vera. Blood 116, 2812-2821.

64. Pettersson, A., Boketoft, A., Sabirsh, A., Nilsson, N. E., Kotarsky, K., Olde, B., and Owman, C. (2000). First-generation monoclonal antibodies identifying the human leukotriene B (4) receptor-1. Biochem Biophys Res Commun 279, 520-525.

65. Pizzitola, I., Anjos-Afonso, F., Rouault-Pierre, K., Lassailly, F., Tettamanti, S., Spinelli, O., Biondi, A., Biagi, E., and Bonnet, D. (2014). Chimeric antigen receptors against CD33/CD123 antigens efficiently target primary acute myeloid leukemia cells in vivo. Leukemia 28, 1596-1605.

66. Pulte, D., Gondos, A., and Brenner, H. (2008). Improvements in survival of adults diagnosed with acute myeloblastic leukemia in the early 21st century. Haematologica 93, 594-600.

67. Ravandi, F., Estey, E. H., Appelbaum, F. R., Lo-Coco, F., Schiffer, C. A., Larson, R. A., Burnett, A. K., and Kantarjian, H. M. (2012). Gemtuzumab ozogamicin: time to resurrect? J Clin Oncol 30, 3921-3923.

68. Ritchie, D. S., Neeson, P. J., Khot, A., Peinert, S., Tai, T., Tainton, K., Chen, K., Shin, M., Wall, D. M., Honemann, D., et al. (2013). Persistence and efficacy of second generation CAR T cell against the LeY antigen in acute myeloid leukemia. Mol Ther 21, 2122-2129.

69. Russler-Germain, D. A., Spencer, D. H., Young, M. A., Lamprecht, T. L., Miller, C. A., Fulton, R., Meyer, M. R., Erdmann-Gilmore, P., Townsend, R. R., Wilson, R. K., and Ley, T. J. (2014). The R882H DNNIT3A mutation associated with AML dominantly inhibits wild-type DNNIT3A by blocking its ability to form active tetramers. Cancer cell 25, 442-454.

70. Sadelain, M. (2015). CAR therapy: the CD19 paradigm. J Clin Invest 125, 3392-3400.

71. Saito, Y., Kitamura, H., Hijikata, A., Tomizawa-Murasawa, M., Tanaka, S., Takagi, S., Uchida, N., Suzuki, N., Sone, A., Najima, Y., et al. (2010). Identification of therapeutic targets for quiescent, chemotherapy-resistant human leukemia stem cells. Sci Transl Med 2, 17ra19.

72. Samuelsson, B., Dahlen, S. E., Lindgren, J. A., Rouzer, C. A., and Serhan, C. N. (1987). Leukotrienes and lipoxins: structures, biosynthesis, and biological effects. Science 237, 1171-1176.

73. Shaffer, D. R., Savoldo, B., Yi, Z., Chow, K. K., Kakarla, S., Spencer, D. M., Dotti, G., Wu, M. F., Liu, H., Kenney, S., and Gottschalk, S. (2011). T cells redirected against CD70 for the immunotherapy of CD70-positive malignancies. Blood 117, 4304-4314.

74. Shlush, L. I., Zandi, S., Mitchell, A., Chen, W. C., Brandwein, J. M., Gupta, V., Kennedy, J. A., Schimmer, A. D., Schuh, A. C., Yee, K. W., et al. (2014a). Identification of pre-leukaemic haematopoietic stem cells in acute leukaemia. Nature 506, 328-333.

75. Shlush, L. I., Zandi, S., Mitchell, A., Chen, W. C., Brandwein, J. M., Gupta, V., Kennedy, J. A., Schimmer, A. D., Schuh, A. C., Yee, K. W., et al. (2014b). Identification of pre-leukaemic haematopoietic stem cells in acute leukaemia. Nature 506, 328-333.

76. Showell, H. J., Conklyn, M. J., Alpert, R., Hingorani, G. P., Wright, K. F., Smith, M. A., Stam, E., Salter, E. D., Scampoli, D. N., Meltzer, S., et al. (1998). The preclinical pharmacological profile of the potent and selective leukotriene B4 antagonist CP-195543. J Pharmacol Exp Ther 285, 946-954.

77. Showell, H. J., Pettipher, E. R., Cheng, J. B., Breslow, R., Conklyn, M. J., Farrell, C. A., Hingorani, G. P., Salter, E. D., Hackman, B. C., Wimberly, D. J., and et al. (1995). The in vitro and in vivo pharmacologic activity of the potent and selective leukotriene B4 receptor antagonist CP-105696. J Pharmacol Exp Ther 273, 176-184.

78. So, C. W., Karsunky, H., Passegue, E., Cozzio, A., Weissman, I. L., and Cleary, M. L. (2003). MLL-GAS7 transforms multipotent hematopoietic progenitors and induces mixed lineage leukemias in mice. Cancer Cell 3, 161-171.

79. Strassberger, V., Gutbrodt, K. L., Krall, N., Roesli, C., Takizawa, H., Manz, M. G., Fugmann, T., and Neri, D. (2014). A comprehensive surface proteome analysis of myeloid leukemia cell lines for therapeutic antibody development. J Proteomics 99, 138-151.

80. Taussig, D. C., Pearce, D. J., Simpson, C., Rohatiner, A. Z., Lister, T. A., Kelly, G., Luongo, J. L., Danet-Desnoyers, G. A., and Bonnet, D. (2005). Hematopoietic stem cells express multiple myeloid markers: implications for the origin and targeted therapy of acute myeloid leukemia. Blood 106, 4086-4092.

81. Uhlen, M., Fagerberg, L., Hallstrom, B. M., Lindskog, C., Oksvold, P., Mardinoglu, A., Sivertsson, A., Kampf, C., Sjostedt, E., Asplund, A., et al. (2015). Proteomics. Tissue-based map of the human proteome. Science 347, 1260419.
82. Wang, Q. S., Wang, Y., Lv, H. Y., Han, Q. W., Fan, H., Guo, B., Wang, L. L., and Han, W. D. (2015). Treatment of CD33-directed chimeric antigen receptor-modified T cells in one patient with relapsed and refractory acute myeloid leukemia. Mol Ther 23, 184-191.
83. Wilhelm, M., Schlegl, J., Hahne, H., Moghaddas Gholami, A., Lieberenz, M., Savitski, M. M., Ziegler, E., Butzmann, L., Gessulat, S., Marx, H., et al. (2014). Mass-spectrometry-based draft of the human proteome. Nature 509, 582-587.
84. Yan, X. J., Xu, J., Gu, Z. H., Pan, C. M., Lu, G., Shen, Y., Shi, J. Y., Zhu, Y. M., Tang, L., Zhang, X. W., et al. (2011). Exome sequencing identifies somatic mutations of DNA methyltransferase gene DNMT3A in acute monocytic leukemia. Nature genetics 43, 309-315.
85. Yi Luo, L.-J. C., Yongxian Hu, Lujia Dong, Guoqing Wei and He Huang (2015). First-in-Man CD123-Specific Chimeric Antigen Receptor-Modified T Cells for the Treatment of Refractory Acute Myeloid Leukemia. ASH meeting abstract
86. Yokomizo, T., Izumi, T., Chang, K., Takuwa, Y., and Shimizu, T. (1997). A G-protein-coupled receptor for leukotriene B4 that mediates chemotaxis. Nature 387, 620-624.
87. Yokomizo, T., Kato, K., Terawaki, K., Izumi, T., and Shimizu, T. (2000). A second leukotriene B (4) receptor, BLT2. A new therapeutic target in inflammation and immunological disorders. J Exp Med 192, 421-432.
88. Yokota, Y., Inoue, H., Matsumura, Y., Nabeta, H., Narusawa, M., Watanabe, A., Sakamoto, C., Hijikata, Y., Iga-Murahashi, M., Takayama, K., et al. (2012). Absence of LTB4/BLT1 axis facilitates generation of mouse GM-CSF-induced long-lasting antitumor immunologic memory by enhancing innate and adaptive immune systems. Blood 120, 3444-3454.
89. Zhou, G., and Levitsky, H. (2012). Towards curative cancer immunotherapy: overcoming posttherapy tumor escape. Clin Dev Immunol 2012, 124187.

Example 2

To rapidly obtain two fully human high-quality single-chain fragments (scFvs) targeting LTB4R1 and EMR2, in-house next-generation, premade, fully human, phage display scFv libraries is first utilized. The advantages include phage stability, rapid production, the fact that intrinsic properties such as immunogenicity, affinity, specificity and stability of antibodies can be improved by various mutagenesis technologies. The antibody genes are expressed and the gene products displayed on the surface of filamentous bacteriophage as fusion proteins, thus creating a link between antibody phenotype and its encoded genotype (Pansri, BMC Biotechnol, 9:6, 2009; Farajnia, Immunopharmacol Immunotoxicol, 36:297-308, 2014).

Example 3

To expand the validation cohort of the targets within primary AML patient samples, at least 50 samples, bearing frequently recurring genetic abnormalities, including DNMT3a mutation, are analyzed by flow cytometry.

Leukotriene B4 (LTB4), an eicosanoid derivative of arachidonic acid metabolism produced by the sequential action of 5-lipoxygenase and leukotriene A4-hydrolase, is a leukocyte chemoattractant30. LTB4 signals through two G protein—coupled seven-transmembrane domain receptors, LTB4 receptor (BLT1) and BLT2, the high- and low-affinity receptors, respectively (Yokomizo, Nature, 387:620-624, 1997; Yokomizo, J Exp Med, 192:421-432, 2000). BLT1 is a mediator of inflammation (Kim, J Exp Med, 203:829-835, 2006). In sharp contrast to BLT2, which is expressed ubiquitously, BLT1 is predominantly expressed in granulocytes. Yokota et al. used a GM-CSF based tumor vaccine setting in BALB/c leukemia model and showed better primary and recall immune responses in the BLT1-/- mice (Yokota, Blood, 210:3444-3453, 2012).

EMR2 is a new member of the EGF-TM7 family of proteins, containing a total of five tandem EGF-like domains and shares strikingly similar molecular characteristics with CD97. Unlike CD97, which is ubiquitously expressed in most cell types, EMR2 expression is restricted to monocytes/macrophages and granulocytes. EMR2 fails to interact with CD55, the cellular ligand for CD97 and may therefore have a unique function in the myeloid lineage (Lin, Genomics, 67:188-200, 2000).

Example 4

To assemble the antibody-targeting domains into second-generation CARs (bearing a single costimulatory element within the endoplasmic domain with the activating CD3ζ domain) or CCR (fusion molecule coupling antigen specificity to T cell co-stimulatory signaling without activating domains). The combinations of CAR/CCR are retrovirally expressed in T cells and the efficacy in damaging AML cells is evaluated compared to normal cells in a panel of representative cell lines by cytotoxic lymphocyte assays.

Example 5—Probing the Acute Myeloid Leukemia Surfaceome for Chimeric Antigen Receptor Targets Summary Chimeric antigen receptor (CAR) therapy targeting CD19 has yielded remarkable outcomes in patients with acute lymphoblastic leukemia. To identify potential CAR targets in acute myeloid leukemia (AML), the AML surfaceome was probed for over-expressed molecules absent from vital tissues. Large transcriptomics and proteomics data sets were integrated from malignant and normal tissues, and developed an algorithm to identify potential targets expressed in leukemia stem cells, but not in normal CD34+CD38− hematopoietic cells, T cells or vital tissues. As these investigations did not uncover candidate targets with a profile as favorable as CD19, a generalizable combinatorial targeting strategy fulfilling stringent efficacy and safety criteria were developed. The findings indicate that several target pairings hold great promise for CAR therapy of AML.

INTRODUCTION

An ideal CAR target should be expressed at high density, in most if not all tumor cells including cancer stem cells, and in a large fraction of patients (Table 3). Unlike native T cells, which are known to signal through the TCR in response to very low antigen density, CAR T cells require higher antigen densities to fully activate effector functions (Turatti et al., 2007; Walker et al., 2017; Weijtens et al., 2000). High absolute antigen expression that is easily detected by FACS analysis is thus much preferred for CAR target selection. Clonal heterogeneity creates complex tumors that are prone to escape targeted therapies. Expression of the target in normal tissues may be tolerable (transient or partial elimination of non-vital cell types) or unacceptable (destruction of vital tissues, hematopoietic stem cell depletion). To prevent undue toxicity, the ideal tumor target should not be expressed on any normal tissue/organ of, or at least not in vital tissues (heart, liver, CNS, lung and other tissues that cannot withstand transient damage) nor in closely related normal cellular counterparts, i.e., CD34+ hematopoietic stem/progenitor cells (HSPCs) in the case of AML. The target antigen should also not be expressed in CAR T cells to obviate fratricide elimination (Table 3). It is therefore imperative to carefully evaluate candidate targets not just in tumor cells, but across all normal tissues. Consequently, this task requires comprehensive sources of antigen annotation, as well as analytical tools specifically designed to identify potential CAR target antigens.

TABLE 3

Features of an ideal CAR target

| Goal | Activity | Expression |
| --- | --- | --- |
| Efficient recognition and targeting by CAR T cells | High on-tumor | in all tumor cells at high level in many patients |
| Safe discrimination of target cells by CAR T cells | Low off-tumor | NOT in: any normal tissue, especially vital tissues normal counterparts (eg HSPCs for AML) resting/activated T cells |

To date, searches for CAR targets have largely relied on transcriptome analyses, under the assumption that there exists a direct correspondence between mRNA transcripts and protein expression. The correlation between mRNA and protein expression is complex and potentially unrepresentative of the cell proteome, due to multiple factors including variable half-lives and post transcriptional regulatory mechanisms (Hack, 2004). An integrated and comprehensive analysis of transcriptomic and proteomic data in both malignant and normal cells is therefore needed to capture information lacking from indirect analyses of mRNA or limited protein expression assays (Haider and Pal, 2013). Moreover, advanced proteomic technologies combined with enrichment strategies for identifying plasma cell membrane proteins can provide direct measurements of the surface proteome. Both proteomic and genomic datasets were therefore integrated from AML and normal cell populations, including the surface-specific mass-spectrometry analyses of AML cell lines. After compiling a comprehensive dataset of antigen annotations, in both normal and malignant cells, a multi-step ranking algorithm were developed for the identification of potential CAR targets. These were then validated by flow cytometry in primary AML patient samples, normal bone marrow (BM) HSPCs and peripheral blood (PB) T cells. Here the most promising candidates and candidate pairs that meet stringent criteria for serving as prospective targets in CAR therapies targeting AML were report.

Materials and Methods

Experimental Model and Subject Details

Primary AML specimens were obtained from the Hematology Oncology Tissue Bank (HOTB) of MSKCC (IRB protocol Y2017P026). Patient characteristics are illustrated in Supplemental Table 2.

Primary human bone marrow CD34+ cells were purchased from Stem Cell Technologies (70002.2, 70002.3).

Human T Cells Isolation and Activation

Buffy coats from healthy volunteer donors were obtained from the New York Blood Center. Peripheral blood mononuclear cells were isolated by density gradient centrifugation, and T lymphocytes were then purified using the Pan T cell isolation kit (Miltenyi Biotech). Cells were activated with Dynabeads (1:1 beads:cell) Human T-Activator CD3/CD28 (ThermoFisher) in X-vivo 15 medium (Lonza) supplemented with 5% human serum (Gemini Bioproducts) with 100 U/ml IL-2 (Miltenyi Biotech) at a density of 106 cells/ml. The beads were removed by magnetic separation 48 h after activation. The medium was changed every 2 days, and cells were replated at 106 cells/ml.

AML Cell Lines

THP1, Mono-mac, Kasumi, Molm13, OCI/AML3 and TF-1 cells were maintained in RPMI1640/1-Glutamine (Life Technologies, Inc., Carlsbad, CA), supplemented with 10% FBS (20% for HL60) (Life Technologies) at 37° C. THP1 and Mono-mac lines bear MLL-AF9 translocation, the THP1 line also bears deletion of p16, p53, UTX and rearrangement of RB1; Kasumi bears an AML1-ETO translocation; Molm13 FLT3-ITD, OCI/AML3 a NPM mutation and TF-1 a highly rearranged hyperdiploid karyotype with p53 mutation.

Normal Tissue Proteomics Compilation and Data Retrieval

Expression data for normal tissues was retrieved from three data repositories, the Human Protein Atlas (HPA) (www.proteinatlas.org, normal tissue.csv.zip, accessed Oct. 15, 2016), the Human Proteome Map (HPM) (RRID: SCR_015560, www.humanproteomemap.org, HPM_gene_level_expression_matrix_Kim_et_al_052914.csv accessed Oct. 13, 2016), and the Proteomics Database (PDB) (RRID:SCR_015562, Accessed via the PDB API, available at www.proteomicsdb.org, Oct. 13, 2016). Additionally, subcellular localization data was obtained from the HPA (RRID:SCR_006710, www.proteinatlas.org, subcellular_localization.csv.zip, accessed Oct. 15, 2016) and COMPARTMENTS (RRID:SCR_015561, compartments.jensenlab.org, LOCATE_human_v6_20081121.xml, accessed Oct. 15, 2015) repositories, and transcriptomic data retrieved from the HPA (www.proteinatlas.org, rna_tissue.csv.zip, accessed Oct. 15, 2015) and Bloodspot.eu data archives (RRID:SCR_015563).

Correcting Tissue and Organelle Nomenclature

Due to differing tissue nomenclature among source repositories, each data set was mapped to a set of consensus tissue labels. In cases where multiple tissues from one repository mapped to a single label from another source, the maximum expression value was taken, for instance the PDB's "retina" and "vitreous humor" tissues were collapsed into a single tissue category, "eye." For consistency, fetal and placental tissues were also discarded, resulting in 43 distinct tissue categories (Table 4) shown below: adipose tissue, adrenal, appendix, bladder, blood, bone, brain, breast, bronchus, cerumen, cervix, epididymis, eye, fallopian tube, gallbladder, gut, heart, kidney, esophagus, liver, lung, lymph node, nasopharynx, oropharynx, ovary, pancreas, parathyroid, prostate, rectum, seminal, skeletal muscle, skin, smooth muscle, soft tissue, spinal cord, spleen, stomach, synovial fluid, testis, thyroid, tonsil, uterus, vagina Similarly, maps of subcellular localization labels from the HPA and COMPARTMENTS databases were generated by manually classifying organelle labels as either cell membrane-associated or otherwise unaffiliated, and then applying the resulting dictionary to proteins in both repositories.

TABLE 4

| | Consensus Tissue Name | HPA | HPM | PDB |
|---|---|---|---|---|
| 1 | adipose tissue | 'adipose tissue' | | 'adipocyte' |
| 2 | adrenal | 'adrenal gland' | 'Adult.Adrenal' | 'adrenal gland' |
| 3 | appendix | 'appendix' | | |
| 4 | bladder | 'urinary bladder' | 'Adult.Urinary.Bladder' | 'urinary bladder', 'urine' |
| 5 | blood | | 'B.Cells', 'CD4.Cells', 'CD8.Cells', 'Monocytes', 'NK.Cells', 'Platelets' | 'B-lymphocyte', 'blood', 'blood platelet', 'cytotoxic T-lymphocyte', 'helper T-lymphocyte', 'monocyte', 'natural killer cell', 'serum' |
| 6 | bone | 'bone marrow' | | 'bone', 'bone marrow stromal cell', 'mesenchymal stem cell' |
| 7 | brain | 'cerebellum', 'cerebral cortex', 'hippocampus', 'lateral ventricle' | 'Adult.Frontal.Cortex' | 'brain', 'cerebral cortex', 'prefrontal cortex' |
| 8 | breast | 'breast' | | 'breast' |
| 9 | bronchus | 'bronchus' | | |
| 10 | cerumen | | | 'cerumen' |
| 11 | cervix | 'cervix, uterine' | | 'cervical epithelium', 'cervical mucosa', 'uterine cervix', 'uterus' |
| 12 | epididymis | 'epididymis' | | |
| 13 | eye | | 'Adult.Retina' | 'retina', 'vitreous humor' |
| 14 | fallopian tube | 'fallopian tube' | | |
| 15 | gallbladder | 'gallbladder' | 'Adult.Gallbladder' | 'gall bladder' |
| 16 | gut | 'colon', 'duodenum', 'small intestine' | 'Adult.Colon' | 'colon', 'colon muscle', 'colonic epithelial cell', 'gut', 'ileum epithelial cell' |
| 17 | heart | 'heart muscle' | 'Adult.Heart' | 'heart', 'proximal fluid (coronary sinus)' |
| 18 | kidney | 'kidney' | 'Adult.Kidney' | 'kidney' |
| 19 | eesophagus | 'esophagus' | 'Adult.Esophagus' | 'esophagus' |
| 20 | liver | 'liver' | 'Adult.Liver' | 'bile', 'liver' |
| 21 | lung | 'lung' | 'Adult.Lung' | 'lung' |
| 22 | lymph node | 'lymph node' | | 'lymph node' |

TABLE 4-continued

| | Consensus Tissue Name | HPA | HPM | PDB |
|---|---|---|---|---|
| 23 | nasopharynx | 'nasopharynx' | | 'nasopharynx' |
| 24 | oropharynx | 'oral mucosa', 'salivary gland' | | 'oral epithelium', 'saliva', 'salivary gland' |
| 25 | ovary | 'ovary' | 'Adult.Ovary' | 'ovary' |
| 26 | pancreas | 'pancreas' | 'Adult.Pancreas' | 'pancreas', 'pancreatic islet', 'pancreatic juice' |
| 27 | parathyroid | 'parathyroid gland' | | |
| 28 | prostate | 'prostate' | 'Adult.Prostate' | 'prostate gland' |
| 29 | rectum | 'rectum' | 'Adult.Rectum' | 'rectum' |
| 30 | seminal | 'seminal vesicle' | | 'seminal plasma', 'seminal vesicle', 'spermatozoon' |
| 31 | skeletal muscle | 'skeletal muscle' | | |
| 32 | skin | 'skin', 'skin 1', 'skin 2' | | 'hair follicle', 'skin' |
| 33 | smooth muscle | 'smooth muscle' | | |
| 34 | soft tissue | 'soft tissue 1', 'soft tissue 2' | | |
| 35 | spinal cord | | 'Adult.Spinal.Cordc' | 'cerebrospinal fluid', 'spinal cord' |
| 36 | spleen | 'spleen' | | 'spleen' |
| 37 | stomach | 'stomach', 'stomach 1', 'stomach 2' | | 'cardia', 'stomach' |
| 38 | synovial fluid | | | 'synovial fluid' |
| 39 | testis | 'testis' | 'Adult.Testis' | 'testis' |
| 40 | thyroid | 'thyroid gland' | | 'thyroid gland' |
| 41 | tonsil | 'tonsil' | | 'tonsil' |
| 42 | uterus | 'endometrium', 'endometrium 1', 'endometrium 2' | | 'myometrium' |
| 43 | vagina | 'vagina' | | |

Calculation of Distribution Metrics

In the interest of facilitating subsequent selection steps, expression entries were classified into three categories: "not detected", "low", "medium", and "high", the native format in which HPA protein and RNA data was made available. To accomplish the binning, both the HPM and PDB datasets were first log 10 transformed, after HPM data was then temporarily corrected for the purpose of abundance distribution estimation so as to minimize artifactual cases in which LC-MS/MS peptide fragment masses were underdetermined, resulting in multiple gene assignments. This was accomplished by collapsing protein entries originating from the same experiment and occurring with precisely the same spectral abundance measure, into a single entry during the curve fitting process (after which all entries were restored). To fit normal curves of best fit to the observed distributions, the Broyden-Fletcher-Goldfarb-Shanno algorithm was applied (Team, 2016), after which the peak maximum and standard deviation measure was recorded for each curve.

Gene Nomenclature Conversion

Gene identification labels for all data sources not natively provided in Ensembl gene format were then converted using the biomaRt and mygene R packages, as well as the Proteomics Database API to ensure comprehensive mapping between differing nomenclatures (Adam Mark, 2014; Durinck et al., 2009). In cases where multiple entries from a given data source mapped to the same gene ID only the highest expression value for each tissue was retained. And in cases where entries mapped to more than one Ensembl Gene ID, duplicate entries for each ID were made.

For each unique (protein, tissue, repository) entry, the maximum expression value was retained and the remaining expression values, which arose from native IDs mapped to two Ensembl Gene IDs, were discarded.

Generation of Repository Metrics

The number of available data sources for every unique (protein, tissue) entry was then recorded and the maximum binned expression abundance for each unique (protein, tissue) entry was then computed.

Expression and Binning

Expression values within one standard deviation and above normal peaks were considered to be of "medium" (2) abundance, expression values above this threshold were considered of "high" (3) abundance. Similarly, expression values within one standard deviation and below the normal peak were considered of "low" (1) abundance, and abundance values falling below one standard deviation considered to have an expression level low enough to consider "not detected" (0), for the purpose of epitope selection.

AML/Normal HSPCs Ratio Analysis

The experiment-normalized RNA data obtained from Bloodspot.eu was exponentiated using a base of two as the data was natively provided in log 2 format, after which the maximum values taken for each unique (gene-cell type) entry. Data was then divided into two groups, AML and normal HSPCs, with the AML group consisting of the following subtypes: -5/7(Q), -9Q, 7, 8, ABN(3Q), COMPLEX, COMPLEX_DEL(5Q), COMPLEX_UNTYPICAL, DEL(5Q), DEL(7Q)/7Q-, DEL(9Q), INV(16), INV(3), nan, NORMAL, OTHER, T(1;3), T(11Q23)/MLL, T(6;9), T(8; 16), T(8;21), T(9;11), T(9;22), TRISOMY 11, TRISOMY 13, and TRISOMY 8. The normal HSPCs group consisting of the following cell types: HSC, MPP, CMP, GMP, and MEP. A mean expression value for each gene in the AML group was then calculated by averaging across the five normal cell types. The resulting mean values were then taken as devisors for expression ratios in which the dividends were each cell type's RNA abundance. The base ten logarithm was then taken for each expression ratio and normal curves were fit to the observed distribution using the Broyden-Fletcher-Goldfarb-Shanno algorithm, after which the peak maximum and standard deviation measure was recorded for each curve. A threshold of two standard deviations above the distribution maximum was then applied, and any protein candidate with a ratio above this threshold recorded for later use.

Target Selection

Step 0—Surface Proteomics

Only proteins found during surface-biotinylation proteomics assays performed on six AML cell lines, THP1, Mono-mac, Kasumi, Molm13, OCI/AML3 and TF-1, those reported by Strassberger et al., or a select list of 359 previously reported molecules, including CLEC12A, IL3RA, FOLR2, FUT3, CD33, and CD38 were kept for further study.

Step 1—RNA

Further, exclusively molecules whose ratio of RNA expression in AML samples versus normal HSPCs cells was greater than or equal to 2 SD above the mean were retained.

Step 2—QC

Only protein entries reported only in two or more normal tissue proteomics databases were retained for further study. Additionally, proteins were discarded from further consideration if the locations reported in either the HPA or COMPARTMENTS databases were not on the cell membrane.

Step 3—Exclude High Expressors

Any protein entry whose mean expression across all normal tissues exceeded the classification threshold as a "medium" (2) expressor was excluded from further study. Further, all proteins whose expression was classified as high (3) for any tissue type, in any dataset, apart from those originating from blood and bone were excluded from further study.

Combinatorial Selection

Pairwise Exclusion 9 candidates, in addition to CLEC12A, IL3RA and CD33, were then assessed as combinatorial pairs by evaluating their expression each tissue sites at once. Vital and non-vital tissues were then assessed using distinct criteria, which all tissues possessing a given protein were required to pass. Due to their high concentration of hematopoietic cells, the appendix, bone, blood, and spleen tissues were not considered for the purposes of selection. Criteria for vital tissues (adipose tissue, adrenal, bladder, brain, bronchus, eye, gut, heart, kidney, esophagus, liver, lung, nasopharynx, oropharynx, pancreas, rectum, skeletal muscle, skin, smooth muscle, soft tissue, spinal cord, and stomach) required at least one of the tissue pairs to possess no detectable expression. Criteria for non-vital tissues (breast, cerumen, cervix, epididymis, fallopian tube, gallbladder, lymph node, ovary, parathyroid, prostate, seminal, spleen, synovial fluid, testis, thyroid, tonsil, uterus, and vagina) permit tissue expression in both antigens in a pair to exhibit "low" expression, or to possess no detectable expression, as qualified above.

Surface Proteomics

Cell surface biotinylation of six (THP1, Mono-mac, Kasumi, Molm13, OCI/AML3 and TF-1) human AML cell lines were performed, which was used for mass spectrometric analysis.

For the isolation and collection of surface proteins, the Pierce® Cell Surface Protein Isolation Kit #89881 (Thermo Scientific 89881) were used. $6 \times 10^6$ cells were cultured in 75 cm$^2$ flasks. Prior to surface protein biotinylation, all reagents were cooled to 4° C. The cells were washed four times with ice-cold phosphate buffered saline (PBS) followed by incubation with 0.25 mg/mL Sulfo-NHS-SS-Biotin in 10 mL ice-cold PBS per flask on a rocking platform for 30 minutes at 4° C. The biotinylation reaction was quenched by adding 500 µL of the provided quenching solution (Pierce). Centrifuge cells at 500×g for 5 minutes and discard supernatant. Cells were washed with ice-cold PBS, harvested by gentle scraping and pelleted by centrifugation. The cells were lysed using the provided lysis buffer (Pierce) containing a protease inhibitor cocktail (Sigma) for 30 minutes on ice with intermittent vortexing. Lysates were centrifuged at 16,000×g for 2 minutes at 4° C. The clarified supernatant was used for purification of biotinylated proteins on NeutrAvidin Agarose. Before use, 500 µL of NeutrAvidin Agarose slurry was washed three times with Pierce wash buffer in a provided column (Pierce). The clarified supernatant was added to the slurry and incubated for 2 h at room temperature in the closed column using an end-over-end tumbler to mix vigorously and allow the biotinylated proteins to bind to the NeutrAvidin Agarose slurry. Unbound proteins were removed by repetitive washing; three times with 500 μL Pierce Wash Buffer in a provided column (Pierce), three times with 500 μL (50 mM Ammonium bicarbonate) and eight times with 500 μL digestion buffer (50 mM Tric-Cl, pH 7.5, 1 mM $CaCl_2$). Finally bounded proteins on biotin-NeutrAvidin Agarose were digested with 4 μg of trypsin (prepared in digestion buffer) over night at 37° C. in shaking incubator (~750 rpm). The next day, digested peptides were filtered through column and protease reaction was stopped by of 0.5% TFA. Samples were cleared by centrifuging 10 min at 14,000×g, 15° C. and desalted by stage tips. Desalted peptides were dry down by speed vac and re-suspended in 10 μl of 3% acetonitrile/0.1% formic acid for LC-MS/MS analysis.

LC-MS/MS Analysis

Desalted peptides were dissolved in 3% acetonitrile/0.1% formic acid and injected onto a C18 capillary column on a nano ACQUITY UPLC system (Water) which was coupled to the Q Exactive mass spectrometer (Thermo Scientific). Peptides were eluted with a non-linear 200 min gradient of 2-35% buffer B (0.1% (v/v) formic acid, 100% acetonitrile) at a flow rate of 300 nl/min. After each gradient, the column was washed with 90% buffer B for 5 min and re-equilibrated with 98% buffer A (0.1% formic acid, 100% HPLC-grade water) for 4 min. MS data were acquired with an automatic switch between a full scan and 10 scan data-dependent MS/MS scan (TopN method). Target value for the full scan MS spectra was $3\times10^6$ charges in the 380-1800 m/z range with a maximum injection time of 30 ms and resolution of 70,000 at 200 m/z in profile mode. Isolation of precursors was performed with 2.0 m/z. Precursors were fragmented by higher-energy C-trap dissociation (HCD) with a normalized collision energy of 27 eV. MS/MS scans were acquired at a resolution of 17,500 at 200 m/z with an ion target value of $5\times10^4$ maximum injection time of 60 ms and dynamic exclusion for 60 s in centroid mode.

Protein Identification

MS raw files were converted into MGF by Proteome Discover (Thermo Scientific) and processed using Mascot 2.4 (Matrix Science, U.K.) by searching against the Uniport human Database (version 2014 with 20209 protein entries) supplemented with common contaminant proteins. Search criteria included 10 ppm mass tolerance for MS spectra, 0.8 Da mass tolerance for MS/MS spectra, a maximum of two allowed missed cleavages, fixed carbamidomethylation of cysteine modifications, variable methionine oxidation and N-terminal protein acetylation, Mascot significance threshold of 0.05, and a false discovery rate of <0.01. Mascot data were assembled by Scaffold and X!-Tandem software and search criteria for identification 2 minimum peptides and 1% FDR at the peptide, and protein level.

Flow-Cytometric Analysis

The following antibodies were used to define antigen expression by flow-cytometry:

CD82-PE (Biolegend, 342103); CD120b (TNF-RII)-PE (Miltenyi, 130-107-740); EMR2-FITC, -APC (Miltenyi, 130-104-654, 130-104-656); ITGB5-PE (Biolegend, 345203); CCR1-PE, -APC (Miltenyi, 130-100-367, 130-100-358); CD96-APC (Miltenyi, 130-101-031); PTPRJ (CD148)-PE (life technologies, A15799); CD70-PE, -FITC (Biolegend, 355104, 355106); CD85d (ILT4)-PE-APC (Miltenyi, 130-100-567, 130-100-559); LTB4R1-AF700 (Novus Biologicals, FAB099N); CD85h (ILT1)-APC (Miltenyi, 130-100-920); TLR2-APC (Miltenyi, 130-099-020); CR1 (aka CD35)-APC (Miltenyi, 130-099-923); ITGAX (CD11c)-APC (Biolegend, 301613); EMB (abcam, 179801); EMC10 (abcam PA5-25112); LILRB3-PE (Miltenyi, 130-101-662); LILRB4-APC (R&D, FAB24251A); DAGLB (abcam, PA5-26331); P2RY13 (Novus, NBP2-37382); LILRA6-APC (Miltenyi, 130-101-665); SLC30A1 (Alomone labs, AZT-011); SLC6A6 (LSBio, LS-C179237); SEMA4A (R&D, FAB4694A); CD123-PE (BD Biosciences, 555644); CLEC12A-PE (Miltenyi 130-106-482); CD33-APC (Miltenyi, 130-098-864); CD38-BV421 (BD Biosciences, 562444); CD34-PE/Cy7 (Biolegend, 343515); CD4SRA-BV640 (Biolegend, 304135); CD90-FITC (BD Biosciences, 555595).

Quantification and Statistical Analysis

Student's t-test was used for significance testing in the bar graphs using a two-sample, normally distributed equal-variance model. P values less than 0.05 were considered to be significant. Graphs and error bars reflect means and standard deviations. All statistical analyses were carried out using GraphPad Prism 4.0 and the R statistical environment. (*) 0.03, () 0.0021, (*) 0.0002, (****) 0.0001.

Allowing for a 20% margin, a sufficient single-tailed estimate of arbitrarily large population size can be assessed at 95% confidence with 23 patients. A sample size of 30 was chosen to further narrow the window of uncertainty.

Data and Software Availability

Proteomic data were submitted (ProteomeXchange Submission) to PRIDE database on Jul. 31, 2017. A temporary ticket has been assigned [px-submission #204296].

Results

Assembling a Comprehensive Dataset of AML Surface Molecule Annotations

Figure 11A:
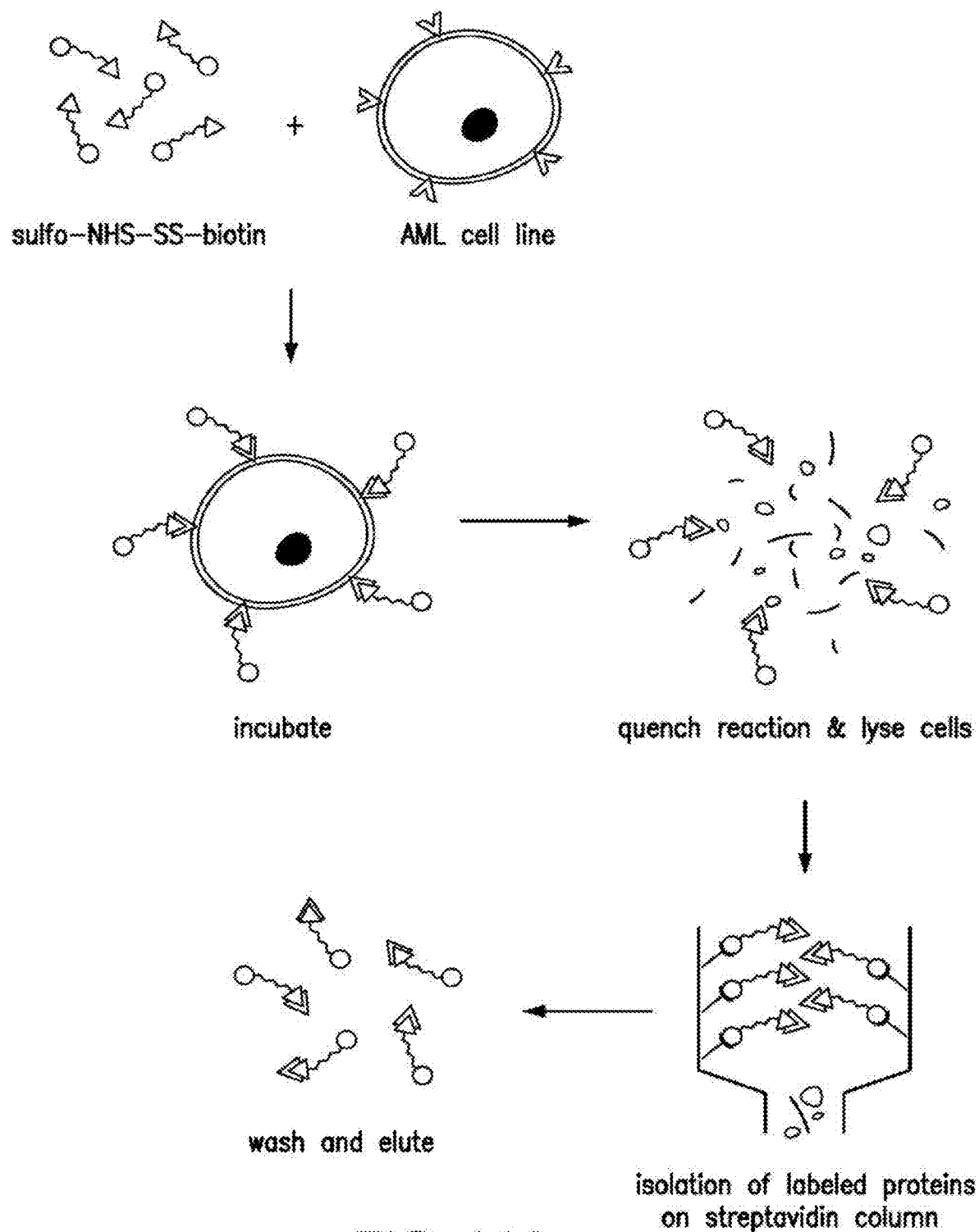
FIGS. 11A-11B depict the AML surface proteomics. A) Simplified diagram depicting the principle of surface-specific proteomic analyses performed in a panel of AML cell lines B) Venn diagram comparing molecules identified by surface biotinylation in AML cells and reported surface markers in AML.
Figure 11B:
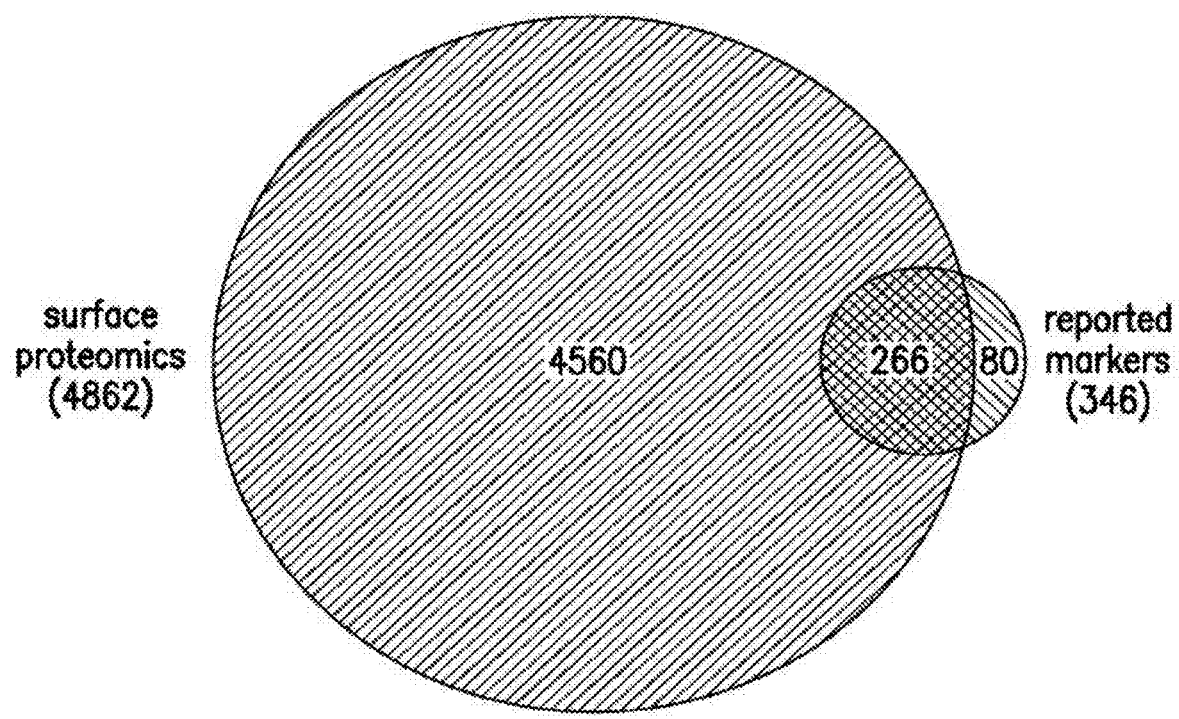

To search for potential CAR targets, surface-specific proteomic studies were first performed in a diverse panel of AML (THP1, Mono-mac, Kasumi, Molm13, OCI/AML3 and TF-1) cell lines. After biotinylating the cell surface (FIG. 11), mass-spectrometric analysis were performed and 4,942 proteins were identified. In order to generate the largest possible inclusive data set, the findings of surface-specific proteomic studies conducted in other human myeloid leukemia lines (NB4, HL60, THP1, PLB985, K562) (Strassberger et al., 2014) and all previously reported surface proteins, such as CD123 (Jordan et al., 2000), CLL1 (Bakker et al., 2004), CD33 (Taussig et al., 2005), CD44 (Jin et al., 2006), CD96 (Hosen et al., 2007), CD47 (Majeti et al., 2009), CD32 and CD25 (Saito et al., 2010), TIM3 (Kikushige et al., 2010), CD99 (Chung et al., 2017) were further added to this list, adding another 80 proteins (FIG. 6—orange boxes).

To annotate the expression of these molecules in normal tissues, data from the Human Protein Atlas (HPA) (Uhlen et al., 2015), the Human Proteome Map (HPM) (Kim et al., 2014) and the Proteomics Database (PD) (Wilhelm et al., 2014) were integrated. These data sources provided protein expression information for several normal tissues/organs, including liver, gallbladder, pancreas, stomach, gut, duodenum, colon, rectum, testis, epididymis, prostate, breast, vagina, uterus, ovary, skin, skeletal and smooth muscle, cerebral cortex, hippocampus, lateral ventricle, cerebellum, thyroid, bronchus, lung, heart, retina, vitreous humor, bone marrow, lymphocytes, lymph nodes, tonsil, synovial fluid and others, listed in Table 4. Data in the atlases were obtained by antibody-based immunohistochemistry (HPA) or protein Mass Spectrometry (HPM and PD) (FIG. 6—green boxes). To focus the study on molecules specifically annotated to the membrane, two subcellular localization data sources, the HPA's subcellular annotation and the Jensen Lab's Compartments repository were relied on (FIG. 6—yellow boxes).

Figure 6:
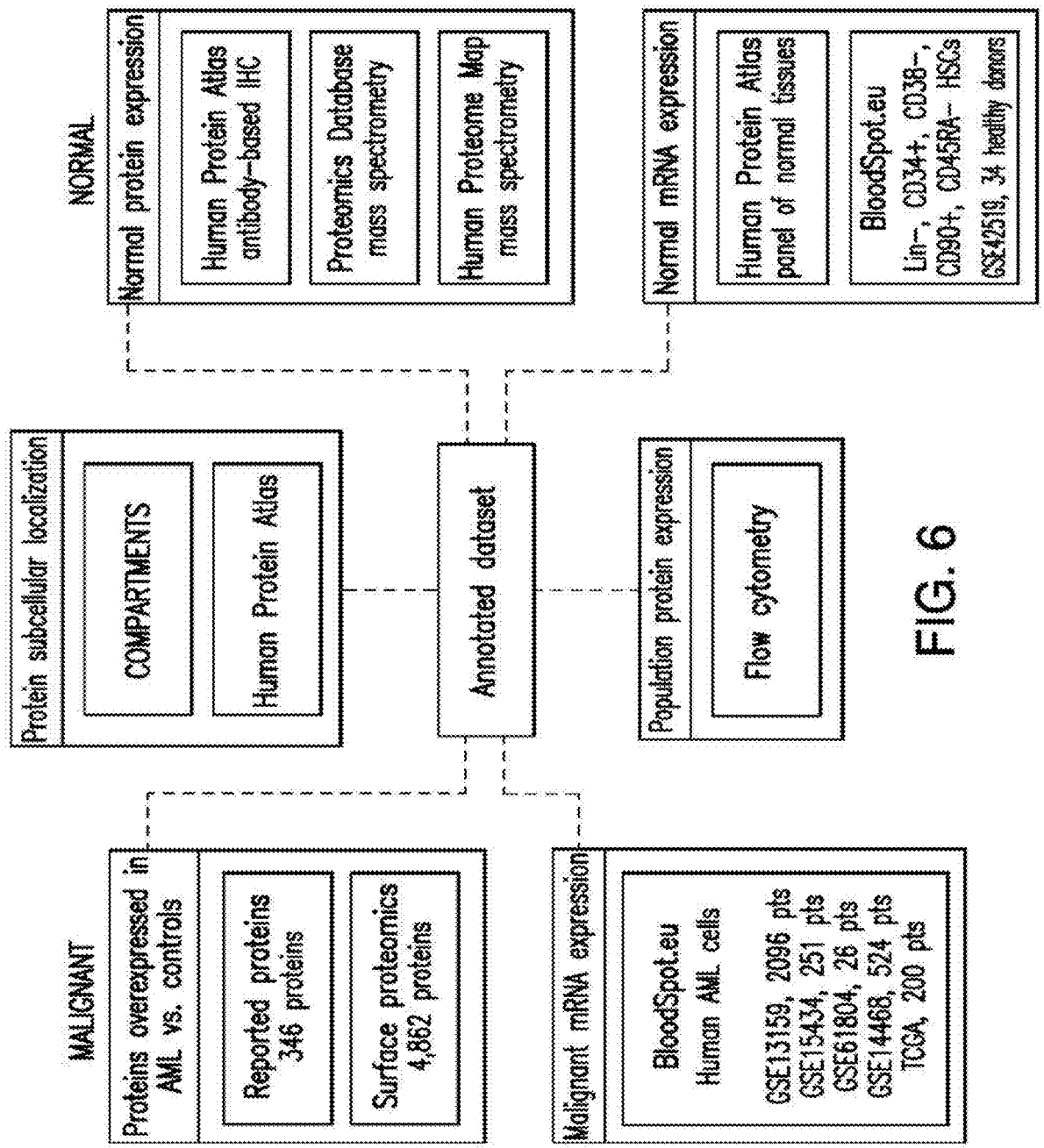
FIG. 6 depicts the generation of a comprehensive dataset of surface molecule annotations. On the left side the data sources related to malignant (AML) cells and on the right the data sources related to normal cells. Orange boxes represent the information derived from either previous studies (346) or in-house surface proteomics studies (4,862) in a panel of AML cell lines. Yellow boxes represent the data sources providing information regarding subcellular localization. Green boxes represent three distinct published repositories of protein expression levels in several normal tissues and the platform in which data was generated. Pink boxes represent RNA data either from normal (right side) or AML cells (left side). The blue box represents the expression data obtained by flow-cytometry in multiple distinct subsets of hematopoietic cells. The center grey box represents the combined annotation repository.

To remove surface molecules that are not over-expressed in AML cells compared to normal counterparts, publicly available gene expression analyses in normal bone marrow CD34+CD38-CD90+CD45RA-HSCs and Lin-CD34+CD38–CD90–CD45RA– multipotent progenitors (MPP), Lin-CD34+CD38+CD45RA–CD123+ common myeloid progenitor cells (CMP), Lin-CD34+CD38+CD45RA+CD123+ granulocyte monocyte progenitors (GMP), Lin-CD34+CD38+CD45RA–CD123– megakaryocyte-erythroid progenitor cells (MEP) from healthy donors (GSE42519) and 3,097 primary AML patient samples clustered in 26 distinct subtypes based on specific cytogenetics such as del5q, t(8;21), t(11q23)/MLL, inv(16)/t(16;16) etc (GSE13159, GSE15434, GSE61804, GSE14468 and the Cancer Genome Atlas) (Bagger et al., 2016) were utilized (FIG. 6—pink boxes). In the final stage of the study, the expression of candidate targets selected by the algorithms were characterized and described below, in a panel of 30 primary AML patient samples based on flow-cytometric analyses (FIG. 6A—blue box). This compilation (FIG. 6—grey box) represents the most comprehensive repository of AML surface protein annotation assembled to date.

Design of an Algorithm to Identify CAR Targets

Figure 7A:
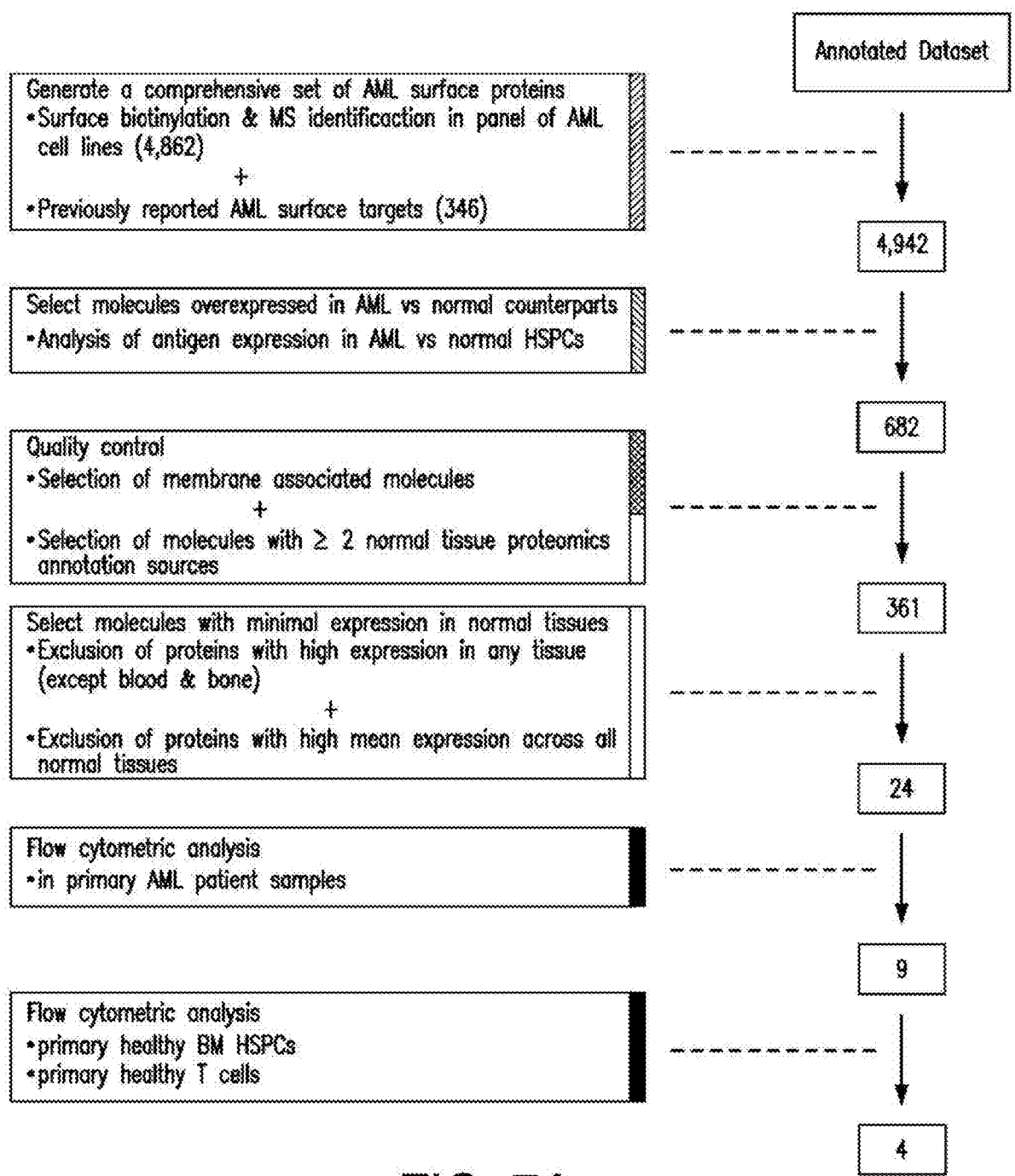
FIGS. 7A-7B depicts an algorithm to identify candidates for CAR therapy. A) The algorithm shows the steps, which identify surface molecules in AML and molecules, which are overexpressed in AML compared to normal HSPCs; the quality control; the step, which identifies targets with minimal expression in a large panel of normal tissues and flow-cytometric analysis. Step descriptions color-coded relative to data sources in FIG. 6. Indicated to the right of each box, the number of molecules resulting from each analytical step. B) Heatmap showing the expression profile of 24 selected candidates in a large panel of normal tissues as well as previously identified CAR targets in AML and CD19. *Only PDB distinguishes between CD44 and CD44v6, shown is an aggregate of CD44 isoforms. If one excluded high expression in the normal spleen from the analysis, both CD33 and CLEC12A would be included amongst the top 24 CAR candidate targets (as illustrated in FIG. 14).

Starting from an annotated dataset of 23,118 Ensembl gene entries (19,876 unique HUGO gene identities) including 4,943 surface molecules, an algorithm to select CAR targets were designed (FIG. 7A). Given that an ideal target should be over-expressed in tumor cells compared to normal tissue counterparts, a log 10 expression ratio were first computed between AML cells and normal HSPCs per molecule by comparing RNA expression levels in 26 genetically defined subtypes of AML, to normal BM CD34+CD38-CD90+CD45RA-HSCs, MPP, CMP, GMP, and MEP progenitor cells. A mean expression value for each molecule in both malignant and normal groups was calculated and a normal distribution fit to the AML/normal HSPCs ratios. A threshold of two standard deviations above the distribution peak maximum was applied, leaving 823 Ensembl gene entries corresponding to 682 unique HUGO entries. Antigens were then prioritized with a membrane-associated sub-localization and redundant protein expression data in at least 2 of the 3 databases (HPA, HPM and PDB) that annotate expression levels in normal tissues. This "quality control" step further removed 321 molecules, leaving us with 361 candidates.

Figure 7B:
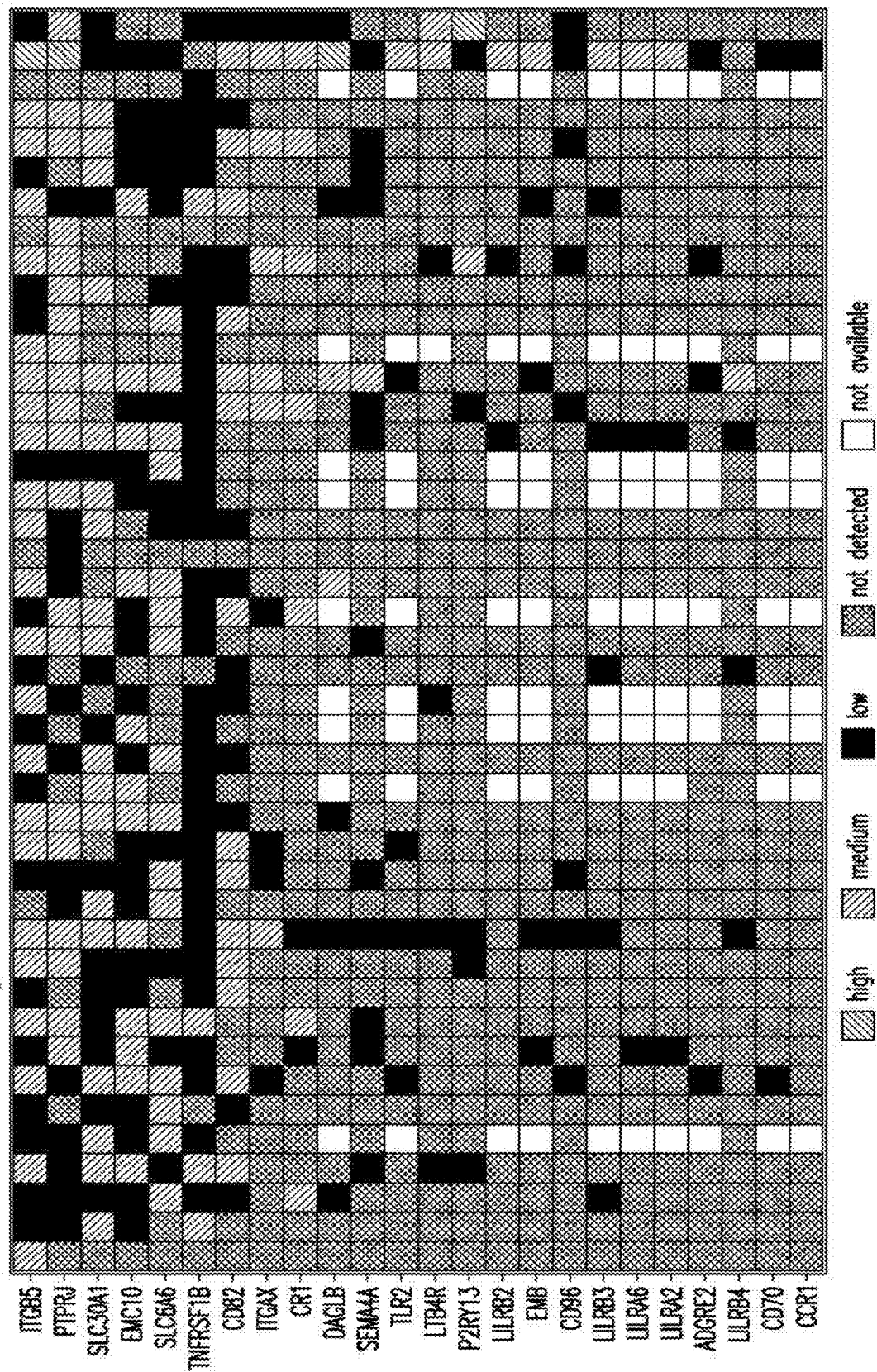
Figure 12B:
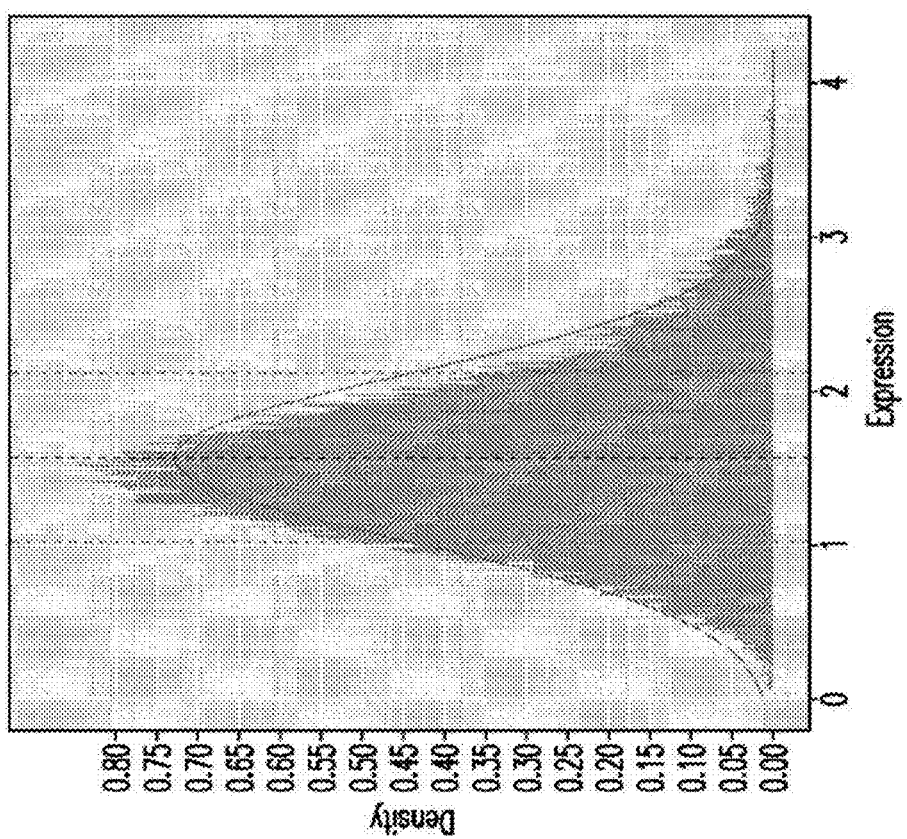
FIGS. 12A-12B depict the calculation of distribution metrics in PDB and HPM datasets. A) PDB, the log 10 expression density, plotted with normal curve overlay. Dashed black line placed at peak maximum and dashed purple lines at one standard deviation above and below peak max. B) HPM, ordered log 10 expression. Dashed black line placed at peak maximum and dashed purple lines at one standard deviation above and below peak max.
Figure 12A:
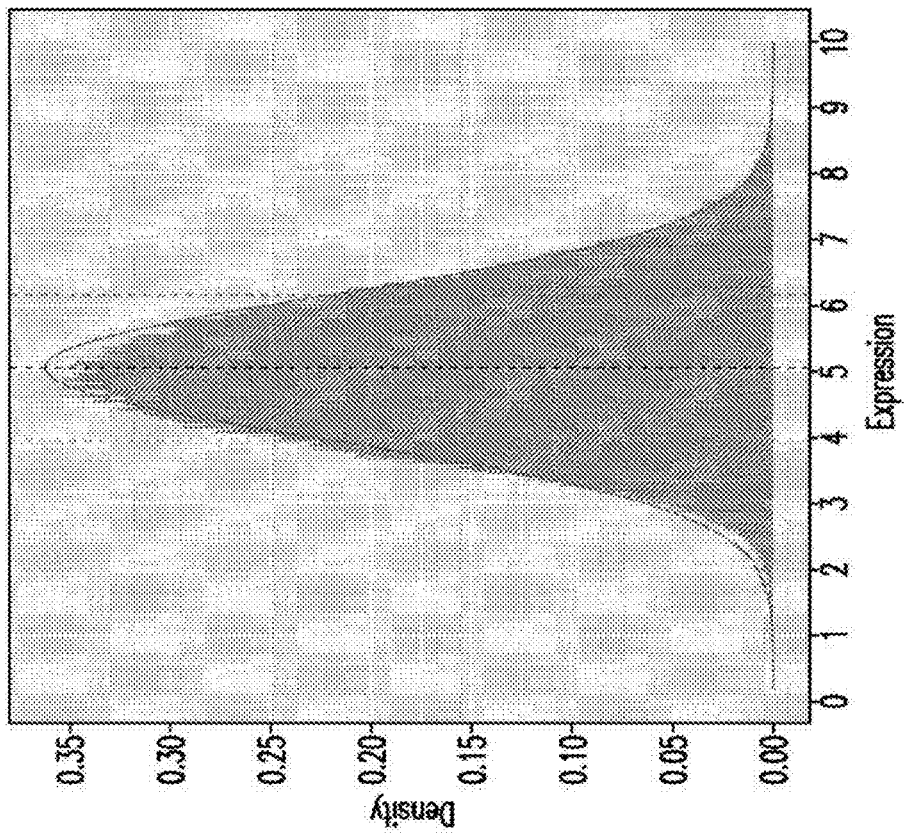
Figure 14:
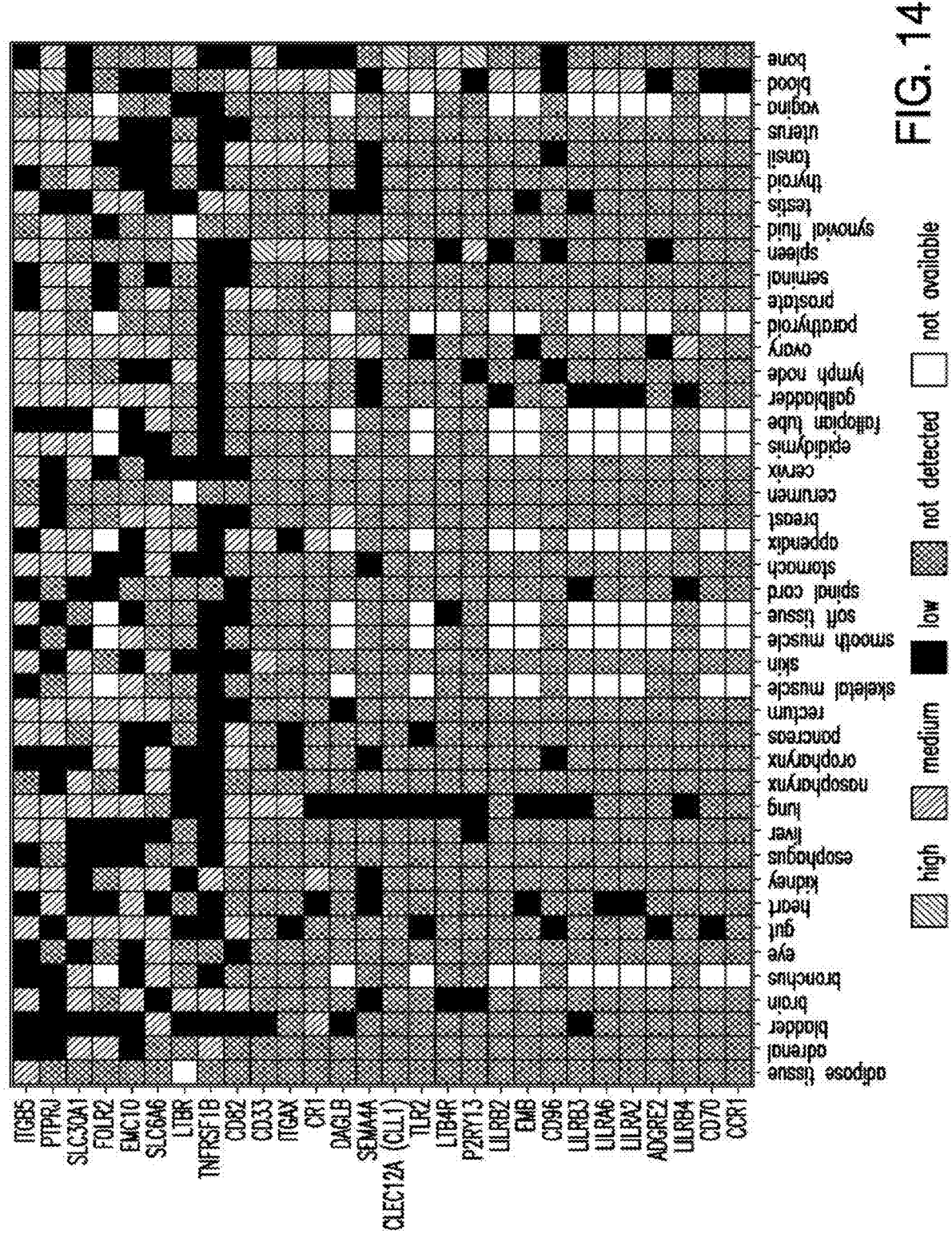
FIG. 14 depicts the expression profile of CAR targets in normal tissues. Heatmap showing the expression profile of selected candidates with no high (3) expression in a large panel of normal tissues, except blood, bone marrow and spleen.
Figure 15:
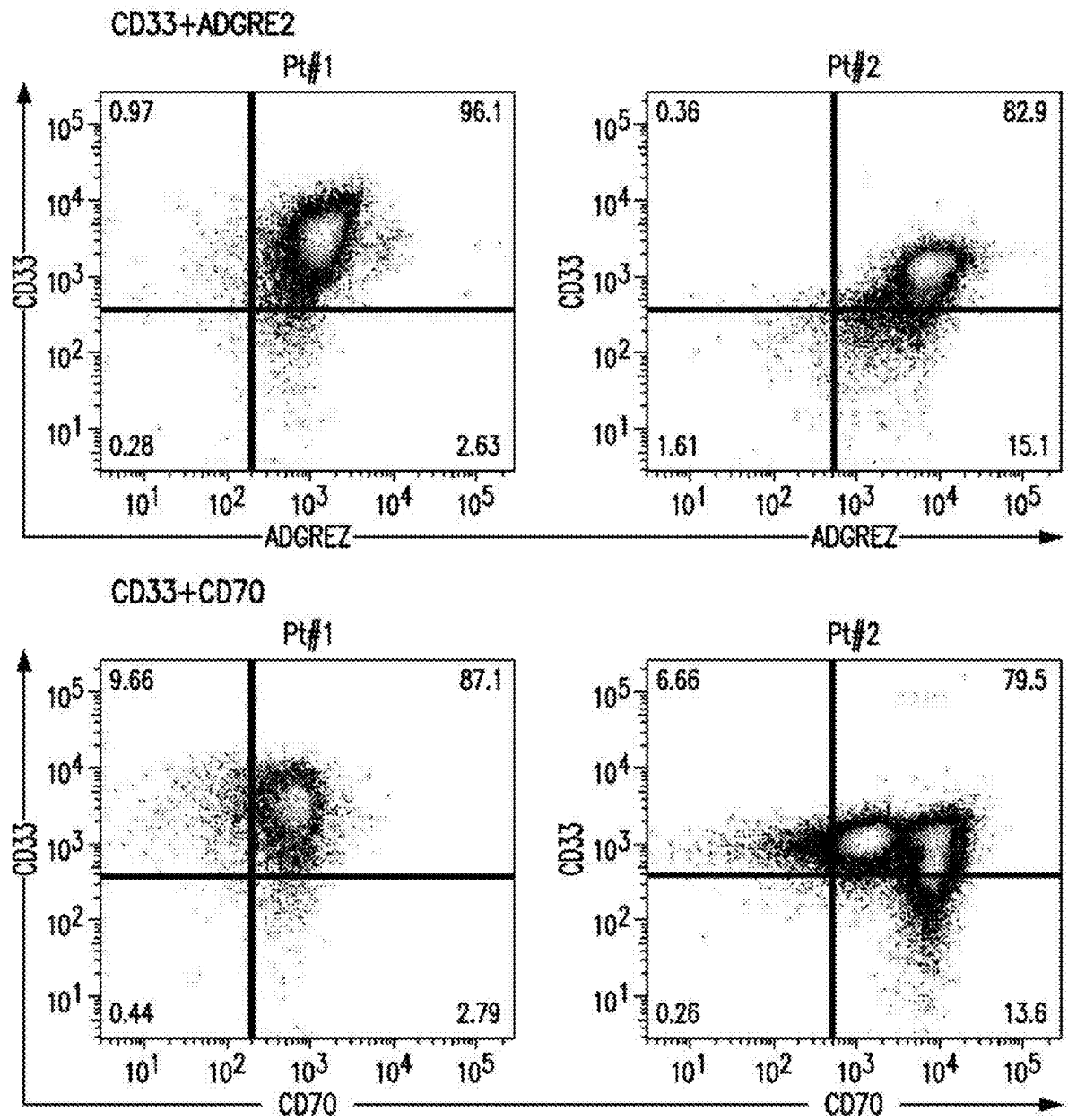
FIG. 15 depicts the scatter plots of the expressions of AML targets in patient. First row shows 2 scatter plots of ADGRE2+CD33 pair from 2 patients. Second row shows 2 scatter plots of CD70+CD33 pair from 2 patients. Third row shows 2 scatter plots of CCR1+CLEC12A pair from 2 patients and fourth row shows 2 scatter plots of LILRB2+ CLEC12A pair from 2 patients. The presented data were acquired on different days and from different patients and analyzed in comparison to their specific controls.
Figure 15:
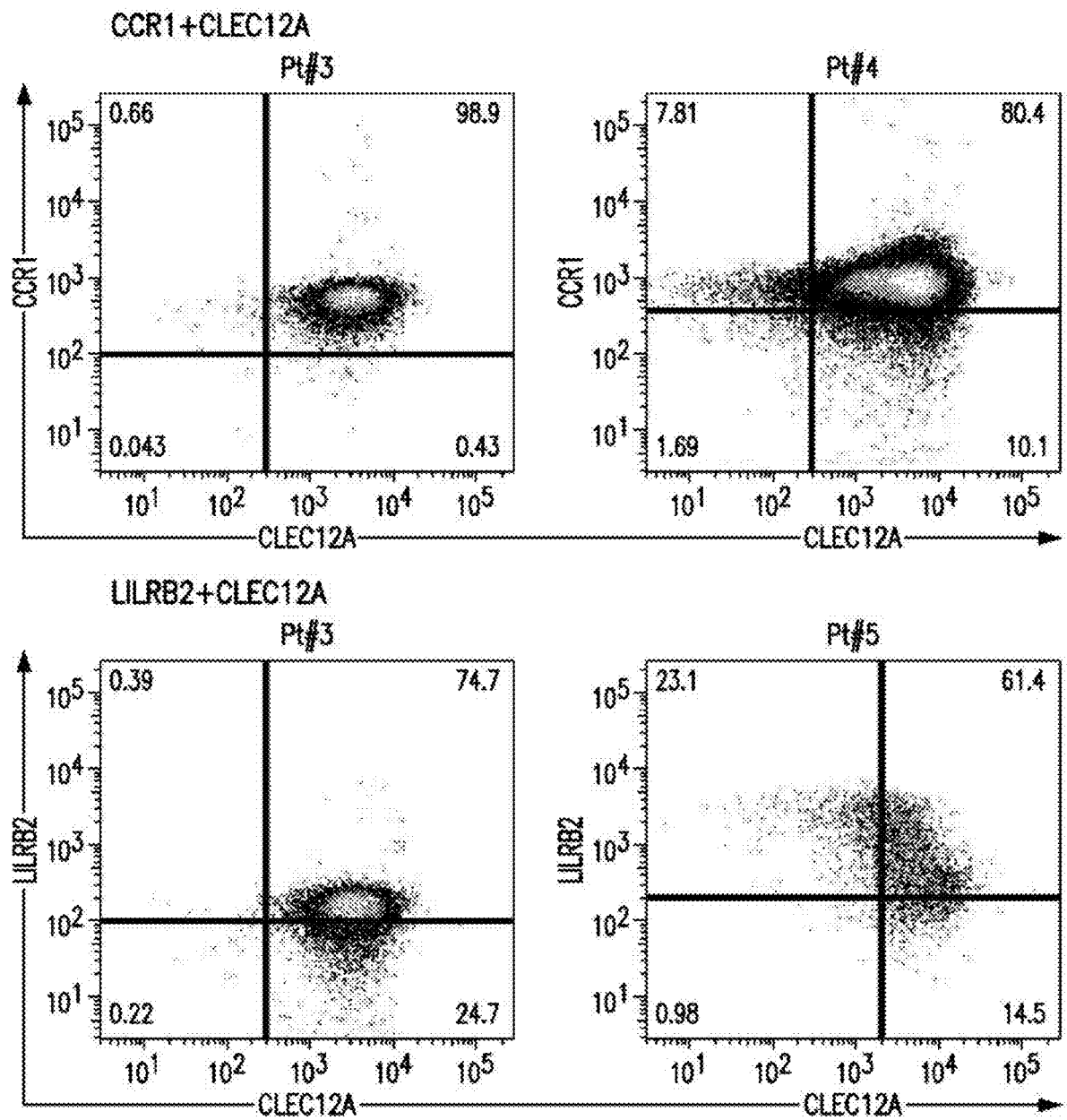

To eliminate any molecule highly expressed in normal tissues, protein expression data in normal tissues from HPA, HPM and PDB were merged, ranging from 0 (below the level of detection) to 3 (high) (FIG. 12). Molecules exhibiting high average expression (>2) across all normal tissues as well as molecules exhibiting high expression (3) in any normal tissue were excluded, except for blood and bone/bone marrow. With this algorithm, 24 molecules overexpressed in AML vs. their normal counterparts were identified and with no high expression in clusters of normal tissues, except for blood and bone marrow (FIG. 7B). Further exclusion of the spleen would additionally include CD33 and CLEC12A amongst the top 24 CAR candidate targets (FIG. 14).

Expression Analyses in Primary AML Samples and Normal Hematopoietic Cells

Figure 8A:
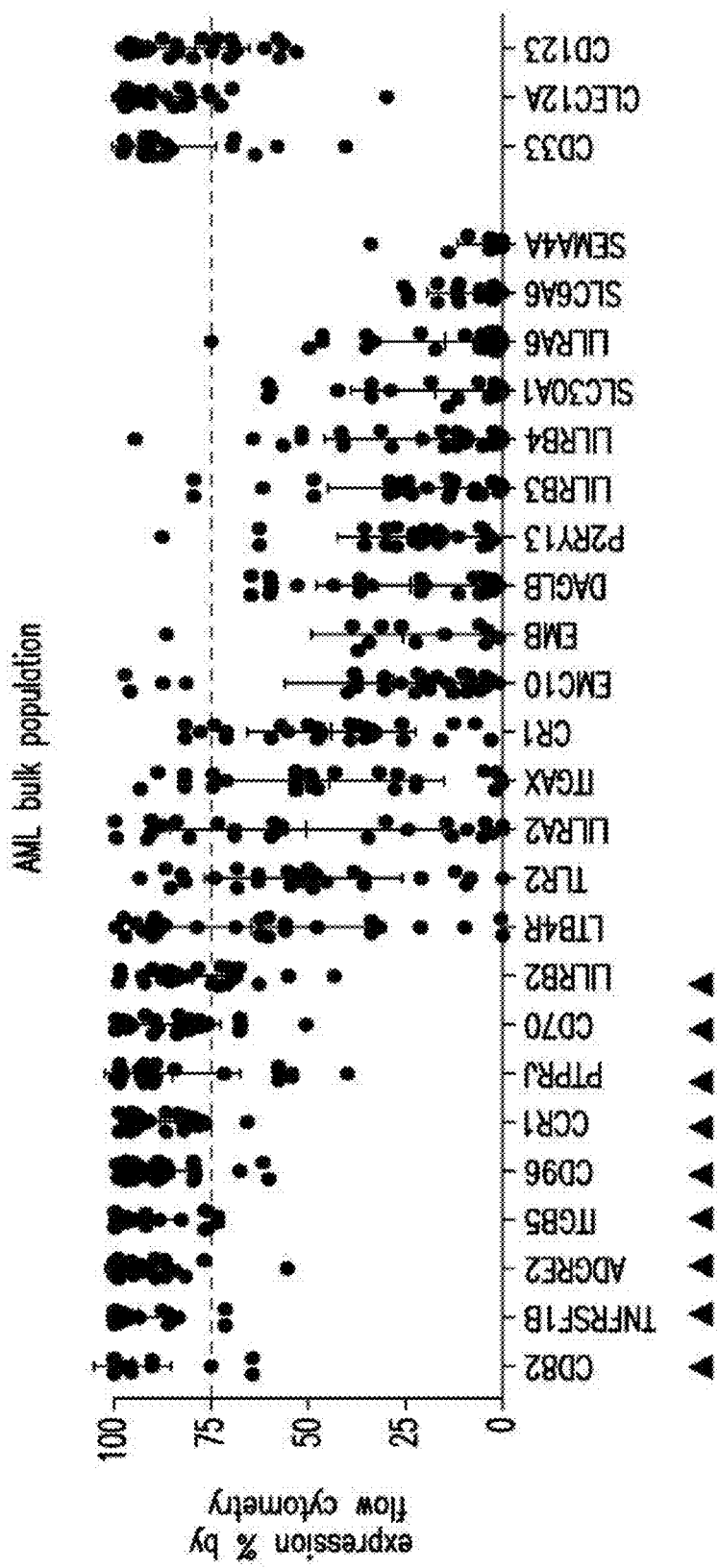
FIGS. 8A-8E depict the flow-cytometric analysis in primary AML patient samples and normal hematopoietic cells. A) Percentage of cells expressing candidate antigens in AML bulk population with respect to 3 CAR targets (CD123, CD33 and CLEC12A) in current clinical investigations by flow-cytometry B) Percentage of cells expressing candidate antigens in Leukemic CD34+CD38+ stem cell population by flow-cytometry C) Percentage of cells expressing candidate antigens in normal bone marrow CD34+CD38-CD45RA-CD90+ HSCs and CD34+CD38+ progenitor cells by flow-cytometry. D) Percentage of cells expressing candidate antigens in normal CD3+ T cells at two time points (freshly purified and upon activation) by flow-cytometry E) Summary expression levels of 4 top targets in AML bulk population, LSCs, normal HSCs and T cells. **** corresponds to P value <0.0001 by Student's t-test.

Expression levels of the 24 candidates were analyzed by flow cytometry in 30 primary specimens of relapsed AML, enriched for AML harboring genetic abnormalities predisposing to clinical relapse (Table 4). These samples bear frequently recurring genetic abnormalities, including mutations in DNMT3A (14), CEBPα (12), IDH2 (11), FLT3-ITD (9), NPM1 (7), IDH1 (7), WT1 (4), RUNX1 (4), ASXL1 (4), SUZ12 (3), KRas (2), TET2 (2), p53 (1) and CBL (1). Nine of the 24 candidate targets were present in all analyzed patient specimens and detected in >75% cells: CD82, TNFRSF1B (aka CD120b), ADGRE2 (aka EMR2 or CD312), ITGB5, CCR1 (aka CD191), CD96, PTPRJ (aka CD148), CD70, and LILRB2 (aka CD85d). In the analyses CD123 (IL3RA), CLEC12A (CLL1) and CD33 were also included, as these molecules are targets in current AML clinical trials. These antigens were also found to be expressed in >75% of AML cells in all patients (FIG. 8A).

Figure 8B:
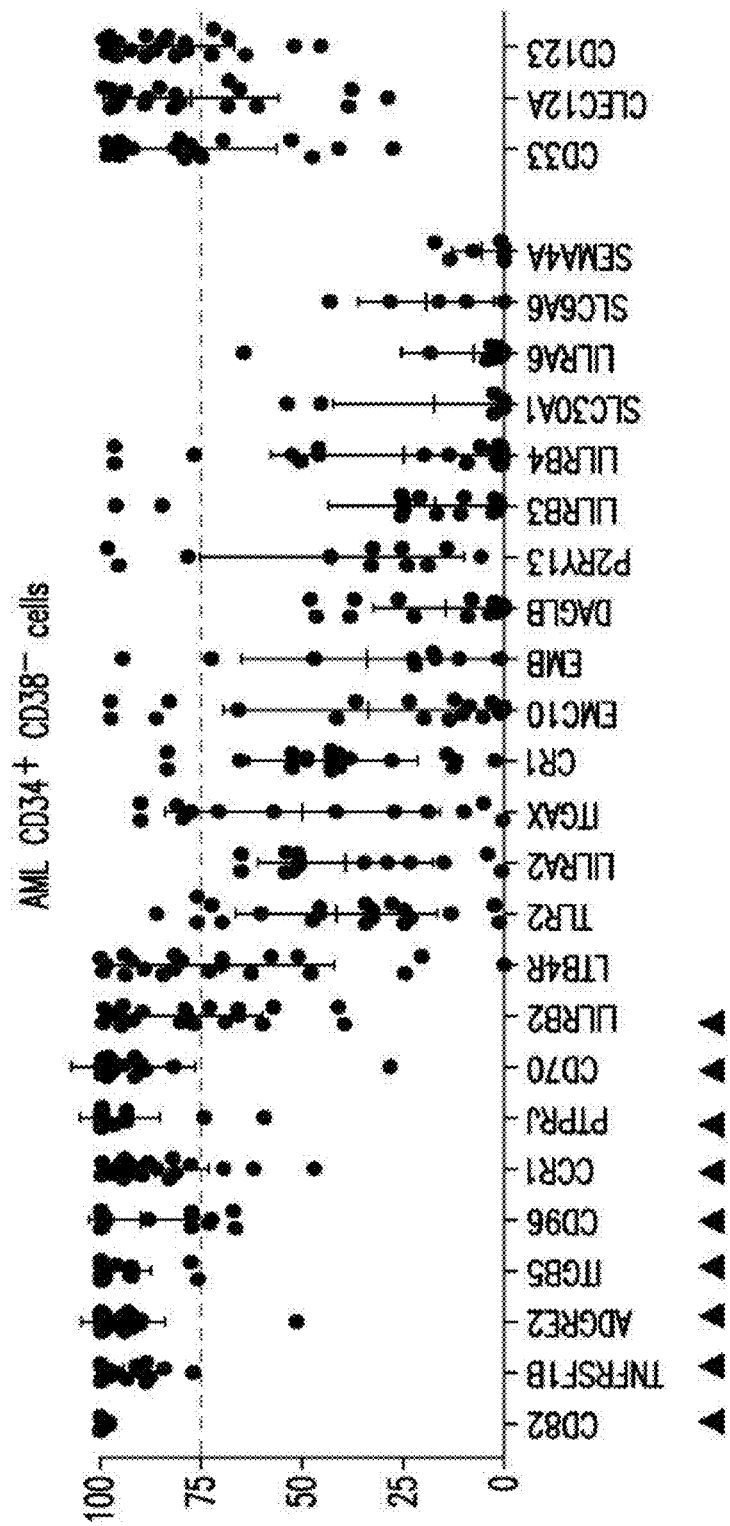
Figure 8C:
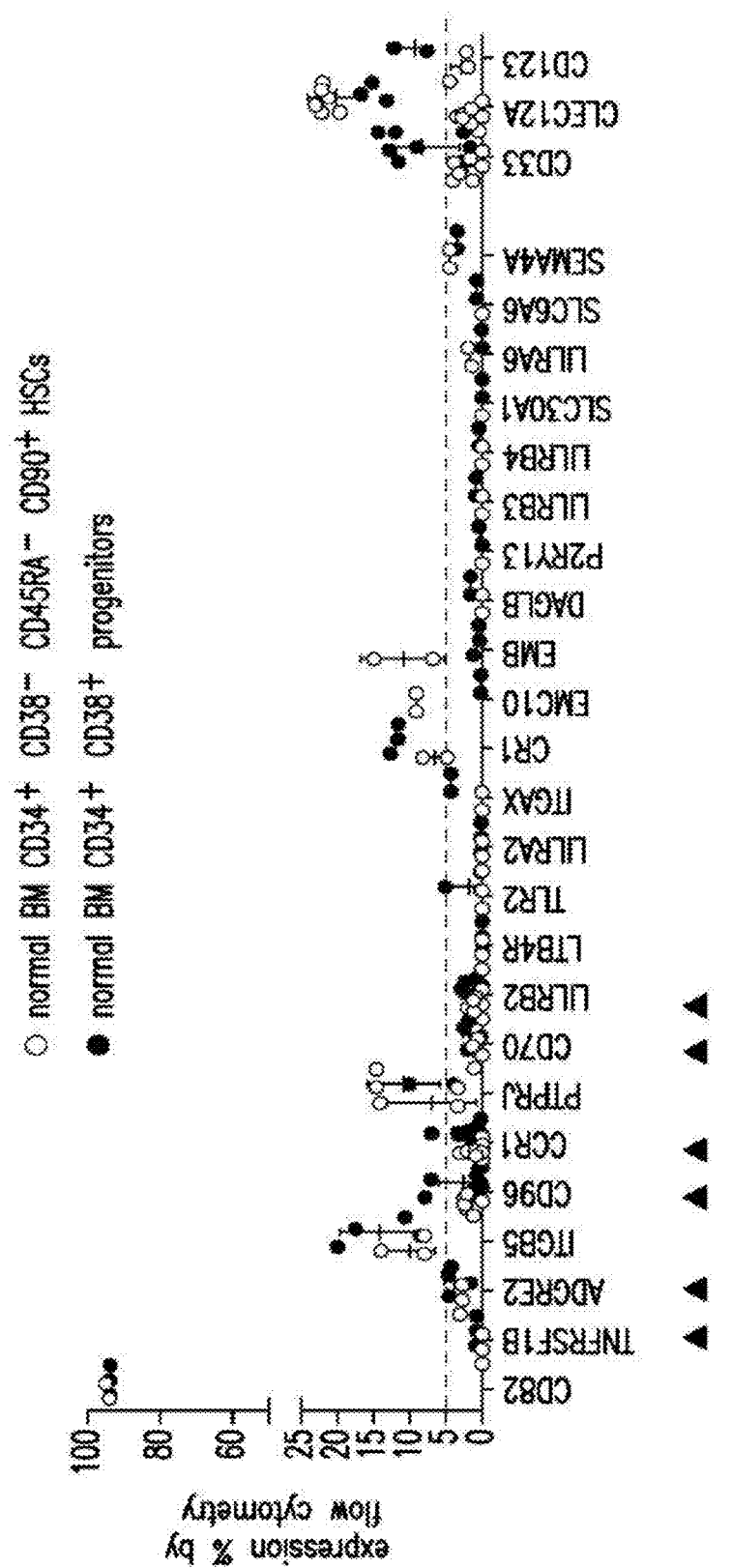

As an ideal CAR target should be expressed in leukemic stem cells (LSCs) (Table 3), the expression of our selected markers in AML CD34+CD38-cells were further examined using flow cytometry. All 9 targets were also highly expressed (>75%) in this essential AML cell subset (FIG. 8B). Their mean expression levels (range 78-99%) were comparable to that of CD123 (mean 82%) and slightly higher than that of CLEC12A (mean 77%) and CD33 (mean 77%) in LSCs. Flow-cytometric analyses in normal BM CD34+CD38-CD90+CD45RA-HSCs and CD34+CD38+ progenitor cells showed that 6 out of 9 molecules (TNFRSF1B, ADGRE2, CCR1, CD96, CD70 and LILRB2) were expressed at low levels (<5%) in normal HSPCs (FIG. 8C). CD123, CLEC12A and CD33 were present at higher levels in these normal progenitor cells (9%, 20% and 8%, respectively) (FIG. 8C).

Figure 8D:
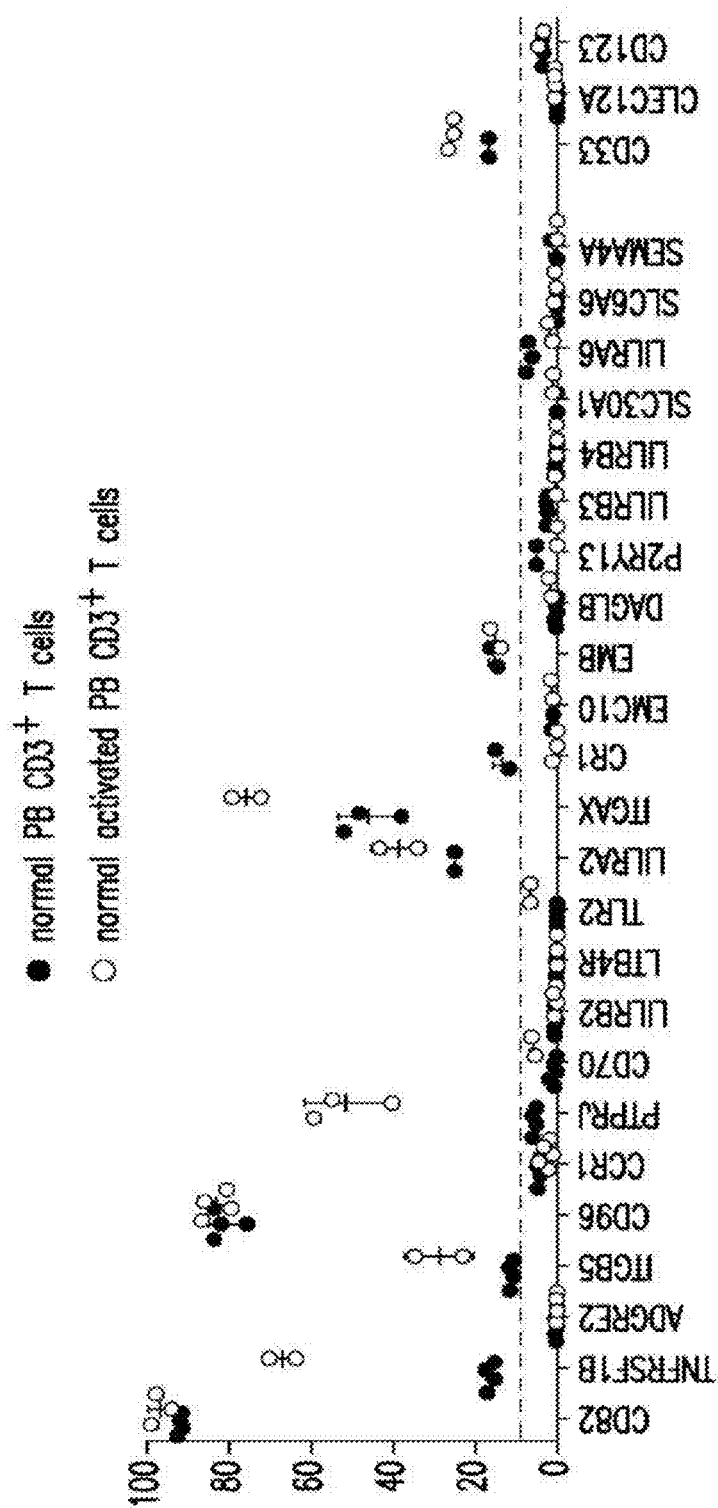

As CAR therapy requires the sustained activity of functional CAR T cells, expression of these antigens in freshly purified and activated T cells from healthy donors were investigated. Four of the latter 6 candidates (ADGRE2, CCR1, CD70 and LILRB2) showed low-level expression (<5%) in T cells (FIG. 8D). TNFRSF1B and CD96 were more abundant (up to 67% and 83%, respectively), which may complicate the generation or activity of CAR T cells and would require adapted strategies (e.g., target gene ablation) if one were to pursue these antigens in a CAR therapy.

Figure 8E:
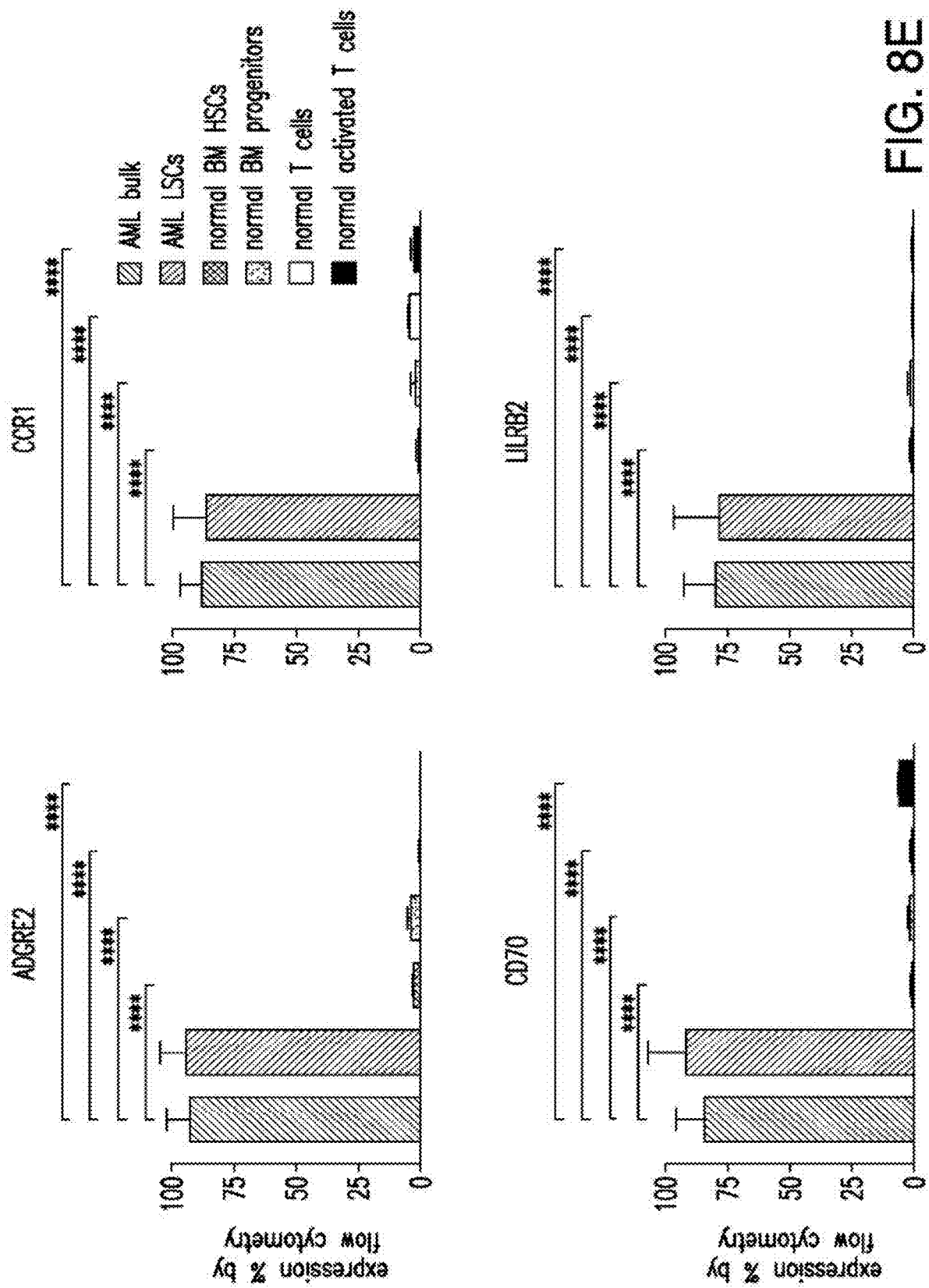

In summary, the selection process identified 4 potential CAR targets with high expression in AML bulk cells and AML LSCs (FIG. 8A-B) and low expression in normal tissues (FIG. 7B), normal HSPCs (FIG. 8C) and resting/activated T cells (FIG. 8D), as depicted in FIG. 8E. These expression profiles compare favorably with CD123, which is highly expressed in AML, especially LSCs (FIG. 8A-B), but is also abundant in multiple normal tissues (FIG. 7B). CD33 and CLEC12A are also highly expressed in AML (FIG. 8A), although they exhibit a high degree of expression in normal hematopoietic progenitor cells (FIG. 8C), consistent with their RNA expression levels (Bagger et al., 2016). Integrated systemic proteomics data indicate that CD33 is more abundant in the lung, prostate and skin (FIG. 7B).

It is noteworthy that none of these molecules showed a profile comparable to that of CD19, which is expressed at high levels in virtually all B cell leukemia cells, remains completely absent from HSPCs and T cells, and undetectable systemically. The absence of a target expression profile similarly favorable to CD19 thus prompted us to leverage the annotated database to explore combinatorial targeting strategies.

Combinatorial Pairing of Candidate Targets

Figures 9A, 9B, 9C:
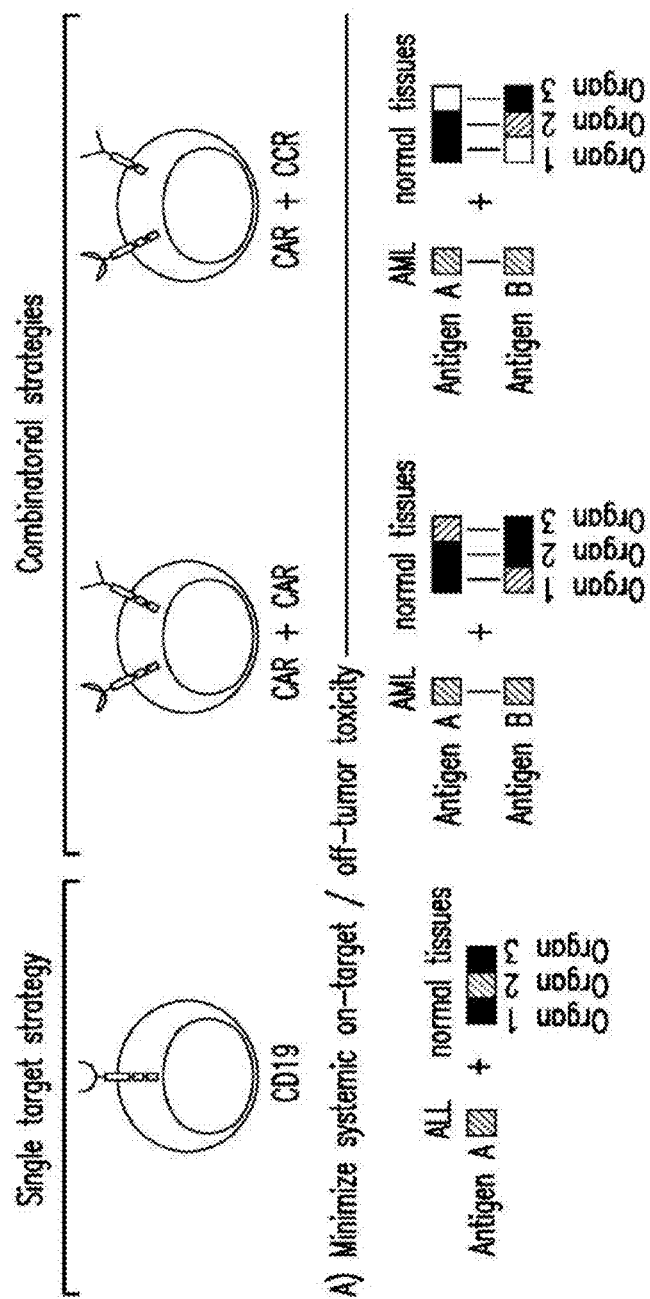

Combinatorial strategies fall in two major categories (FIG. 9). One is based on cumulative CAR targeting through the generation of bi-specific T cells that co-express two CARs (or a dual-specific CAR (Duong et al., 2011; Grada et al., 2013; Wilkie et al., 2012; Zah et al., 2016). The other takes advantage of split signaling (Alvarez-Vallina and Hawkins, 1996; Krause et al., 1998) to target two antigens, using one antigen to direct costimulation to enhance or rescue the suboptimal function of a CAR or TCR targeting the other antigen (Kloss et al., 2013; Krause et al., 1998). In the former approach (CAR/CAR, FIG. 9), T cells recognize target cells that express any of two given antigens and will thus engage tissues expressing either antigen alone. Some low or moderate expression in normal tissues, albeit not optimal, may be tolerable depending on the tissues in question. In the latter approach (CAR/CCR, FIG. 9), T cells are more restricted to dual-antigen positive tumor cells, thus relaxing the expression criteria for at least one of the paired antigens (FIG. 9A). This approach however requires pan-tumor expression of the CAR target to avert antigen escape (FIG. 9D). In both instances, target pairings depend on the systemic expression and co-expression of the two prospective matches to minimize cumulative expression in normal tissues.

To further improve the targeting of AML (approaching 100% FACS positivity in all tumor cells as is seen with CD19 in ALL (Kong et al., 2008)), a software package was written to pair antigens minimizing the potential for systemic on-target/off-tumor activity by avoiding cumulative target expression in normal organ/tissues (FIG. 9A). Two other related safety requirements are the avoidance of normal HSC (FIG. 9B) and T cell recognition (FIG. 9C). The considerations for a combinatorial approach are however more complex and entail additional, concurrent principles for selecting preferred target combinations. Thus, with regards to increasing therapeutic efficacy, the first principle is to maximize the number of targetable tumor cells, addressing the challenge of clonal heterogeneity (FIG. 9D). Another priority is to target LSCs, without which a CAR therapy would not stand a chance of being potentially curative (FIG. 9E). Finally, pairing choices should favor redundant expression of the two targets in the tumor in order to minimize the risk of antigen escape (FIG. 9F). These principles were applied to a pool of 12 molecules, including the 9 top single targets defined in FIG. 7, to which CD123, CD33 and CLEC12A were added, which represent 66 possible combinations.

Figure 10A:
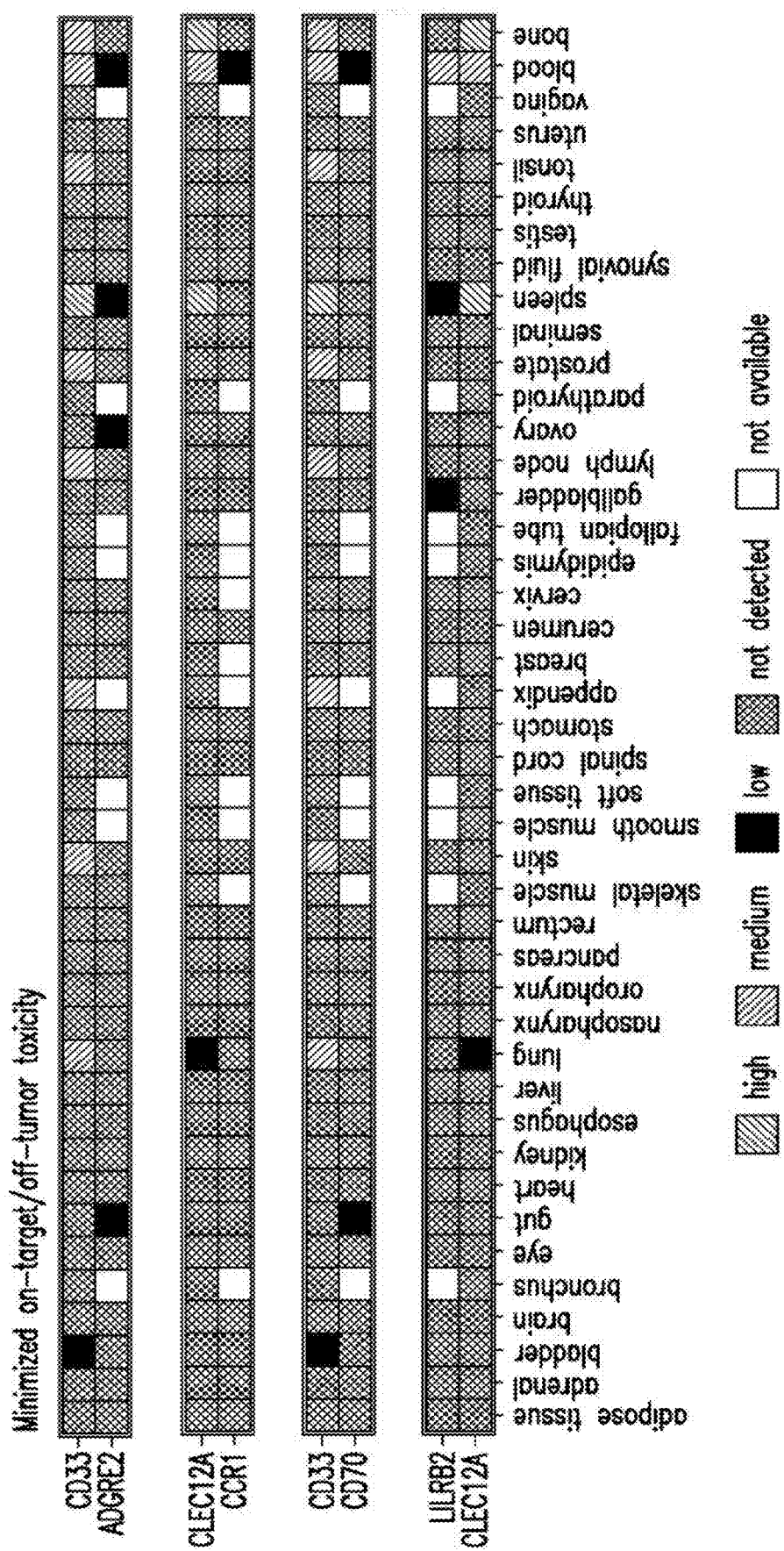
FIGS. 10A-10D depict the combinatorial pairs of targets. A) 4 combinatorial pairs, defined by evaluating the expression of tissue sites together. Criteria for vital tissues require at least one antigen in the pair to possess no detectable expression in any tissue. Criteria for non-vital tissues permit tissue expression to exhibit "low" expression. B) Total percent expression of cells with either antigens in the pair compared to expression levels of each antigen alone in primary AML samples C) Levels of co-expression (intersection) of two targets compared to total (union) expression levels. Data are represented as mean±standard deviation. D) Expression levels of the pairs in AML cells compared to normal BM HSCs and T cells.
Figure 16:
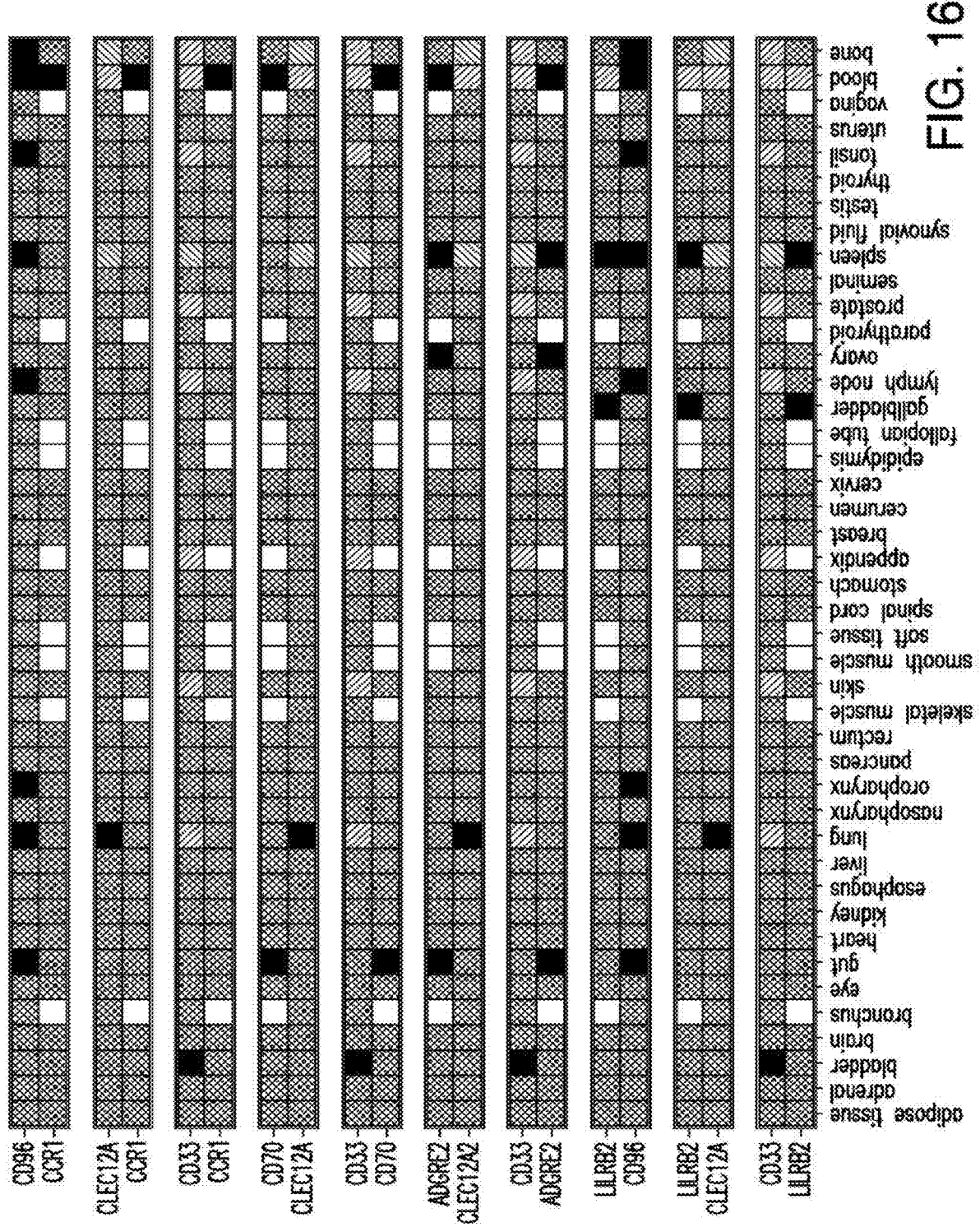
FIG. 16 depicts ten combinatorial pairs with non-overlapping expression in normal tissues.

The first step was to identify antigen pairs that did not increase systemic on-target/off-tumor tissue targeting, addressing the principle illustrated in FIG. 9A. To this end, a script that pairs targets with non-overlapping expression in normal tissues were generated, wherein expression levels in vital and non-vital tissues were weighted. Pairing in vital tissues required that at least one of two antigens be "not-detected" (0) in each tissue. Pairing in non-vital tissues allowed both and one of the two antigens to exhibit "low" (1) expression. Our top 4 targets (ADGRE2, CCR1, CD70 and LILRB2), did not present overlapping expression in normal tissues (other than myeloid-rich tissues-bone, blood, spleen, appendix) when paired with CD33, CLEC12A or CD96. Thus, several pairings appeared not to increase toxicity based on this cumulative targeting criterion alone (FIG. 16). As CD96 was removed from final pairing because of its high expression in T cells (FIG. 8D) and failure to meet the FIG. 9C principle, the following 4 combinations were further pursued for validation in primary AML samples: ADGRE2+CD33, CCR1$^+$CLEC12A, CD70$^+$CD33 and LILRB2+CLEC12A (FIG. 10A).

Figure 10B:
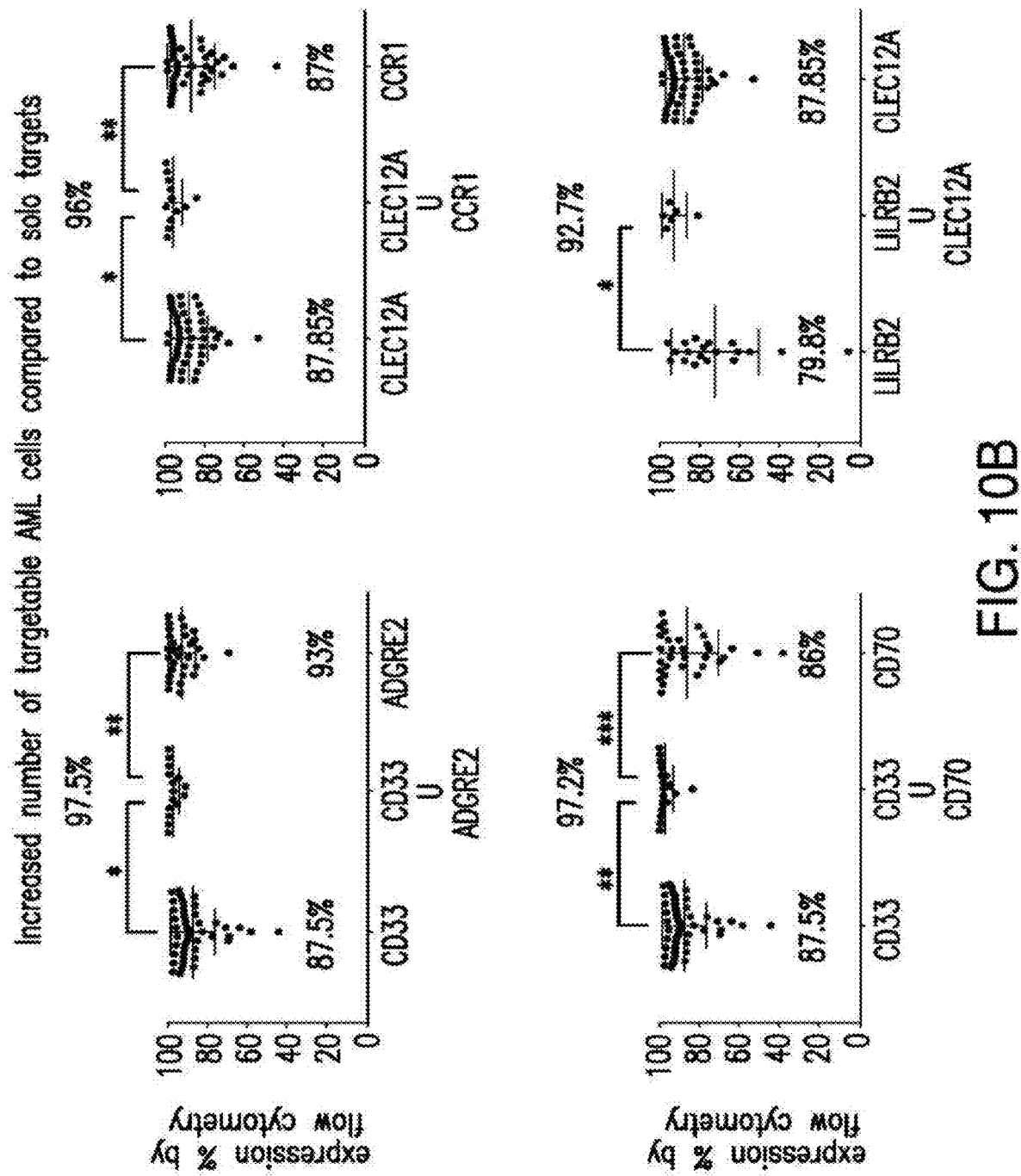

The pairing must also aim for maximum efficacy against AML and prevent antigen escape, strive to recognize all AML cells in a given clinical specimen, prioritizing LSCs and favoring redundancy (FIG. 9D-F). All four combinations increased the rate of targeted targeting, reaching nearly 100% FACS positivity in all AML cells. For each one of these pairs, the dual targeting exceeds the targeting of either antigen alone: (ADGRE2+CD33=97.5%) vs ADGRE2 (93%) and CD33 (87.5%); (CLEC12A+CCR1=96%) vs CLEC12A (87.8%) and CCR1 (87%); (CD70+ CD33=97.2%) vs CD70 (86%) and CD33 (87.5%); (LILRB2+CLEC12A=92.7%) vs LILRB2 (79.8%) (FIG. 10B).

Figure 10C:
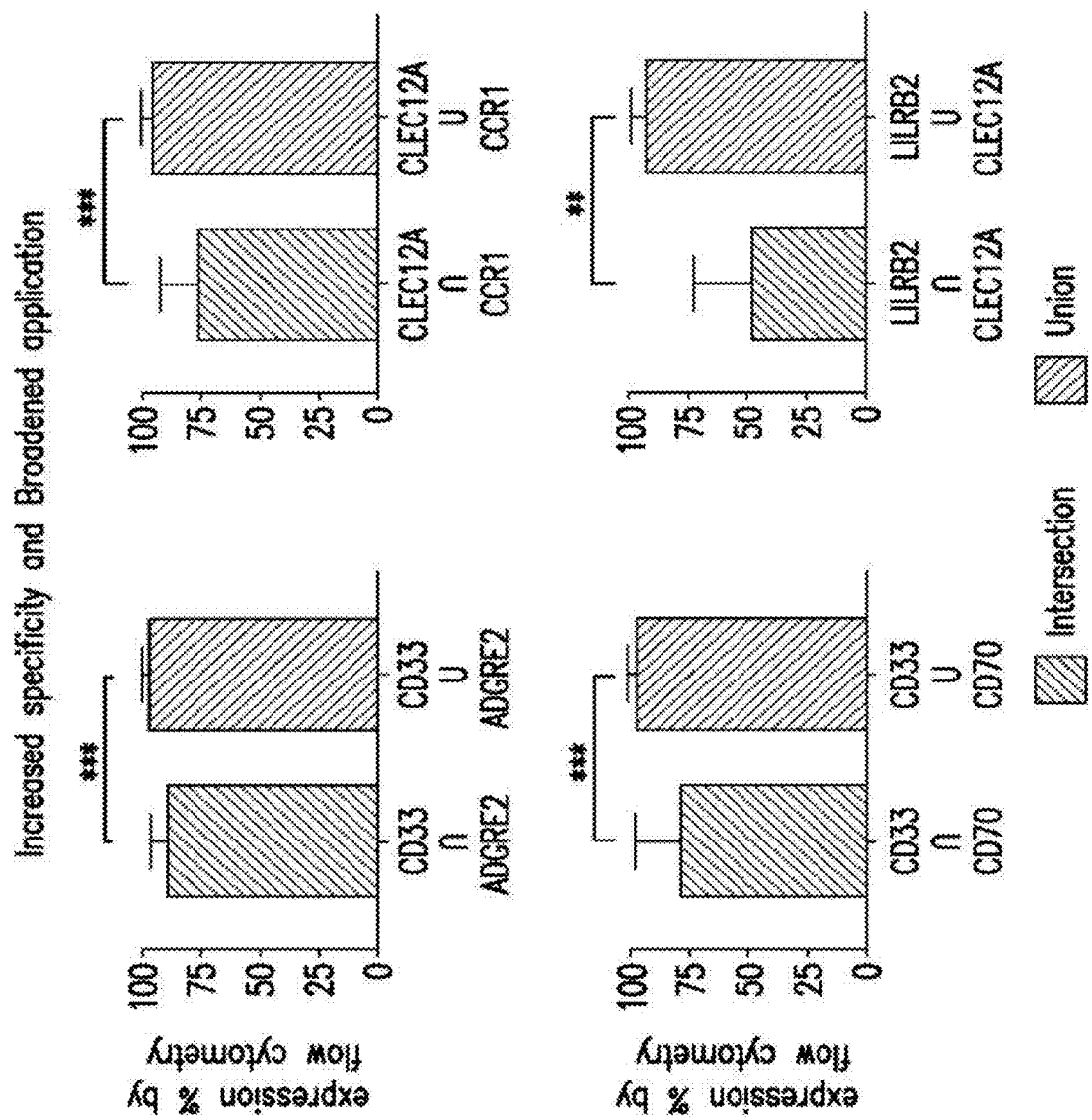

The co-expression of two given targets (which would serve to prevent antigen escape, principle FIG. 9F) were further analyzed in comparison to the sum of each one's expression (which would serve to target multiple cancer clones, principle FIG. 9D). Most of the AML cell populations expressed both antigens in these best pairing (FIG. 10C). It is however noteworthy that total positivity (union) was significantly higher than dual-positivity (intersection) (FIG. 10C), suggesting the presence of minor clones expressing one antigen only. This finding is consistent with clonal heterogeneity and favors using these antigen pairs in the dual-targeting approach (CAR/CAR, FIG. 9). A CAR/CCR combinatorial targeting approach might in this instance increase the risk of relapse and antigen escape and disease relapse (FIG. 9).

Figure 10D:
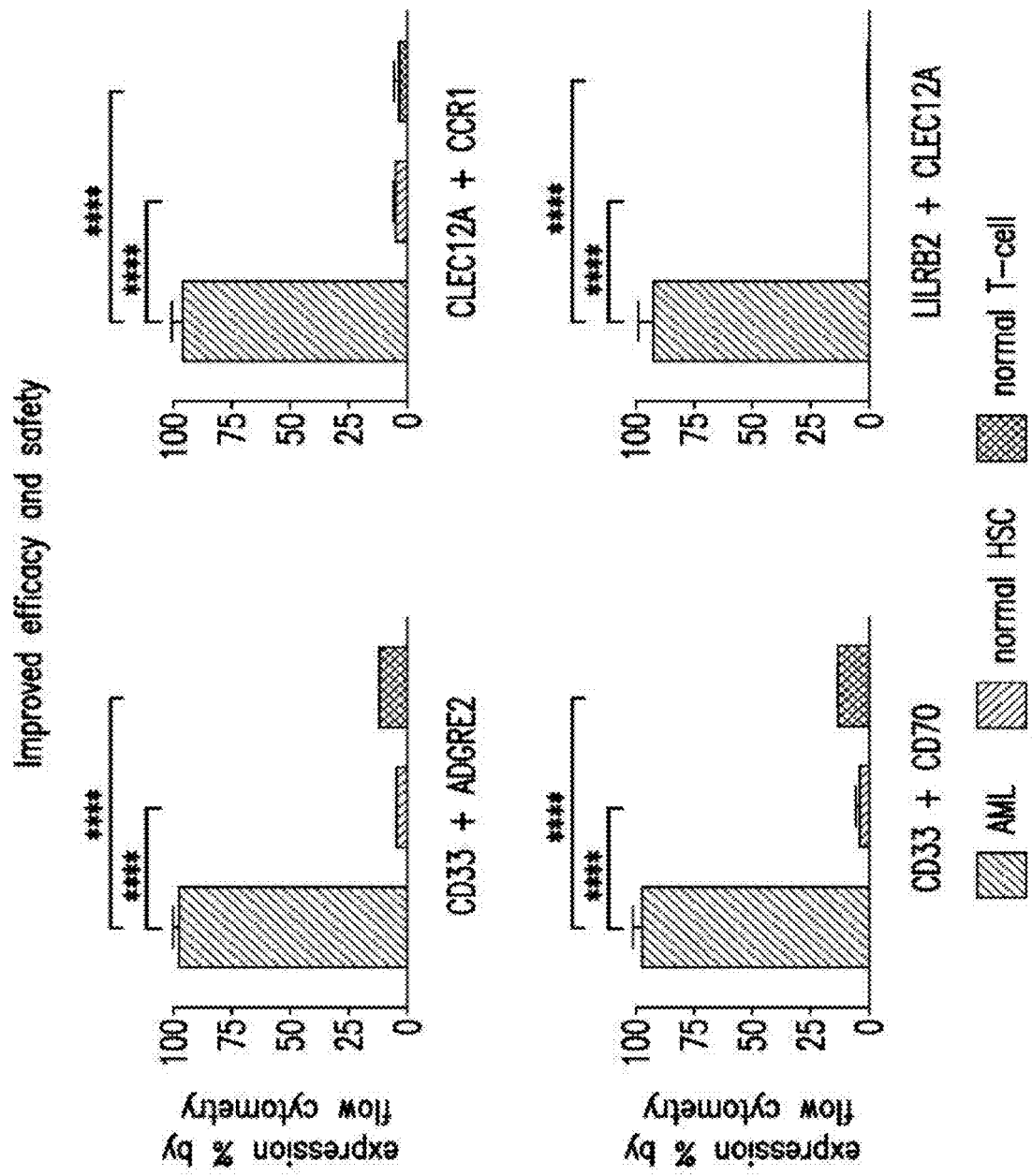

Finally, expression levels of our 4 combinations in normal bone marrow HSPCs and peripheral blood T cells was low (FIG. 10D), confirming that one can maximize AML recognition without increasing the risk of toxicity towards normal hematopoietic cells.

DISCUSSION

CAR therapy is a novel approach to cancer immunotherapy that has demonstrated great potential against relapsed B-cell malignancies, in particular ALL. One may hope for a comparable outcome in AML, if targets as effective as CD19 are identified. A platform that relies on large data sets of protein and RNA expression in malignant and normal tissues were generated, from which new candidate targets for AML CAR therapy were identified. However, neither these nor previously described CAR targets sufficiently fulfill the criteria for a suitable CAR target (Table 3). This led to instead employ the platform to identify combinatorial pairings which can target nearly all AML cells within a tumor sample, including LSCs, but without increasing off-target activity above the level encountered with single targets. Here several target pairs identified using this algorithm were reported, which exhibit non-overlapping expression in normal tissues that would minimize systemic on-target/off-tumor activity (FIGS. 9A and 10A), spare normal HSCs and T cells (FIG. 9B-C) and allow redundant targeting to nearly all AML cells, including LSCs with high redundancy, thereby addressing the challenges of clonal heterogeneity and antigen escape (FIG. 9D-F and 10B-C).

Figure 13:
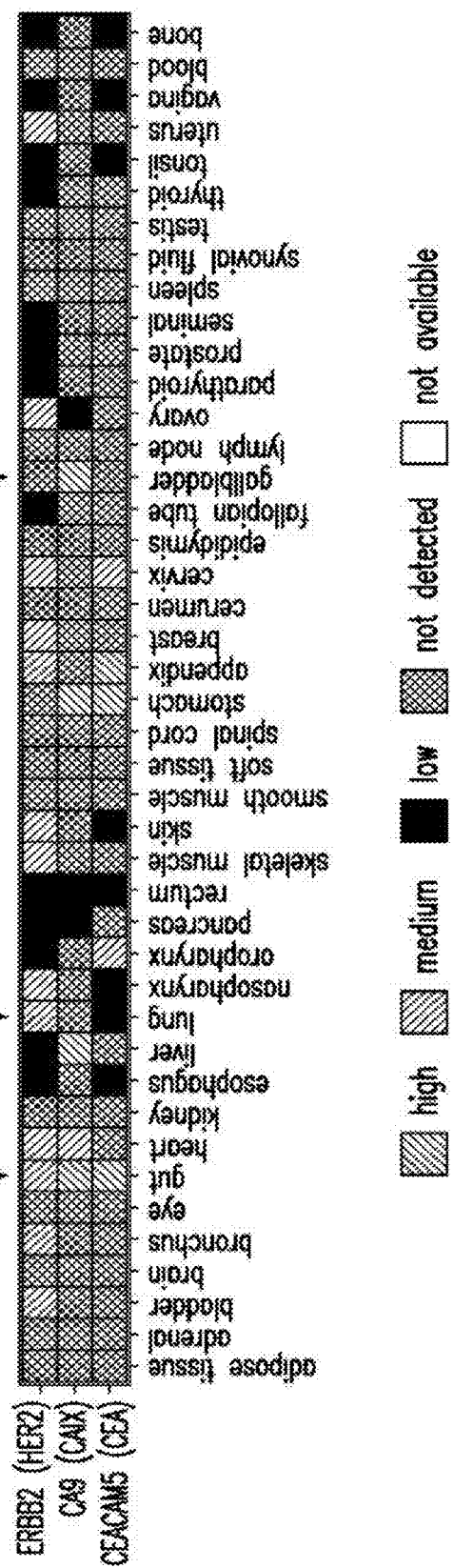
FIG. 13 depicts the expression analysis of T cell targets with proven off-tumor toxicity in normal tissues. Expression profile of ERBB2, targeted in breast cancer and related to toxicity in the lung (arrow); CAIX, targeted in renal cell carcinoma, and related to toxicity in the biliary system (arrow at the site of gallbladder); CEACAM5, targeted in colon cancer and related to hemorrhagic colitis. High expression was found in the normal colon (arrow) as well as stomach and esophagus. Adoptively transferred T cells were found at these sites in treated patients.

An extensive AML surfaceome dataset were assembled, combining public protein repositories and our own cell-surface proteomics performed in 6 AML cell lines, thus generating an inclusive list of AML-associated cell surface proteins. Studies on candidate targets typically focus on one molecule, comparing expression in cancer cells to their normal counterparts, but rarely do they take into account the systemic expression of the candidate target, risking underestimation of the toxicity across normal organs. To address body-wide protein expression, three extensive proteomics databases were combined, which map the human proteome. Both immuno-histochemical assays and mass spectrometry data were combined, increasing confidence especially for low levels of expression. This database included annotations of each candidate molecule in a large panel of normal tissues, in addition to AML and normal HSP cells. Notably, the inventors' integrated database confirmed the presence of normal tissues adversely affected in earlier trials targeting CAIX (Lamers et al., 2013; Lamers et al., 2006), CEA (Parkhurst et al., 2011) and ERBB2 (Morgan et al., 2010), including gallbladder, gut and lung, respectively (FIG. 13). Conversely, CD19, whose only reported on-target/off-tumor toxicity is the induction of B cell aplasia, exhibited a profile of expression limited to the expected lymphoid-rich tissues (FIG. 7B).

Figure 7B:
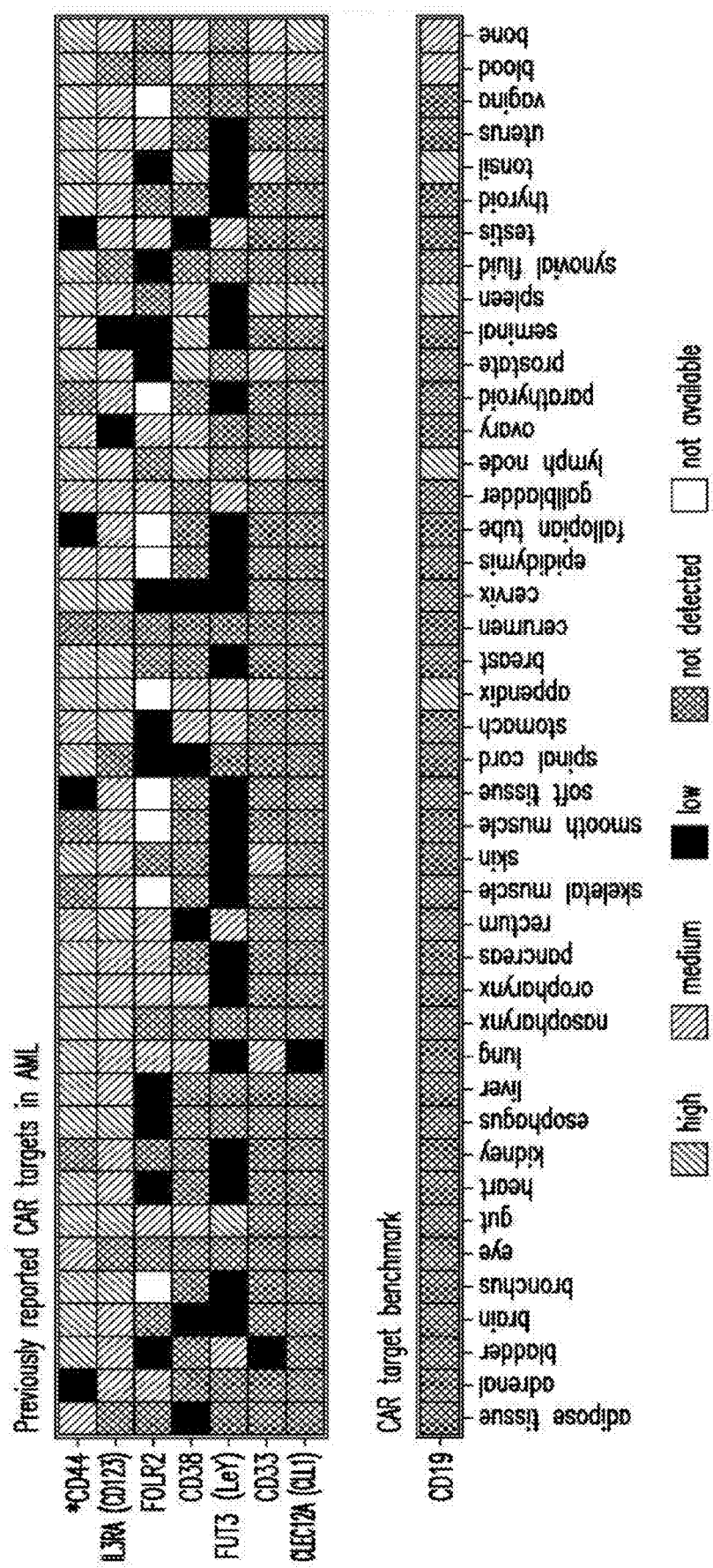

Starting from over 5,000 Ensembl gene IDs (4,942 hgnc), the algorithm identified 24 candidates with features potentially suitable for CAR targeting (FIG. 7). It should be noted, four of these targets, all present in our cell surface proteomics, were G-protein coupled receptors (G-PCRs): ADGRE2, CCR1, LTB4R and P2RY13. Prior studies based on RNA-seq have found these G-PCRs to be amongst the most highly expressed G-PCRs in AML cells (Maiga et al., 2016). A possible role for G-PCRs in leukemic cell behavior has been suggested for chemokine receptors (such as CCR1), adhesion receptors (such as ADGRE2) and purine receptors (including P2RY13) (Wilhelm et al., 2011). The FACS analyses conducted for all 24 candidates in a panel of 30 primary AML samples and AML LSCs, further shortened our candidate list to nine molecules, based on positive detection by FACS analysis in most patients and in >75% cells per clinical specimen. Six of these molecules exhibited low levels of expression in normal bone marrow CD34+ CD38-CD45RA-CD90+ HSCs: TNFRSF1B, ADGRE2, CCR1, CD96, CD70 and LILRB2. TNFRSF1B and CD96 were found to be expressed at high levels in T cells (FIG. 8D), which may result in CAR T cell self-elimination. The expression of TNFRSF1B and CD96 in T cells could be eliminated by gene editing, however this would impose additional CAR T cell manufacturing steps (Riviere and Sadelain, 2017).

The remaining four candidate targets identified by our algorithm were ADGRE2, CCR1, CD70 and LILRB2. ADGRE2 (aka EMR2) is a member of the epidermal growth factor (EGF)-TM7 family of proteins, along with EMR1 (Baud et al., 1995), F4/80 and CD97 (Lin et al., 1997). Like CD97, ADGRE2/EMR2 possesses calcium-binding EGF domains (Downing et al., 1996), but unlike CD97, which is ubiquitously expressed in many cell types, EMR2 expression is restricted to monocytes/macrophages and granulocytes and is not up-regulated in activated T and B cells (Lin et al., 2000)(FIG. 8E). ADGRE2 was found to be expressed at low levels in the gut, ovary and spleen; conversely, its expression levels in AML were higher compared to normal BM HSCs.

CCR1 (aka CD191) is a G-PCR that binds to members of the C—C chemokine family. An immunohistochemical analysis of 944 hematolymphoid neoplasias previously identified CCR1 expression in a subset of AML, B and T cell lymphomas, plasma cell myeloma, and Hodgkin lymphoma (Anderson et al., 2010). CCR1 presents the lowest overall expression in normal tissues while the majority of the AML cases showed strong CCR1 expression, averaging 88% positivity by FACS in all specimens.

CD70 is a member of the TNF-family and the ligand of the CD27 T cell costimulatory receptor (Bowman et al., 1994; Goodwin et al., 1993). It is expressed in multiple tumor types and serves as a target for antibody and drug-conjugated antibody depletion in both renal cell carcinoma and non-Hodgkin lymphoma (Law et al., 2006; McEarchern et al., 2007; McEarchern et al., 2008; Ryan et al., 2010). CD70-specific CARs have been shown to induce sustained regression of established Raji Burkitt lymphoma xenografts (Shaffer et al., 2011). CD70 to be expressed at low levels in the gut and the FACS analyses detected CD70 in ~86% of cells in all patient specimens.

LILRB2 (aka CD85d) is a member of the leukocyte immunoglobulin-like receptor (LIR) family. The encoded protein is expressed on myeloid and B cells, acting to suppress the immune response. It is also expressed on NSCLC cells (Sun et al., 2008). LILRB2 to be expressed in the gallbladder and spleen at low levels and the FACS analyses detected LILRB2 in ~76% of cells in most patient specimens. This finding supports the notion that HSCs can express immune inhibitors of innate and adaptive immunity to evade potential immune surveillance (Zheng et al., 2012).

Seven targets have been previously reported as potential AML CAR targets. None of these meet our criteria for optimal single CAR targeting (Table 3), however they may nonetheless prove effective while remaining within acceptable levels of toxicity. Expression profiles for these seven targets in normal tissues are shown in FIG. 7B. CD33 is a myeloid-specific sialic acid-binding receptor, targeted by gentuzumab ozogamicin (GO) (Administration, 2010) with demonstrated survival benefit in AML patients (Hills et al., 2014; Ravandi et al., 2012). Vadastuximab talirine, a CD33-directed antibody-drug conjugated in phase III clinical development (2016), was recently halted following 5 serious adverse events in patients with AML. Preclinical studies evaluating CD33 CARs have shown reduction of myeloid progenitors (Kenderian et al., 2015; Pizzitola et al., 2014). Two clinical trials targeting CD33 are currently active (NCT01864902 and NCT02799680). One AML patient was treated with CD33 CAR T cells at the Chinese PLA General Hospital, showing transient efficacy and mild fluctuations in bilirubin (Wang et al., 2015). CD33 was found to be detected at higher levels than other myeloid markers, as reflected in its higher expression in lung, skin, and prostate (FIG. 7B). The FACS analyses detected CD33 in ~87% of cells from all patient specimens. CLEC12A (aka CLL1, CD371), a type II transmembrane receptor family containing a C-type lectin/C-type lectin-like domain, is over-expressed in LSCs (van Rhenen et al., 2007). The FACS analyses detected CLEC12A in the lung at low levels and in ~87% of cells in most patient specimens. It is expressed in committed progenitor cells, consistent with RNA expression levels (Bakker et al., 2004) and our flow cytometry results (FIG. 8C). CLEC12A plays a role as a negative regulator of granulocyte and monocyte function. CLEC12A CAR T cells have been shown to be effective against HL60 (Tashiro et al., 2017), but exhibited modest activity against primary AML xenografts (Kenderian et al., 2016). Lewis (Le)-Y, a difucosylated carbohydrate antigen, has been targeted in four patients with relapsed AML. Infusion of second-generation CD28-based CAR T cells resulted in stable/transient remission of three patients, all of whom ultimately progressed, despite T cell persistence (Ritchie et al., 2013), suggesting possible antigen escape. Le-Y was found to be highly expressed in the gut (FIG. 7) and thus did not consider it for further analysis. Two trials for CARs targeting CD123 (NCT02159495 and NCT02623582), the high-affinity interleukin-3 receptor α-chain, are in progress. In one instance, partial remission was induced in a patient with FLT3-ITD+ AML treated with a third generation CD123-specific CAR (Luo et al., 2015). Preclinical studies however have revealed significant myeloablation in one study (Gill et al., 2014) but not another (Pizzitola et al., 2014). CD123 is expressed at high levels in several normal tissues (FIG. 7B), which resulted in its elimination by our algorithm. Low affinity CARs may mitigate some of the on-target/off-tumor toxicity (Arcangeli et al., 2017). Moreover, folate receptor β and CD44v6, the isoform variant 6 of the adhesive receptor CD44, other myeloid-lineage antigens (Bendall et al., 2000; Legras et al., 1998; Lynn et al., 2016; Lynn et al., 2015) that were found to be expressed in multiple normal tissues (FIG. 7B). CD44v6 is found in AML stem cells (Casucci et al., 2013) and some epithelial tissues, particularly skin keratinocytes (Heider et al., 2004). Reports of CD44v6 expression are conflicting, depending on antibody usage (Bendall et al., 2000). CD38 is a non-lineage-restricted, type II transmembrane glycoprotein targeted by Daratumumab, the first U.S. Food and Drug Administration-approved anti-CD38 antibody (Dimopoulos et al., 2016; Lonial et al., 2016) the activity of which on AML is limited without ATRA (Yoshida et al., 2016). It is expressed in all normal hematopoietic progenitor cells, T cell and NK cells. More recently, Drent et al. generated ~124 antibodies specific for CD38 spanning over 2 logs of affinity and demonstrated that CAR T cells bearing scFvs with reduced affinity can strongly lyse $CD38^{++}$ myeloma cells (on-target/on-tumor effect), while sparing $CD38^{+}$ normal hematopoietic cells (on-target/off-tumor effect) (Drent et al., 2017). These findings extend previous reports showing a correlation between scFv affinity and CAR activity (Caruso et al., 2015; Hudecek et al., 2013; Liu et al., 2015).

While several of the above targets have therapeutic potential, none was found with an expression profile comparable favorable to CD19. Lesser abundant expression of these candidates in AML cells or LSCs as measured by FACS analysis suggests a higher risk of antigen escape and AML relapse than seen with CD19 CAR therapy. These considerations prompted exploration of combinatorial targeting strategies. Combinatorial strategies differ in both intent and approach (Sun and Sadelain, 2015; Wu et al., 2015). Some combine activating receptors (CAR/CAR), which enables T cells to recognize target cells that express any of two given antigens. This approach broadens T cell reactivity in the context of a heterogeneous disease like AML and likely decreases the risk of antigen escape, but at the cost of potentially accumulating toxicity associated with each target. In contrast, a combinatorial approach that restricts T cell function to dual-positive tumor cells will avert T cell activity against normal tissues that express either target alone (Alvarez-Vallina and Hawkins, 1996; Kloss et al., 2013), but requires pan-expression of the CAR target in AML cells. The analyses (FIG. 10B-C and FIG. 14), however, did not identify suitable CAR targets to implement this strategy.

6 principles (FIG. 9) were laid out to guide combinatorial CAR pairing with the purpose of enhancing AML targeting (FIG. 9D-F, FIG. 10B-D) without increasing the potential for off-tumor toxicity (FIGS. 9A-C and 10A). From a pool of 12 promising molecules, pairwise combination results in 66 distinct pairs, from which several possible combinations were suitable for further analysis. Four of these, CD33+ ADGRE2, CLEC12A+CCR1, CD33+CD70 and LILRB2+ CLEC12A, were studied in greater depth, by looking at their expression in primary AML specimens. Three of these pairings positively stained >97% of cells in AML samples, (LILRB2+CLEC12A scored slightly lower, averaging 93%, FIG. 10B), while all stained <5% of normal HSCs and T cells. Thus, the aggregate staining of ADGRE2 and CD33 increased the rate of FACS recognition to 97%. CD33 is a relatively abundant myeloid marker, more abundant in lung, skin, and prostate than other myeloid markers, however this combinatorial pairing would not be expected to exacerbate on-target/off-tumor activity (FIG. 10A). Similarly, the combined targeting of CCR1 and CLEC12A is not predicted to increase off-tumor targeting in the lung (FIG. 10A). In pairing targets with non-overlapping expression in normal tissues, one may leverage a co-targeting strategy with minimal cumulative antigen expression in non-tumor cells (FIG. 9A).

This present study represents a new approach to the discovery of CAR targets and rests on two central concepts. First, the use of a composite high-throughput annotation database, including both proteomics and transcriptomics, for evaluating many candidates simultaneously. And second the application of six principles to guide combinatorial pairings, which are the basis for the algorithm applied here. This paradigm will help advance the development of CAR therapy for AML and other cancers including solid tumors.

REFERENCES (2016). ADCs Show Promise in Leukemias. Cancer Discov 6, 939.

Adam Mark, R. T., Cyrus Afrasiabi and Chunlei Wu (2014).

Anderson, M. W., Zhao, S., Ai, W. Z., Tibshirani, R., Levy, R., Lossos, I. S., and Natkunam, Y. (2010). C—C chemokine receptor 1 expression in human hematolymphoid neoplasia. Am J Clin Pathol 133, 473-483.

Arcangeli, S., Rotiroti, M. C., Bardelli, M., Simonelli, L., Magnani, C. F., Biondi, A., Biagi, E., Tettamanti, S., and Varani, L. (2017). Balance of Anti-CD123 Chimeric Antigen Receptor Binding Affinity and Density for the Targeting of Acute Myeloid Leukemia. Mol Ther.

Bagger, F. O., Sasivarevic, D., Sohi, S. H., Laursen, L. G., Pundhir, S., Sonderby, C. K., Winther, O., Rapin, N., and Porse, B. T. (2016). BloodSpot: a database of gene expression profiles and transcriptional programs for healthy and malignant haematopoiesis. Nucleic Acids Res 44, D917-924.

Bakker, A. B., van den Oudenrijn, S., Bakker, A. Q., Feller, N., van Meijer, M., Bia, J. A., Jongeneelen, M. A., Visser, T. J., Bijl, N., Geuijen, C. A., et al. (2004). C-type lectin-like molecule-1: a novel myeloid cell surface marker associated with acute myeloid leukemia. Cancer Res 64, 8443-8450.

Baud, V., Chissoe, S. L., Viegas-Pequignot, E., Diriong, S., N'Guyen, V. C., Roe, B. A., and Lipinski, M. (1995). EMR1, an unusual member in the family of hormone receptors with seven transmembrane segments. Genomics 26, 334-344.

Becker, P. S., Kantarjian, H. M., Appelbaum, F. R., Petersdorf, S. H., Storer, B., Pierce, S., Shan, J., Hendrie, P. C., Pagel, J. M., Shustov, A. R., et al. (2011). Clofarabine with high dose cytarabine and granulocyte colony-stimulating factor (G-CSF) priming for relapsed and refractory acute myeloid leukaemia. Br J Haematol 155, 182-189.

Bendall, L. J., Bradstock, K. F., and Gottlieb, D. J. (2000). Expression of CD44 variant exons in acute myeloid leukemia is more common and more complex than that observed in normal blood, bone marrow or CD34+ cells. Leukemia 14, 1239-1246.

Bowman, M. R., Crimmins, M. A., Yetz-Aldape, J., Kriz, R., Kelleher, K., and Herrmann, S. (1994). The cloning of CD70 and its identification as the ligand for CD27. J Immunol 152, 1756-1761.

Breems, D. A., Van Putten, W. L., Huijgens, P. C., Ossenkoppele, G. J., Verhoef, G. E., Verdonck, L. F., Vellenga, E., De Greef, G. E., Jacky, E., Van der Lelie, J., et al.

(2005). Prognostic index for adult patients with acute myeloid leukemia in first relapse. J Clin Oncol 23, 1969-1978.

Brentjens, R. J., Davila, M. L., Riviere, I., Park, J., Wang, X., Cowell, L. G., Bartido, S., Stefanski, J., Taylor, C., Olszewska, M., et al. (2013). CD19-targeted T cells rapidly induce molecular remissions in adults with chemotherapy-refractory acute lymphoblastic leukemia. Sci Transl Med 5, 177ra138.

Cancer Genome Atlas Research, N. (2013). Genomic and epigenomic landscapes of adult de novo acute myeloid leukemia. N Engl J Med 368, 2059-2074.

Casucci, M., Nicolis di Robilant, B., Falcone, L., Camisa, B., Norelli, M., Genovese, P., Gentner, B., Gullotta, F., Ponzoni, M., Bernardi, M., et al. (2013). CD44v6-targeted T cells mediate potent antitumor effects against acute myeloid leukemia and multiple myeloma. Blood 122, 3461-3472.

Chung, S. S., Eng, W. S., Hu, W., Khalaj, M., Garrett-Bakelman, F. E., Tavakkoli, M., Levine, R. L., Carroll, M., Klimek, V. M., Melnick, A. M., and Park, C. Y. (2017). CD99 is a therapeutic target on disease stem cells in myeloid malignancies. Sci Transl Med 9.

Couzin-Frankel, J. (2013). Breakthrough of the year 2013. Cancer immunotherapy. Science 342, 1432-1433.

Curran, K. J., Pegram, H. J., and Brentjens, R. J. (2012). Chimeric antigen receptors for T cell immunotherapy: current understanding and future directions. J Gene Med 14, 405-415.

Davila, M. L., Kloss, C. C., Gunset, G., and Sadelain, M. (2013). CD19 CAR-targeted T cells induce long-term remission and B Cell Aplasia in an immunocompetent mouse model of B cell acute lymphoblastic leukemia. PLoS One 8, e61338.

Davila, M. L., Riviere, I., Wang, X., Bartido, S., Park, J., Curran, K., Chung, S. S., Stefanski, J., Borquez-Ojeda, O., Olszewska, M., et al. (2014). Efficacy and toxicity management of 19-28z CAR T cell therapy in B cell acute lymphoblastic leukemia. Sci Transl Med 6, 224ra225.

Dimopoulos, M. A., Oriol, A., Nahi, H., San-Miguel, J., Bahlis, N. J., Usmani, S. Z., Rabin, N., Orlowski, R. Z., Komarnicki, M., Suzuki, K., et al. (2016). Daratumumab, Lenalidomide, and Dexamethasone for Multiple Myeloma. N Engl J Med 375, 1319-1331.

Downing, A. K., Knott, V., Werner, J. M., Cardy, C. M., Campbell, I. D., and Handford, P. A. (1996). Solution structure of a pair of calcium-binding epidermal growth factor-like domains: implications for the Marfan syndrome and other genetic disorders. Cell 85, 597-605.

Drent, E., Themeli, M., Poels, R., de Jong-Korlaar, R., Yuan, H., de Bruijn, J., Martens, A. C. M., Zweegman, S., van de Donk, N., Groen, R. W. J., et al. (2017). A Rational Strategy for Reducing On-Target Off-Tumor Effects of CD38-Chimeric Antigen Receptors by Affinity Optimization. Mol Ther.

Duong, C. P., Westwood, J. A., Berry, L. J., Darcy, P. K., and Kershaw, M. H. (2011). Enhancing the specificity of T-cell cultures for adoptive immunotherapy of cancer. Immunotherapy 3, 33-48.

Durinck, S., Spellman, P. T., Birney, E., and Huber, W. (2009). Mapping identifiers for the integration of genomic datasets with the R/Bioconductor package biomaRt. Nat Protoc 4, 1184-1191.

Estey, E., Kornblau, S., Pierce, S., Kantarjian, H., Beran, M., and Keating, M. (1996). A stratification system for evaluating and selecting therapies in patients with relapsed or primary refractory acute myelogenous leukemia. Blood 88, 756.

Gardner, R., Wu, D., Cherian, S., Fang, M., Hanafi, L. A., Finney, O., Smithers, H., Jensen, M. C., Riddell, S. R., Maloney, D. G., and Turtle, C. J. (2016). Acquisition of a CD19-negative myeloid phenotype allows immune escape of MLL-rearranged B-ALL from CD19 CAR-T-cell therapy. Blood 127, 2406-2410.

Gill, S., Tasian, S. K., Ruella, M., Shestova, O., Li, Y., Porter, D. L., Carroll, M., Danet-Desnoyers, G., Scholler, J., Grupp, S. A., et al. (2014). Preclinical targeting of human acute myeloid leukemia and myeloablation using chimeric antigen receptor-modified T cells. Blood 123, 2343-2354.

Goodwin, R. G., Alderson, M. R., Smith, C. A., Armitage, R. J., VandenBos, T., Jerzy, R., Tough, T. W., Schoenborn, M. A., Davis-Smith, T., Hennen, K., and et al. (1993). Molecular and biological characterization of a ligand for CD27 defines a new family of cytokines with homology to tumor necrosis factor. Cell 73, 447-456.

Hack, C. J. (2004). Integrated transcriptome and proteome data: the challenges ahead. Brief Funct Genomic Proteomic 3, 212-219.

Haider, S., and Pal, R. (2013). Integrated analysis of transcriptomic and proteomic data. Curr Genomics 14, 91-110.

Heider, K. H., Kuthan, H., Stehle, G., and Munzert, G. (2004). CD44v6: a target for antibody-based cancer therapy. Cancer Immunol Immunother 53, 567-579.

Hills, R. K., Castaigne, S., Appelbaum, F. R., Delaunay, J., Petersdorf, S., Othus, M., Estey, E. H., Dombret, H., Chevret, S., Ifrah, N., et al. (2014). Addition of gemtuzumab ozogamicin to induction chemotherapy in adult patients with acute myeloid leukaemia: a meta-analysis of individual patient data from randomised controlled trials. Lancet Oncol 15, 986-996.

Hosen, N., Park, C. Y., Tatsumi, N., Oji, Y., Sugiyama, H., Gramatzki, M., Krensky, A. M., and Weissman, I. L. (2007). CD96 is a leukemic stem cell-specific marker in human acute myeloid leukemia. Proc Natl Acad Sci USA 104, 11008-11013.

Jacoby, E., Nguyen, S. M., Fountaine, T. J., Welp, K., Gryder, B., Qin, H., Yang, Y., Chien, C. D., Seif, A. E., Lei, H., et al. (2016). CD19 CAR immune pressure induces B-precursor acute lymphoblastic leukaemia lineage switch exposing inherent leukaemic plasticity. Nat Commun 7, 12320.

Jensen, M. C., and Riddell, S. R. (2015). Designing chimeric antigen receptors to effectively and safely target tumors. Curr Opin Immunol 33, 9-15.

Jin, L., Hope, K. J., Zhai, Q., Smadja-Joffe, F., and Dick, J. E. (2006). Targeting of CD44 eradicates human acute myeloid leukemic stem cells. Nat Med 12, 1167-1174.

Jordan, C. T., Upchurch, D., Szilvassy, S. J., Guzman, M. L., Howard, D. S., Pettigrew, A. L., Meyerrose, T., Rossi, R., Grimes, B., Rizzieri, D. A., et al. (2000). The interleukin-3 receptor alpha chain is a unique marker for human acute myelogenous leukemia stem cells. Leukemia 14, 1777-1784.

Kenderian, S. S., Ruella, M., Shestova, O., Klichinsky, M., Aikawa, V., Morrissette, J. J., Scholler, J., Song, D., Porter, D. L., Carroll, M., et al. (2015). CD33-specific chimeric antigen receptor T cells exhibit potent preclinical activity against human acute myeloid leukemia. Leukemia 29, 1637-1647.

Kikushige, Y., Shima, T., Takayanagi, S., Urata, S., Miyamoto, T., Iwasaki, H., Takenaka, K., Teshima, T., Tanaka, T., Inagaki, Y., and Akashi, K. (2010). TIM-3 is a promising target to selectively kill acute myeloid leukemia stem cells. Cell Stem Cell 7, 708-717.

Kim, M. S., Pinto, S. M., Getnet, D., Nirujogi, R. S., Manda, S. S., Chaerkady, R., Madugundu, A. K., Kelkar, D. S., Isserlin, R., Jain, S., et al. (2014). A draft map of the human proteome. Nature 509, 575-581.

Kloss, C. C., Condomines, M., Cartellieri, M., Bachmann, M., and Sadelain, M. (2013). Combinatorial antigen recognition with balanced signaling promotes selective tumor eradication by engineered T cells. Nat Biotechnol 31, 71-75.

Kochenderfer, J. N., Dudley, M. E., Carpenter, R. O., Kassim, S. H., Rose, J. J., Telford, W. G., Hakim, F. T., Halverson, D. C., Fowler, D. H., Hardy, N. M., et al. (2013). Donor-derived CD19-targeted T cells cause regression of malignancy persisting after allogeneic hematopoietic stem cell transplantation. Blood 122, 4129-4139.

Kochenderfer, J. N., Dudley, M. E., Kassim, S. H., Somerville, R. P., Carpenter, R. O., Stetler-Stevenson, M., Yang, J. C., Phan, G. Q., Hughes, M. S., Sherry, R. M., et al. (2015). Chemotherapy-refractory diffuse large B-cell lymphoma and indolent B-cell malignancies can be effectively treated with autologous T cells expressing an anti-CD19 chimeric antigen receptor. J Clin Oncol 33, 540-549.

Kong, Y., Yoshida, S., Saito, Y., Doi, T., Nagatoshi, Y., Fukata, M., Saito, N., Yang, S. M., Iwamoto, C., Okamura, J., et al. (2008). CD34+CD38+CD19+ as well as CD34+CD38-CD19+ cells are leukemia-initiating cells with self-renewal capacity in human B-precursor ALL. Leukemia 22, 1207-1213.

Lamers, C. H., Sleijfer, S., van Steenbergen, S., van Elzakker, P., van Krimpen, B., Groot, C., Vulto, A., den Bakker, M., Oosterwijk, E., Debets, R., and Gratama, J. W. (2013). Treatment of metastatic renal cell carcinoma with CAIX CAR-engineered T cells: clinical evaluation and management of on-target toxicity. Mol Ther 21, 904-912.

Lamers, C. H., Sleijfer, S., Vulto, A. G., Kruit, W. H., Kliffen, M., Debets, R., Gratama, J. W., Stoter, G., and Oosterwijk, E. (2006). Treatment of metastatic renal cell carcinoma with autologous T-lymphocytes genetically retargeted against carbonic anhydrase IX: first clinical experience. J Clin Oncol 24, e20-22.

Law, C. L., Gordon, K. A., Toki, B. E., Yamane, A. K., Hering, M. A., Cerveny, C. G., Petroziello, J. M., Ryan, M. C., Smith, L., Simon, R., et al. (2006). Lymphocyte activation antigen CD70 expressed by renal cell carcinoma is a potential therapeutic target for anti-CD70 antibody-drug conjugates. Cancer Res 66, 2328-2337.

Le, D. T., Uram, J. N., Wang, H., Bartlett, B. R., Kemberling, H., Eyring, A. D., Skora, A. D., Luber, B. S., Azad, N. S., Laheru, D., et al. (2015). PD-1 Blockade in Tumors with Mismatch-Repair Deficiency. N Engl J Med 372, 2509-2520.

LeBien, T. W., and Tedder, T. F. (2008). B lymphocytes: how they develop and function. Blood 112, 1570-1580.

Lee, D. W., Kochenderfer, J. N., Stetler-Stevenson, M., Cui, Y. K., Delbrook, C., Feldman, S. A., Fry, T. J., Orentas, R., Sabatino, M., Shah, N. N., et al. (2015). T cells expressing CD19 chimeric antigen receptors for acute lymphoblastic leukaemia in children and young adults: a phase 1 dose-escalation trial. Lancet 385, 517-528.

Legras, S., Gunthert, U., Stauder, R., Curt, F., Oliferenko, S., Kluin-Nelemans, H. C., Marie, J. P., Proctor, S., Jasmin, C., and Smadja-Joffe, F. (1998). A strong expression of CD44-6v correlates with shorter survival of patients with acute myeloid leukemia. Blood 91, 3401-3413.

Lin, H. H., Stacey, M., Hamann, J., Gordon, S., and McKnight, A. J. (2000). Human EMR2, a novel EGF-TM7 molecule on chromosome 19p13.1, is closely related to CD97. Genomics 67, 188-200.

Lin, H. H., Stubbs, L. J., and Mucenski, M. L. (1997). Identification and characterization of a seven transmembrane hormone receptor using differential display. Genomics 41, 301-308.

Lonial, S., Weiss, B. M., Usmani, S. Z., Singhal, S., Chari, A., Bahlis, N. J., Belch, A., Krishnan, A., Vescio, R. A., Mateos, M. V., et al. (2016). Daratumumab monotherapy in patients with treatment-refractory multiple myeloma (SIRIUS): an open-label, randomised, phase 2 trial. Lancet 387, 1551-1560.

Lynn, R. C., Feng, Y., Schutsky, K., Poussin, M., Kalota, A., Dimitrov, D. S., and Powell, D. J., Jr. (2016). High-affinity FRbeta-specific CAR T cells eradicate AML and normal myeloid lineage without HSC toxicity. Leukemia.

Lynn, R. C., Poussin, M., Kalota, A., Feng, Y., Low, P. S., Dimitrov, D. S., and Powell, D. J., Jr. (2015). Targeting of folate receptor beta on acute myeloid leukemia blasts with chimeric antigen receptor-expressing T cells. Blood 125, 3466-3476.

Maiga, A., Lemieux, S., Pabst, C., Lavallee, V. P., Bouvier, M., Sauvageau, G., and Hebert, J. (2016). Transcriptome analysis of G protein-coupled receptors in distinct genetic subgroups of acute myeloid leukemia: identification of potential disease-specific targets. Blood Cancer J 6, e431.

Majeti, R., Chao, M. P., Alizadeh, A. A., Pang, W. W., Jaiswal, S., Gibbs, K. D., Jr., van Rooijen, N., and Weissman, I. L. (2009). CD47 is an adverse prognostic factor and therapeutic antibody target on human acute myeloid leukemia stem cells. Cell 138, 286-299.

Maude, S. L., Frey, N., Shaw, P. A., Aplenc, R., Barrett, D. M., Bunin, N. J., Chew, A., Gonzalez, V. E., Zheng, Z., Lacey, S. F., et al. (2014a). Chimeric antigen receptor T cells for sustained remissions in leukemia. N Engl J Med 371, 1507-1517.

Maude, S. L., Shpall, E. J., and Grupp, S. A. (2014b). Chimeric antigen receptor T-cell therapy for ALL. Hematology Am Soc Hematol Educ Program 2014, 559-564.

McEarchern, J. A., Oflazoglu, E., Francisco, L., McDonagh, C. F., Gordon, K. A., Stone, I., Klussman, K., Turcott, E., van Rooij en, N., Carter, P., et al. (2007). Engineered anti-CD70 antibody with multiple effector functions exhibits in vitro and in vivo antitumor activities. Blood 109, 1185-1192.

McEarchern, J. A., Smith, L. M., McDonagh, C. F., Klussman, K., Gordon, K. A., Morris-Tilden, C. A., Duniho, S., Ryan, M., Boursalian, T. E., Carter, P. J., et al. (2008). Preclinical characterization of SGN-70, a humanized antibody directed against CD70. Clin Cancer Res 14, 7763-7772.

McGranahan, N., Furness, A. J., Rosenthal, R., Ramskov, S., Lyngaa, R., Saini, S. K., Jamal-Hanjani, M., Wilson, G. A., Birkbak, N. J., Hiley, C. T., et al. (2016). Clonal neoantigens elicit T cell immunoreactivity and sensitivity to immune checkpoint blockade. Science 351, 1463-1469.

Morgan, R. A., Yang, J. C., Kitano, M., Dudley, M. E., Laurencot, C. M., and Rosenberg, S. A. (2010). Case report of a serious adverse event following the administration of T cells transduced with a chimeric antigen receptor recognizing ERBB2. Mol Ther 18, 843-851.

Parkhurst, M. R., Yang, J. C., Langan, R. C., Dudley, M. E., Nathan, D. A., Feldman, S. A., Davis, J. L., Morgan, R. A., Merino, M. J., Sherry, R. M., et al. (2011). T cells targeting carcinoembryonic antigen can mediate regression of metastatic colorectal cancer but induce severe transient colitis. Mol Ther 19, 620-626.

Paszkiewicz, P. J., Frassle, S. P., Srivastava, S., Sommermeyer, D., Hudecek, M., Drexler, I., Sadelain, M., Liu, L., Jensen, M. C., Riddell, S. R., and Busch, D. H. (2016). Targeted antibody-mediated depletion of murine CD19 CAR T cells permanently reverses B cell aplasia. J Clin Invest 126, 4262-4272.

Pegram, H. J., Lee, J. C., Hayman, E. G., Imperato, G. H., Tedder, T. F., Sadelain, M., and Brentjens, R. J. (2012). Tumor-targeted T cells modified to secrete IL-12 eradicate systemic tumors without need for prior conditioning. Blood 119, 4133-4141.

Perna, F., Sadelain, M. (2016). Myeloid leukemia switch as immune escape from CD19 chimeric antigen receptor (CAR) therapy. Transl Cancer Res 5, S221-S225.

Pizzitola, I., Anjos-Afonso, F., Rouault-Pierre, K., Lassailly, F., Tettamanti, S., Spinelli, O., Biondi, A., Biagi, E., and Bonnet, D. (2014). Chimeric antigen receptors against CD33/CD123 antigens efficiently target primary acute myeloid leukemia cells in vivo. Leukemia 28, 1596-1605.

Pulte, D., Gondos, A., and Brenner, H. (2008). Improvements in survival of adults diagnosed with acute myeloblastic leukemia in the early 21st century. Haematologica 93, 594-600.

Qasim, W., Zhan, H., Samarasinghe, S., Adams, S., Amrolia, P., Stafford, S., Butler, K., Rivat, C., Wright, G., Somana, K., et al. (2017). Molecular remission of infant B-ALL after infusion of universal TALEN gene-edited CAR T cells. Sci Transl Med 9.

Ravandi, F., Estey, E. H., Appelbaum, F. R., Lo-Coco, F., Schiffer, C. A., Larson, R. A., Burnett, A. K., and Kantarjian, H. M. (2012). Gemtuzumab ozogamicin: time to resurrect? J Clin Oncol 30, 3921-3923.

Ritchie, D. S., Neeson, P. J., Khot, A., Peinert, S., Tai, T., Tainton, K., Chen, K., Shin, M., Wall, D. M., Honemann, D., et al. (2013). Persistence and efficacy of second generation CAR T cell against the LeY antigen in acute myeloid leukemia. Mol Ther 21, 2122-2129.

Riviere, I., and Sadelain, M. (2017). Chimeric Antigen Receptors: A Cell and Gene Therapy Perspective. Mol Ther 25, 1117-1124.

Rizvi, N. A., Hellmann, M. D., Snyder, A., Kvistborg, P., Makarov, V., Havel, J. J., Lee, W., Yuan, J., Wong, P., Ho, T. S., et al. (2015). Cancer immunology. Mutational landscape determines sensitivity to PD-1 blockade in non-small cell lung cancer. Science 348, 124-128.

Ryan, M. C., Kostner, H., Gordon, K. A., Duniho, S., Sutherland, M. K., Yu, C., Kim, K. M., Nesterova, A., Anderson, M., McEarchern, J. A., et al. (2010). Targeting pancreatic and ovarian carcinomas using the auristatin-based anti-CD70 antibody-drug conjugate SGN-75. Br J Cancer 103, 676-684.

Sadelain, M. (2015). CAR therapy: the CD19 paradigm. J Clin Invest 125, 3392-3400.

Sadelain, M. (2016). Chimeric antigen receptors: driving immunotherapy towards synthetic biology. Curr Opin Immunol 41, 68-76.

Sadelain, M., Riviere, I., and Riddell, S. (2017). Therapeutic T cell engineering. Nature 545, 423-431.

Saito, Y., Kitamura, H., Hijikata, A., Tomizawa-Murasawa, M., Tanaka, S., Takagi, S., Uchida, N., Suzuki, N., Sone, A., Najima, Y., et al. (2010). Identification of therapeutic targets for quiescent, chemotherapy-resistant human leukemia stem cells. Sci Transl Med 2, 17ra19.

Shaffer, D. R., Savoldo, B., Yi, Z., Chow, K. K., Kakarla, S., Spencer, D. M., Dotti, G., Wu, M. F., Liu, H., Kenney, S., and Gottschalk, S. (2011). T cells redirected against CD70 for the immunotherapy of CD70-positive malignancies. Blood 117, 4304-4314.

Snyder, A., Makarov, V., Merghoub, T., Yuan, J., Zaretsky, J. M., Desrichard, A., Walsh, L. A., Postow, M. A., Wong, P., Ho, T. S., et al. (2014). Genetic basis for clinical response to CTLA-4 blockade in melanoma. N Engl J Med 371, 2189-2199.

Sotillo, E., Barrett, D. M., Black, K. L., Bagashev, A., Oldridge, D., Wu, G., Sussman, R., Lanauze, C., Ruella, M., Gazzara, M. R., et al. (2015). Convergence of Acquired Mutations and Alternative Splicing of CD19 Enables Resistance to CART-19 Immunotherapy. Cancer Discov 5, 1282-1295.

Strassberger, V., Gutbrodt, K. L., Krall, N., Roesli, C., Takizawa, H., Manz, M. G., Fugmann, T., and Neri, D. (2014). A comprehensive surface proteome analysis of myeloid leukemia cell lines for therapeutic antibody development. J Proteomics 99, 138-151.

Sun, J., and Sadelain, M. (2015). The quest for spatio-temporal control of CAR T cells. Cell Res 25, 1281-1282.

Sun, Y., Liu, J., Gao, P., Wang, Y., and Liu, C. (2008). Expression of Ig-like transcript 4 inhibitory receptor in human non-small cell lung cancer. Chest 134, 783-788.

Tashiro, H., Sauer, T., Shum, T., Parikh, K., Mamonkin, M., Omer, B., Rouce, R. H., Lulla, P., Rooney, C. M., Gottschalk, S., and Brenner, M. K. (2017). Treatment of Acute Myeloid Leukemia with T Cells Expressing Chimeric Antigen Receptors Directed to C-type Lectin-like Molecule 1. Mol Ther.

Taussig, D. C., Pearce, D. J., Simpson, C., Rohatiner, A. Z., Lister, T. A., Kelly, G., Luongo, J. L., Danet-Desnoyers, G. A., and Bonnet, D. (2005). Hematopoietic stem cells express multiple myeloid markers: implications for the origin and targeted therapy of acute myeloid leukemia. Blood 106, 4086-4092.

Team, B. B. a. R. D. C. (2016). Tools for General Maximum Likelihood Estimation.

Turatti, F., Figini, M., Balladore, E., Alberti, P., Casalini, P., Marks, J. D., Canevari, S., and Mezzanzanica, D. (2007). Redirected activity of human antitumor chimeric immune receptors is governed by antigen and receptor expression levels and affinity of interaction. J Immunother 30, 684-693.

Turtle, C. J., Hanafi, L. A., Berger, C., Gooley, T. A., Cherian, S., Hudecek, M., Sommermeyer, D., Melville, K., Pender, B., Budiarto, T. M., et al. (2016a). CD19 CAR-T cells of defined CD4+:CD8+ composition in adult B cell ALL patients. J Clin Invest 126, 2123-2138.

Turtle, C. J., Hanafi, L. A., Berger, C., Hudecek, M., Pender, B., Robinson, E., Hawkins, R., Chaney, C., Cherian, S., Chen, X., et al. (2016b). Immunotherapy of non-Hodgkin's lymphoma with a defined ratio of CD8+ and CD4+ CD19-specific chimeric antigen receptor-modified T cells. Sci Transl Med 8, 355ra116.

Uhlen, M., Fagerberg, L., Hallstrom, B. M., Lindskog, C., Oksvold, P., Mardinoglu, A., Sivertsson, A., Kampf, C., Sjostedt, E., Asplund, A., et al. (2015). Proteomics. Tissue-based map of the human proteome. Science 347, 1260419.

Van Allen, E. M., Miao, D., Schilling, B., Shukla, S. A., Blank, C., Zimmer, L., Sucker, A., Hillen, U., Geukes Foppen, M. H., Goldinger, S. M., et al. (2015). Genomic correlates of response to CTLA-4 blockade in metastatic melanoma. Science 350, 207-211.

van Rhenen, A., van Dongen, G. A., Kelder, A., Rombouts, E. J., Feller, N., Moshaver, B., Stigter-van Walsum, M., Zweegman, S., Ossenkoppele, G. J., and Jan Schuurhuis, G. (2007). The novel AML stem cell associated antigen CLL-1 aids in discrimination between normal and leukemic stem cells. Blood 110, 2659-2666.

Walker, A. J., Majzner, R. G., Zhang, L., Wanhainen, K., Long, A. H., Nguyen, S. M., Lopomo, P., Vigny, M., Fry, T. J., Orentas, R. J., and Mackall, C. L. (2017). Tumor Antigen and Receptor Densities Regulate Efficacy of a Chimeric Antigen Receptor Targeting Anaplastic Lymphoma Kinase. Mol Ther.

Wang, Q. S., Wang, Y., Lv, H. Y., Han, Q. W., Fan, H., Guo, B., Wang, L. L., and Han, W. D. (2015). Treatment of CD33-directed chimeric antigen receptor-modified T cells in one patient with relapsed and refractory acute myeloid leukemia. Mol Ther 23, 184-191.

Wang, Z., Wu, Z., Liu, Y., and Han, W. (2017). New development in CAR-T cell therapy. J Hematol Oncol 10, 53.

Weijtens, M. E., Hart, E. H., and Bolhuis, R. L. (2000). Functional balance between T cell chimeric receptor density and tumor associated antigen density: CTL mediated cytolysis and lymphokine production. Gene Ther 7, 35-42.

Wilhelm, B. T., Briau, M., Austin, P., Faubert, A., Boucher, G., Chagnon, P., Hope, K., Girard, S., Mayotte, N., Landry, J. R., et al. (2011). RNA-seq analysis of 2 closely related leukemia clones that differ in their self-renewal capacity. Blood 117, e27-38.

Wilhelm, M., Schlegl, J., Hahne, H., Moghaddas Gholami, A., Lieberenz, M., Savitski, M. M., Ziegler, E., Butzmann, L., Gessulat, S., Marx, H., et al. (2014). Mass-spectrometry-based draft of the human proteome. Nature 509, 582-587.

Wilkie, S., van Schalkwyk, M. C., Hobbs, S., Davies, D. M., van der Stegen, S. J., Pereira, A. C., Burbridge, S. E., Box, C., Eccles, S. A., and Maher, J. (2012). Dual targeting of ErbB2 and MUC1 in breast cancer using chimeric antigen receptors engineered to provide complementary signaling. J Clin Immunol 32, 1059-1070.

Wu, C. Y., Roybal, K. T., Puchner, E. M., Onuffer, J., and Lim, W. A. (2015). Remote control of therapeutic T cells through a small molecule-gated chimeric receptor. Science 350, aab4077.

Yoshida, T., Mihara, K., Takei, Y., Yanagihara, K., Kubo, T., Bhattacharyya, J., Imai, C., Mino, T., Takihara, Y., and Ichinohe, T. (2016). All-trans retinoic acid enhances cytotoxic effect of T cells with an anti-CD38 chimeric antigen receptor in acute myeloid leukemia. Clin Transl Immunology 5, e116.

Yu, H., Sotillo, E., Harrington, C., Wertheim, G., Paessler, M., Maude, S. L., Rheingold, S. R., Grupp, S. A., Thomas-Tikhonenko, A., and Pillai, V. (2017). Repeated loss of target surface antigen after immunotherapy in primary mediastinal large B cell lymphoma. Am J Hematol 92, E11-E13.

Zah, E., Lin, M. Y., Silva-Benedict, A., Jensen, M. C., and Chen, Y. Y. (2016). T Cells Expressing CD19/CD20 Bispecific Chimeric Antigen Receptors Prevent Antigen Escape by Malignant B Cells. Cancer Immunol Res 4, 498-508.

Zheng, J., Umikawa, M., Cui, C., Li, J., Chen, X., Zhang, C., Huynh, H., Kang, X., Silvany, R., Wan, X., et al. (2012). Inhibitory receptors bind ANGPTLs and support blood stem cells and leukaemia development. Nature 485, 656-660.

Zhou, G., and Levitsky, H. (2012). Towards curative cancer immunotherapy: overcoming posttherapy tumor escape. Clin Dev Immunol 2012, 124187.

From the foregoing description, it will be apparent that variations and modifications may be made to the invention described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

What is claimed is:

1. A method for identifying a target tumor surface antigen comprising:
   i) identifying a plurality of cell-surface expressed proteins in a tumor sample from a proteomics database, a transcriptomics database, surface proteomics analysis of the tumor sample, and flow cytometric analysis of the tumor sample, wherein each protein of said plurality has a redundant expression in at least 2 databases; and
   ii) identifying the target tumor surface antigen from said plurality of cell-surface expressed proteins wherein said target tumor surface antigen has:
      a) an expression level in the tumor sample higher than its expression level in a normal sample of the type of tissue from which the tumor is derived; and
      b) an expression level in a normal tissue sample that is no more than one standard deviation above the normal peak of the protein expression level distribution of a plurality of samples of normal tissues, other than the tissue from which the tumor sample is derived.

2. The method of claim 1, wherein the target tumor surface antigen is identified by having an expression level in a normal tissue sample that is more than about one standard deviation below the normal peak of the protein expression level distribution of the normal tissue sample.

3. The method of claim 1, wherein the target tumor surface antigen is identified by having an expression level in a plurality of samples of normal tissues, other than the tissue from which the tumor sample is derived, that is no more than about one standard deviation above the normal peaks of the protein expression level distributions in the samples of normal tissues.

4. The method of claim 3, wherein the target tumor surface antigen is identified by having an expression level in a plurality of samples of normal tissues, other than the tissue from which the tumor sample is derived, that is more than about one standard deviation below the normal peak of the protein expression level distributions in the samples of normal tissues.

5. The method of claim 1, wherein each or both of the proteomics database and the transcriptomics database is selected from the group consisting of Human Protein Atlas (HPA), the Human Proteome Map (HPM), the Proteomics Database (PD), and combinations thereof.

6. The method of claim 1, wherein the expression level of the tumor surface antigen is the mRNA expression level of the tumor surface antigen.

7. The method of claim 6, wherein the target tumor surface antigen is identified by having the RNA expression level greater than about one standard deviation above the mean expression of the antigen in the samples of normal tissues.

8. The method of claim 1, wherein two tumor surface antigens are identified.

9. The method of claim 8, wherein at least one of the two tumor surface antigens is identified by having a low or no detectable expression in a vital tissue, and wherein no detectable expression is defined as an expression level lower than about one standard deviation below normal peaks of the protein expression level distributions in a plurality of normal tissues, and a low expression is defined as an expression level within about one standard deviation below normal peaks of the protein expression level distributions in a plurality of normal tissues.

10. The method of claim 1, wherein the normal tissue is a vital tissue, and the vital tissue is selected from the group consisting of adipose tissue, adrenal, bladder, brain, bronchus, eye, gut, heart, kidney, esophagus, liver, lung, nasopharynx, oropharynx, pancreas, rectum, skeletal muscle, skin, smooth muscle, soft tissue, spinal cord, stomach, and combinations thereof.

11. The method of claim 1, wherein the normal tissue is a non-vital tissue, and the non-vital tissue is selected from the group consisting of breast, cerumen, cervix, epididymis, fallopian tube, gallbladder, lymph node, ovary, parathyroid, prostate, seminal, spleen, synovial fluid, testis, thyroid, tonsil, uterus, vagina, and combinations thereof.

12. The method of claim 1, wherein the tumor is acute myeloid leukemia (AML).

13. The method of claim 1, wherein the tumor sample is selected from the group consisting of a THP1 cell, a Monomac cell, a Kasumi cell, a Molm13 cell, an OCI/AML3 cell, a TF-1 cell and any combination thereof.

* * * * *